(12) United States Patent
Kim et al.

(10) Patent No.: US 10,749,118 B2
(45) Date of Patent: Aug. 18, 2020

(54) HETEROCYCLIC COMPOUND AND ORGANIC LIGHT-EMITTING DEVICE INCLUDING THE SAME

(71) Applicants: SAMSUNG DISPLAY CO., LTD., Yongin, Gyeonggi-Do (KR); SFC CO., LTD., Cheongju-si, Chungcheongbuk-do (KR)

(72) Inventors: Mi-Kyung Kim, Yongin (KR); Kyung-Hwa Park, Cheongju-si (KR); Bu-Bae Park, Cheongju-si (KR); Ji-Hee Park, Cheongju-si (KR); Bong-Ki Shin, Cheongju-si (KR); Dong-Hyun Kim, Yongin (KR); Se-Hun Kim, Yongin (KR); Hwan-Hee Cho, Yongin (KR)

(73) Assignees: Samsung Display Co., Ltd., Yongin-si (KR); SFC Co., Ltd., Cheongju-si (KR)

( * ) Notice: Subject to any disclaimer, the term of this patent is extended or adjusted under 35 U.S.C. 154(b) by 173 days.

(21) Appl. No.: 14/747,904

(22) Filed: Jun. 23, 2015

(65) Prior Publication Data

US 2015/0380663 A1 Dec. 31, 2015

(30) Foreign Application Priority Data

Jun. 26, 2014 (KR) .................. 10-2014-0079115
Mar. 13, 2015 (KR) .................. 10-2015-0035154

(51) Int. Cl.
*H01L 51/00* (2006.01)
*C07D 495/04* (2006.01)
(Continued)

(52) U.S. Cl.
CPC ...... *H01L 51/0072* (2013.01); *C07D 491/048* (2013.01); *C07D 495/04* (2013.01);
(Continued)

(58) Field of Classification Search
CPC .. C07D 319/08; C07D 327/06; C07D 327/08; C07D 339/08; C07D 405/00;
(Continued)

(56) References Cited

U.S. PATENT DOCUMENTS 4,317,919 A 3/1982 Jones et al.
4,697,022 A 9/1987 Leinert
(Continued)

FOREIGN PATENT DOCUMENTS

KR 1983-0001210 A 4/1983
KR 1984-0009088 A 12/1984
(Continued)

OTHER PUBLICATIONS

Machine Translation of WO2014104665.*
Abstract Publication No. 2008-044923, dated Feb. 28, 2008, for KR 10-2008-0064114 A, 1 page.

*Primary Examiner* — Jennifer A Chriss
*Assistant Examiner* — Sean M DeGuire
(74) *Attorney, Agent, or Firm* — Lewis Roca Rothgerber Christie LLP

(57) ABSTRACT

A heterocyclic compound is represented by Formula 1. In Formulae 1, 1a, and 1b, two adjacent groups among $A_1$ to $A_8$ are each independently connected with a respective * of Formulae 1a or 1b to form a ring, where each * is a carbon atom of Formula 1. An organic light-emitting device includes the heterocyclic compound.

(Continued)

Formula 1

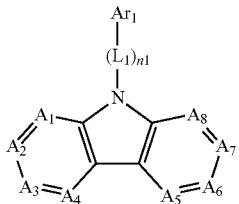

Formula 1a

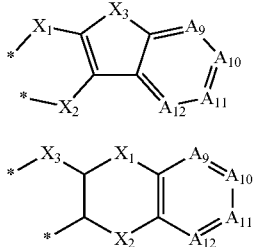

Formula 1b

20 Claims, 1 Drawing Sheet

(51) Int. Cl.
    *C07D 491/048* (2006.01)
    *C07D 495/14* (2006.01)
    *H01L 51/50* (2006.01)
(52) U.S. Cl.
    CPC ........ C07D 495/14 (2013.01); H01L 51/0071 (2013.01); *H01L 51/5016* (2013.01)
(58) Field of Classification Search
    CPC .. C07D 405/02; C07D 405/14; C07D 409/00; C07D 409/02; C07D 409/14; C07D 411/00; C07D 411/02; C07D 411/14; C07D 491/056; C07D 491/47; C07D 495/12; C07D 495/14; C07D 495/22; C07D 497/12; C07D 497/14; C07D 497/22
    See application file for complete search history.

(56) References Cited

U.S. PATENT DOCUMENTS

| | | | |
|---|---|---|---|
| 6,329,086 B1 | 12/2001 | Shi et al. | |
| 2002/0045061 A1 | 4/2002 | Hosokawa | |
| 2004/0135131 A1 | 7/2004 | Treacher et al. | |
| 2006/0063037 A1 | 3/2006 | Kim et al. | |
| 2006/0069235 A1 | 3/2006 | Arnold et al. | |
| 2006/0199943 A1 | 9/2006 | Falcou et al. | |
| 2006/0202194 A1 | 9/2006 | Jeong et al. | |
| 2006/0204785 A1 | 9/2006 | Kim et al. | |
| 2007/0104979 A1 | 5/2007 | Kim et al. | |
| 2007/0104980 A1 | 5/2007 | Kim et al. | |
| 2007/0128468 A1 | 6/2007 | Kim et al. | |
| 2007/0224450 A1 | 9/2007 | Kim et al. | |
| 2007/0267969 A1 | 11/2007 | Nakashima et al. | |
| 2007/0287821 A1 | 12/2007 | Doetz et al. | |
| 2008/0177084 A1 | 7/2008 | Lee et al. | |
| 2008/0191617 A1 | 8/2008 | Chae et al. | |
| 2008/0290795 A1 | 11/2008 | Sado et al. | |
| 2009/0085476 A1 | 4/2009 | Park et al. | |
| 2009/0105416 A1 | 4/2009 | Lee et al. | |
| 2009/0160323 A1 | 6/2009 | Nomura et al. | |
| 2009/0189509 A1 | 7/2009 | Qiu et al. | |
| 2009/0230847 A1 | 9/2009 | Iwaki et al. | |
| 2010/0102714 A1 | 4/2010 | Kim et al. | |
| 2010/0102716 A1 | 4/2010 | Kim et al. | |
| 2010/0133524 A1 | 6/2010 | Kim et al. | |
| 2010/0133994 A1 | 6/2010 | Song et al. | |
| 2010/0237339 A1 | 9/2010 | Nomura et al. | |
| 2011/0133227 A1 | 6/2011 | Lee et al. | |
| 2013/0207082 A1 | 8/2013 | Cho et al. | |
| 2013/0221278 A1 | 8/2013 | Inoue et al. | |
| 2014/0374711 A1* | 12/2014 | Cho | H01L 51/0072 257/40 |

FOREIGN PATENT DOCUMENTS

| | | |
|---|---|---|
| KR | 1998-067504 A | 10/1998 |
| KR | 2001-0044090 A | 6/2001 |
| KR | 2001-0112635 A | 12/2001 |
| KR | 2002-0020204 A | 3/2002 |
| KR | 2002-0026866 A | 4/2002 |
| KR | 2003-0004216 A | 1/2003 |
| KR | 2003-0015435 A | 2/2003 |
| KR | 2003-0092020 A | 12/2003 |
| KR | 10-2005-0073075 A | 7/2005 |
| KR | 10-2005-0089952 A | 9/2005 |
| KR | 10-2006-0051418 A | 5/2006 |
| KR | 10-2006-0098859 A | 9/2006 |
| KR | 10-2006-0098860 A | 9/2006 |
| KR | 10-2007-0011229 A | 1/2007 |
| KR | 10-0662377 B1 | 1/2007 |
| KR | 10-0662378 B1 | 1/2007 |
| KR | 10-0662379 B1 | 1/2007 |
| KR | 10-0662380 B1 | 1/2007 |
| KR | 10-0662381 B1 | 1/2007 |
| KR | 10-0662430 B1 | 1/2007 |
| KR | 10-2007-0048910 A | 5/2007 |
| KR | 10-2007-0058590 A | 6/2007 |
| KR | 10-2007-0083858 A | 8/2007 |
| KR | 10-2007-0097138 A | 10/2007 |
| KR | 10-2007-0097139 A | 10/2007 |
| KR | 10-2007-0105079 A | 10/2007 |
| KR | 10-2007-0105080 A | 10/2007 |
| KR | 10-2007-0108729 A | 11/2007 |
| KR | 10-0779009 B1 | 11/2007 |
| KR | 10-0781921 B1 | 12/2007 |
| KR | 10-2008-0032227 A | 4/2008 |
| KR | 10-2008-0064114 A | 7/2008 |
| KR | 10-2008-0074518 A | 8/2008 |
| KR | 10-2008-0099041 A | 11/2008 |
| KR | 10-2008-0105870 A | 12/2008 |
| KR | 10-2008-0105871 A | 12/2008 |
| KR | 10-2009-0032250 A | 4/2009 |
| KR | 10-2009-0041019 A | 4/2009 |
| KR | 10-2009-0073002 A | 7/2009 |
| KR | 10-2009-0083275 A | 8/2009 |
| KR | 10-2009-0129799 A | 12/2009 |
| KR | 10-2010-0003624 A | 1/2010 |
| KR | 10-2010-0026945 A | 3/2010 |
| KR | 10-2010-0033265 A | 3/2010 |
| KR | 10-2010-0047588 A | 5/2010 |
| KR | 10-2010-0047589 A | 5/2010 |
| KR | 10-2010-0048849 A | 5/2010 |
| KR | 10-2010-0055351 A | 5/2010 |
| KR | 10-2010-0062017 A | 6/2010 |
| KR | 10-2010-0062710 A | 6/2010 |
| KR | 10-2010-0064587 A | 6/2010 |
| KR | 10-2010-0099250 A | 9/2010 |
| KR | 10-2010-0105501 A | 9/2010 |
| KR | 10-2010-0132109 A | 12/2010 |
| KR | 10-2011-0021487 A | 3/2011 |
| KR | 10-2011-0022376 A | 3/2011 |
| KR | 10-2011-0041727 A | 4/2011 |
| KR | 10-2011-0063087 A | 6/2011 |
| KR | 10-2011-0077173 A | 7/2011 |
| KR | 10-2011-0077350 A | 7/2011 |
| KR | 10-2011-0085174 A | 7/2011 |
| KR | 10-2011-0088898 A | 8/2011 |
| KR | 10-2011-0105664 A | 9/2011 |
| KR | 10-2011-0105979 A | 9/2011 |
| KR | 10-2011-0118951 A | 11/2011 |
| KR | 10-2012-0119881 A | 10/2012 |

(56) References Cited

FOREIGN PATENT DOCUMENTS

| | | |
|---|---|---|
| KR | 10-1210934 B1 | 12/2012 |
| KR | 10-2013-0016392 A | 2/2013 |
| KR | 10-2013-0046640 A | 5/2013 |
| KR | 10-2013-0058086 A | 6/2013 |
| KR | 10-2013-0076080 A | 7/2013 |
| KR | 10-2013-0093327 A | 8/2013 |
| KR | 10-2013-0094183 A | 8/2013 |
| KR | 10-2013-0097660 A | 9/2013 |
| KR | 10-2013-0110051 A | 10/2013 |
| KR | 10-2013-0131093 A | 12/2013 |
| KR | 10-2013-0134451 A | 12/2013 |
| WO | WO 2011/125020 A1 | 10/2011 |
| WO | WO2014104665 * | 7/2014 |
| WO | WO-2015034140 A1 * | 3/2015 ......... H01L 51/0058 |

* cited by examiner

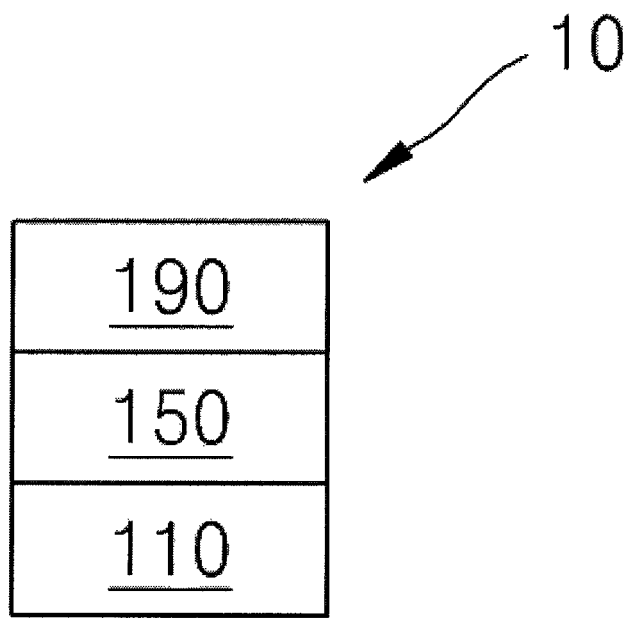

HETEROCYCLIC COMPOUND AND ORGANIC LIGHT-EMITTING DEVICE INCLUDING THE SAME

CROSS-REFERENCE TO RELATED APPLICATIONS

This application claims priority to and the benefit of Korean Patent Application No. 10-2014-0079115, filed on Jun. 26, 2014, and Korean Patent Application No. 10-2015-0035154, filed on Mar. 13, 2015, in the Korean Intellectual Property Office, the entire contents of both of which are incorporated herein by reference.

BACKGROUND

1. Field

One or more example embodiments relate to a heterocyclic compound and an organic light-emitting device including the same.

2. Description of the Related Art

Organic light-emitting devices are self-emitting devices that have wide viewing angles, high contrast ratios, short response times, and excellent luminance, driving voltage, and response speed characteristics, and produce full-color images.

The organic light-emitting device may include a first electrode disposed on a substrate, and a hole transport region, an emission layer, an electron transport region, and a second electrode sequentially formed on the first electrode. Holes injected from the first electrode are transported to the emission layer through the hole transport region, and electrons injected from the second electrode are transported to the emission layer through the electron transport region. Carriers, such as the holes and electrons, recombine in the emission layer to generate excitons. When the excitons drop (relax) from an excited state to a ground state, light is emitted.

SUMMARY

One or more example embodiments include a heterocyclic compound and an organic light-emitting device including the same.

Additional aspects will be set forth in part in the description which follows and, in part, will be apparent from the description, or may be learned by practice of the presented embodiments.

According to one or more example embodiments, there is provided a heterocyclic compound represented by Formula 1 (e.g., represented by Formula 1 with Formula 1a and/or Formula 1b):

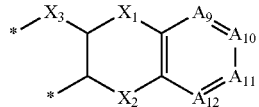

Formula 1

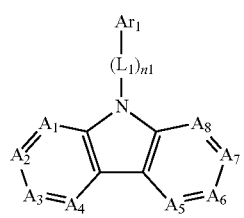

Formula 1a

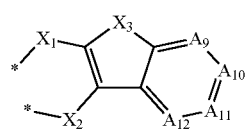

Formula 1b

In Formulae 1, 1a, and 1b, $A_1$ is selected from $CR_1$ and nitrogen, $A_2$ is selected from $CR_2$ and N, $A_3$ is selected from $CR_3$ and N, $A_4$ is selected from $CR_4$ and N, $A_5$ is selected from $CR_5$ and N, $A_6$ is selected from $CR_6$ and N, $A_7$ is selected from $CR_7$ and N, $A_8$ is selected from $CR_8$ and N, $A_9$ is selected from $CR_9$ and N, $A_{10}$ is selected from $CR_{10}$ and N, $A_{11}$ is selected from $CR_{11}$ and N, and $A_{12}$ is selected from $CR_{12}$ and N;

two adjacent groups among $A_1$ to $A_8$ are each independently connected with a respective * in Formulae 1a or 1b, to form a ring, wherein each * is a carbon atom of Formula 1;

$L_1$ is selected from a substituted or unsubstituted $C_3$-$C_{10}$ cycloalkylene, a substituted or unsubstituted $C_1$-$C_{10}$ heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{60}$ heteroarylene, a substituted or unsubstituted divalent non-aromatic condensed polycyclic group, and a substituted or unsubstituted divalent non-aromatic condensed heteropolycyclic group;

n1 is selected from 0, 1, 2, 3, and 4;

$X_1$ is selected from a single bond, $C(R_{13})(R_{14})$, $N(R_{13})$, O, S, Se, Te, Po, $Si(R_{13})(R_{14})$, $Ge(R_{13})(R_{14})$, $P(R_{13})$, $P(R_{13})(=O)$, C=O, and $B(R_{13})$;

$X_2$ is selected from a single bond, $C(R_{15})(R_{16})$, $N(R_{15})$, O, S, Se, Te, Po, $Si(R_{15})(R_{16})$, $Ge(R_{15})(R_{16})$, $P(R_{15})$, $P(R_{15})(=O)$, C=O, and $B(R_{15})$;

$X_3$ is selected from $C(R_{17})(R_{18})$, $N(R_{17})$, O, S, Se, Te, Po, $Si(R_{17})(R_{18})$, $Ge(R_{17})(R_{18})$, $P(R_{17})$, $P(R_{17})(=O)$, C=O, and $B(R_{17})$;

$Ar_1$ and $R_1$ to $R_{18}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

two adjacent groups among $R_1$ to $R_{18}$ are optionally connected with each other (e.g., fused together) to form a ring; and at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_{11}$ to $Q_{17}$, $Q_{21}$ to $Q_{27}$, and $Q_{31}$ to $Q_{37}$ are each independently selected from a hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

According to one or more example embodiments, an organic light-emitting device includes: a first electrode; a second electrode facing the first electrode; and an organic layer between the first electrode and the second electrode and including an emission layer, wherein the organic layer includes at least one of the heterocyclic compound.

BRIEF DESCRIPTION OF THE DRAWING

These and/or other aspects will become apparent and more readily appreciated from the following description of the example embodiments, taken in conjunction with the accompanying drawing which is a schematic view of a structure of an organic light-emitting device according to an example embodiment of the present disclosure.

DETAILED DESCRIPTION

Reference will now be made in detail to example embodiments, an example of which is illustrated in the accompanying drawing. In this regard, the present example embodiments may have different forms and should not be construed as being limited to the descriptions set forth herein. Accordingly, the example embodiments are merely described below, by referring to the accompanying drawing, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As used herein, the singular forms "a", "an", and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

It will be understood that when a layer, region, or component is referred to as being "formed on" another layer, region, or component, it can be directly or indirectly on or formed on the other layer, region, or component. That is, for example, intervening layers, regions, or components may be present.

Sizes of components in the accompanying drawing may be exaggerated for convenience of explanation. In other words, since sizes and thicknesses of components in the accompanying drawing may be arbitrarily illustrated for convenience of explanation, the following embodiments are not limited thereto.

As used herein, the term "substantially," "about," and similar terms are used as terms of approximation and not as terms of degree, and are intended to account for the inherent deviations in measured or calculated values that would be recognized by those of ordinary skill in the art. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein. All such ranges are intended to be inherently described in this specification such that amending to expressly recite any such subranges would comply with the requirements of 35 U.S.C. § 112(a), and 35 U.S.C. § 132(a).

According to an example embodiment, a heterocyclic compound may be represented by Formula 1 (e.g., represented by a combination of Formula 1 and Formula 1a and/or Formula 1b):

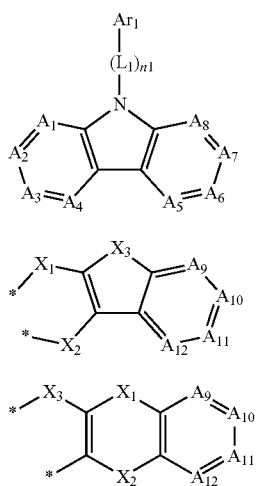

In Formulae 1, 1a, and 1b, $A_1$ may be selected from $CR_1$ and nitrogen (N), $A_2$ may be selected from $CR_2$ and N, $A_3$ may be selected from $CR_3$ and N, $A_4$ may be selected from $CR_4$ and N, $A_5$ may be selected from $CR_5$ and N, $A_6$ may be selected from $CR_6$ and N, $A_7$ may be selected from $CR_7$ and N, $A_8$ may be selected from $CR_8$ and N, $A_9$ may be selected from $CR_9$ and N, $A_{10}$ may be selected from $CR_{10}$ and N, $A_{11}$ may be selected from $CR_{11}$ and N, and $A_{12}$ may be selected from $CR_{12}$ and N;

two adjacent groups among $A_1$ to $A_8$ may be each independently connected with a respective * of Formulae 1a or 1b to form a ring, wherein each * is a carbon atom of Formula 1 (e.g., a carbon atom of one of $A_1$ to $A_8$); and $R_1$ to $R_{12}$ may be as defined in the following description.

For example, in Formulae 1, 1a, and 1b, $A_1$ may be $CR_1$, $A_2$ may be $CR_2$, $A_3$ may be $CR_3$, $A_4$ may be $CR_4$, $A_5$ may be $CR_5$, $A_6$ may be $CR_6$, $A_7$ may be $CR_7$, $A_8$ may be $CR_8$, $A_9$ may be $CR_9$, $A_{10}$ may be $CR_{10}$, $A_{11}$ may be $CR_{11}$, and $A_{12}$ may be $CR_{12}$, but embodiments are not limited thereto.

In Formula 1, $L_1$ may be selected from a substituted or unsubstituted $C_3$-$C_{10}$ cycloalkylene, a substituted or unsubstituted $C_1$-$C_{10}$ heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{89}$ heteroarylene, a substituted or unsubstituted divalent non-aromatic condensed polycyclic group, and a substituted or unsubstituted divalent non-aromatic condensed heteropolycyclic group.

For example, in Formula 1, $L_1$ may be selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a benzoquinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a benzoquinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{60}$ aryloxy group, a $C_6$-$C_{60}$ arylthio group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group, but embodiments are not limited thereto.

For example, in Formula 1, $L_1$ may be selected from a phenylene group, a naphthylene group, a pyridinylene group, a pyrimidinylene group, a quinolinylene group, an isoquinolinylene group, a benzoquinolinylene group, a quinoxalinylene group, a quinazolinylene group, a benzoquinazolinylene group, and a triazinylene group;

a naphthylene group, a pyridinylene group, a pyrimidinylene group, a quinolinylene group, an isoquinolinylene group, a benzoquinolinylene group, a quinoxalinylene group, a quinazolinylene group, a benzoquinazolinylene group, and a triazinylene group, each substituted with at least one of a deuterium, —F, —Cl, —Br, —I, a methyl group, an ethyl group, a tert-butyl group, a methoxy group, an ethoxy group, a tert-butoxy group, a phenoxy group, a phenylthio group, a phenyl group, a naphthyl group, a pyridinyl group, and a pyrimidinyl group, but embodiments are not limited thereto.

For example, in Formula 1, $L_1$ may be selected from groups represented by (e.g., each represented by) Formulae 3-1 to 3-22, but embodiments are not limited thereto:

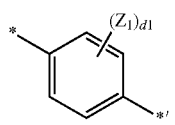

3-1

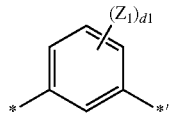

3-2

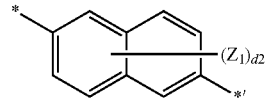

3-3

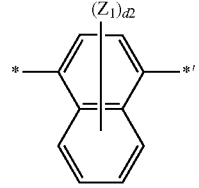

3-4

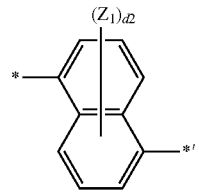

3-5


3-6


3-7

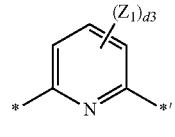

3-8

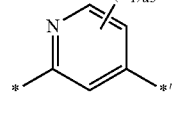

3-9

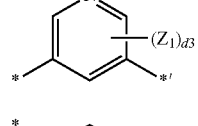

3-10

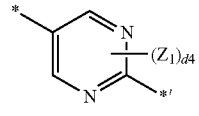

3-11


3-12

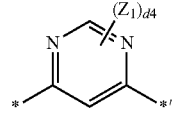

3-13

3-14 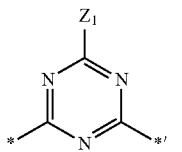

3-15 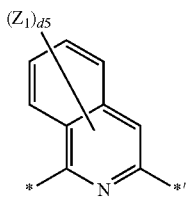

3-16 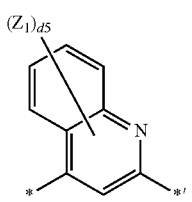

3-17 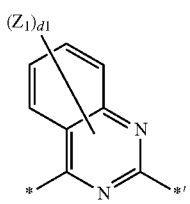

3-18 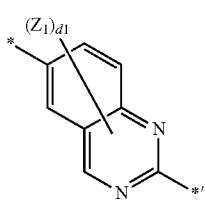

3-19 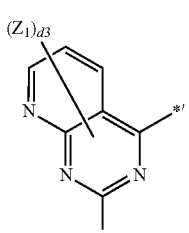

3-20 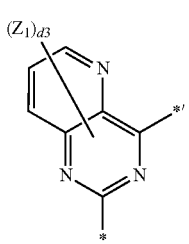

3-21 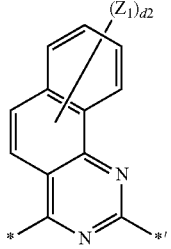

3-22 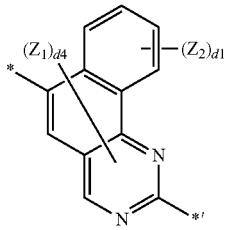

In Formulae 3-1 to 3-22, $Z_1$ and $Z_2$ may be each independently selected from a hydrogen, a deuterium, —F, —Cl, —Br, —I, a methyl group, an ethyl group, a tert-butyl group, a methoxy group, an ethoxy group, a tert-butoxy group, a phenoxy group, a phenylthio group, a phenyl group, a naphthyl group, a pyridinyl group, and a pyrimidinyl group, d1 may be selected from 1, 2, 3, and 4;

d2 may be selected from 1, 2, 3, 4, 5, and 6;

d3 may be selected from 1, 2, and 3;

d4 may be selected from 1 and 2;

d5 may be selected from 1, 2, 3, 4, and 5; and

*and*' may be each independently a binding site to a neighboring atom.

For example, in Formula 1, $L_1$ may be selected from groups represented by (e.g., each represented by) Formulae 4-1 to 4-22, but embodiments are not limited thereto:

4-1 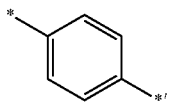

4-2 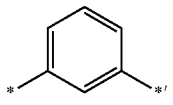

4-3

4-4 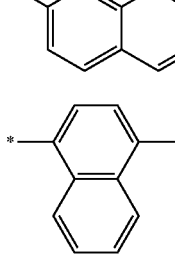

-continued

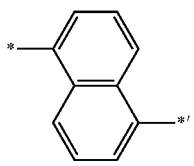
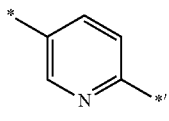

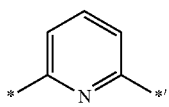
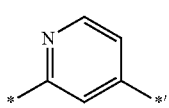
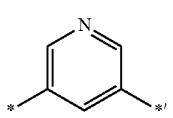
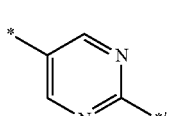
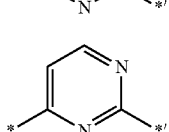
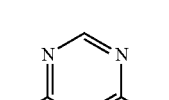
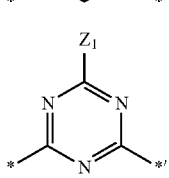
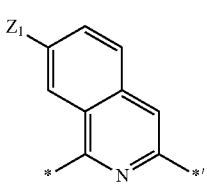
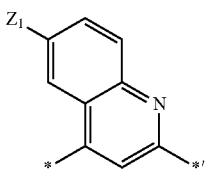

-continued 4-5

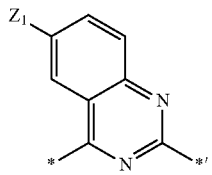

4-6

4-7

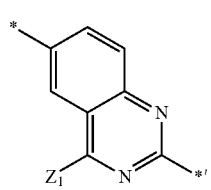

4-8

4-9

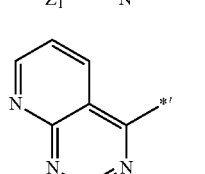

4-10

4-11

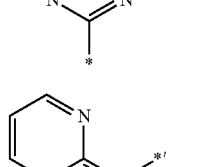

4-12

4-13

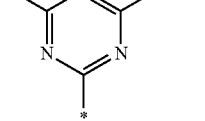

4-14

4-15

4-16

4-17

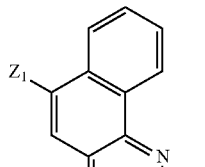

4-18

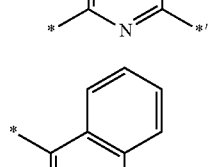

4-19

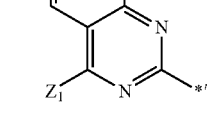

4-20

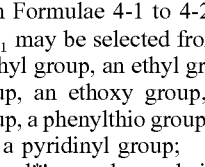

4-21

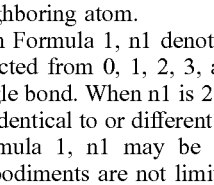

4-22

In Formulae 4-1 to 4-22, $Z_1$ may be selected from a hydrogen, a deuterium, —F, a methyl group, an ethyl group, a tert-butyl group, a methoxy group, an ethoxy group, a tert-butoxy group, a phenoxy group, a phenylthio group, a phenyl group, a naphthyl group, and a pyridinyl group;

*and*' may be each independently a binding site to a neighboring atom.

In Formula 1, n1 denotes the number of $L_1$ and may be selected from 0, 1, 2, 3, and 4. When n1 is 0, $(L_1)_{n1}$ is a single bond. When n1 is 2 or greater, a plurality of $L_1$s may be identical to or different from each other. For example, in Formula 1, n1 may be selected from 0, 1, and 2, but embodiments are not limited thereto. For example, in Formula 1, n1 may be selected from 0 and 1, but embodiments are not limited thereto. For example, in Formula 1, n1 may be 0, but embodiments are not limited thereto.

In Formula 1a, $X_1$ may be selected from a single bond, $C(R_{13})(R_{14})$, $N(R_{13})$, O, S, Se, Te, Po, $Si(R_{13})(R_{14})$, $Ge(R_{13})(R_{14})$, $P(R_{13})$, $P(R_{13})(=O)$, C=O, and $B(R_{13})$;

$R_{13}$ and $R_{14}$ may be connected with each other (e.g., fused together) to form a ring; and $R_{13}$ and $R_{14}$ may be as defined in the following description.

For example, in Formula 1a, $X_1$ may be selected from a single bond, O, and S, but embodiments are not limited thereto.

In Formula 1a, $X_2$ may be selected from a single bond, $C(R_{15})(R_{16})$, $N(R_{15})$, O, S, Se, Te, Po, $Si(R_{15})(R_{16})$, $Ge(R_{15})(R_{16})$, $P(R_{15})$, $P(R_{15})(=O)$, C=O, and $B(R_{15})$;

$R_{15}$ and $R_{16}$ may be connected with each other (e.g., fused together) to form a ring; and $R_{15}$ and $R_{16}$ may be as defined in the following description.

For example, in Formula 1a, $X_2$ may be selected from a single bond, O, and S, but embodiments are not limited thereto.

In Formula 1b, $X_3$ may be selected from $C(R_{17})(R_{18})$, $N(R_{17})$, O, S, Se, Te, Po, $Si(R_{17})(R_{18})$, $Ge(R_{17})(R_{18})$, $P(R_{17})$, $P(R_{17})(=O)$, C=O, and $B(R_{17})$;

$R_{17}$ and $R_{18}$ may be connected with each other (e.g., fused together) to form a ring; and $R_{17}$ and $R_{18}$ may be as defined in the following description.

For example, in Formula 1b, $X_3$ may be selected from $C(R_{17})(R_{18})$ and $N(R_{17})$, but embodiments are not limited thereto.

In Formulae 1, 1a, and 1b, $Ar_1$ and $R_1$ to $R_{18}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and two adjacent groups among $R_1$ to $R_{18}$ may be optionally connected with each other (e.g., fused together) to form a ring.

For example, in Formula 1, $Ar_1$ may be selected from a methyl group, an ethyl group, an n-propyl group, an iso-propyl group, a cyclopentyl group, a cyclohexyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzo-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovaleny group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a pyridoindolyl group, a benzo-quinolinyl group, a phthalazinyl group, a naphthyridinyl group, a quinoxalinyl group, a quinazolinyl group, a ben-zoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophe-nyl group, a dibenzosilolyl group, a benzocarbazolyl group, and a dibenzocarbazolyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzo-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a pyridoindolyl group, a benzo-quinolinyl group, a phthalazinyl group, a naphthyridinyl group, a quinoxalinyl group, a quinazolinyl group, a ben-zoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophe-nyl group, a dibenzosilolyl group, a benzocarbazolyl group, and a dibenzocarbazolyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{60}$ aryloxy group, a $C_6$-$C_{60}$ arylthio group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, but embodiments are not limited thereto.

For example, in Formula 1, $Ar_1$ may be selected from a methyl group, a phenyl group, a naphthyl group, a pyridinyl group, a pyrimidinyl group, a quinolinyl group, an isoquinolinyl group, a carbazolyl group, a pyridoindolyl group, a quinoxalinyl group, a quinazolinyl group, a benzoquinazolinyl group, a benzimidazolyl group, and a triazinyl group; and a phenyl group, a naphthyl group, a pyridinyl group, a pyrimidinyl group, a quinolinyl group, an isoquinolinyl group, a carbazolyl group, a pyridoindolyl group, a quinoxalinyl group, a quinazolinyl group, a benzoquinazolinyl group, a benzimidazolyl group, and a triazinyl group, each substituted with at least one of a deuterium, —F, a methyl group, an ethyl group, an n-propyl group, an iso-propyl group, a tert-butyl group, a methoxy group, an ethoxy group, a tert-butoxy group, a phenoxy group, a phenylthio group, a phenyl group, a naphthyl group, and a pyridinyl group, but embodiments are not limited thereto.

For example, in Formula 1, $Ar_1$ may be selected from groups represented by (e.g., each represented by) Formulae 5-1 to 5-48, but embodiments are not limited thereto:

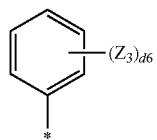

5-1

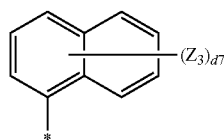

5-2

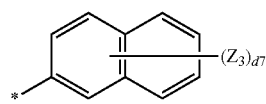

5-3

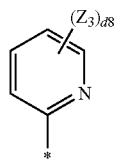

5-4

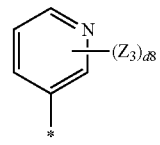

5-5

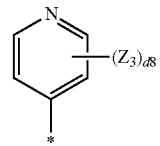

5-6

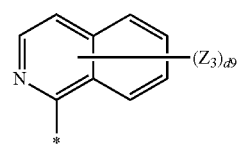

5-7

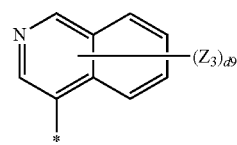

5-8

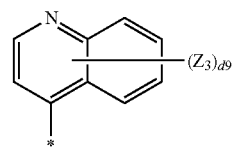

5-9

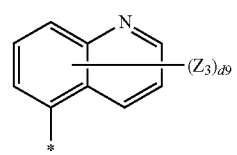

5-10

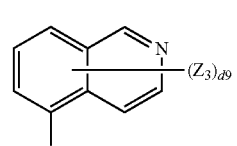

5-11

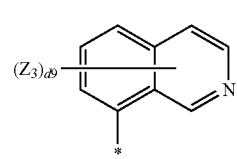

5-12

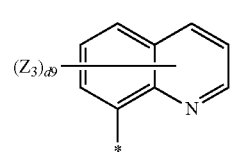

5-13

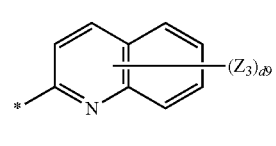

5-14

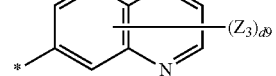

5-15

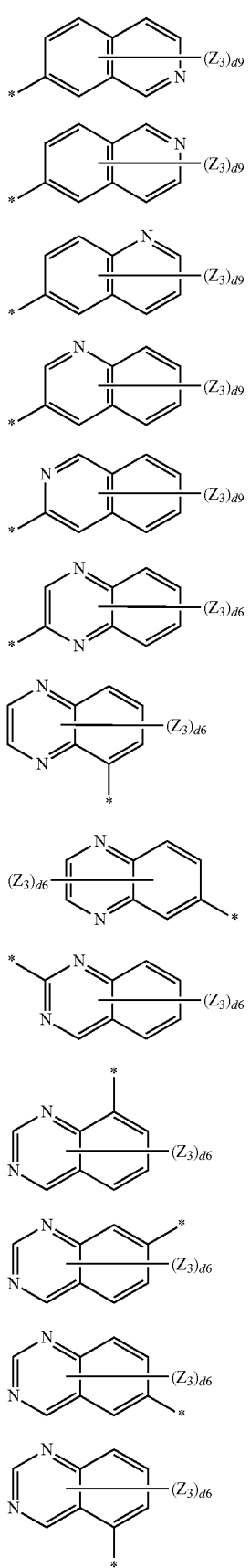
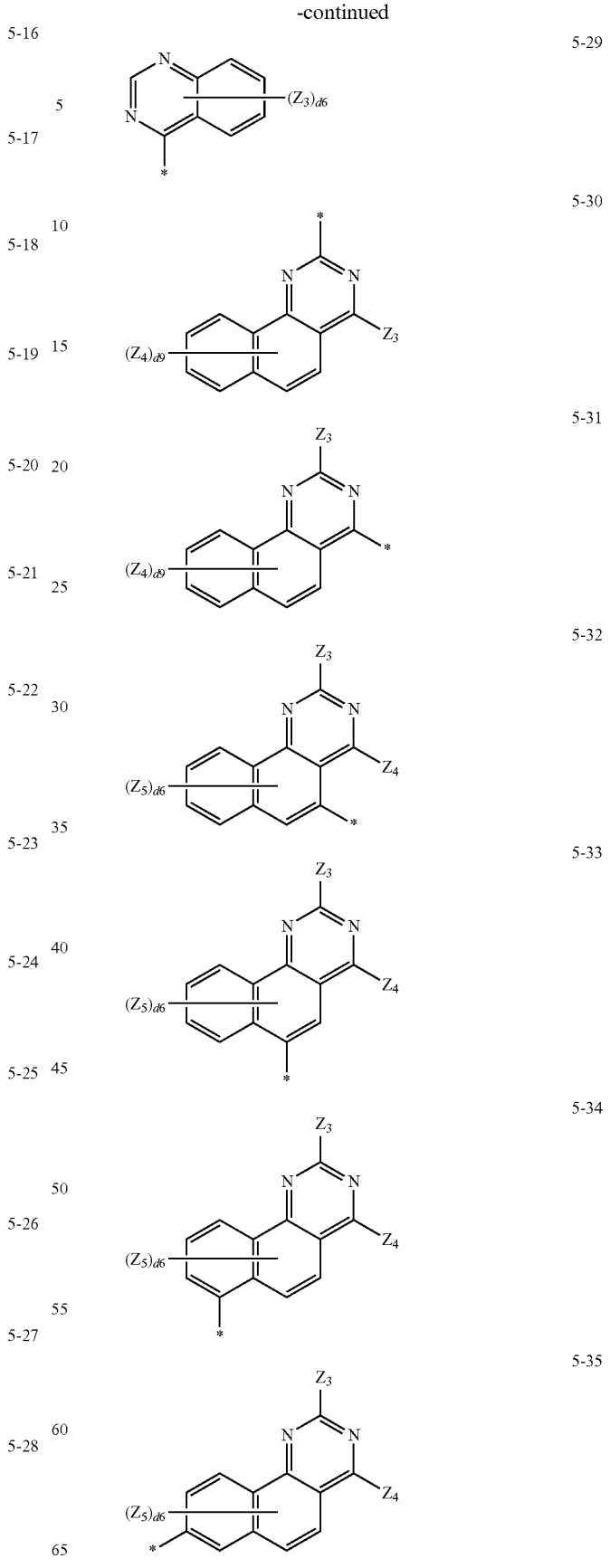

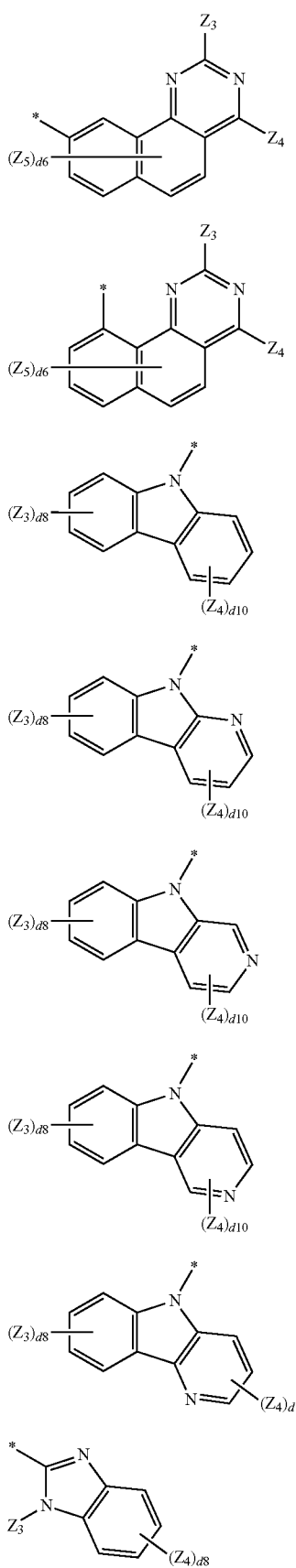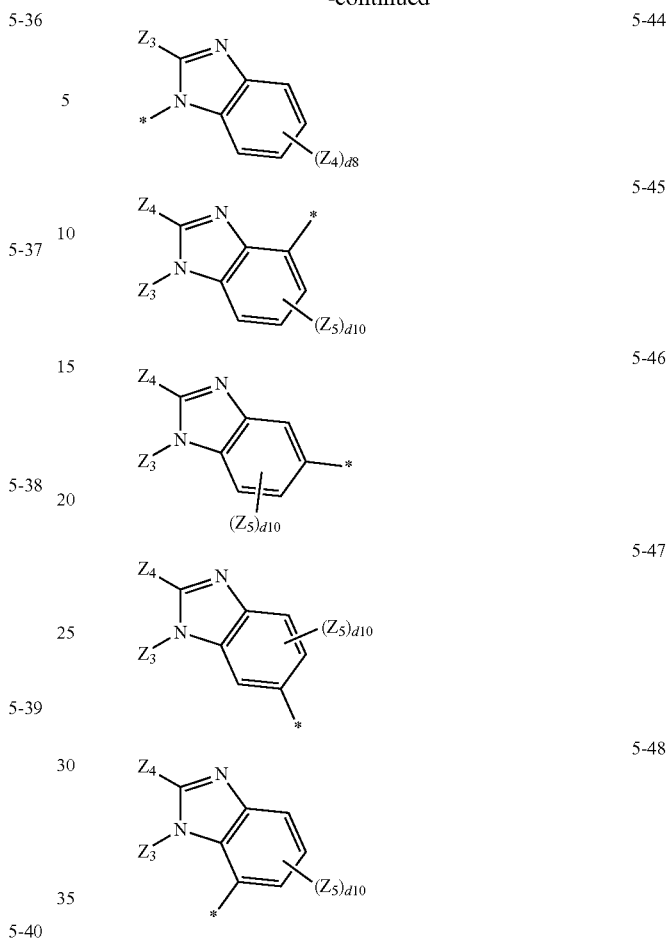

In Formulae 5-1 to 5-48, $Z_3$ to $Z_5$ may be each independently selected from a hydrogen, a deuterium, —F, a methyl group, an ethyl group, an n-propyl group, an iso-propyl group, a tert-butyl group, a methoxy group, an ethoxy group, a tert-butoxy group, a phenoxy group, a phenylthio group, a phenyl group, a naphthyl group, and a pyridinyl group;

d6 may be selected from 1, 2, 3, 4, and 5;
d7 may be selected from 1, 2, 3, 4, 5, 6, and 7;
d8 may be selected from 1, 2, 3, and 4;
d9 may be selected from 1, 2, 3, 4, 5, and 6;
d10 may be selected from 1, 2, and 3; and
* may be a binding site to a neighboring atom.

For example, in Formulae 1, 1a, and 1b, $R_1$ to $R_{18}$ may be each independently selected from a hydrogen, a deuterium, a methyl group, an ethyl group, an n-propyl group, an iso-propyl group, a phenyl group, a naphthyl group, and a pyridinyl group; and a phenyl group, a naphthyl group, and a pyridinyl group, each substituted with at least one of a phenyl group, a naphthyl group, and a pyridinyl group, but embodiments are not limited thereto.

For example, in Formulae 1, 1a, and 1b, $R_1$ to $R_{18}$ may be each independently selected from a hydrogen, a methyl group, an iso-propyl group, a phenyl group, a naphthyl group, and a pyridinyl group; and a phenyl group substituted with a phenyl group, but embodiments are not limited thereto.

For example, the heterocyclic compound may be represented by any one of Formulae 1-1 to 1-12, but embodiments are not limited thereto:

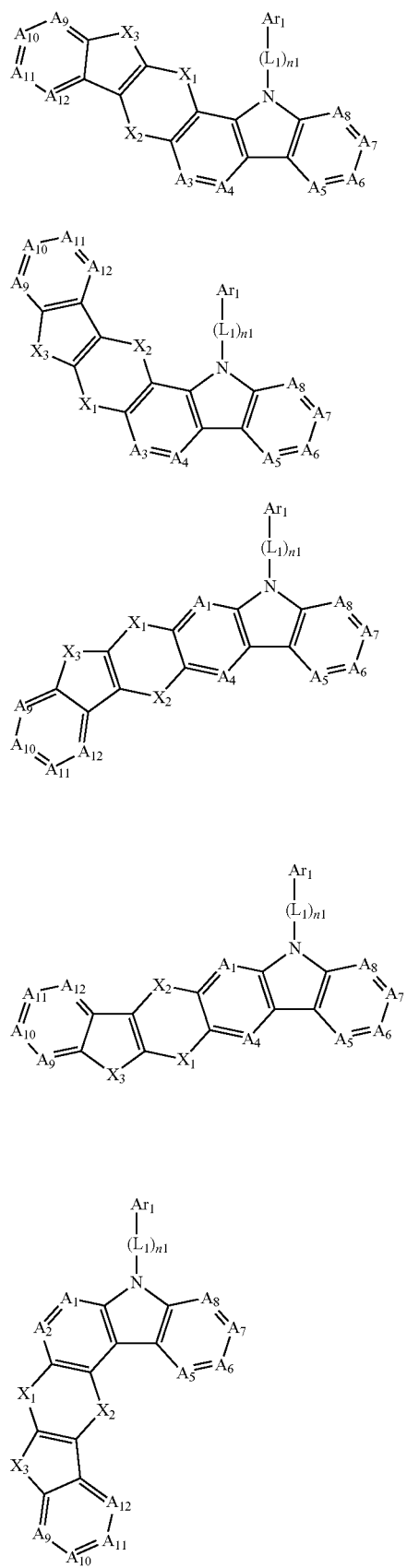
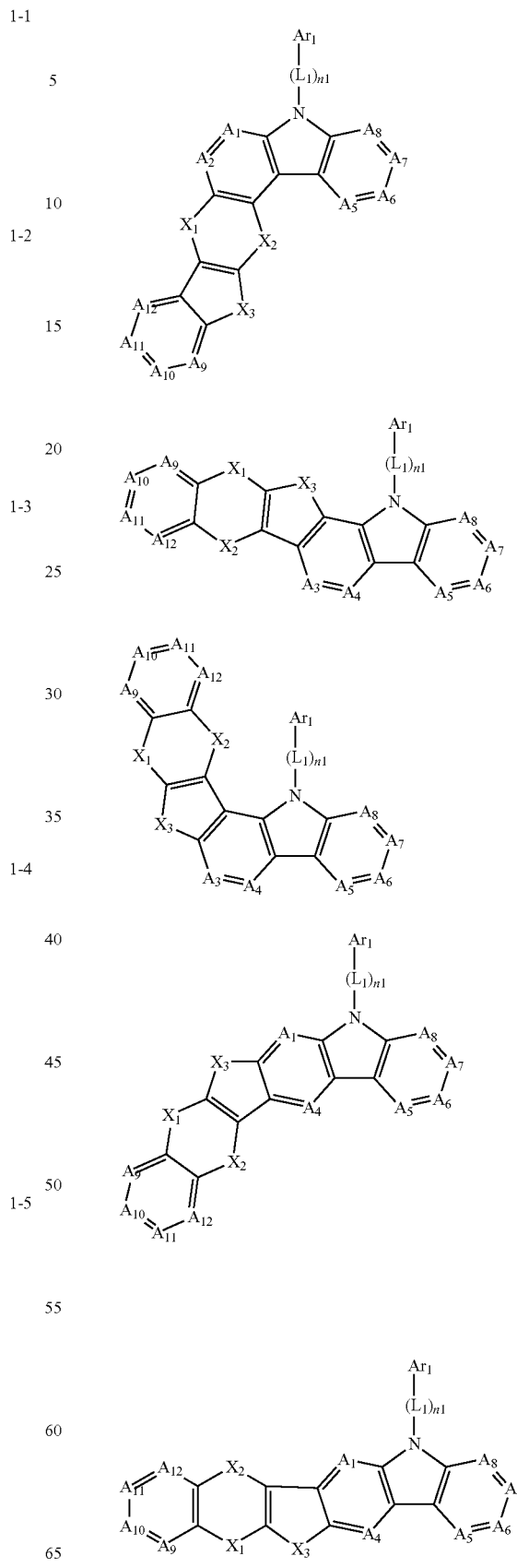

1-11

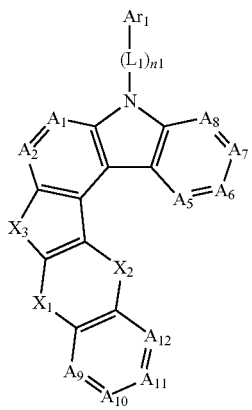

1-12

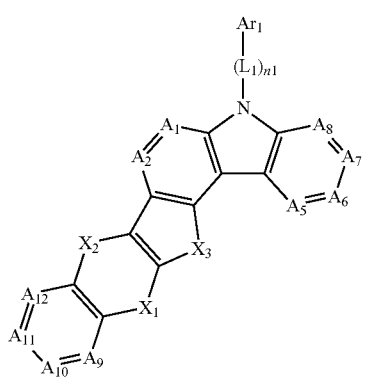

In Formulae 1-1 to 1-12, $A_1$ to $A_{12}$, $L_1$, $n1$, $X_1$, $X_2$, $X_3$, $Ar_1$, and $R_1$ to $R_{12}$ may be defined the same by referring to the description of Formula 1 (e.g., $A_1$ to $A_{12}$, $L_1$, $n1$, $X_1$, $X_2$, $X_3$, $Ar_1$, and $R_1$ to $R_{12}$ may be the same or substantially the same as described with respect to Formula 1).

For example, when the heterocyclic compound is represented by any one of Formulae 1-1 to 1-12 above, $A_1$ may be selected from $CR_1$ and N, $A_2$ may be selected from $CR_2$ and N, $A_3$ may be selected from $CR_3$ and N, $A_4$ may be selected from $CR_4$ and N, $A_5$ may be selected from $CR_5$ and N, $A_6$ may be selected from $CR_6$ and N, $A_7$ may be selected from $CR_7$ and N, $A_8$ may be selected from $CR_8$ and N, $A_9$ may be selected from $CR_9$ and N, $A_{10}$ may be selected from $CR_{10}$ and N, $A_{11}$ may be selected from $CR_{11}$ and N, and $A_{12}$ may be selected from $CR_{12}$ and N;

$L_1$ may be selected from a substituted or unsubstituted $C_3$-$C_{10}$ cycloalkylene, a substituted or unsubstituted $C_1$-$C_{10}$ heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{60}$ heteroarylene, a substituted or unsubstituted divalent non-aromatic condensed polycyclic group, and a substituted or unsubstituted divalent non-aromatic condensed heteropolycyclic group;

$n1$ may be selected from 0, 1, and 2;

$X_1$ and $X_2$ may be each independently selected from O and S;

$X_3$ may be selected from $C(R_{17})(R_{18})$ and $N(R_{17})$; and $Ar_1$ and $R_1$ to $R_{18}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, but embodiments are not limited thereto.

For example, the heterocyclic compound may be represented by any one of Formulae 1-21 to 1-32, but embodiments are not limited thereto:

1-21

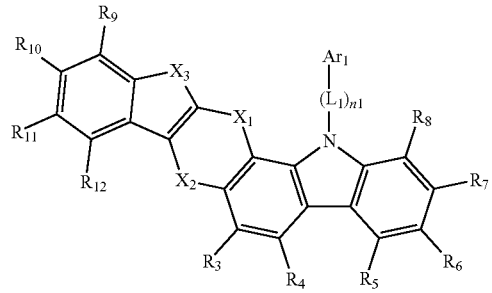

1-22

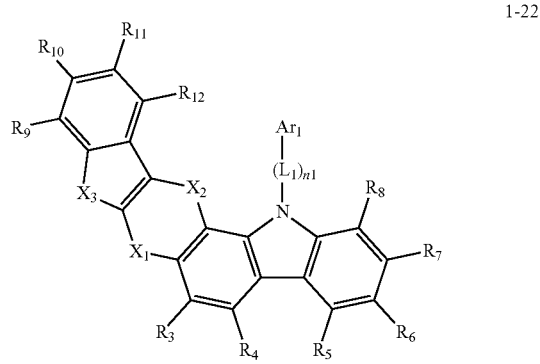

1-23

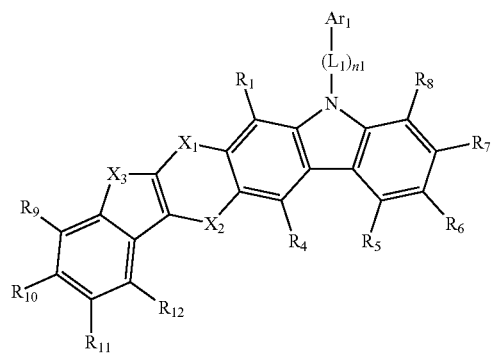

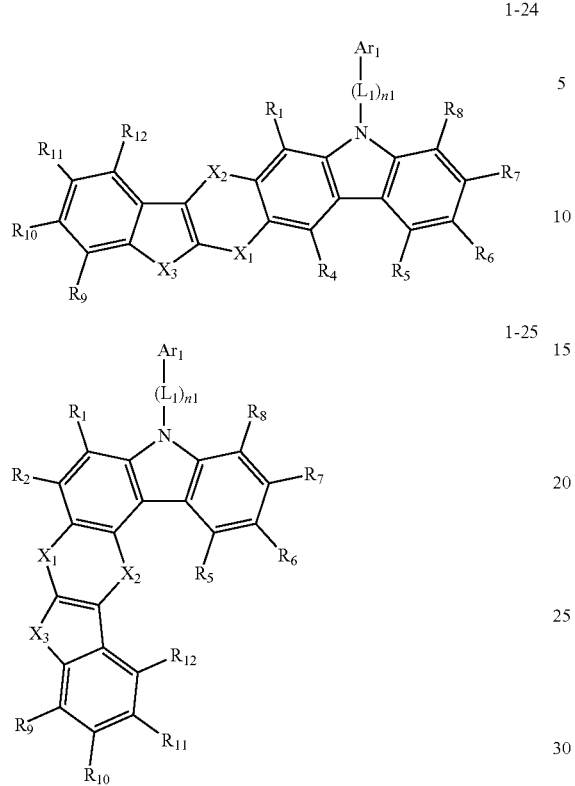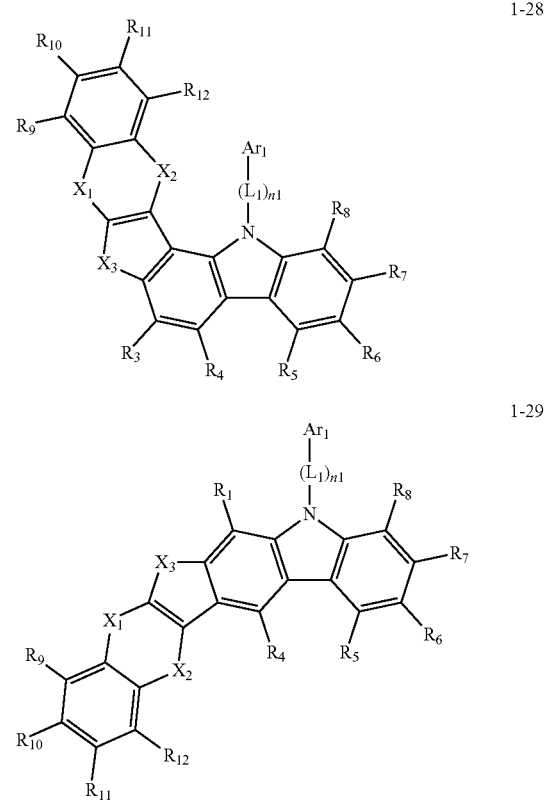

1-32
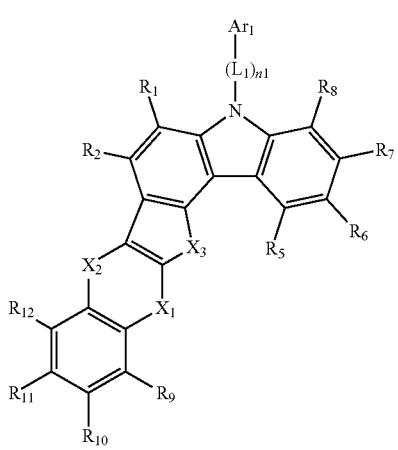
In Formulae 1-21 to 1-32,
L₁ may be selected from groups represented by (e.g., each represented by) Formulae 4-1 to 4-22;
4-1
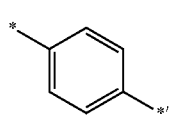
4-2
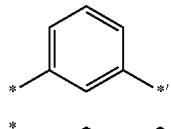
4-3
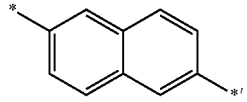
4-4
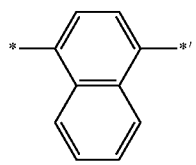
4-5
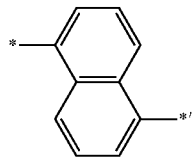
4-6
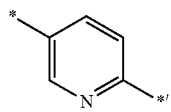
4-7
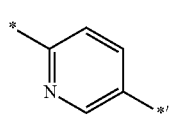
4-8
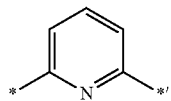
4-9
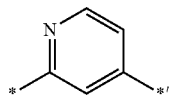
4-10
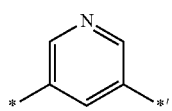
4-11
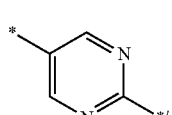
4-12
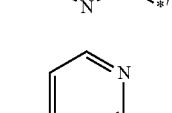
4-13
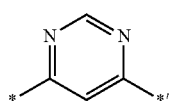
4-14
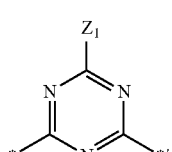
4-15
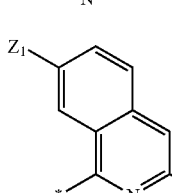
4-16
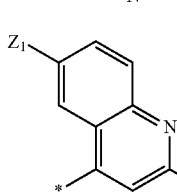
4-17
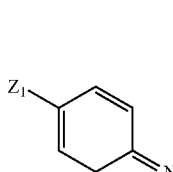
4-18
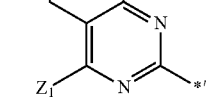

-continued

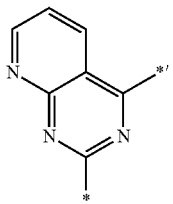
4-19

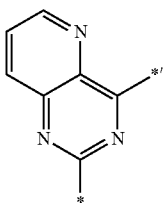
4-20

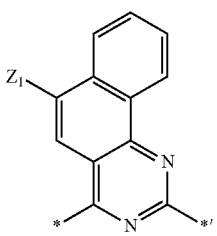
4-21

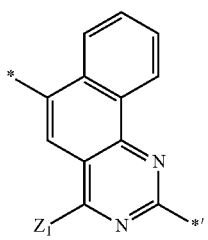
4-22

In Formulae 4-1 to 4-22, $Z_1$ may be selected from a hydrogen, a deuterium, —F, a methyl group, an ethyl group, a tert-butyl group, a methoxy group, an ethoxy group, a tert-butoxy group, a phenoxy group, a phenylthio group, a phenyl group, a naphthyl group, and a pyridinyl group;

*and*' may be each independently a binding site to a neighboring atom;

n1 may be selected from 0, 1, and 2;

$X_1$ and $X_2$ may be each independently selected from O and S;

$X_3$ may be selected from $C(R_{17})(R_{18})$ and $N(R_{17})$;

$Ar_1$ may be selected from a methyl group, a phenyl group, a naphthyl group, a pyridinyl group, a pyrimidinyl group, a quinolinyl group, an isoquinolinyl group, a carbazolyl group, a pyridoindolyl group, a quinoxalinyl group, a quinazolinyl group, a benzoquinazolinyl group, a benzimidazolyl group, and a triazinyl group; and a phenyl group, a naphthyl group, a pyridinyl group, a pyrimidinyl group, a quinolinyl group, an isoquinolinyl group, a carbazolyl group, a pyridoindolyl group, a quinoxalinyl group, a quinazolinyl group, a benzoquinazolinyl group, a benzimidazolyl group, and a triazinyl group, each substituted with at least one of a deuterium, —F, a methyl group, an ethyl group, an n-propyl group, an iso-propyl group, a tert-butyl group, a methoxy group, an ethoxy group, a tert-butoxy group, a phenoxy group, a phenylthio group, a phenyl group, a naphthyl group, and a pyridinyl group; and $R_1$ to $R_{18}$ may be each independently selected from a hydrogen, a deuterium, a methyl group, an ethyl group, an n-propyl group, an iso-propyl group, a phenyl group, a naphthyl group, and a pyridinyl group; and a phenyl group, a naphthyl group, and a pyridinyl group, each substituted with at least one of a phenyl group, a naphthyl group, and a pyridinyl group.

For example, when the heterocyclic compound is represented by any one of Formulae 1-21 to 1-32 above, $L_1$ may be selected from groups represented by (e.g., each represented by) Formulae 4-1 to 4-22;

4-1

4-2

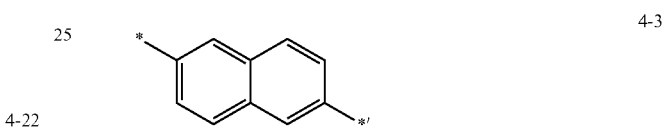
4-3

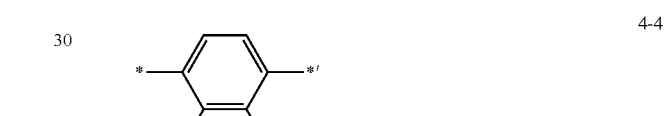
4-4

4-5

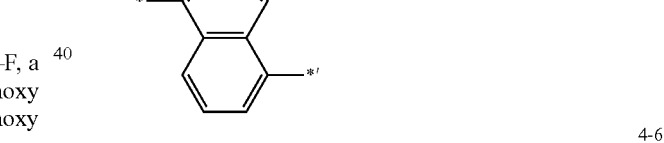
4-6

4-7

4-8

4-9

4-10

-continued

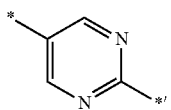
4-11

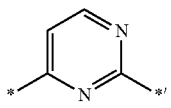
4-12

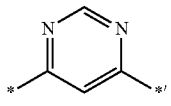
4-13

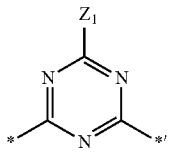
4-14

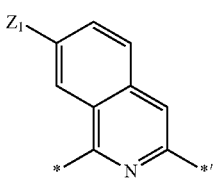
4-15

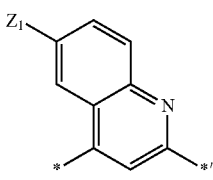
4-16

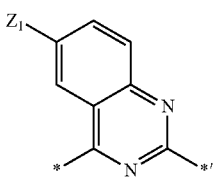
4-17

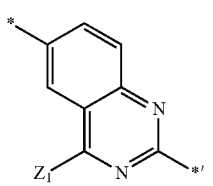
4-18

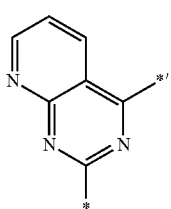
4-19

-continued

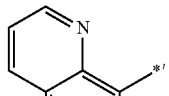
4-20

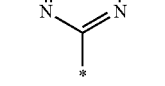

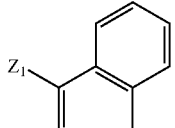
4-21

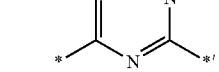

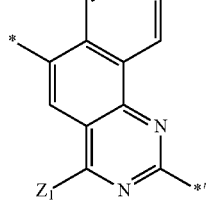
4-22

In Formulae 4-1 to 4-22, $Z_1$ may be selected from a hydrogen, a deuterium, —F, a methyl group, an ethyl group, a tert-butyl group, a methoxy group, an ethoxy group, a tert-butoxy group, a phenoxy group, a phenylthio group, a phenyl group, a naphthyl group, and a pyridinyl group;

*and*' may be each independently a binding site to a neighboring atom;

n1 may be selected from 0, 1, and 2;

$X_1$ and $X_2$ may be each independently O and S;

$X_3$ may be selected from $C(R_{17})(R_{18})$ and $N(R_{17})$; and $Ar_1$ may be selected from groups represented by Formulae 5-1 to 5-48:

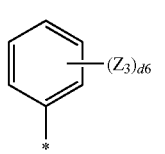
5-1

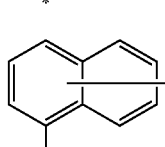
5-2

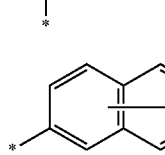
5-3

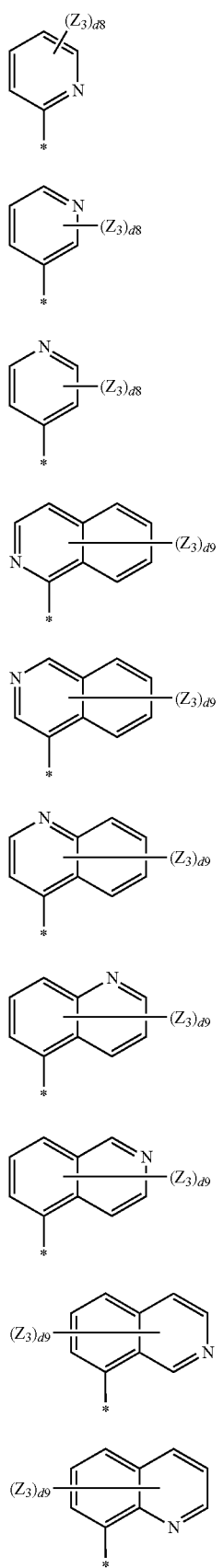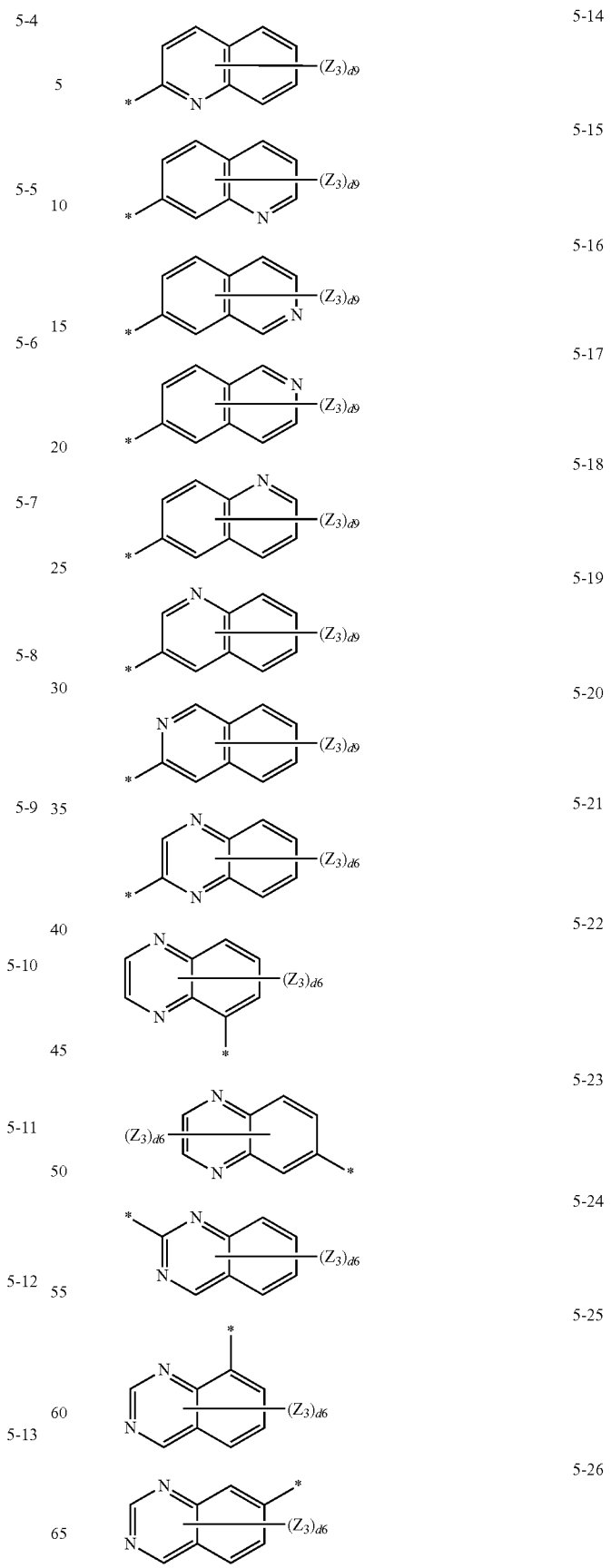

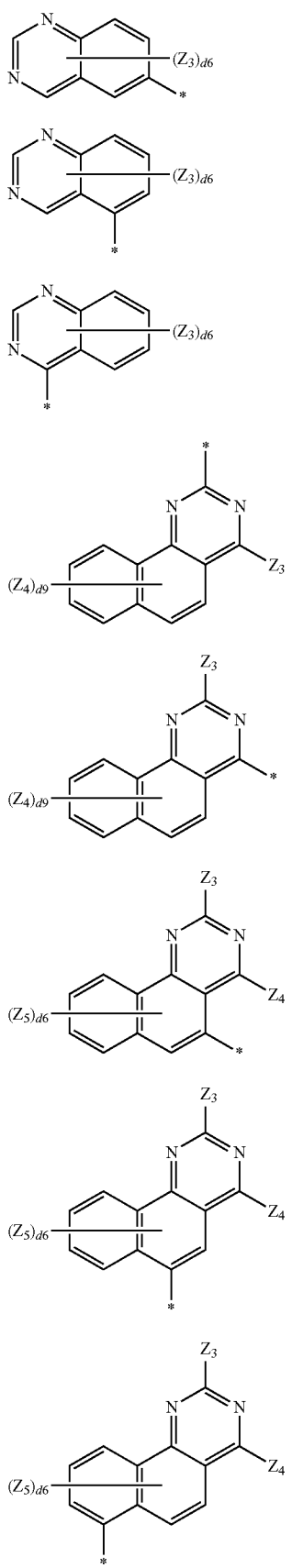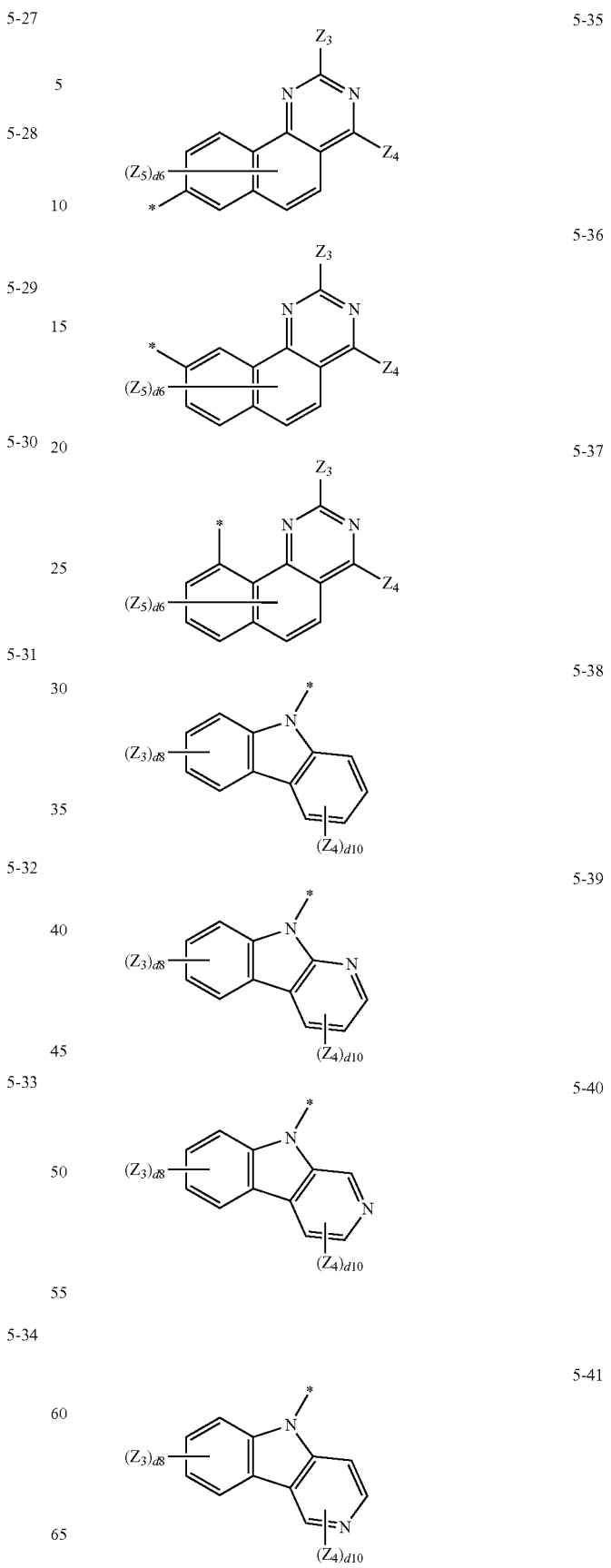

5-42

[Structure: (Z₃)d8 substituted pyrido-indole with (Z₄)d10, * binding site]

5-43

[Structure: benzimidazole with Z₃, (Z₄)d8, * binding site at 2-position]

5-44

[Structure: benzimidazole with Z₃, (Z₄)d8, * binding site on N]

5-45

[Structure: benzimidazole with Z₃, Z₄, (Z₅)d10, * binding site]

5-46

[Structure: benzimidazole with Z₃, Z₄, (Z₅)d10, * binding site]

5-47

[Structure: benzimidazole with Z₃, Z₄, (Z₅)d10, * binding sites]

5-48

[Structure: benzimidazole with Z₃, Z₄, (Z₅)d10, * binding site]

In Formulae 5-1 to 5-48, $Z_3$ to $Z_5$ may be each independently selected from a hydrogen, a deuterium, —F, a methyl group, an ethyl group, an n-propyl group, an iso-propyl group, a tert-butyl group, a methoxy group, an ethoxy group, a tert-butoxy group, a phenoxy group, a phenylthio group, a phenyl group, a naphthyl group, and a pyridinyl group;

d6 may be selected from 1, 2, 3, 4, and 5;
d7 may be selected from 1, 2, 3, 4, 5, 6, and 7;
d8 may be selected from 1, 2, 3, and 4;
d9 may be selected from 1, 2, 3, 4, 5, and 6;
d10 may be selected from 1, 2, and 3;
* may be a binding site to a neighboring atom; and
$R_1$ to $R_{18}$ may be each independently selected from a hydrogen, a deuterium, a methyl group, an ethyl group, an n-propyl group, an iso-propyl group, a phenyl group, a naphthyl group, and a pyridinyl group; and a phenyl group, a naphthyl group, and a pyridinyl group, each substituted with at least one of a phenyl group, a naphthyl group, and a pyridinyl group, but embodiments are not limited thereto.

For example, the heterocyclic compound may be any one of Compounds 2 to 580, but embodiments are not limited thereto:

2

[Structure of Compound 2]

3

[Structure of Compound 3]

4

[Structure of Compound 4]

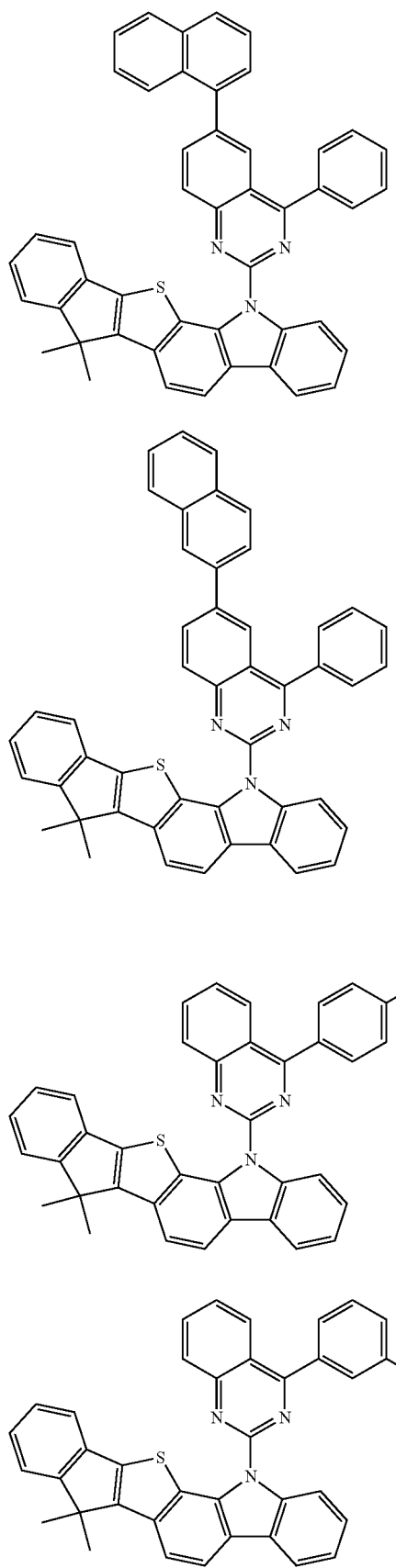
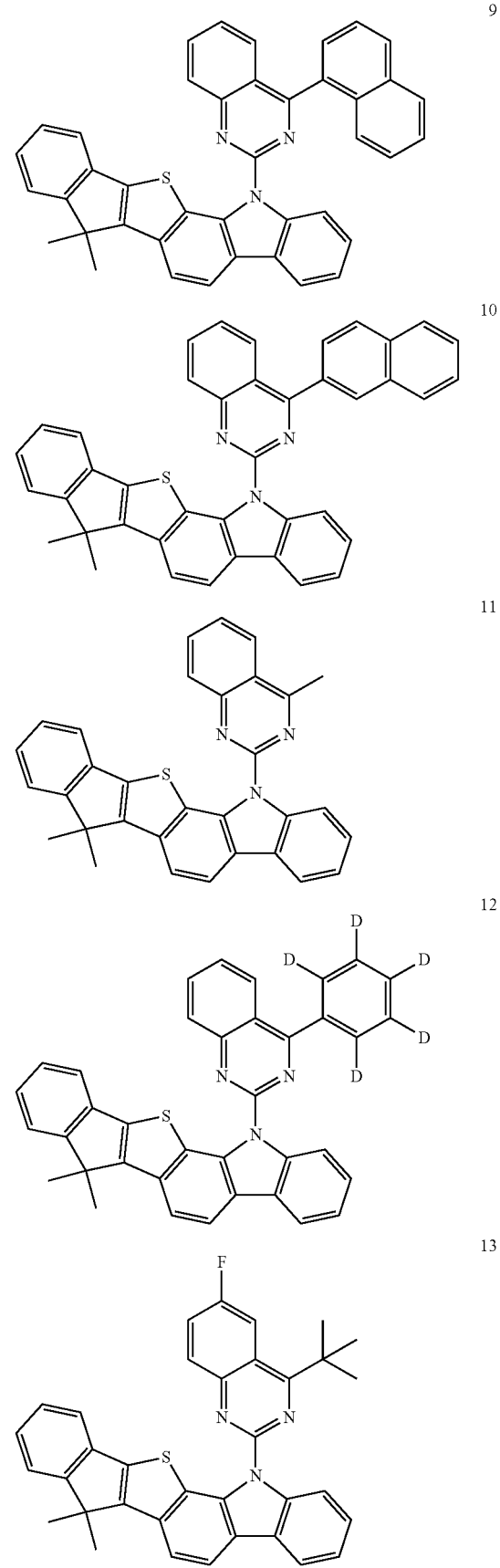

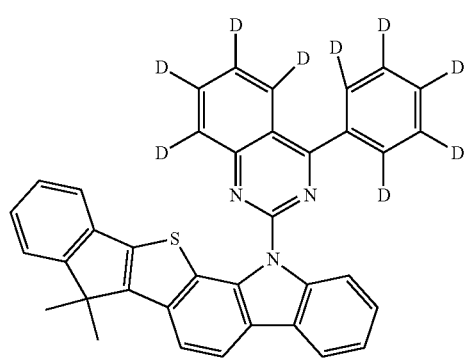
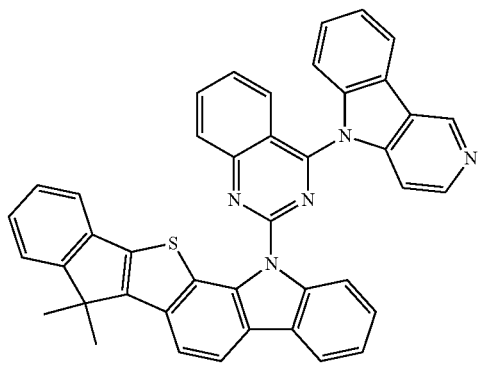

-continued
22
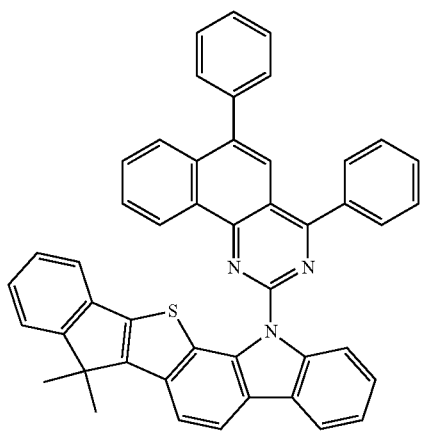
23
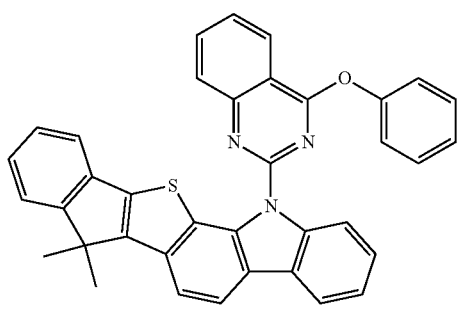
24
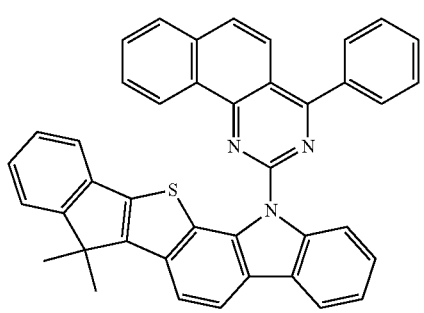
25
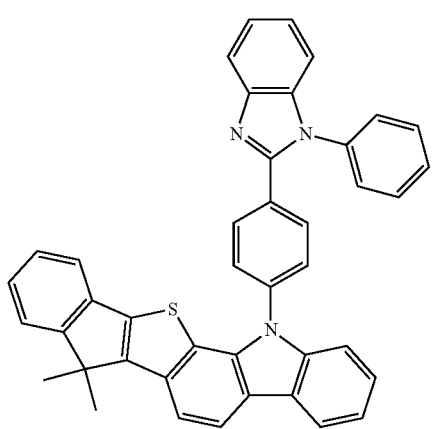
-continued
26
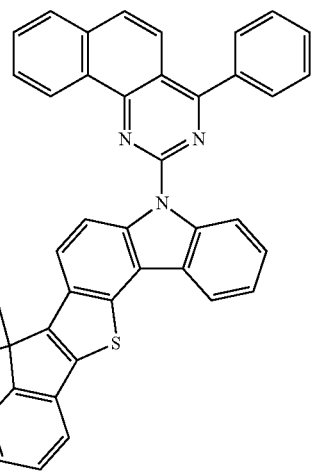
27
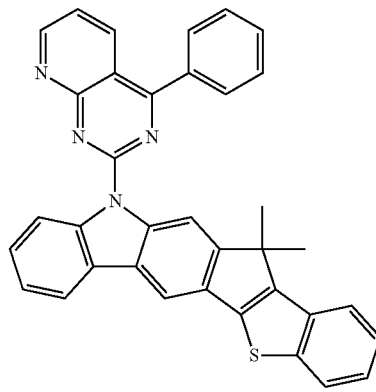
28
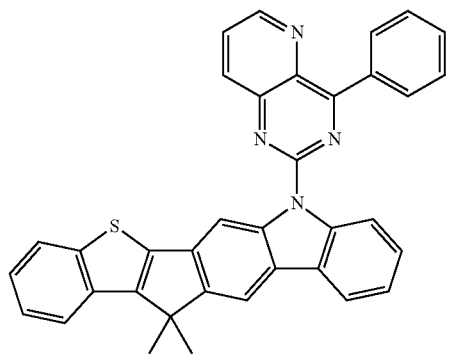
29
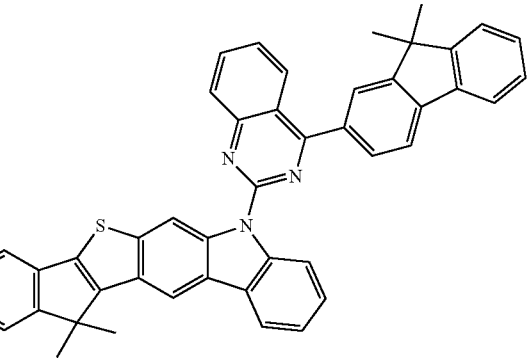

-continued
30
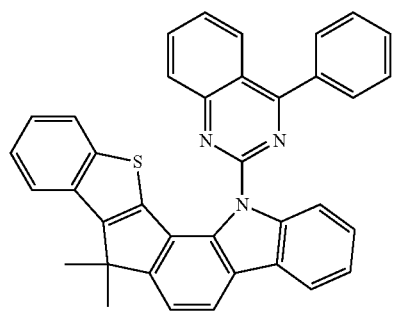
31
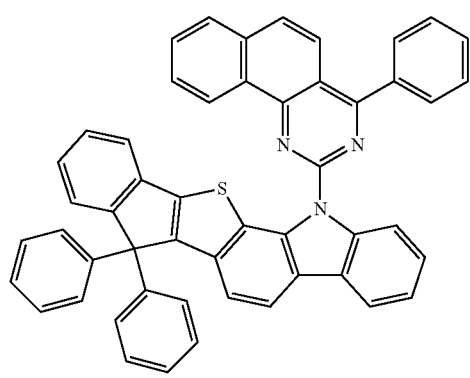
32
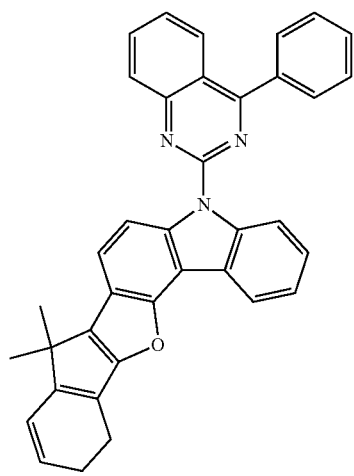
33
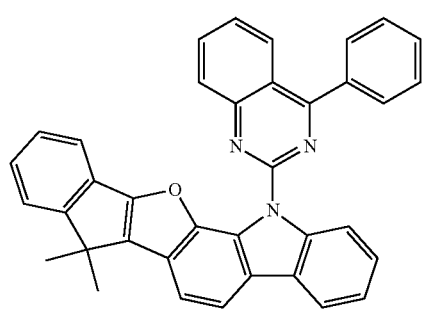
-continued
34
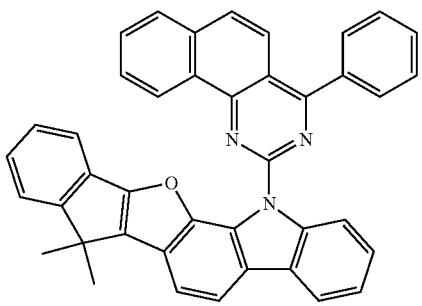
35
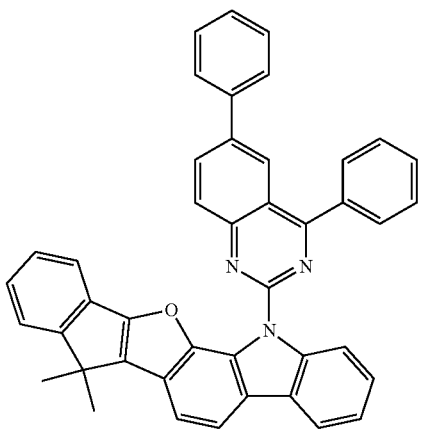
36
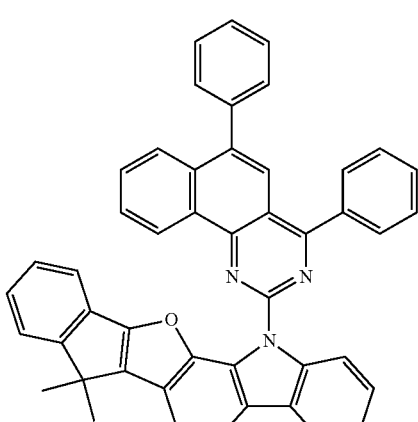
37
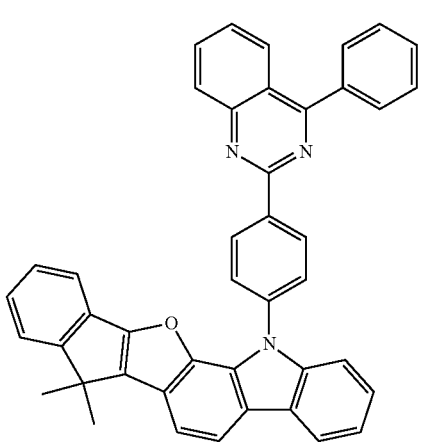

38
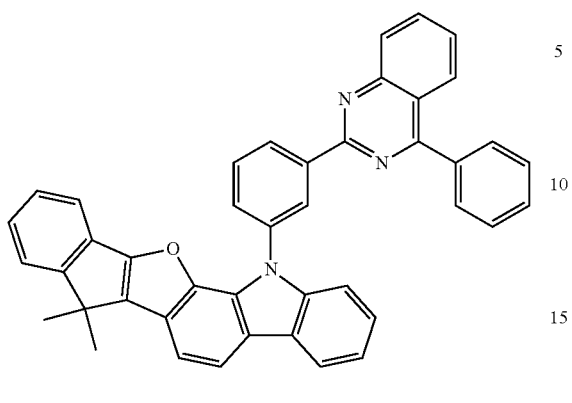
39
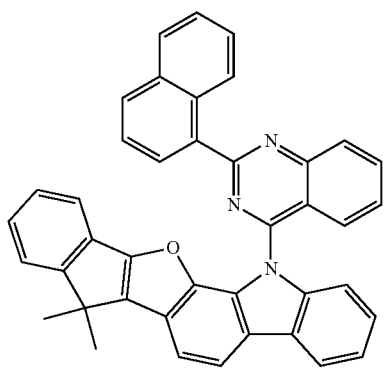
40
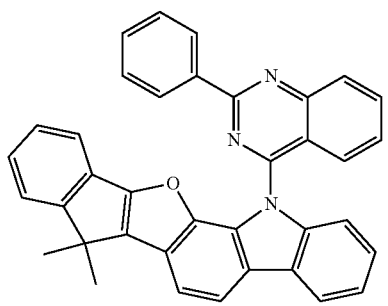
41
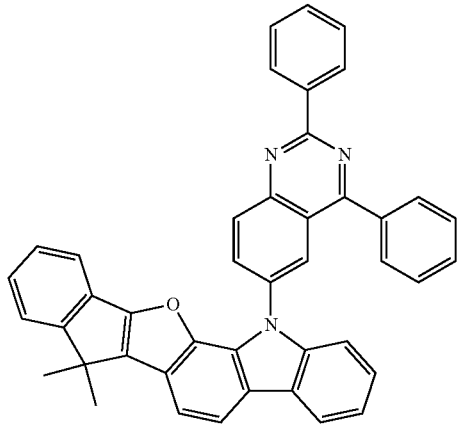
42
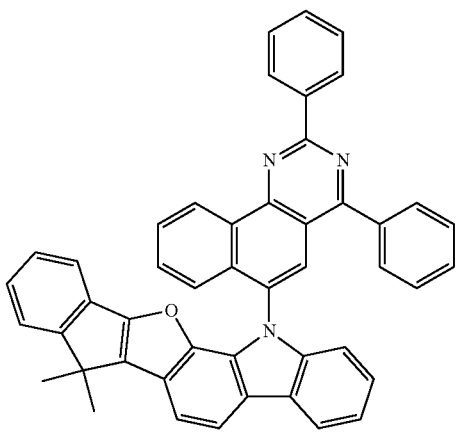
43
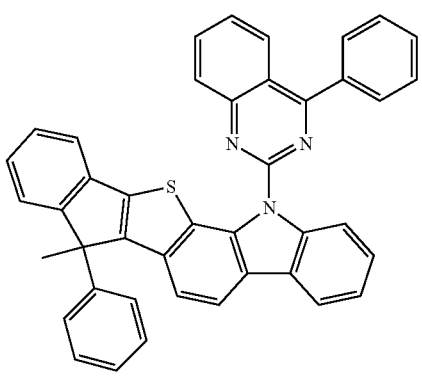
44
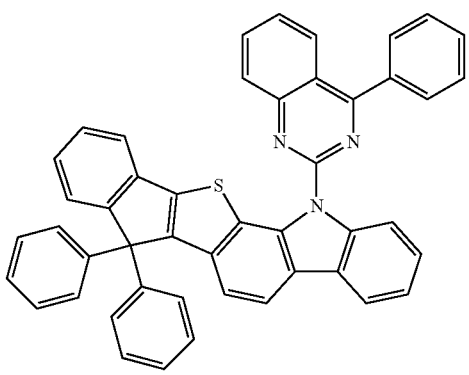
45
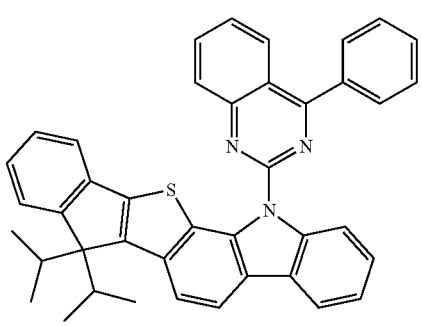

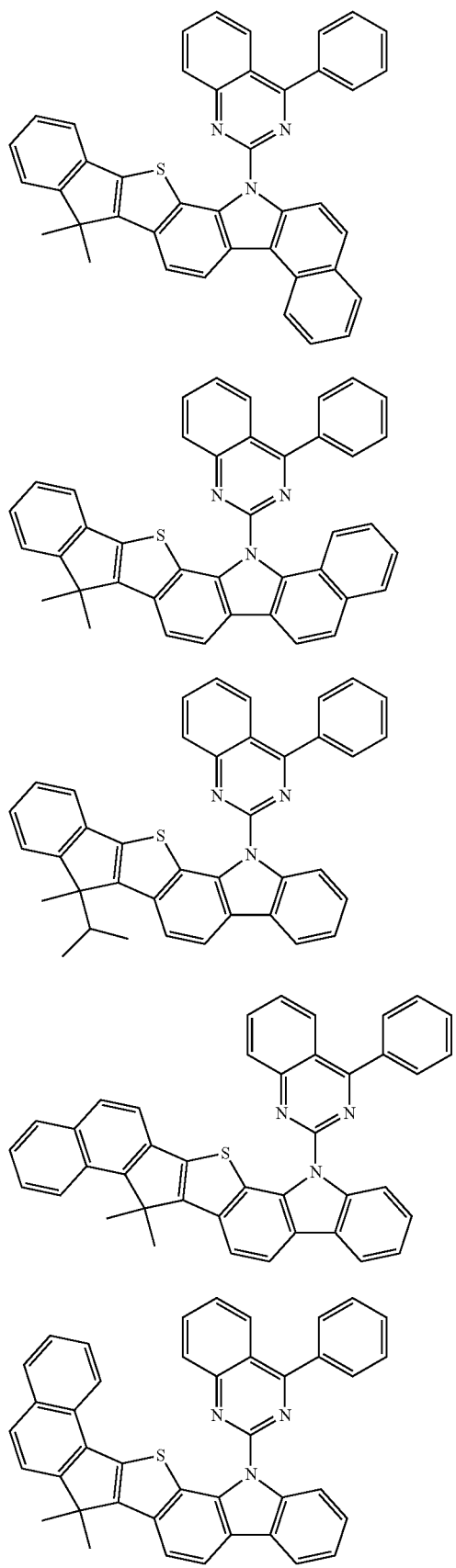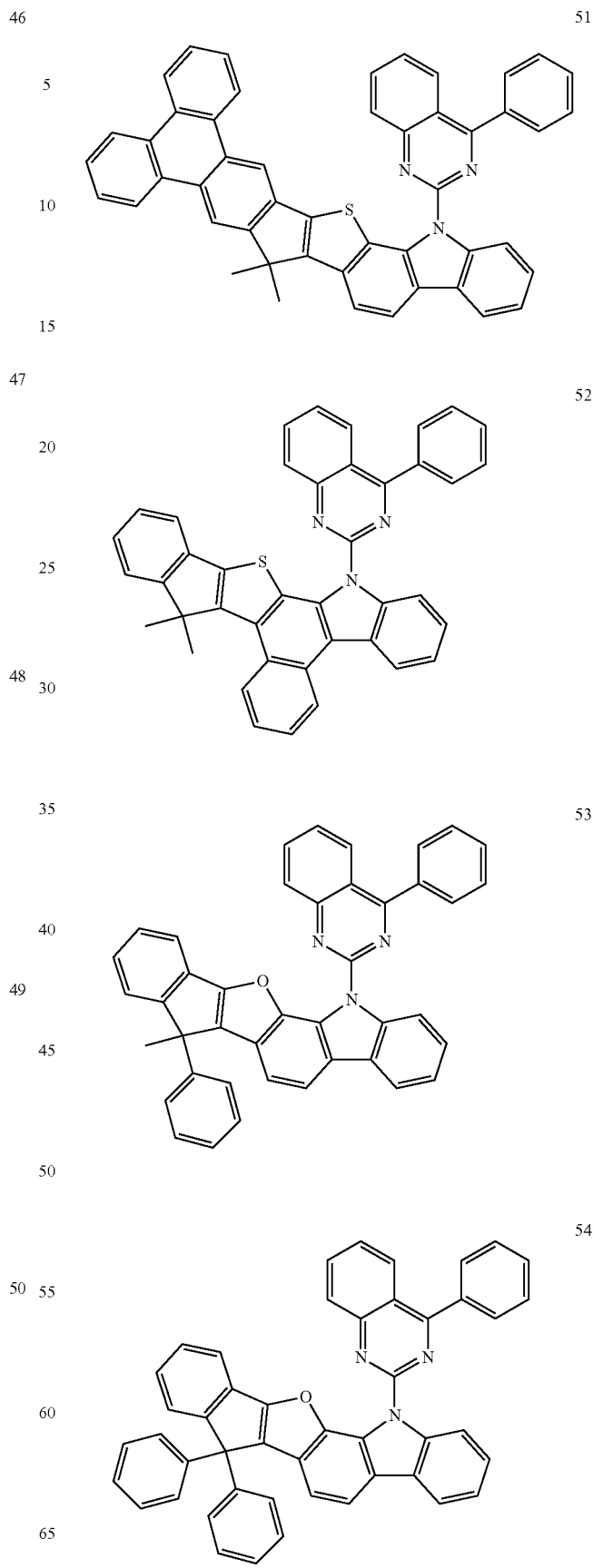

55
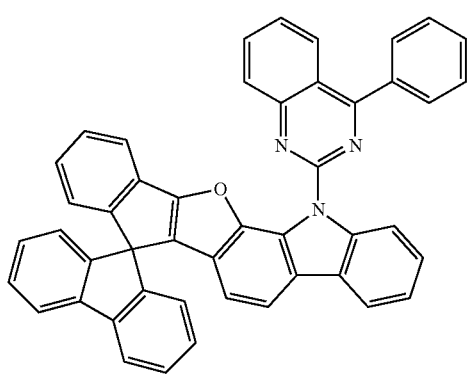
56
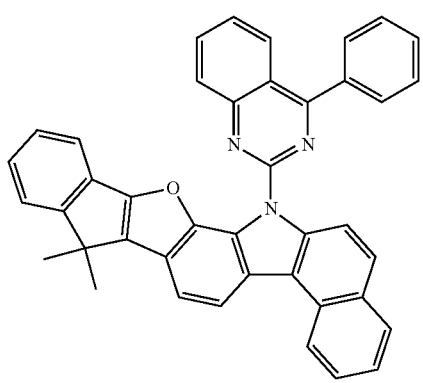
57
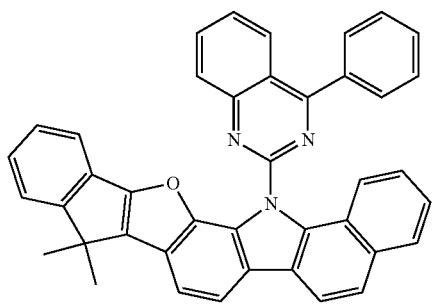
58
59
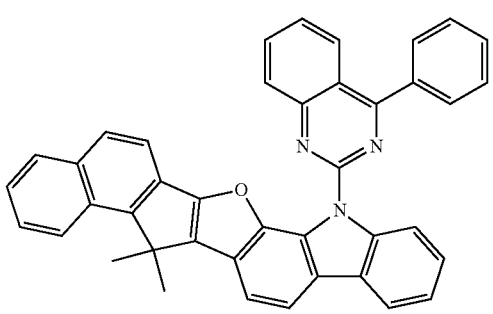
60
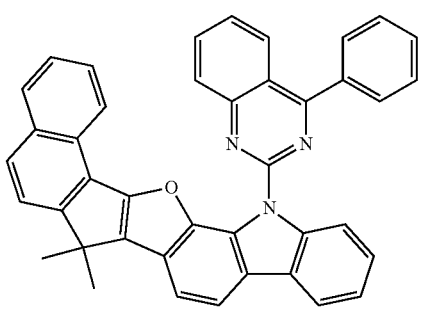
61
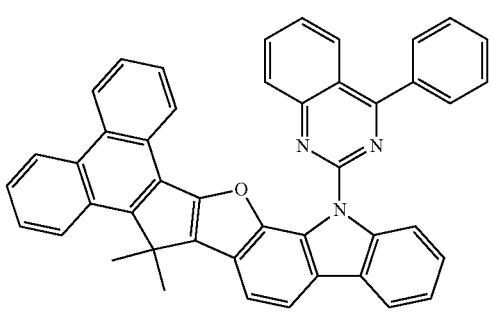
62
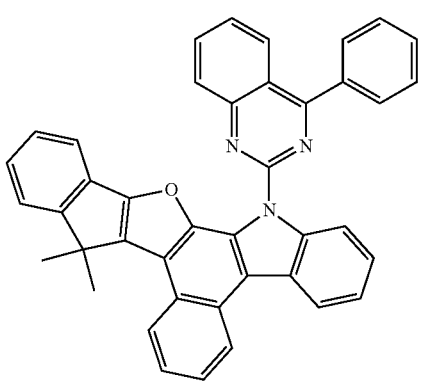

63
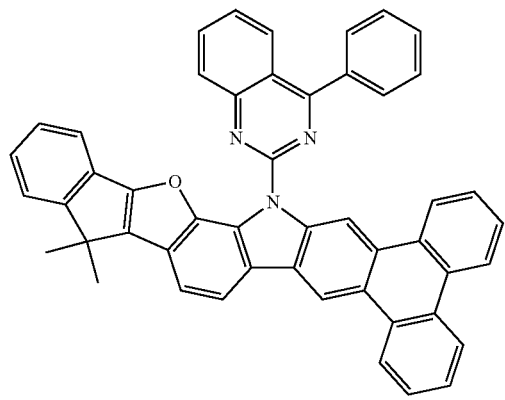
64
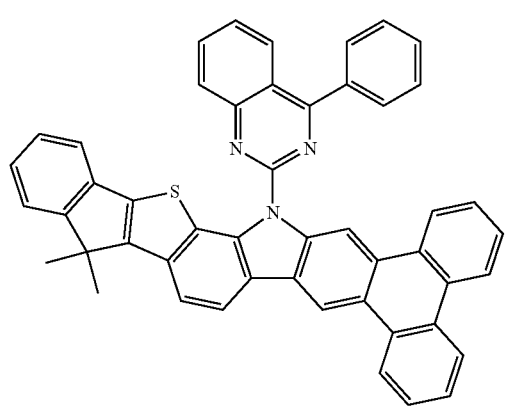
65
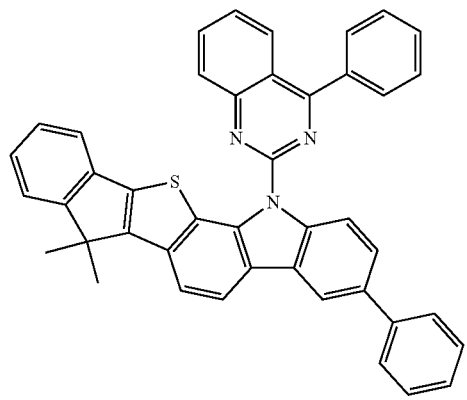
66
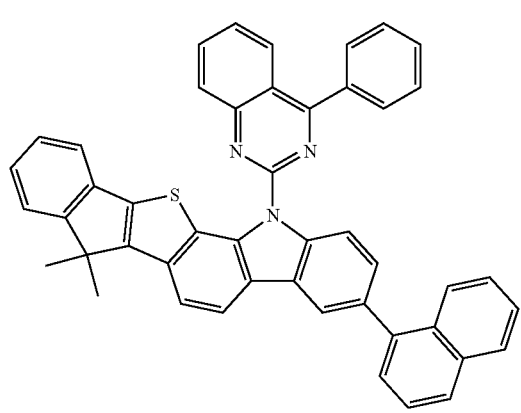
67
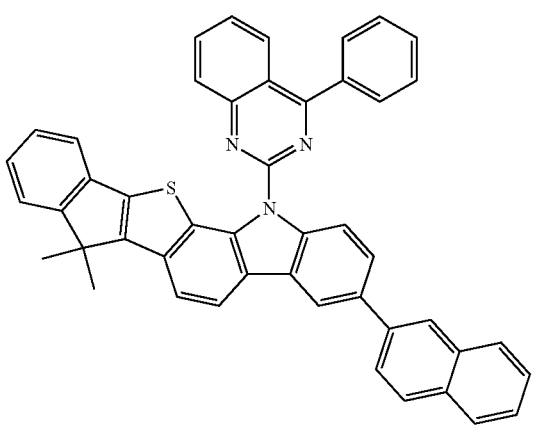
68
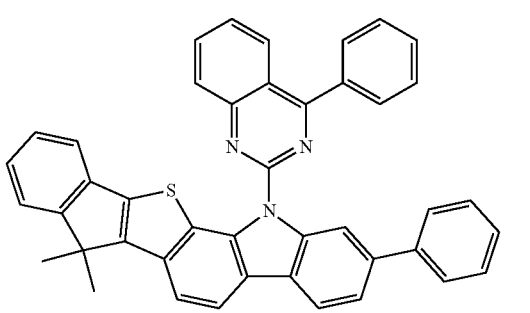
69
70
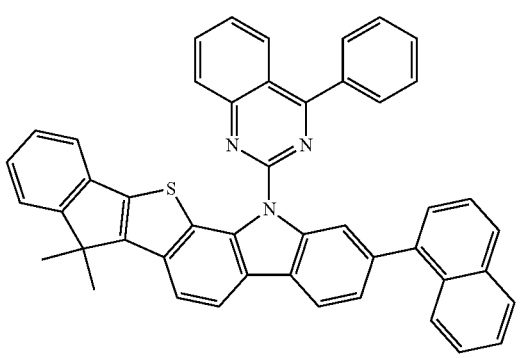

71
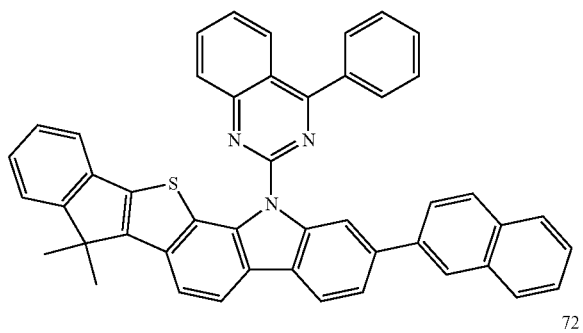
72
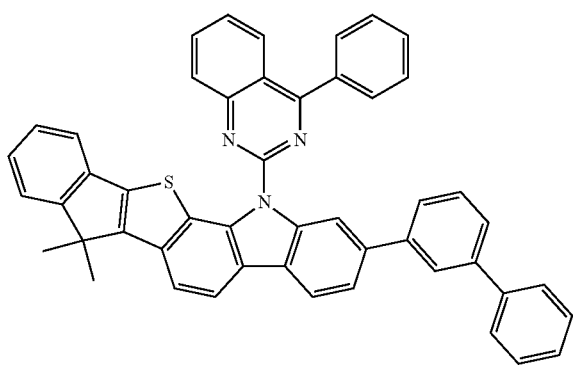
73
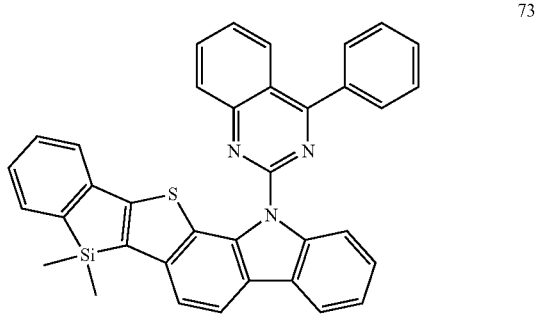
74
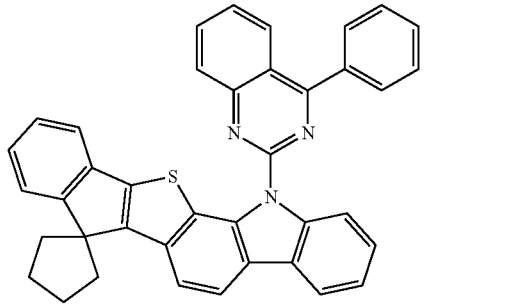
75
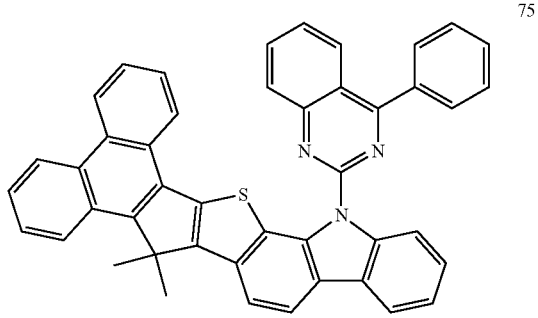
76
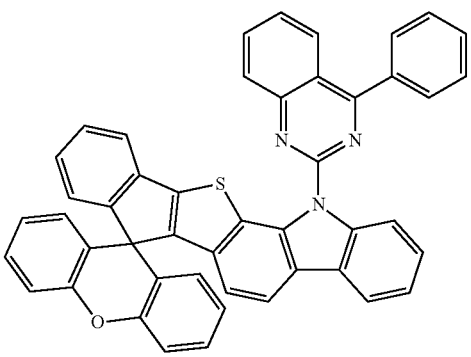
77
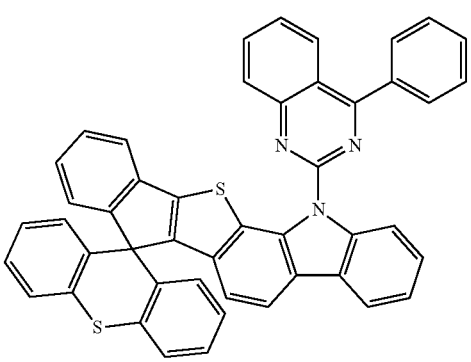
78
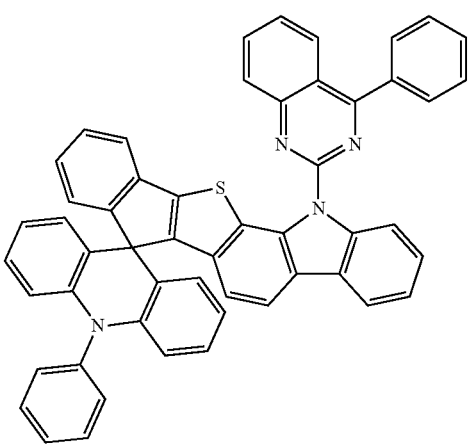
79
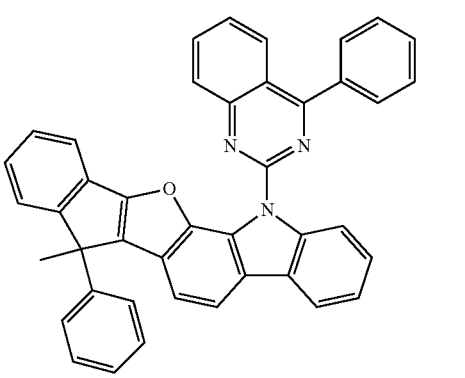

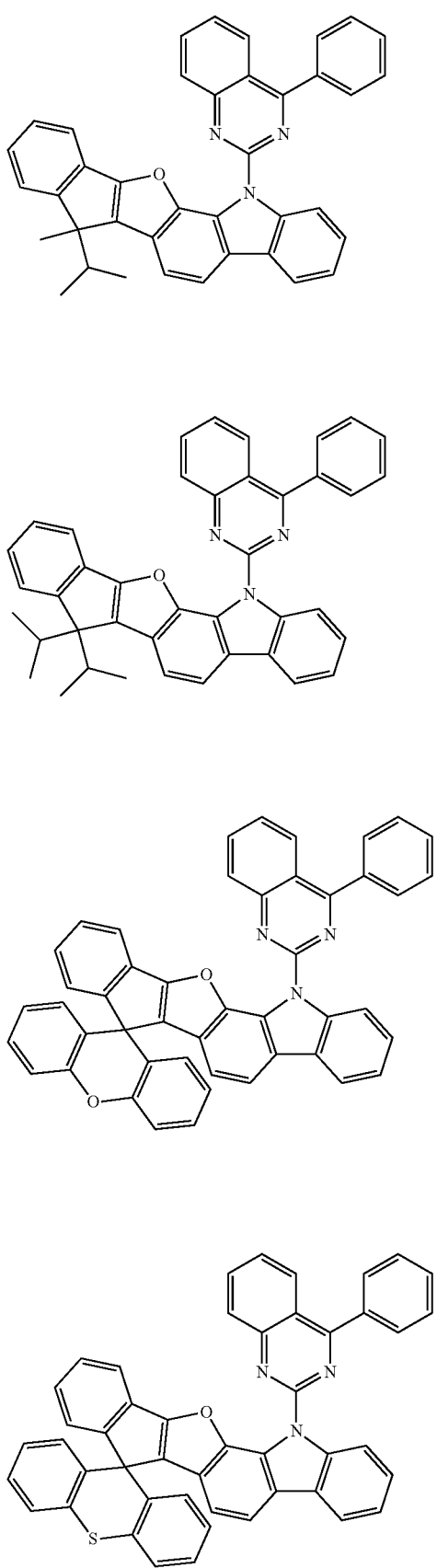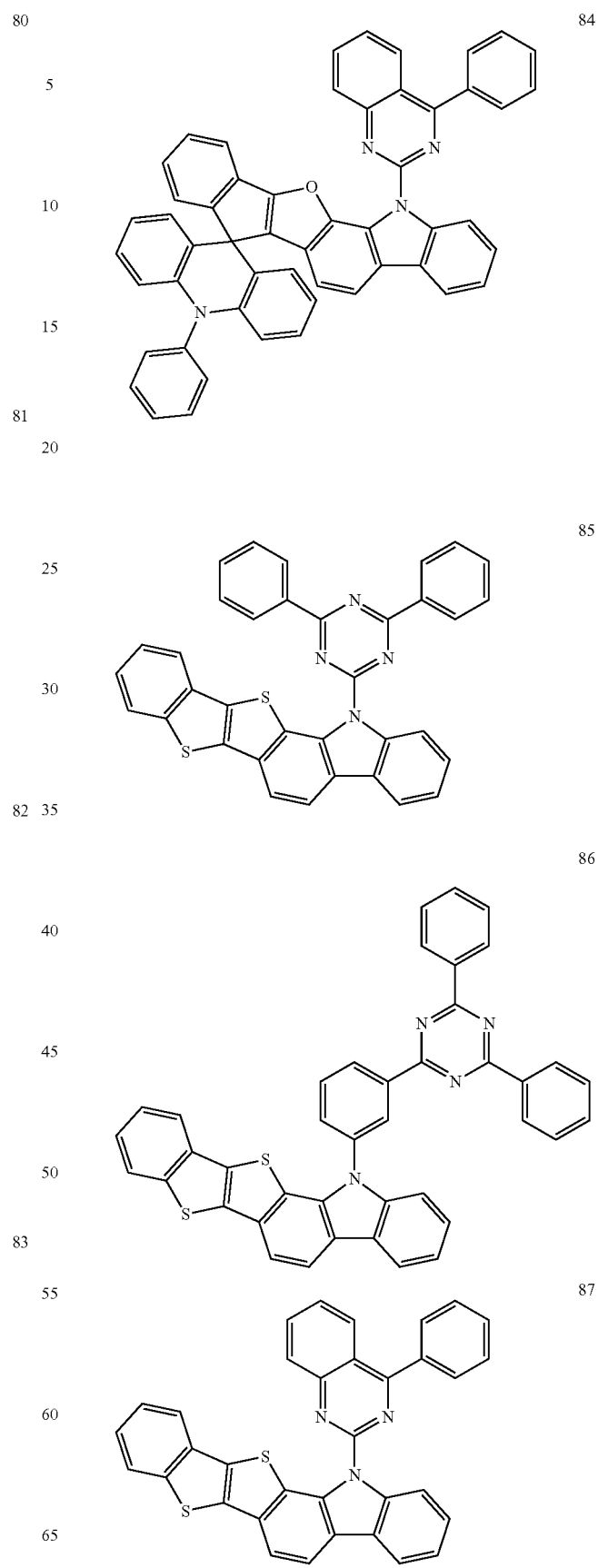

88
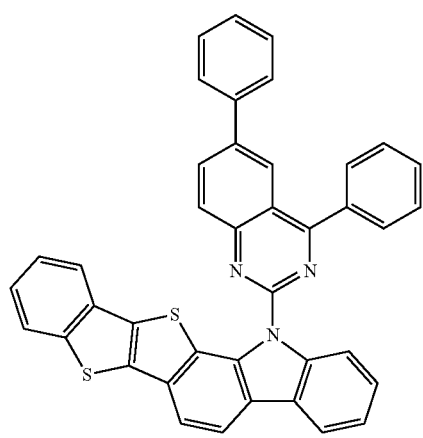
89
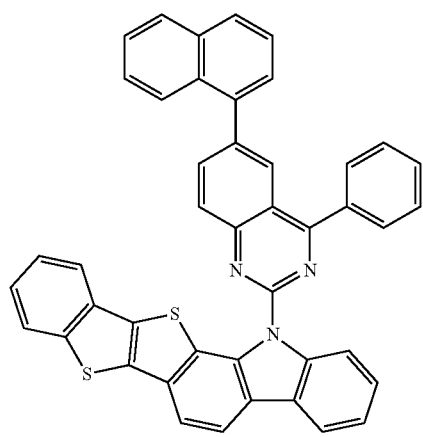
90
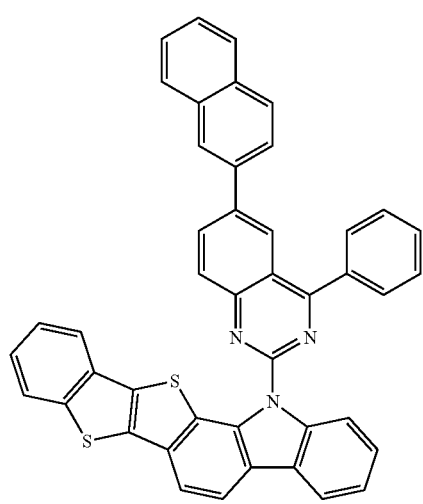
91
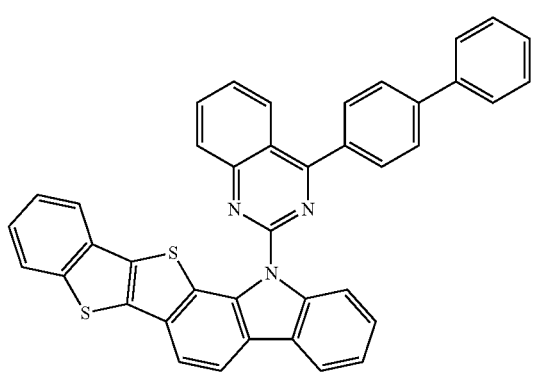
92
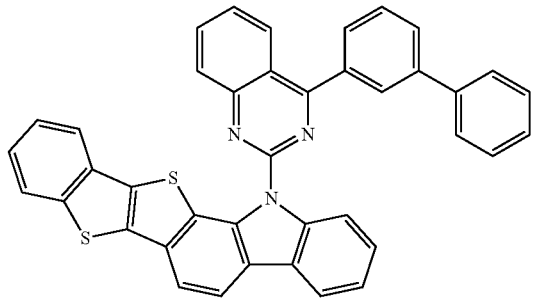
93
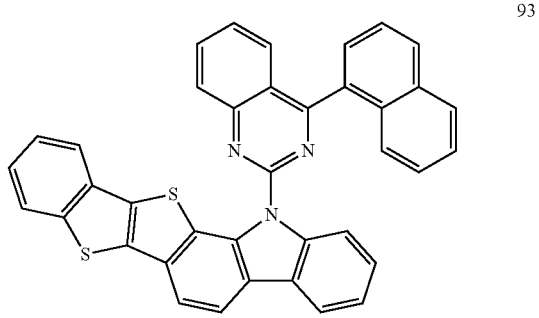
94
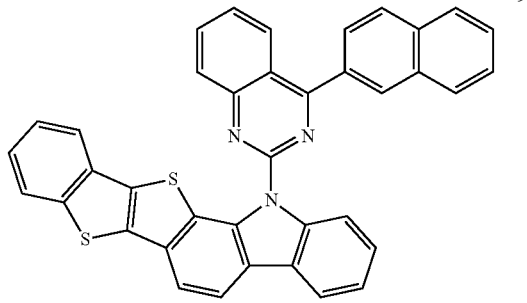
95
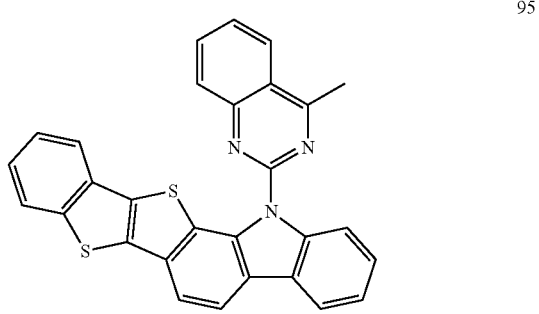

96
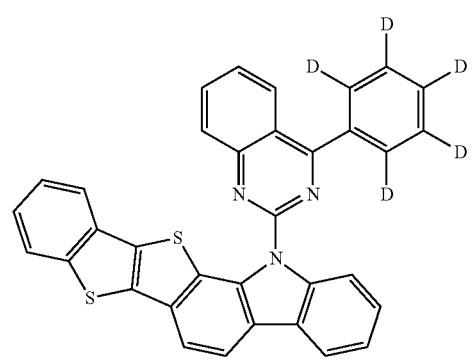
97
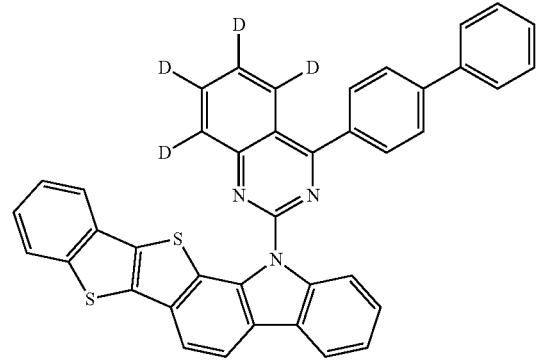
98
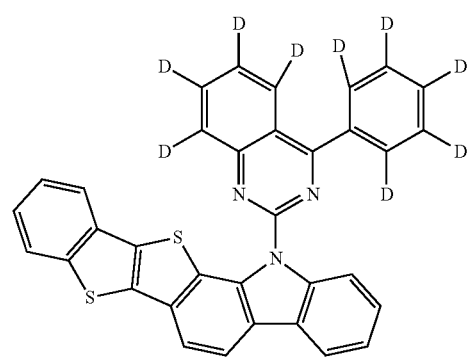
99
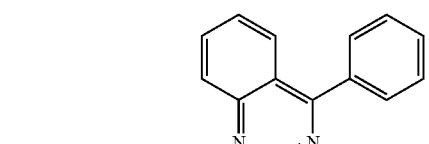
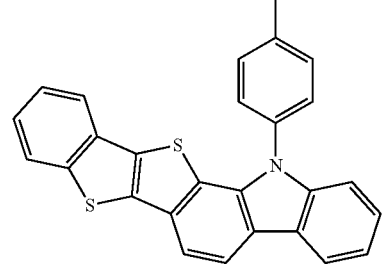
100
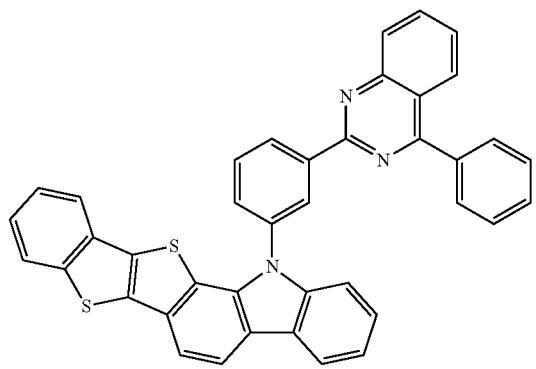
101
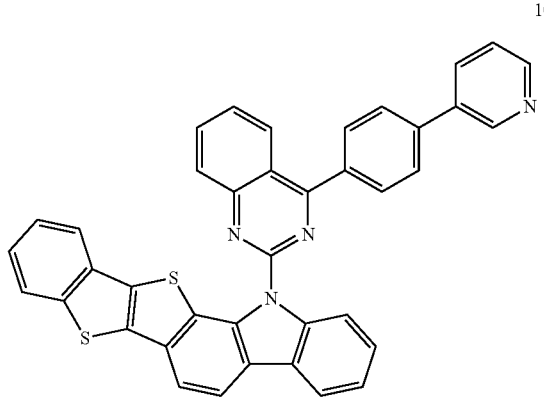
102
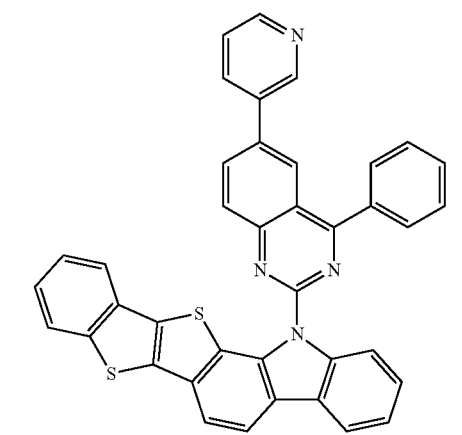
103
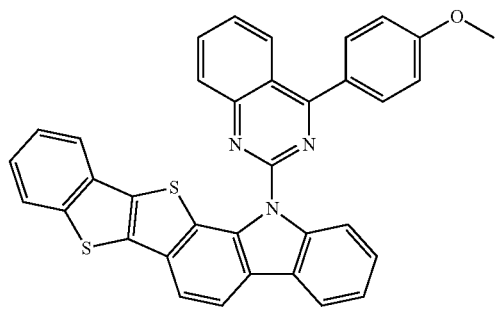

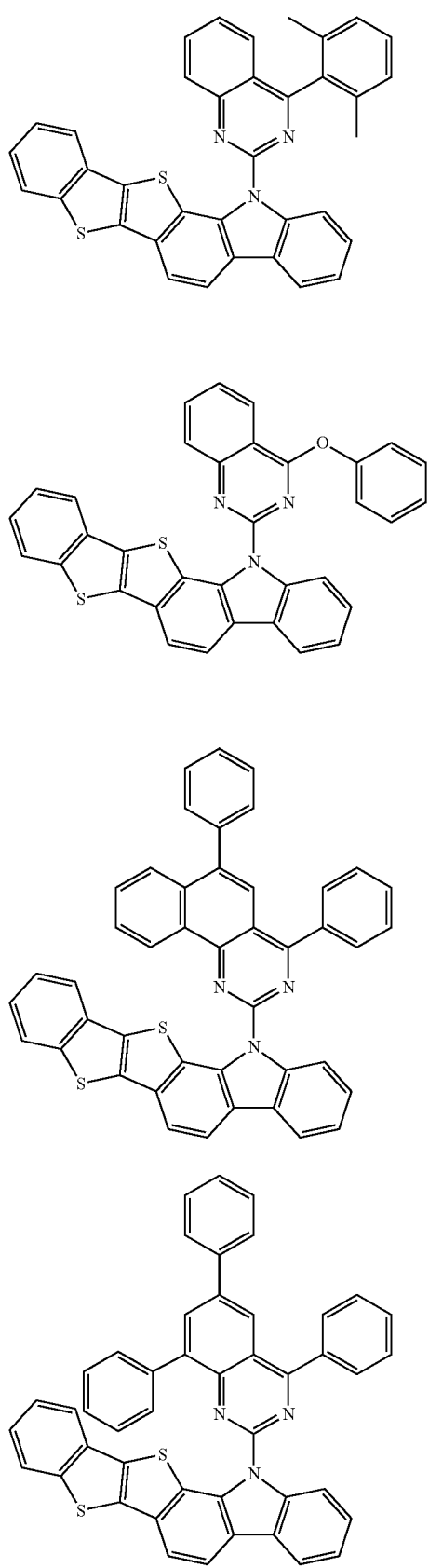
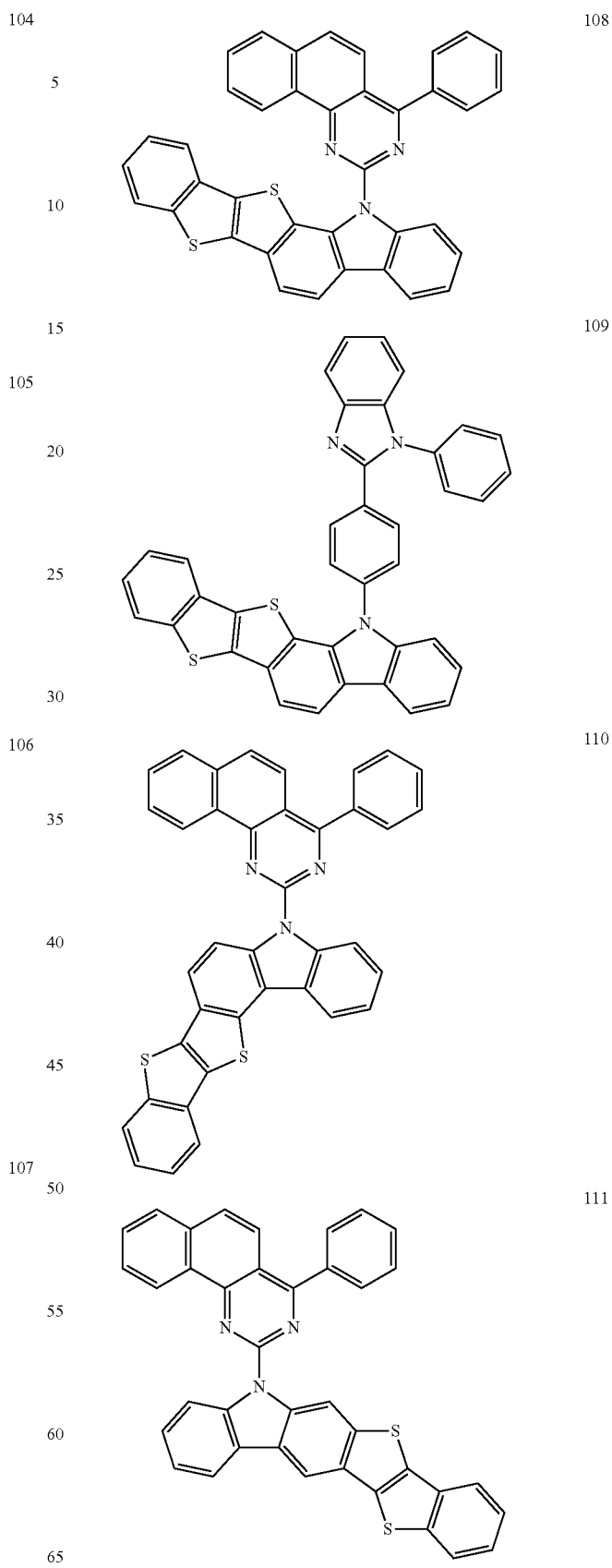

-continued
112
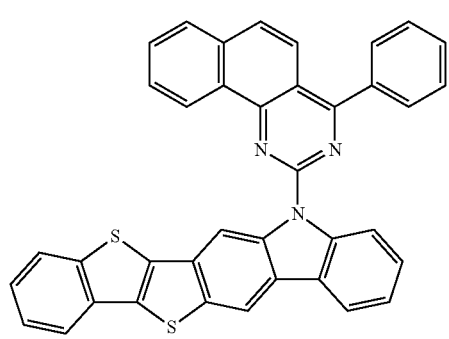
113
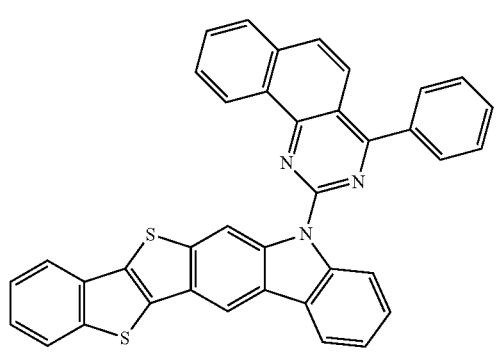
114
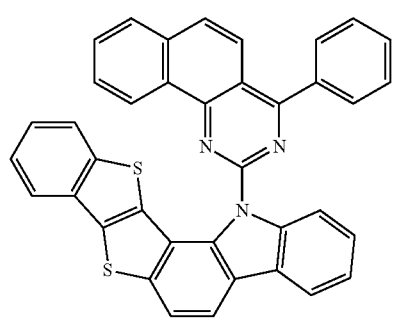
115
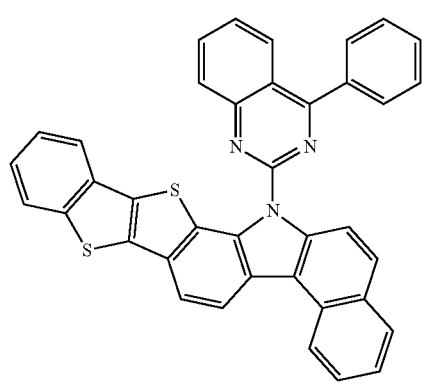
-continued
116
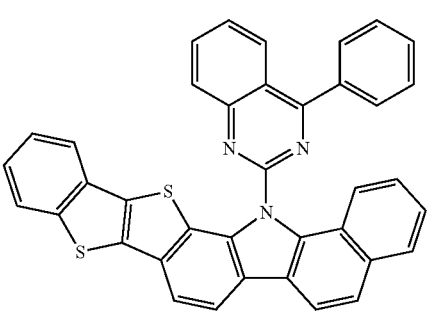
117
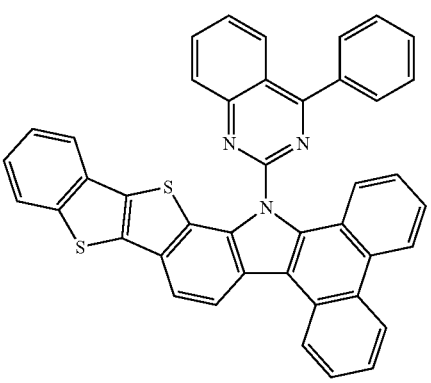
118
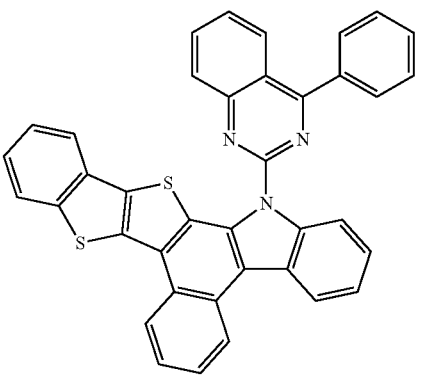
119
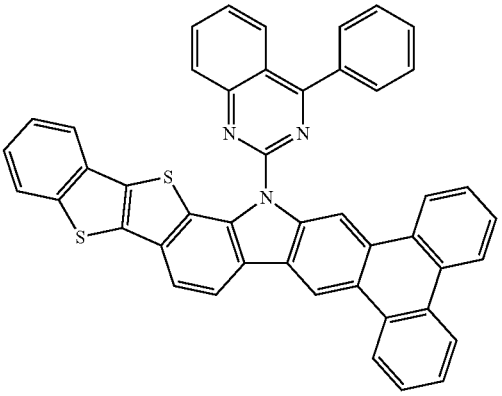

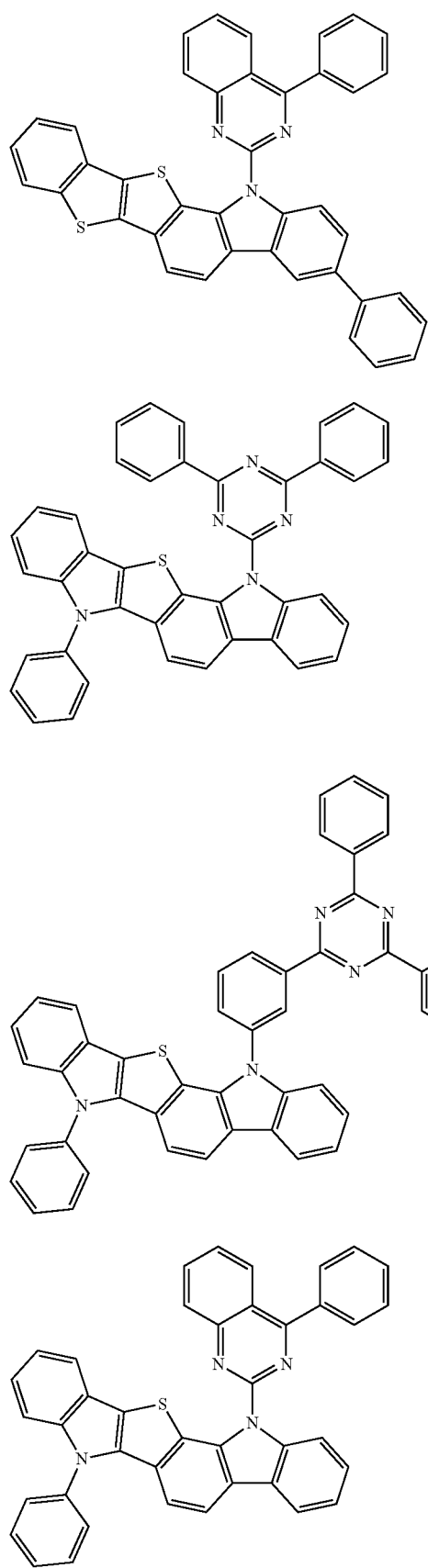
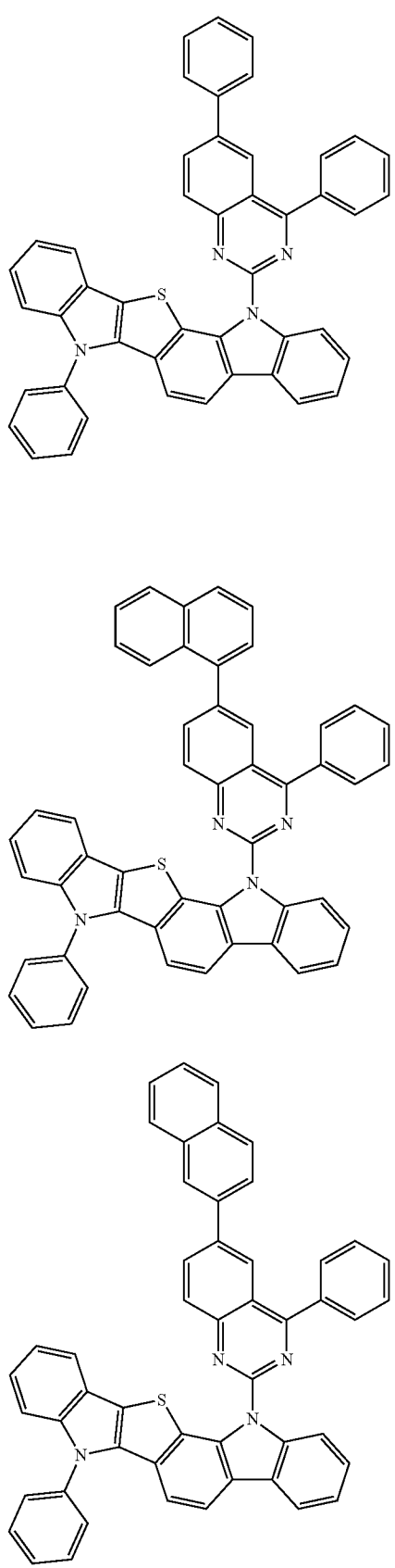

127
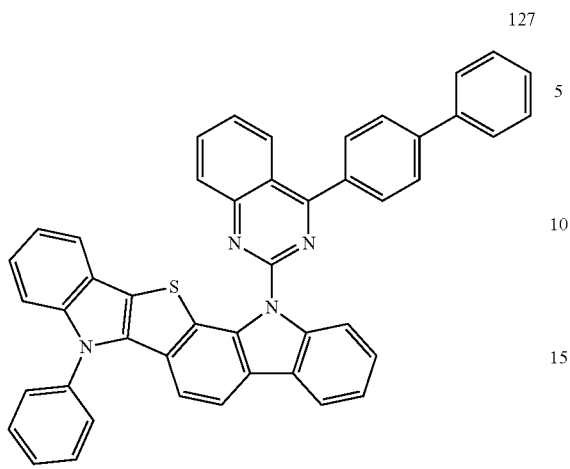
128
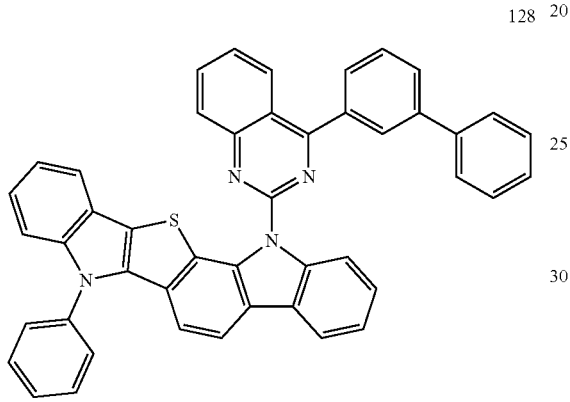
129
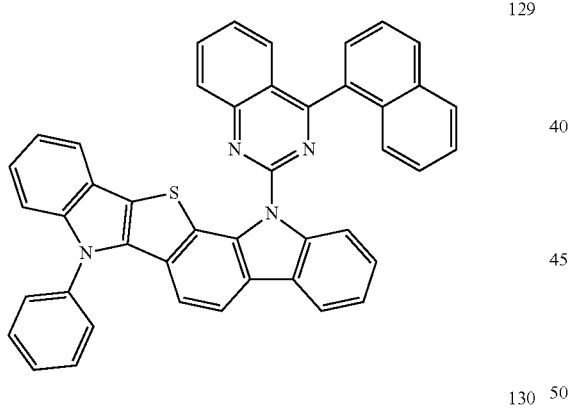
130
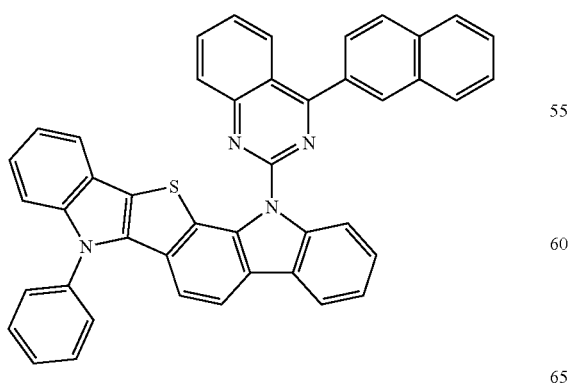
131
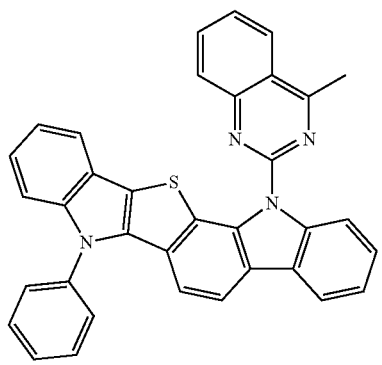
132
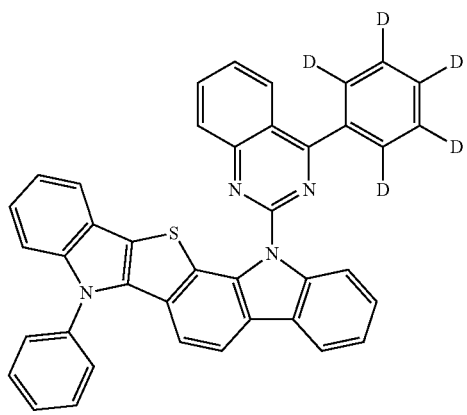
133
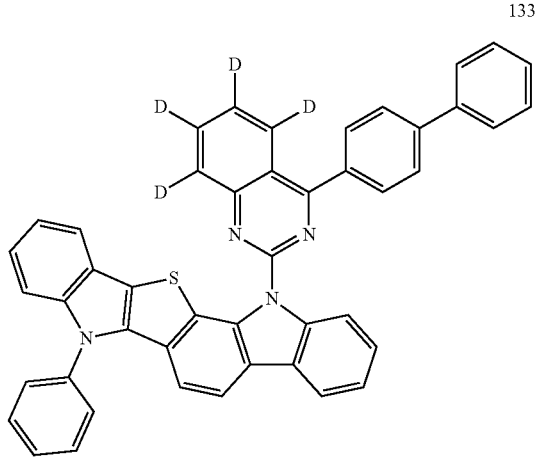
134
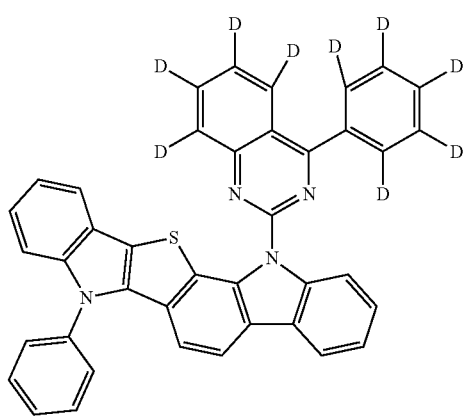

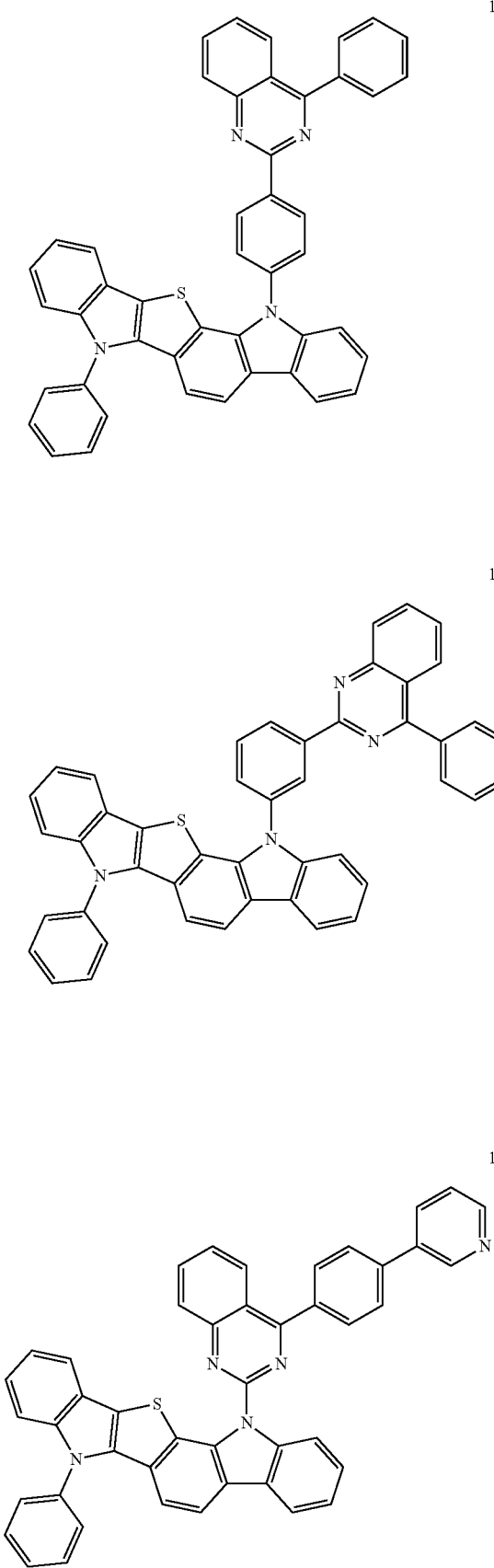
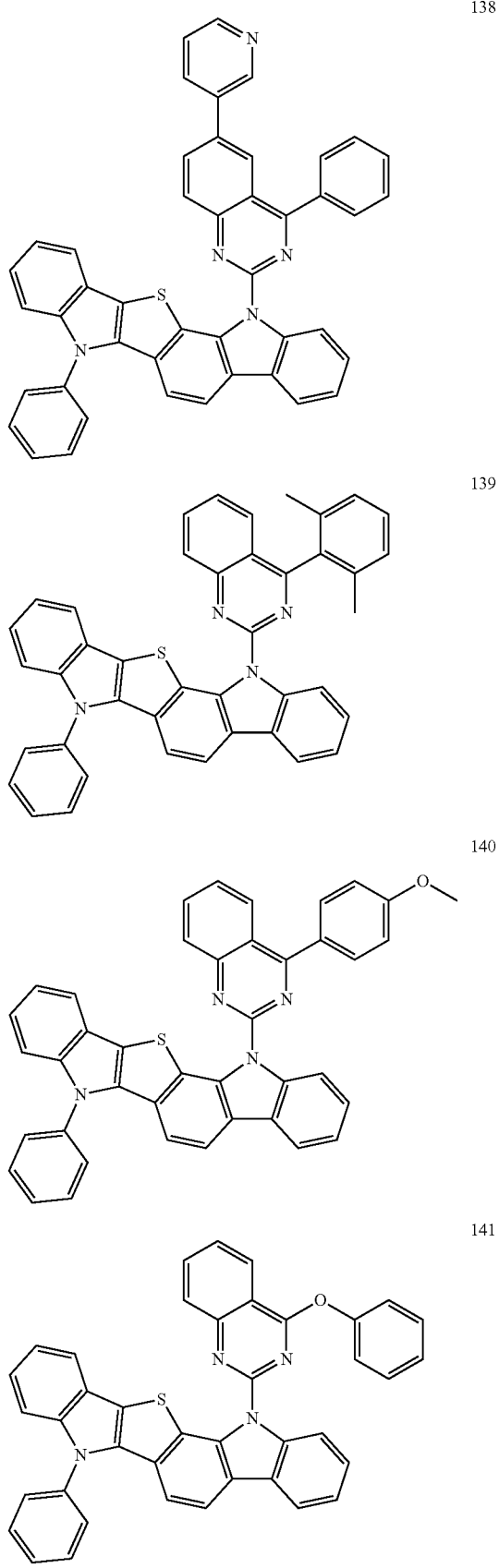

142
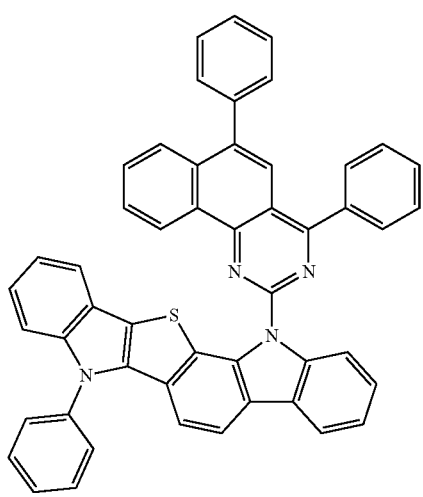
143
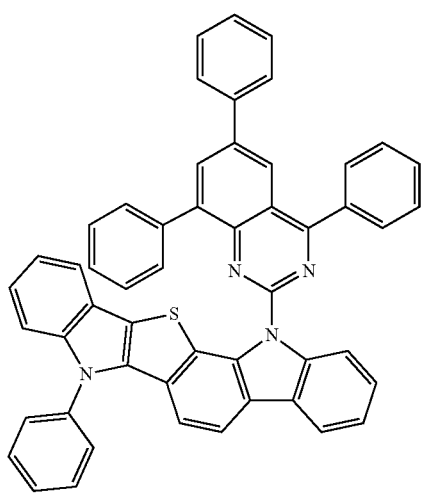
144
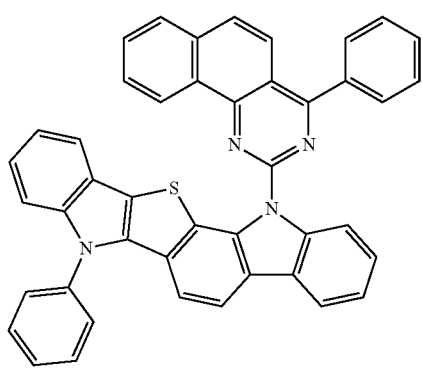
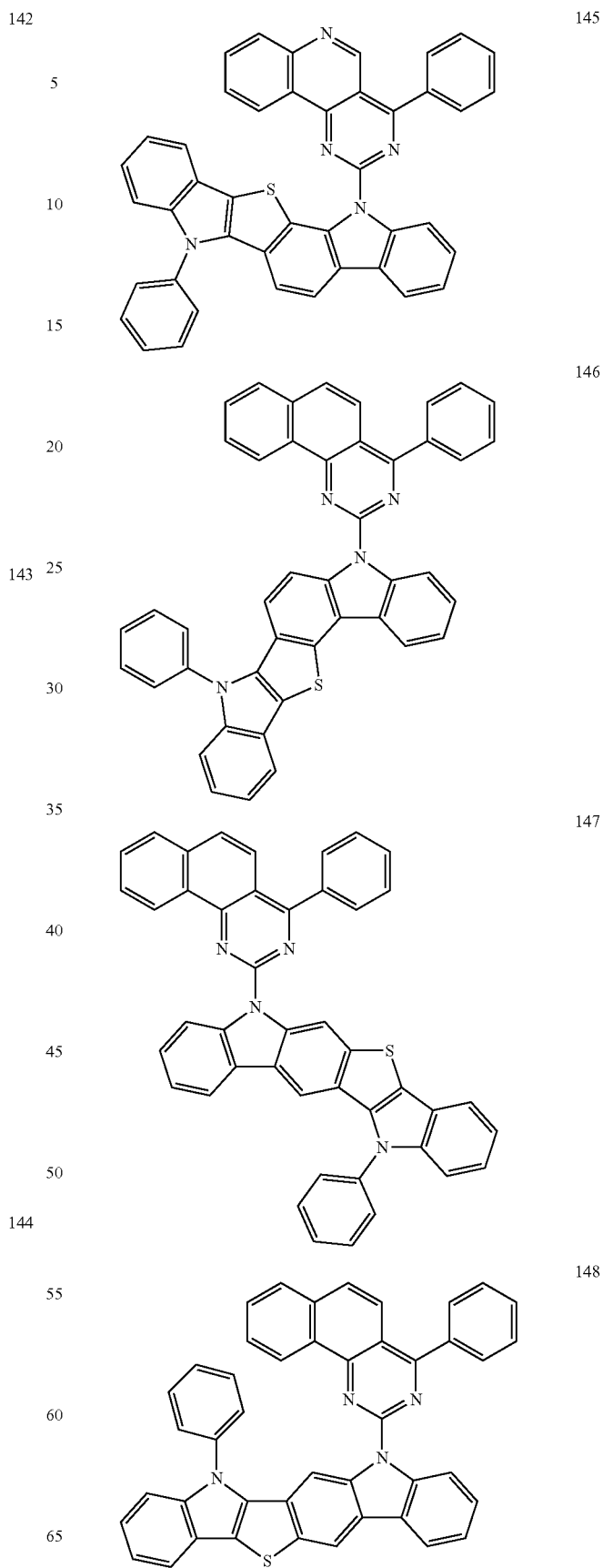

149
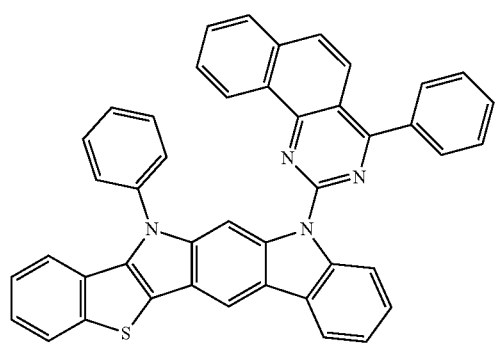
150
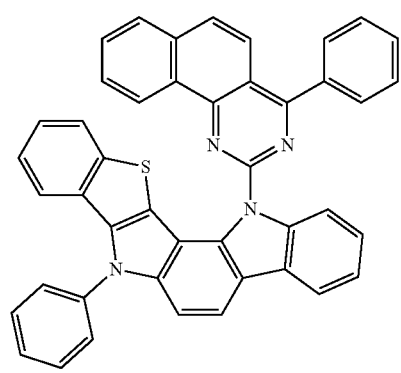
151
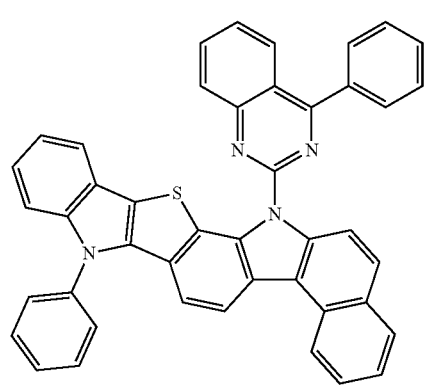
152
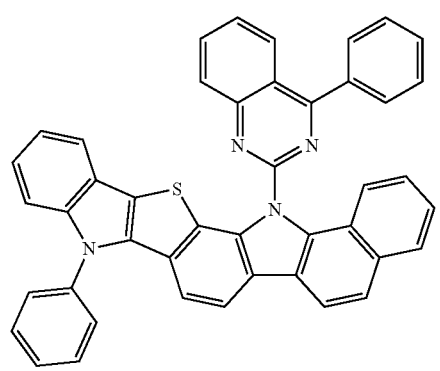
153
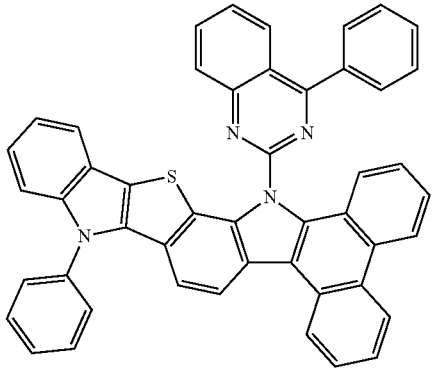
154
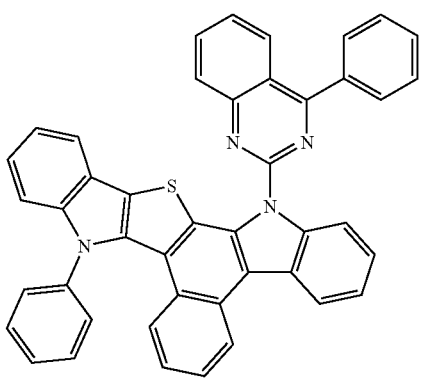
155
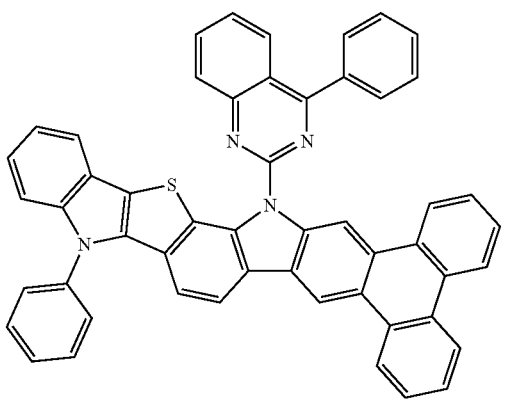
156
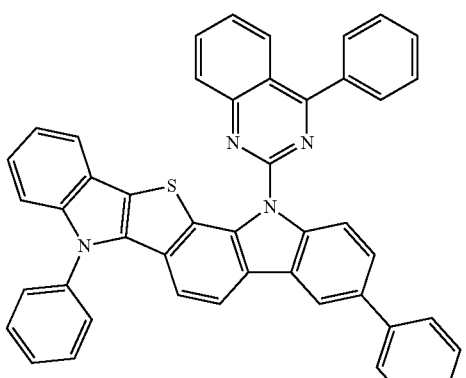

157
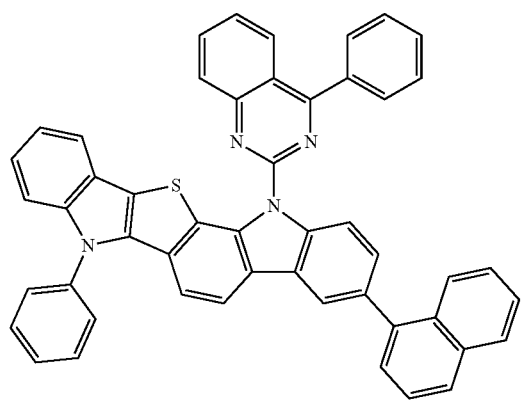
158
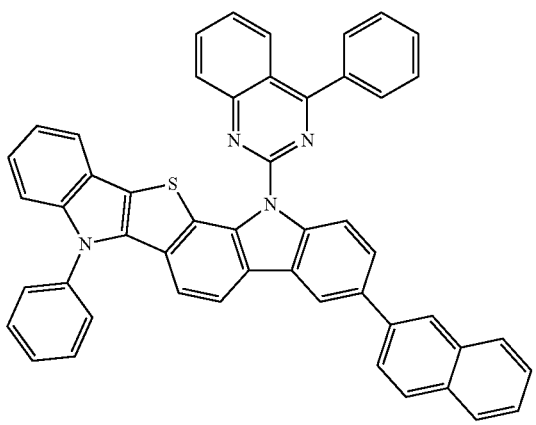
159
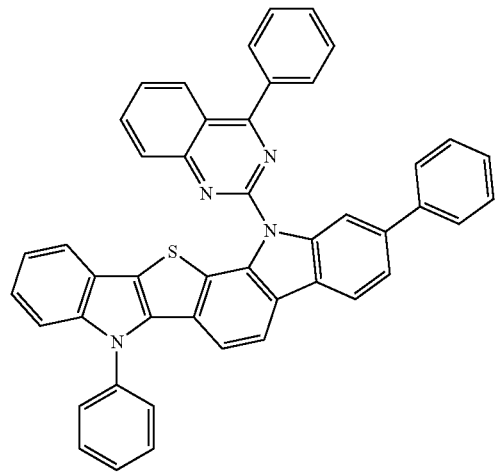
160
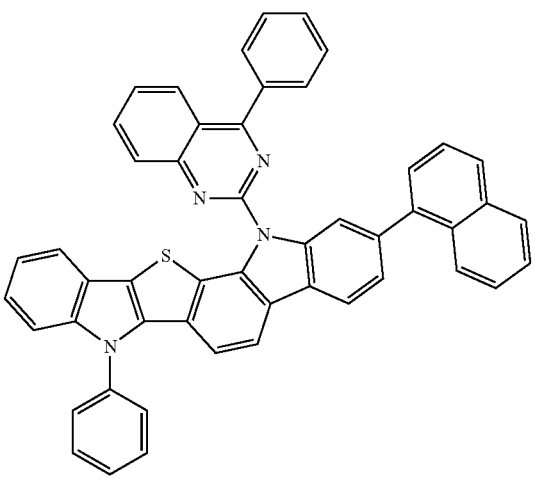
161
162

163
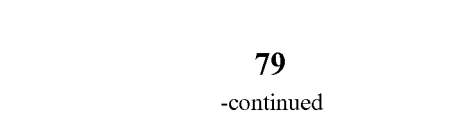
164
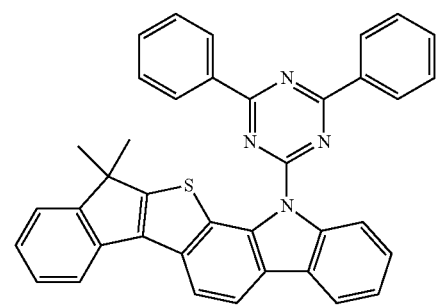
165
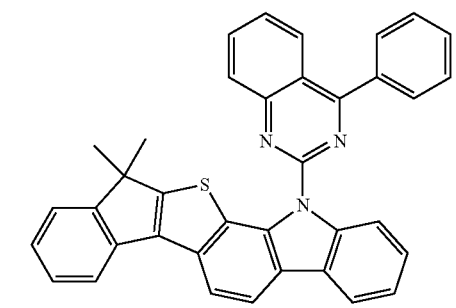
166
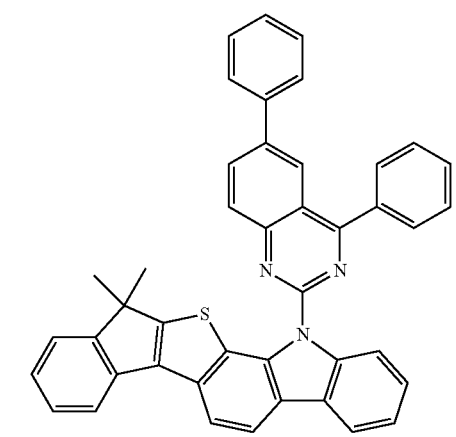
167
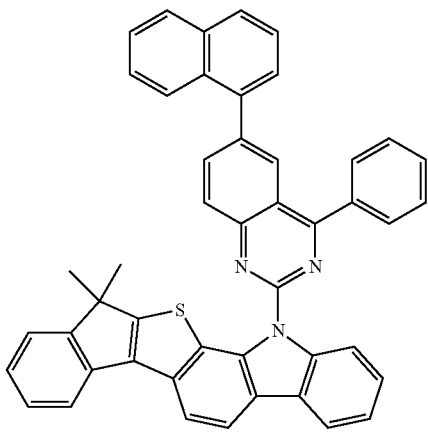
168
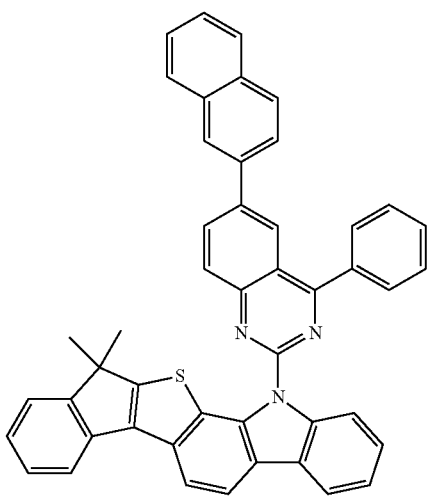
169
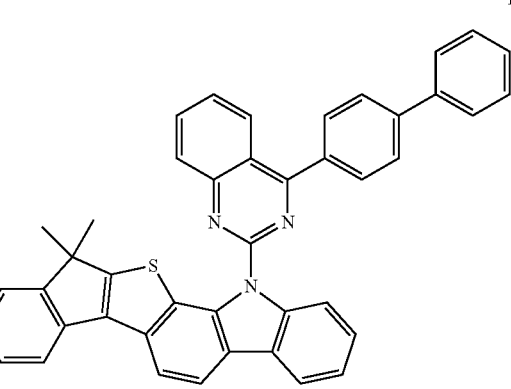
170
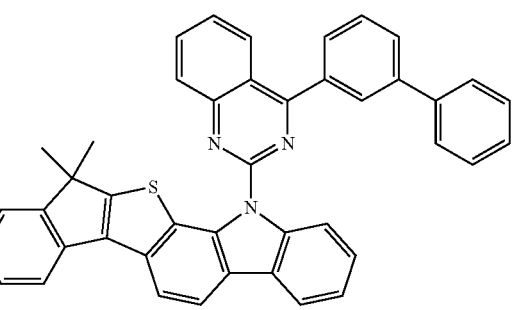

171
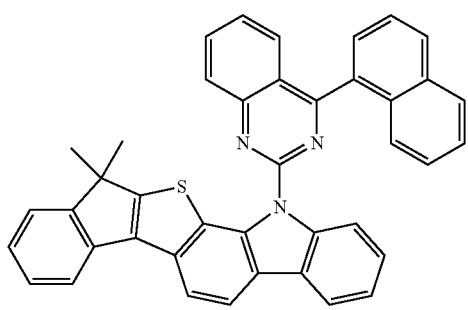
172
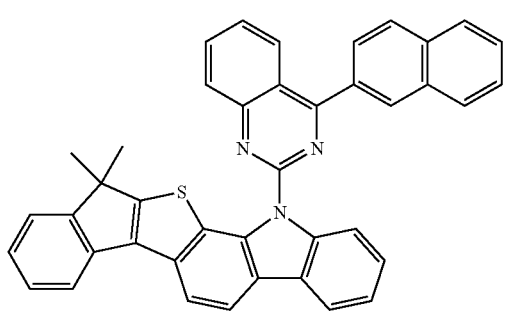
173
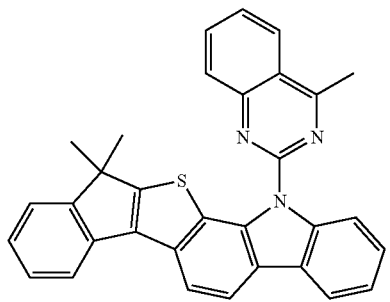
174
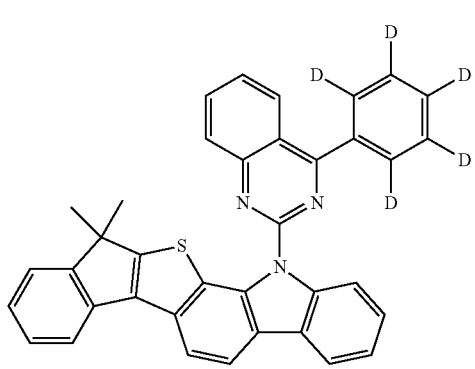
175
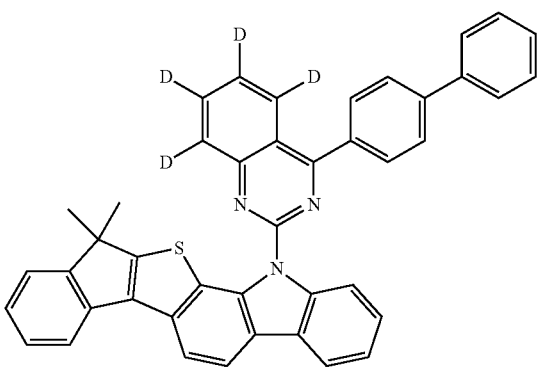
176
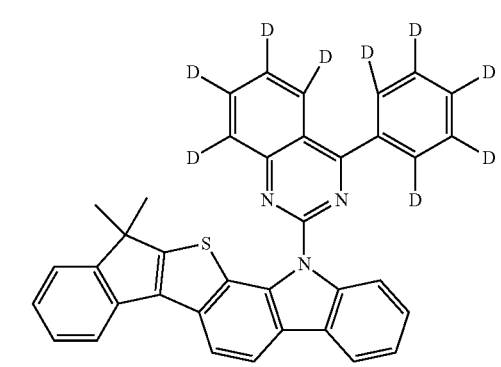
177
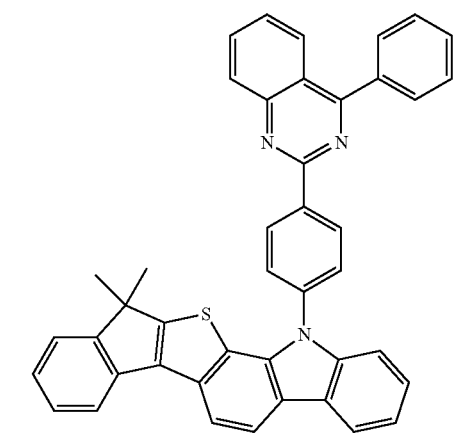
178
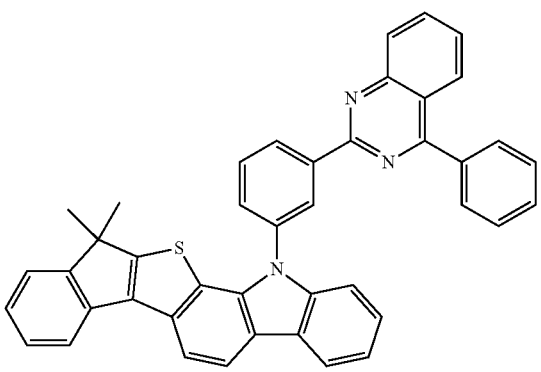

179
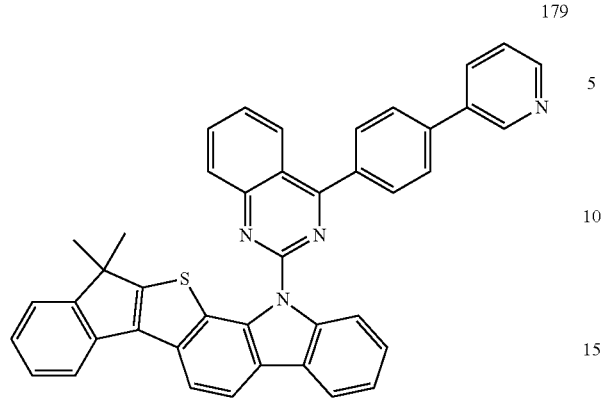
180
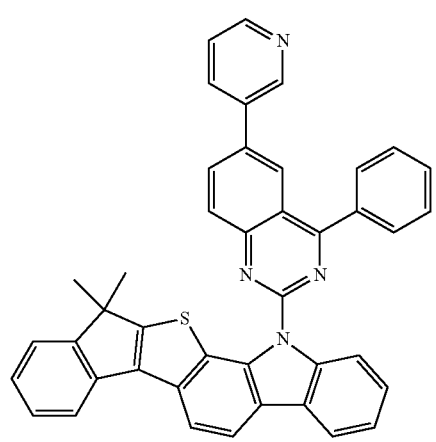
181
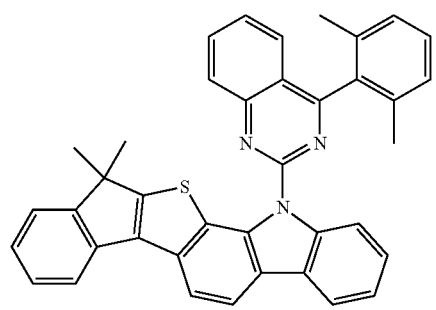
182
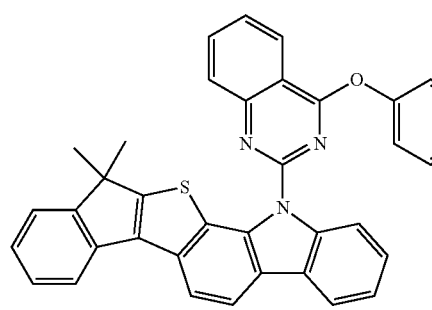
183
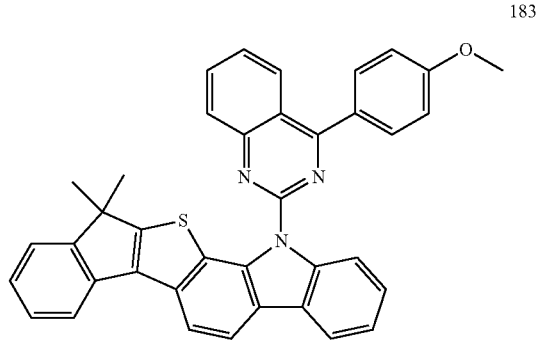
184
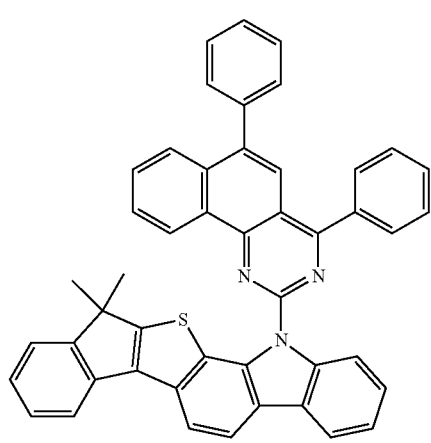
185
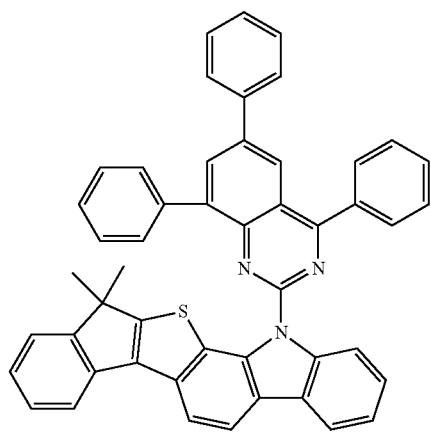
186
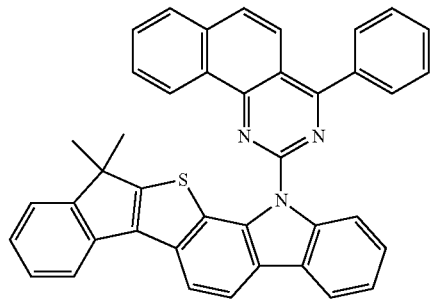

187
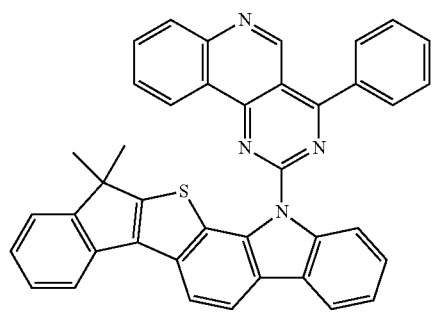
188
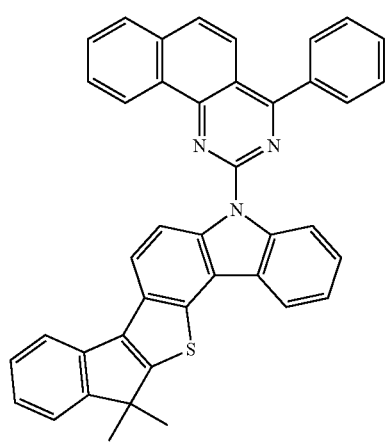
189
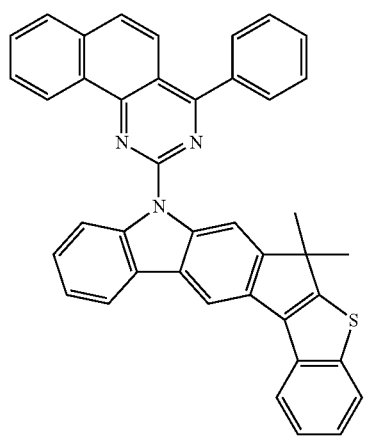
190
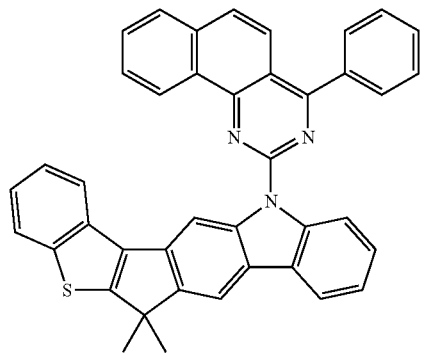
191
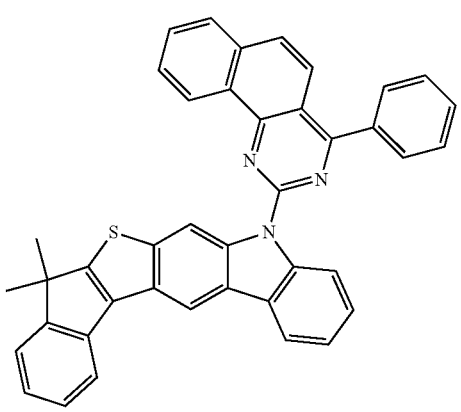
192
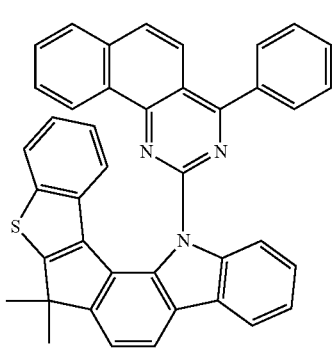
193
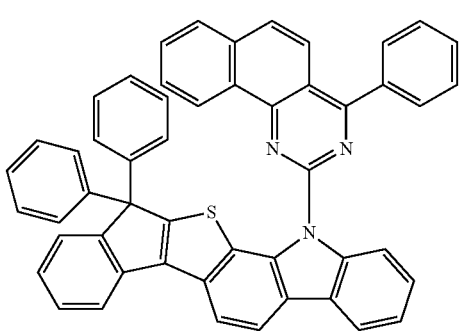
194
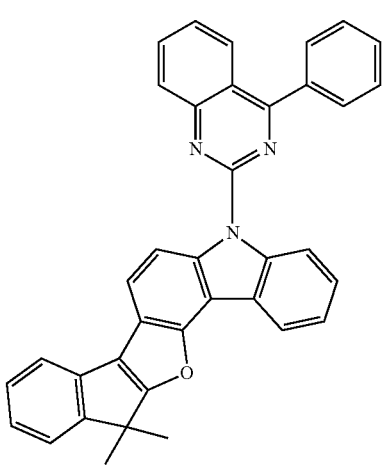

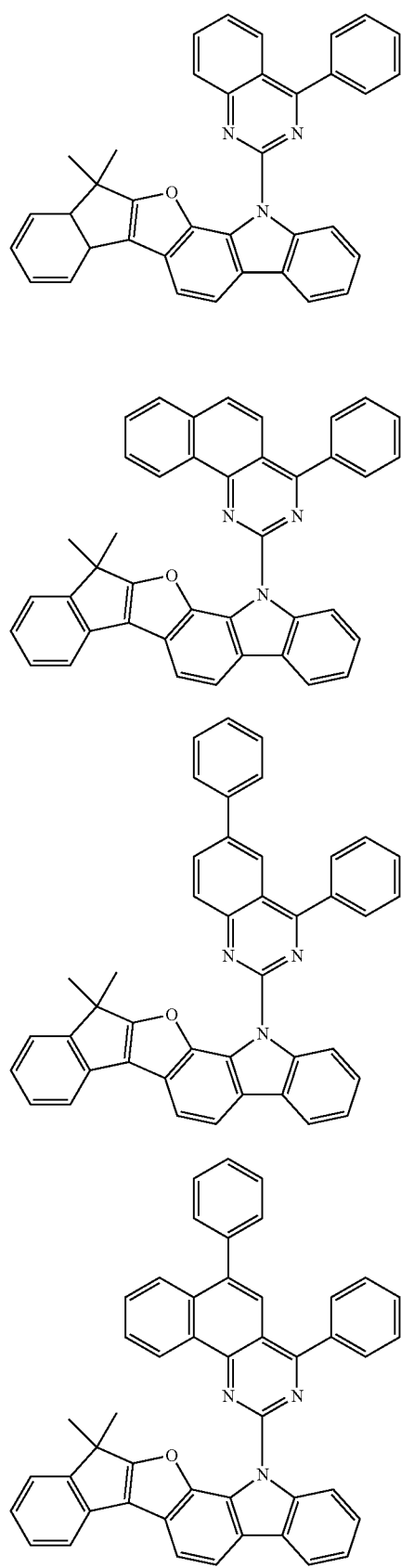

-continued
203
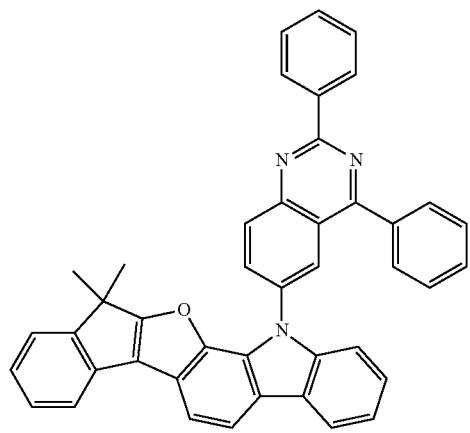
204
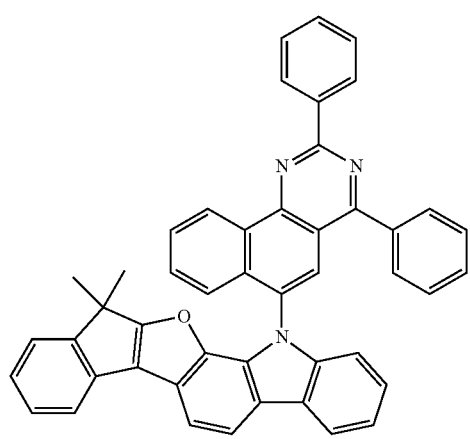
205
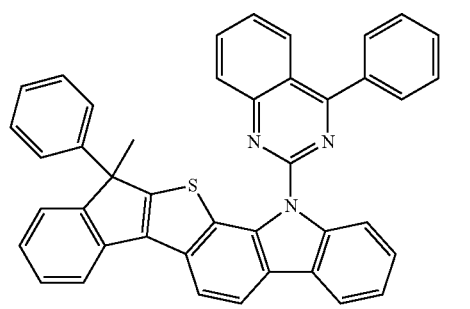
206
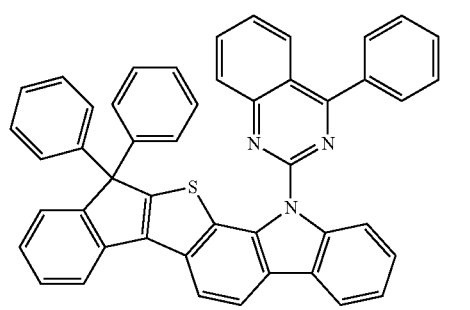
-continued
207
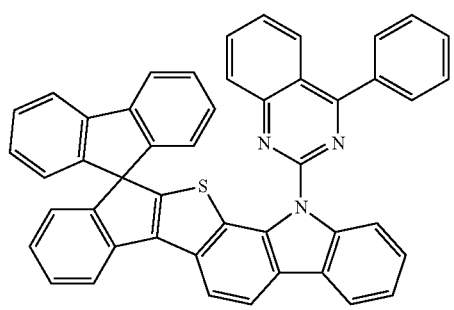
208
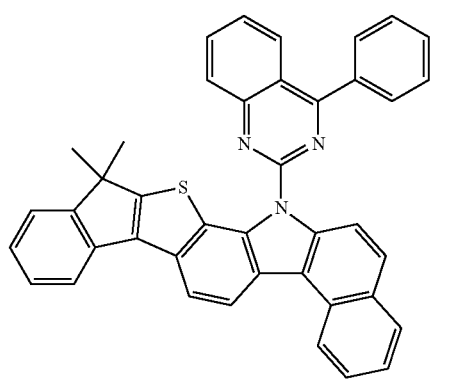
209
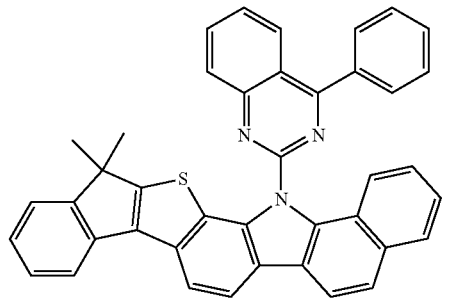
210
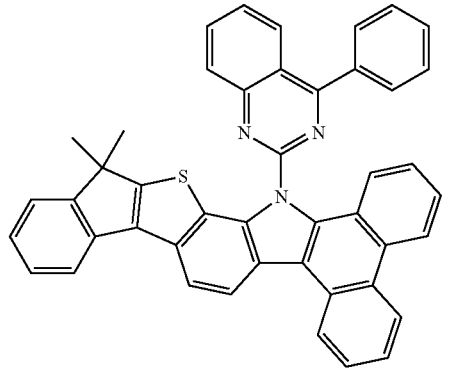

211
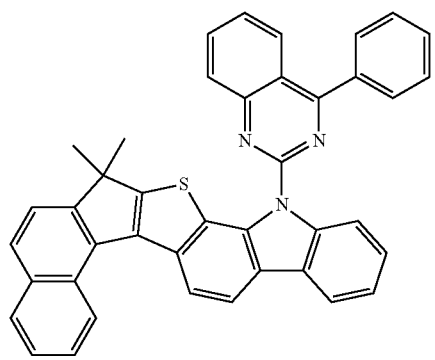
212
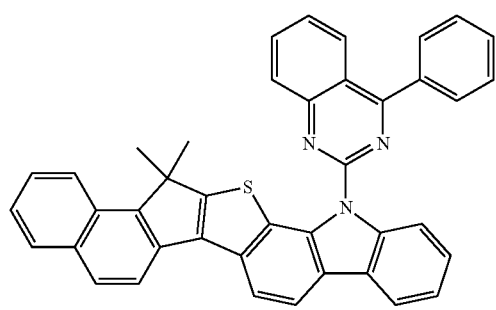
213
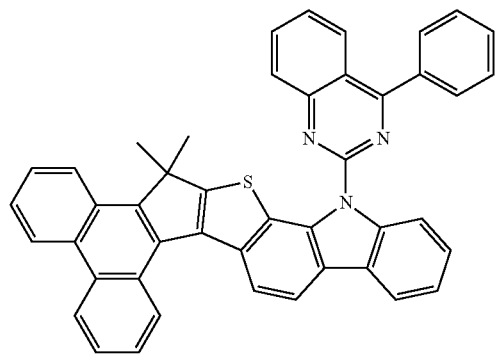
214
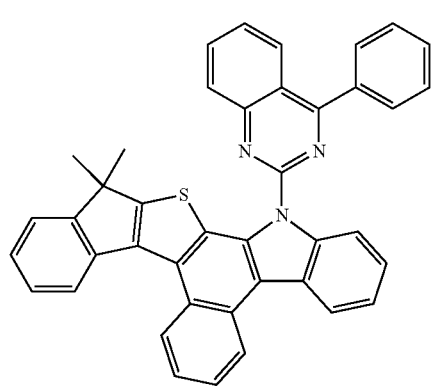
215
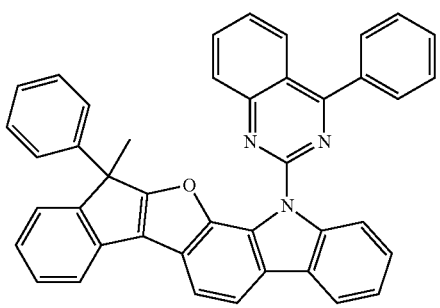
216
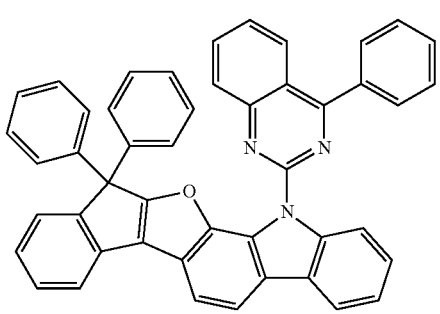
217
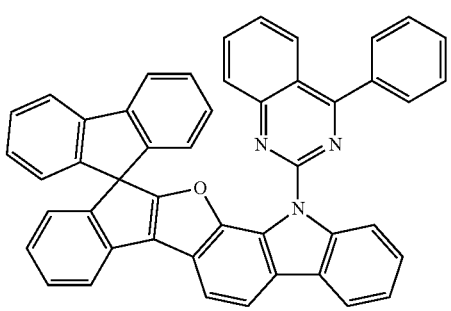
218
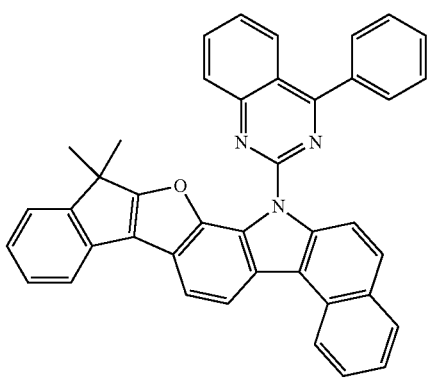
219
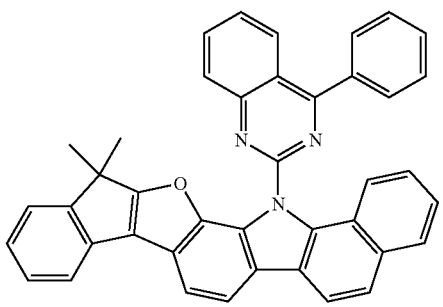

220
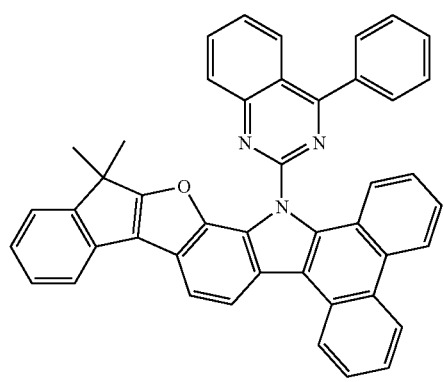
221
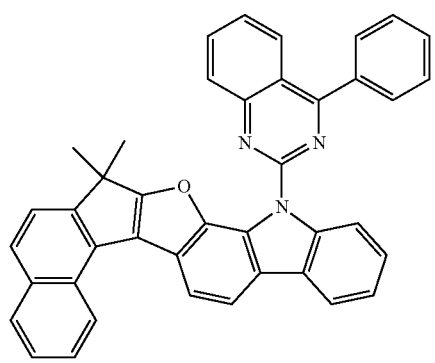
222
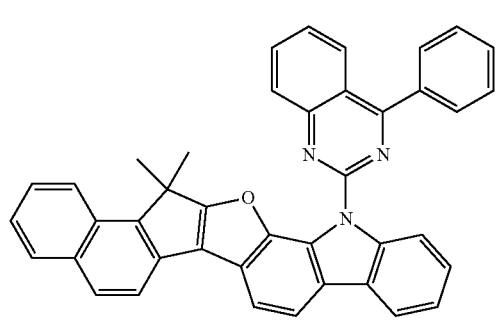
223
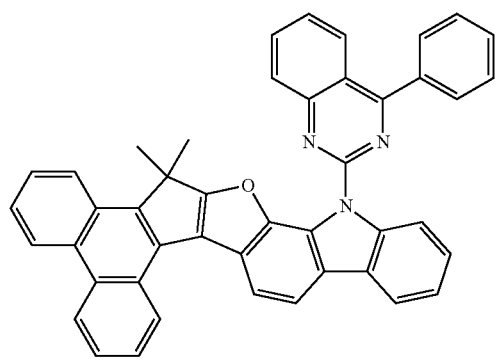
224
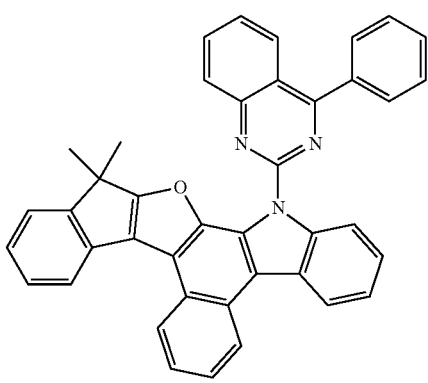
225
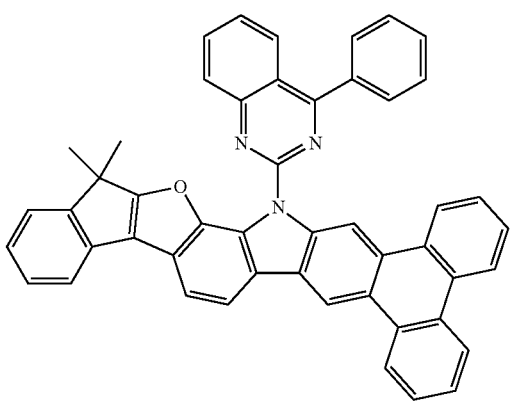
226
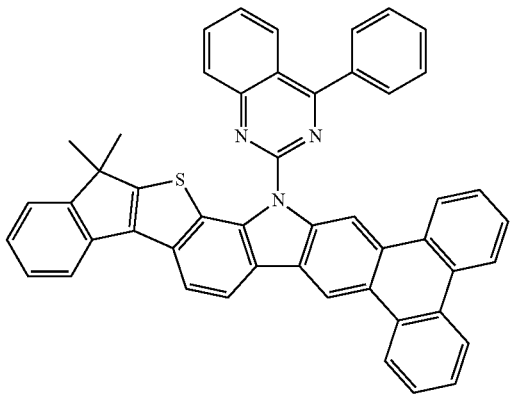
227
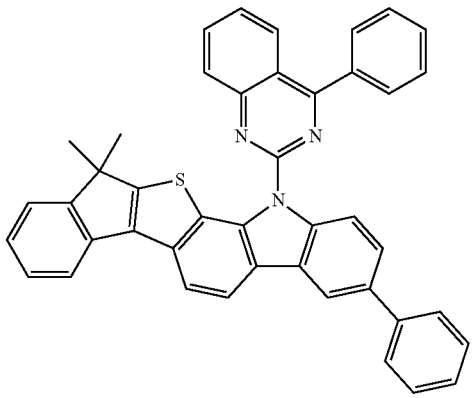

| 228 | 232 |
|---|---|
| 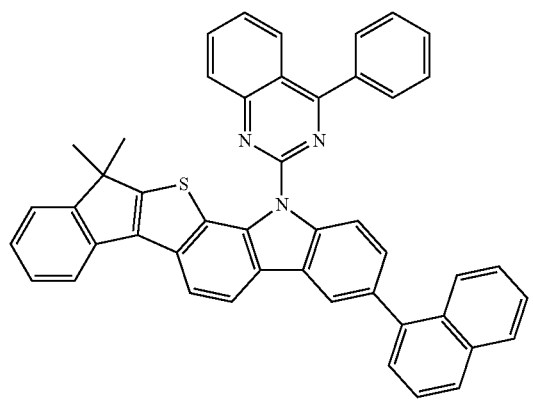 | 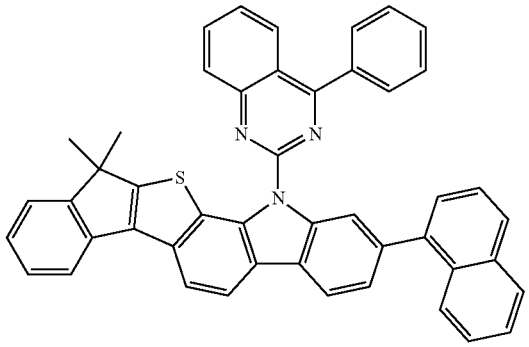 |
| 229 | 233 |
|---|---|
| 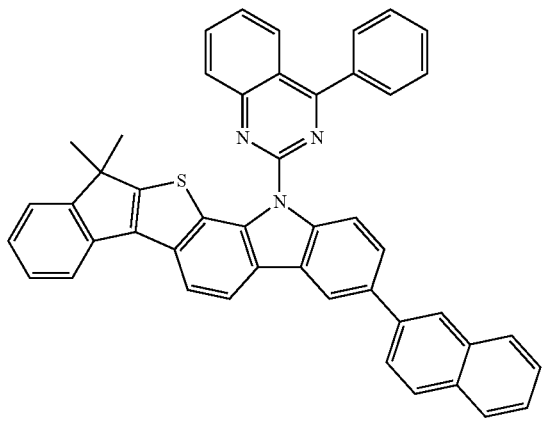 | 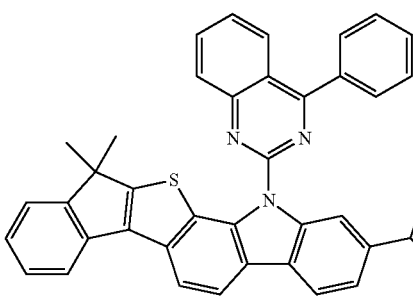 |
| 230 | 234 |
|---|---|
| 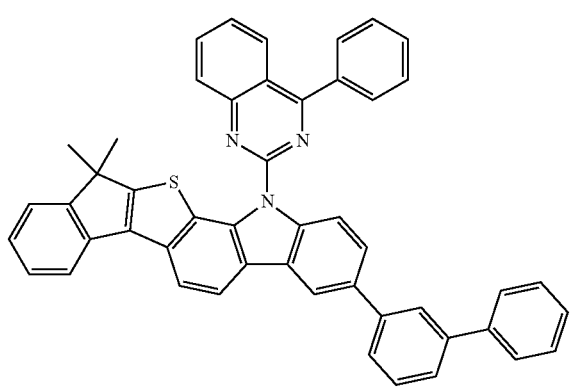 | 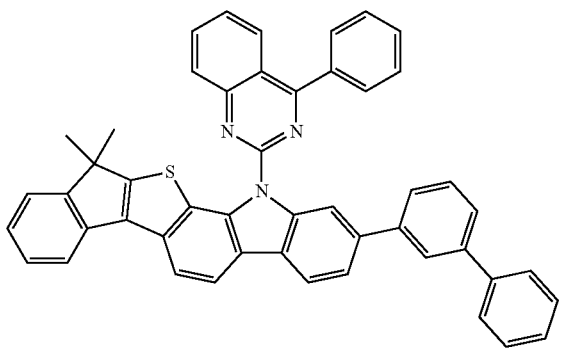 |
| 231 | 235 |
|---|---|
| 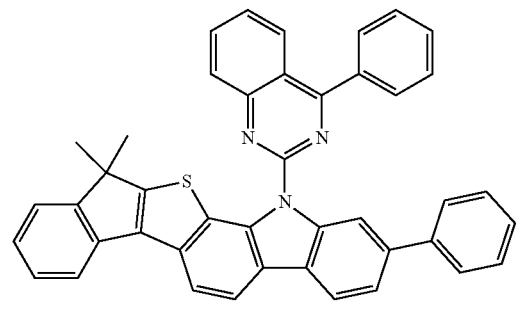 | 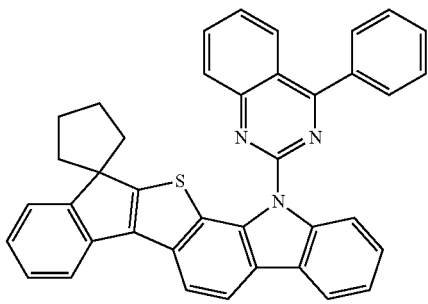 |

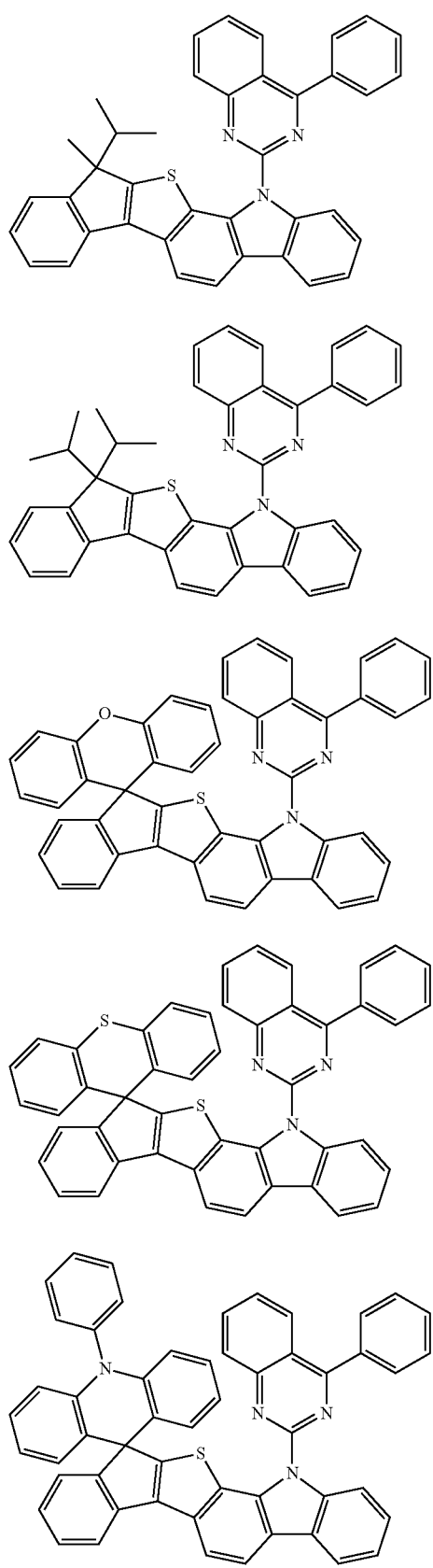
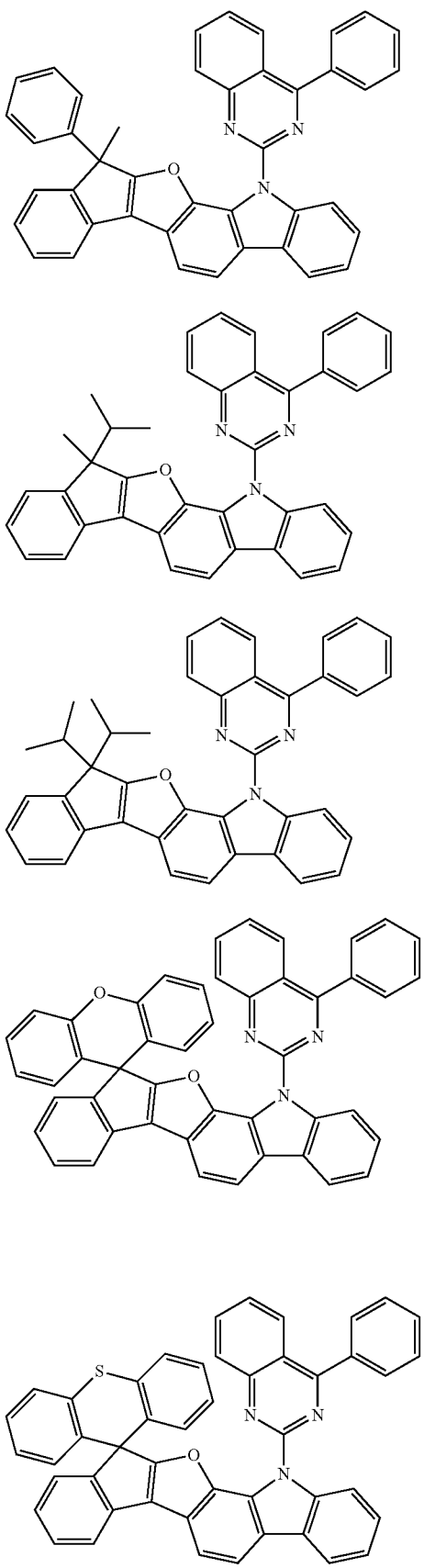

99
-continued
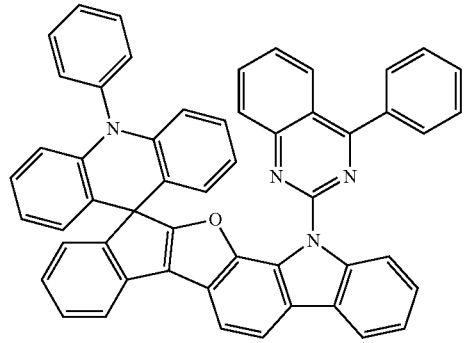
246
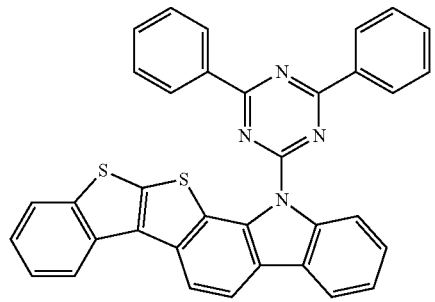
247
248
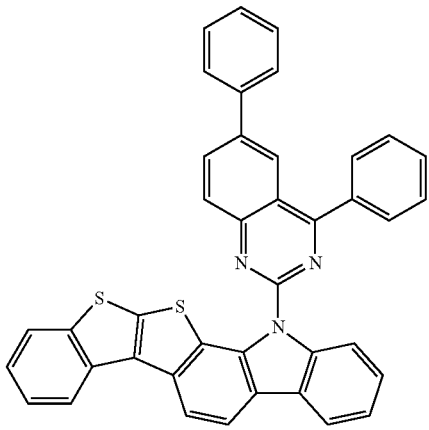
249
100
-continued
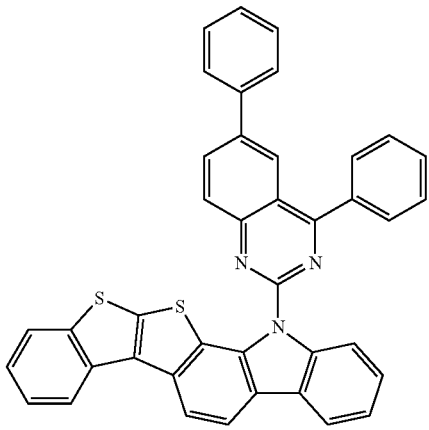
250
251
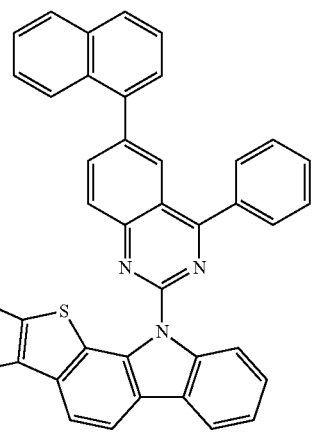
252
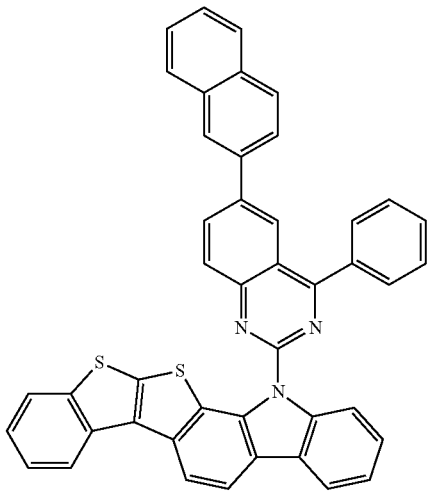

101
-continued
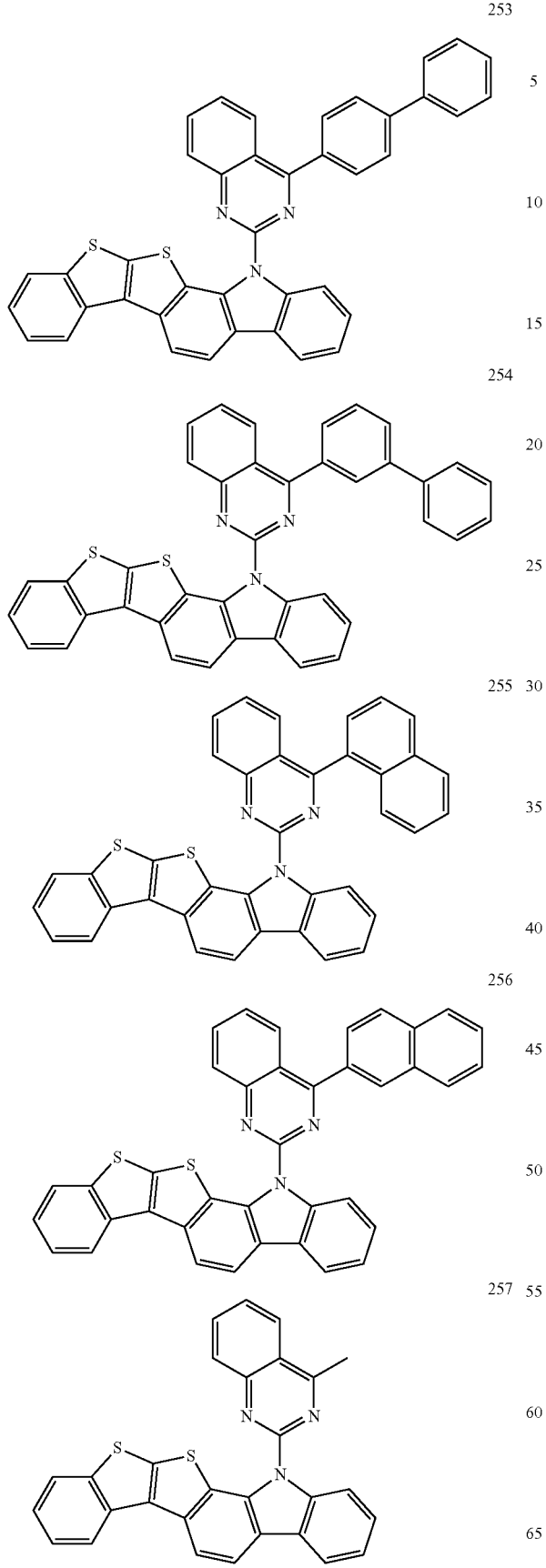
102
-continued
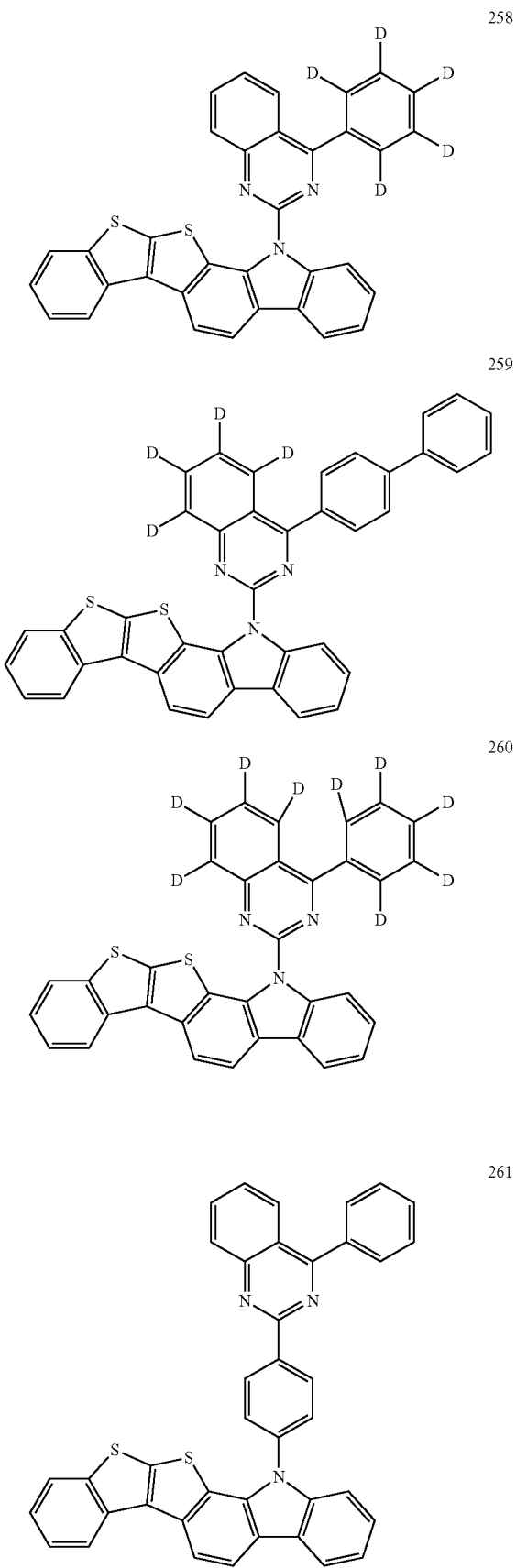

262
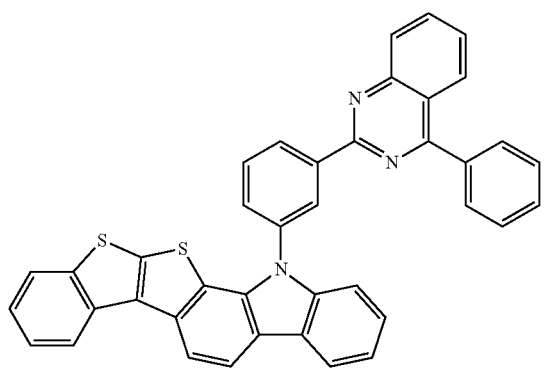
263
264
265
266
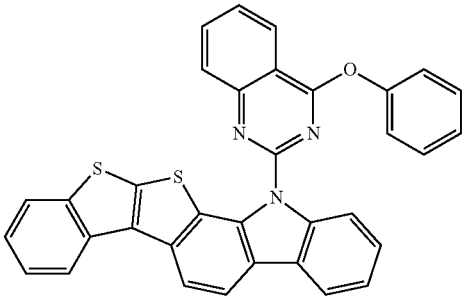
267
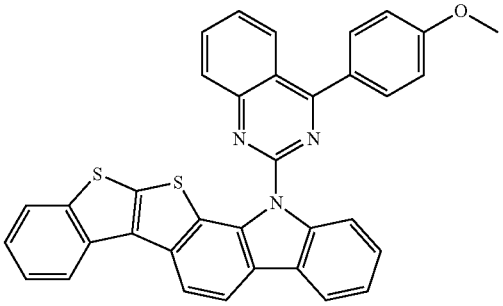
268
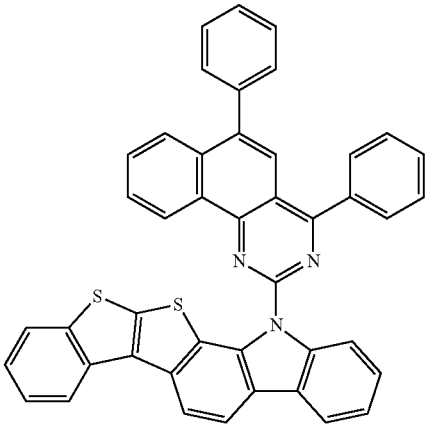
269
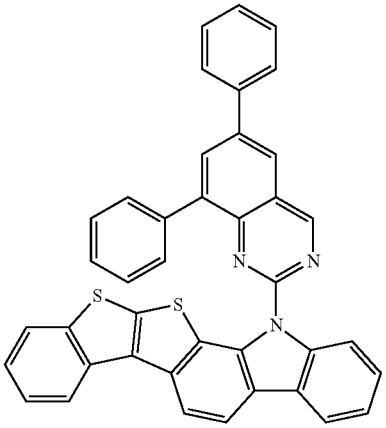

| 270 | 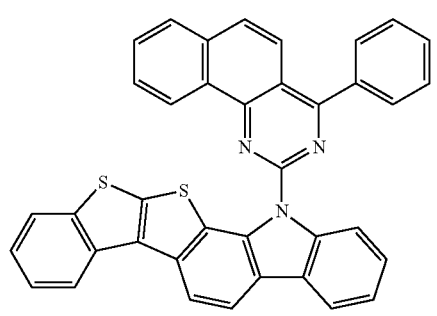 | 274 | 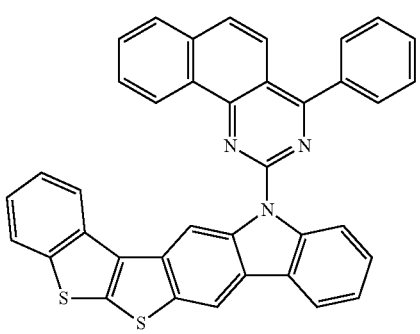 |
| 271 | 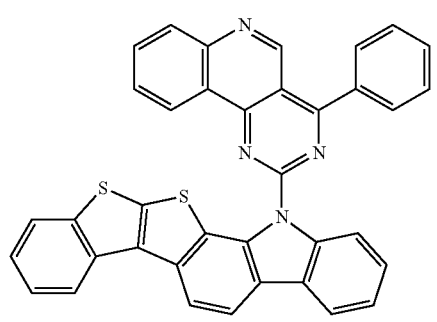 | 275 | 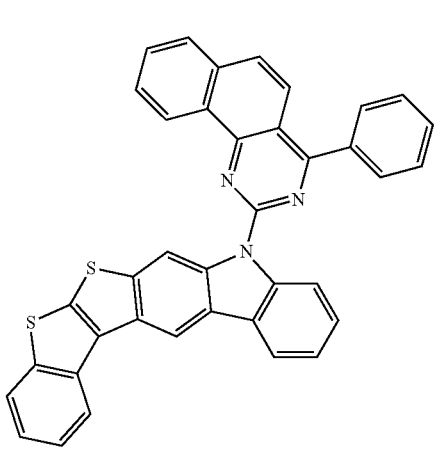 |
| 272 | 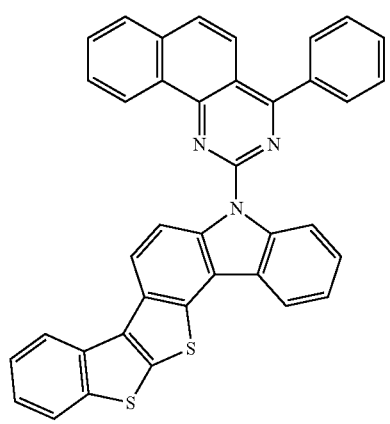 | 276 | 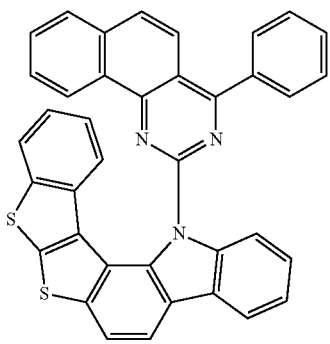 |
| 273 | 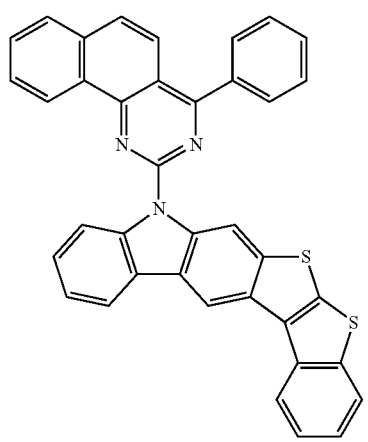 | 277 | 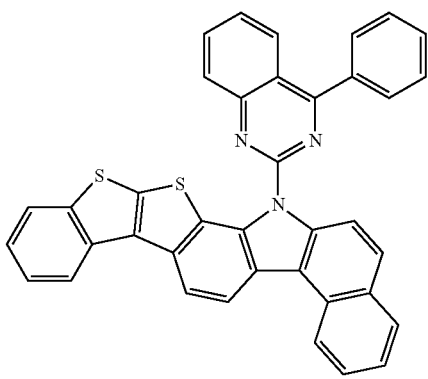 |

278 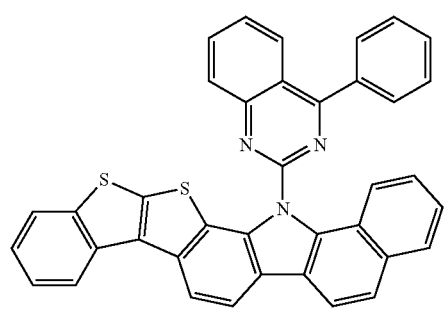
279 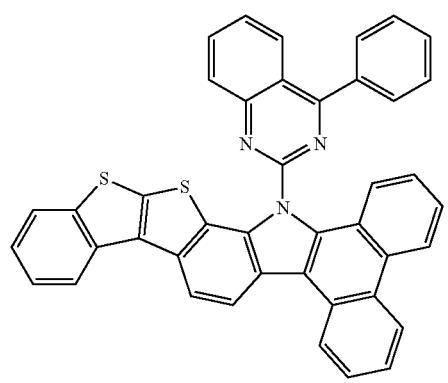
280 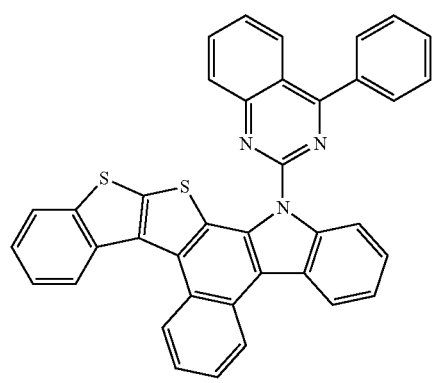
281 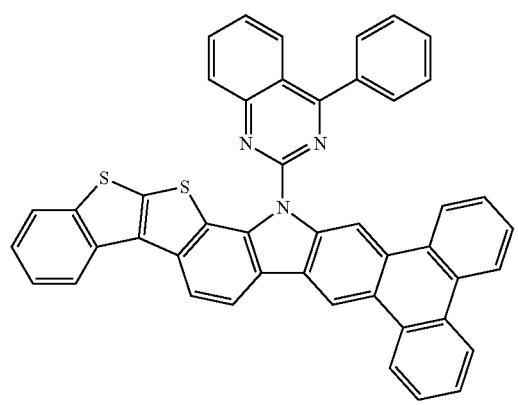
282 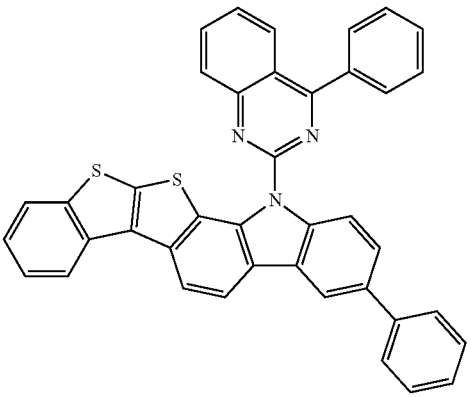
283 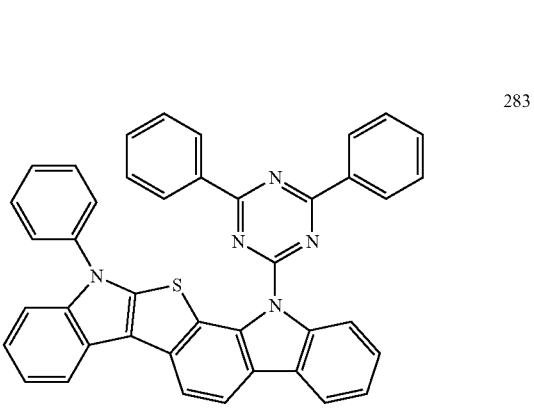
284 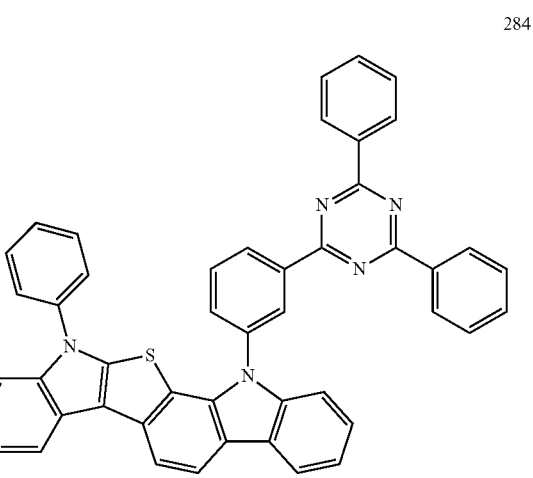
285 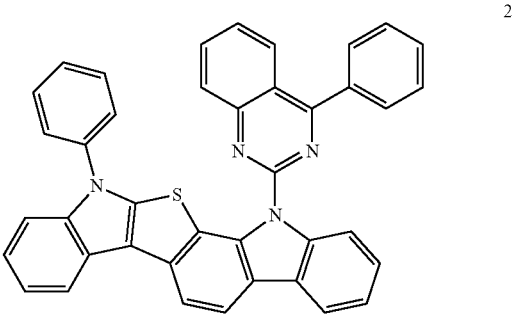

286
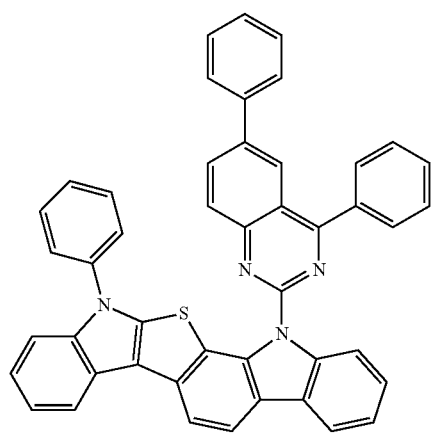
287
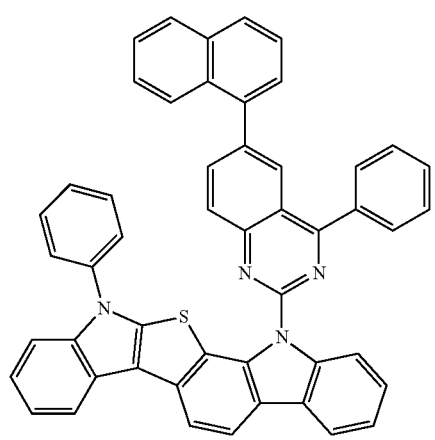
288
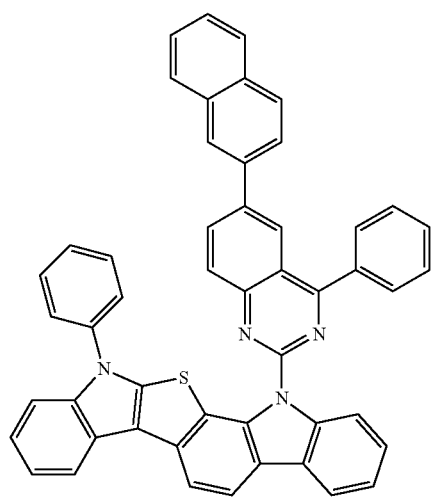
289
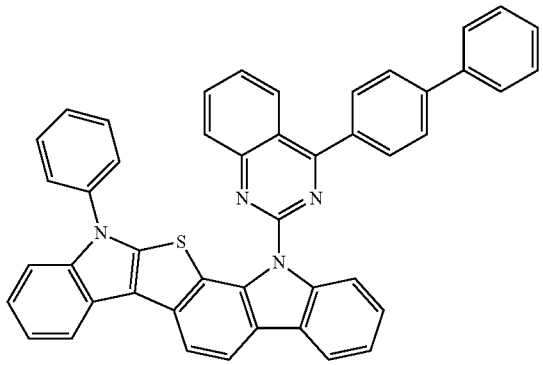
290
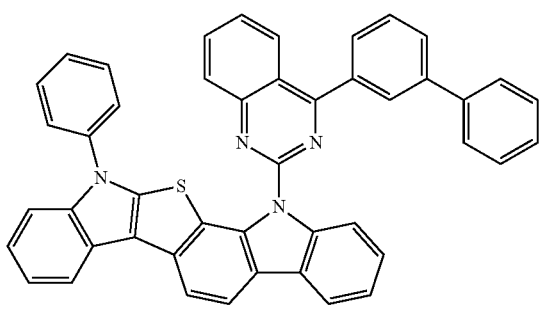
291
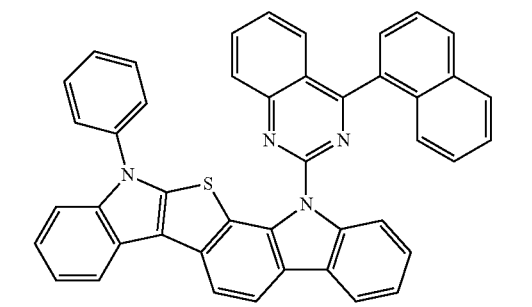
292
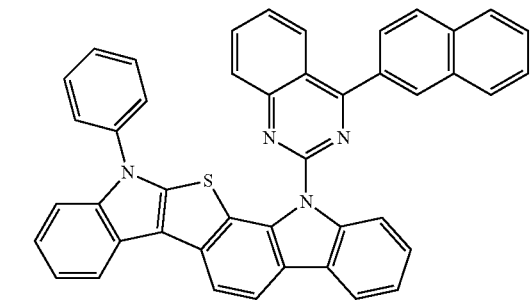
293
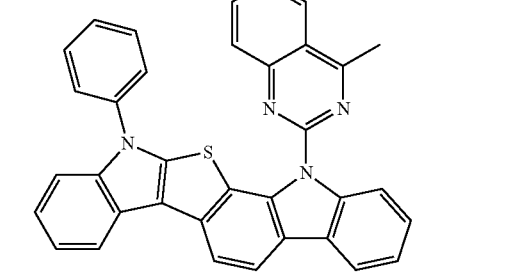

294
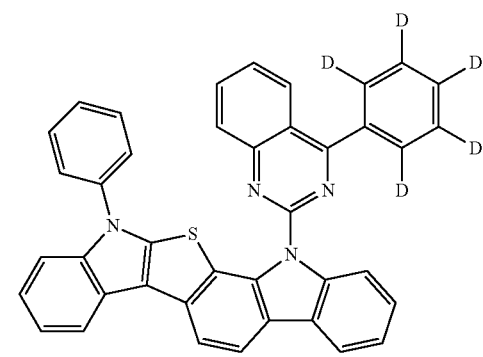
295
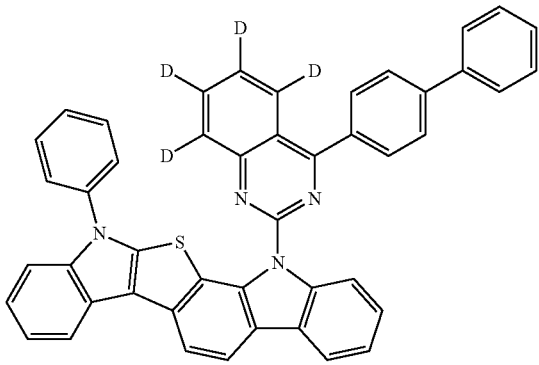
296
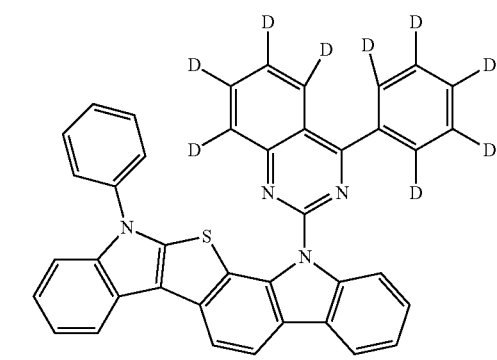
297
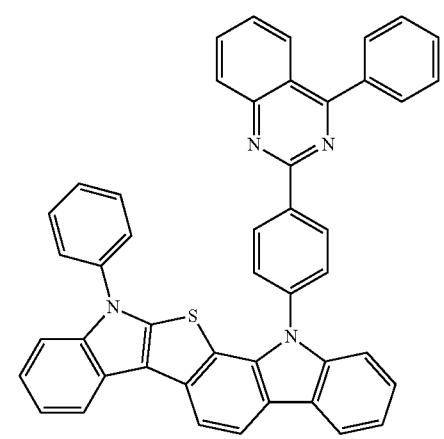
298
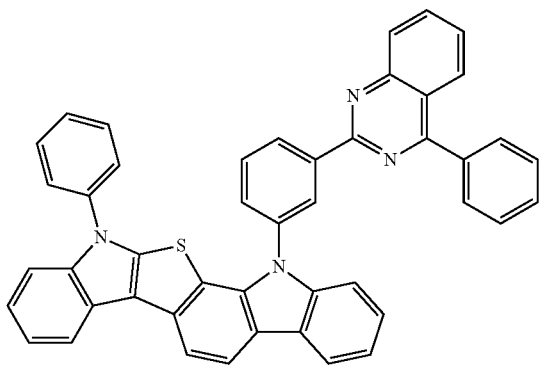
299
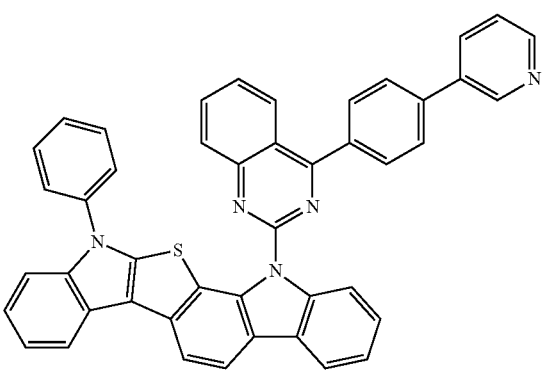
300
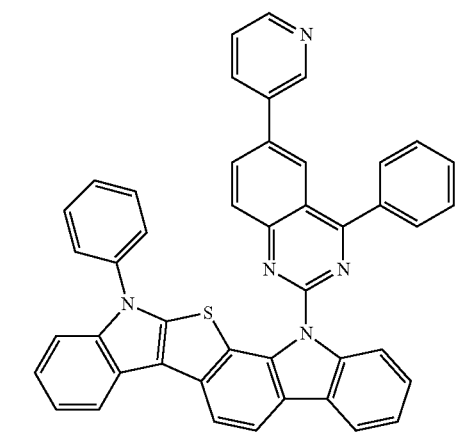
301
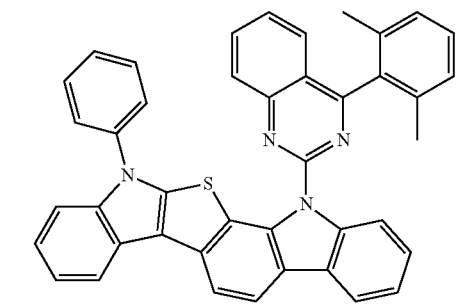

302
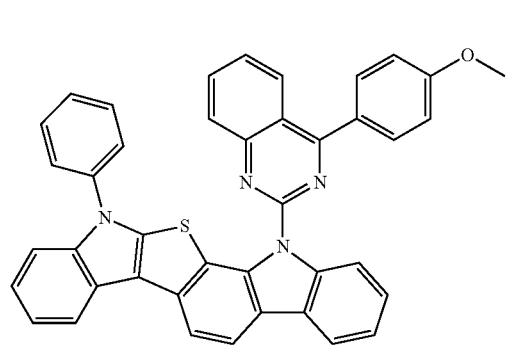
303
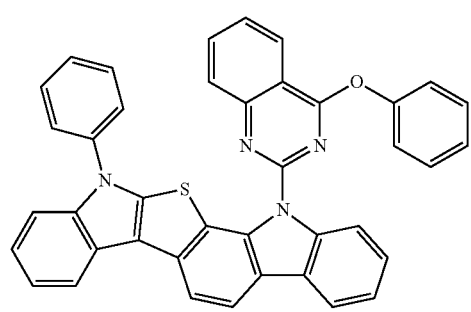
304
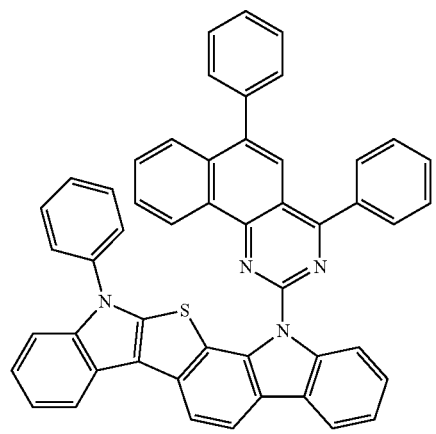
305
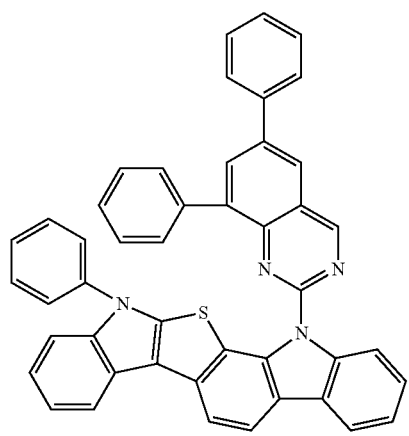
306
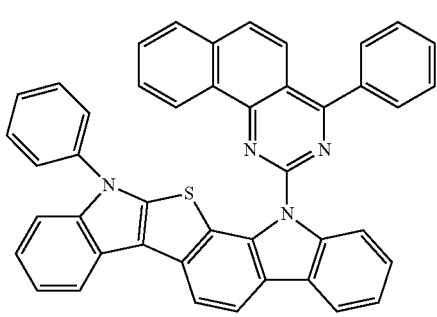
307
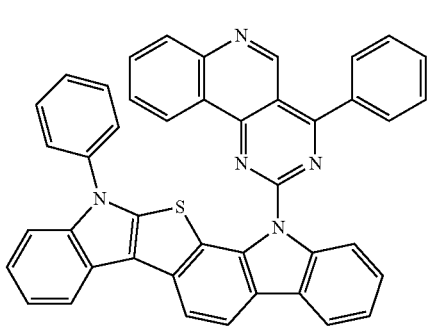
308
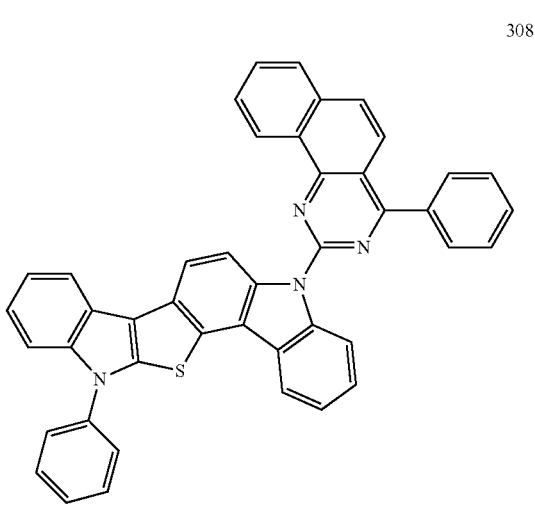
309
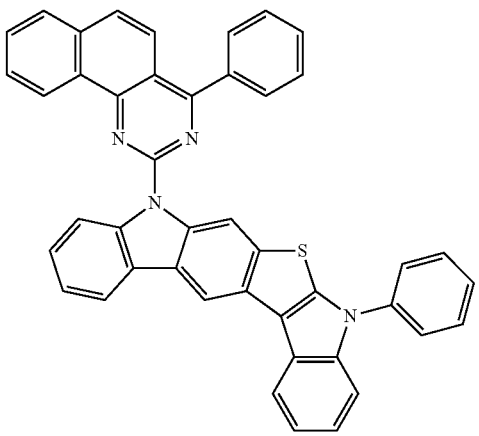

310
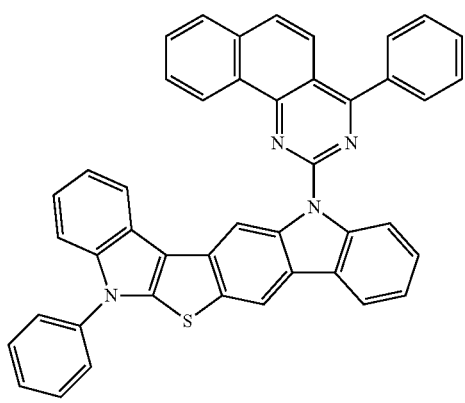
311
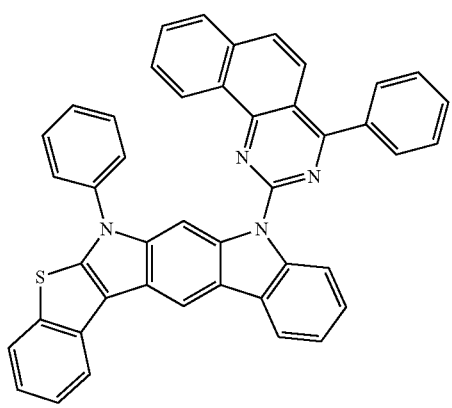
312
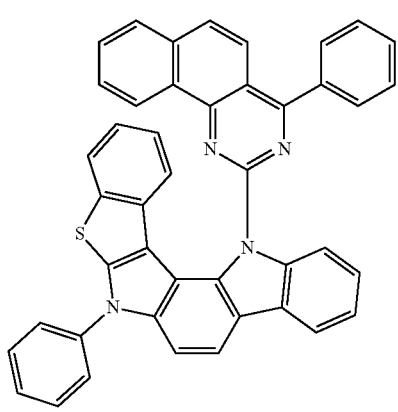
313
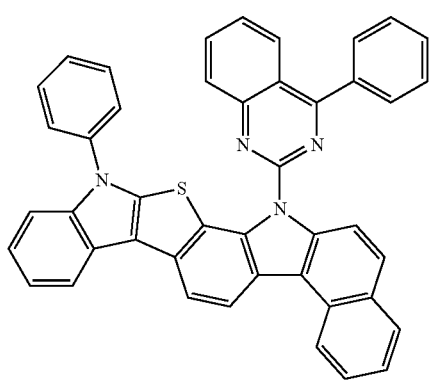
314
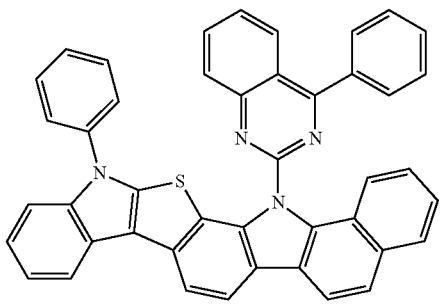
315
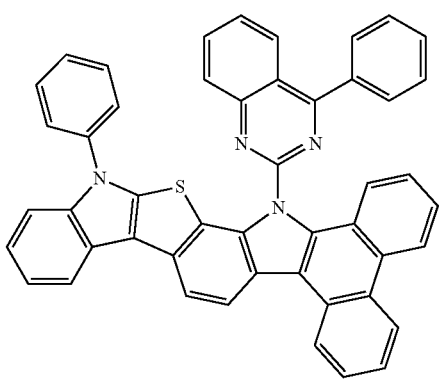
316
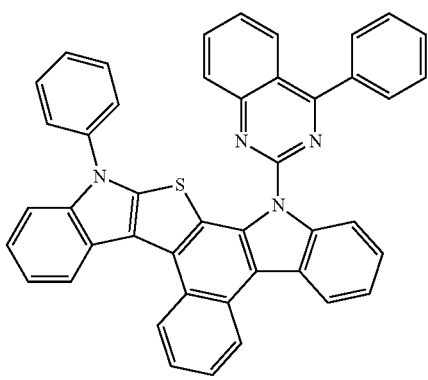
317
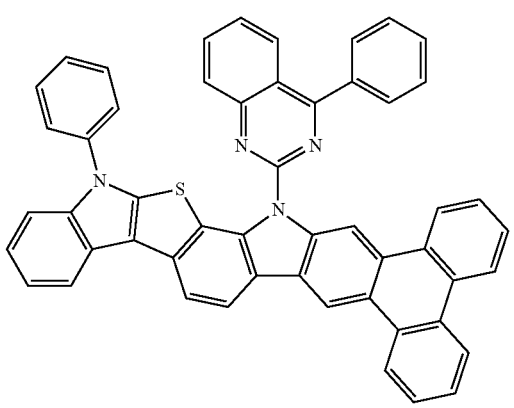

US 10,749,118 B2
117
-continued
318
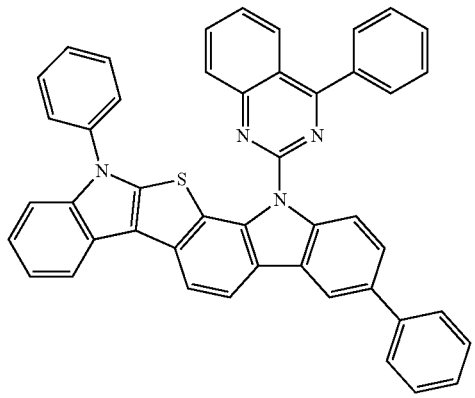
319
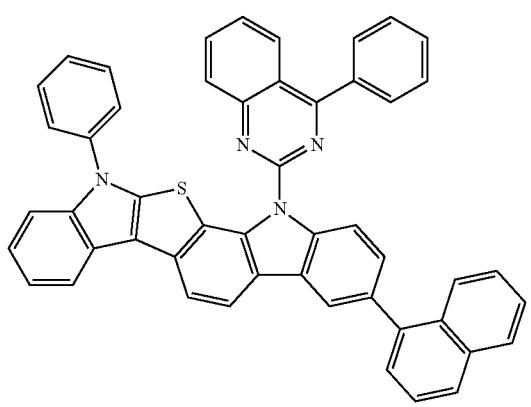
320
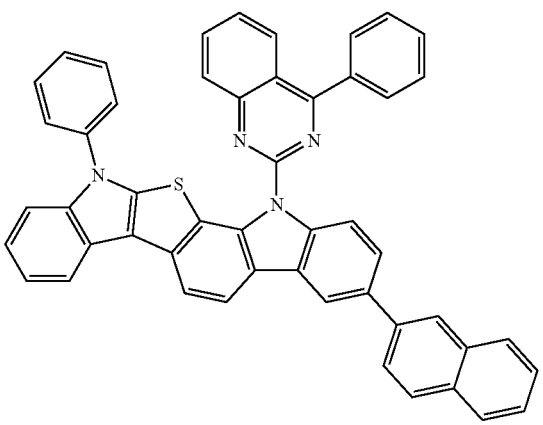
321
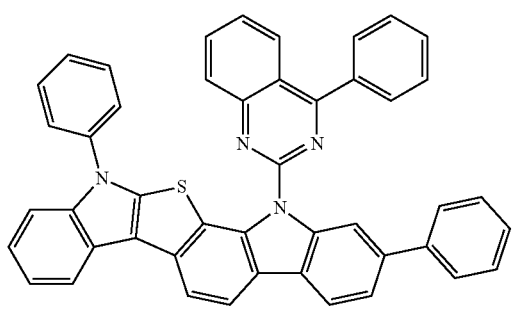
118
-continued
322
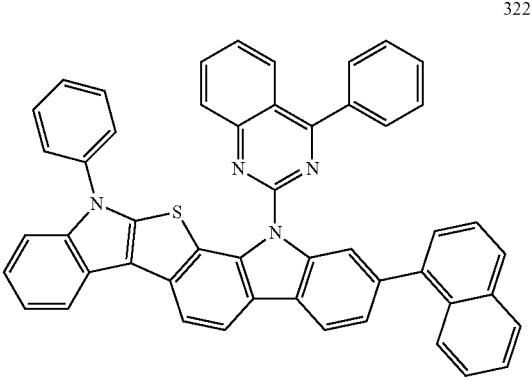
323
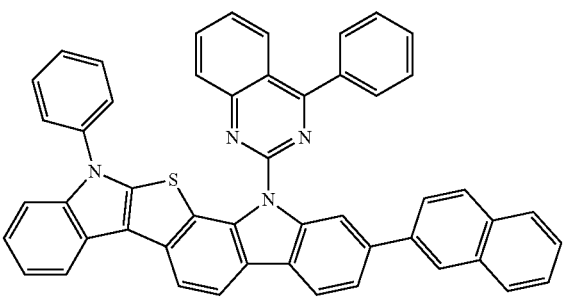
324
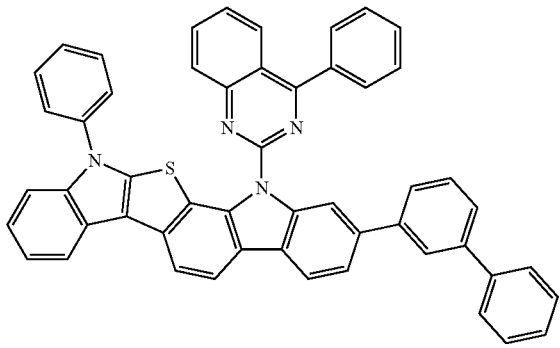
325
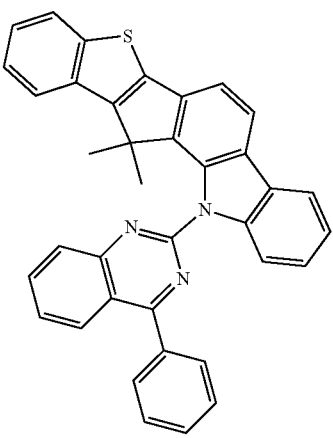

326
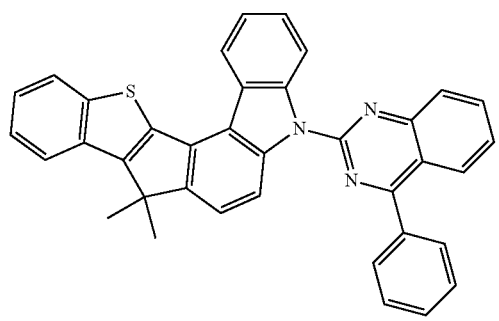
327
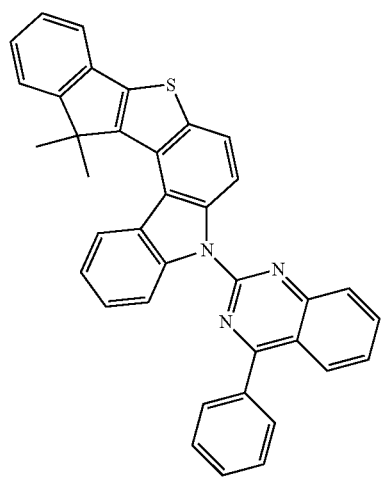
328
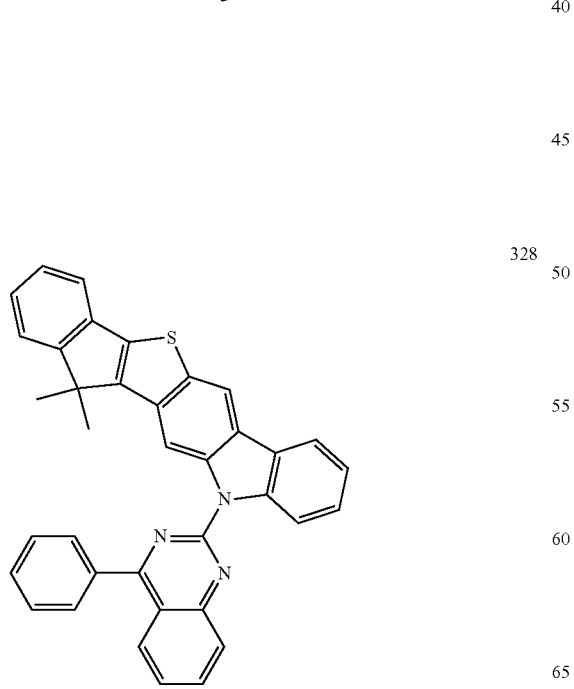
329
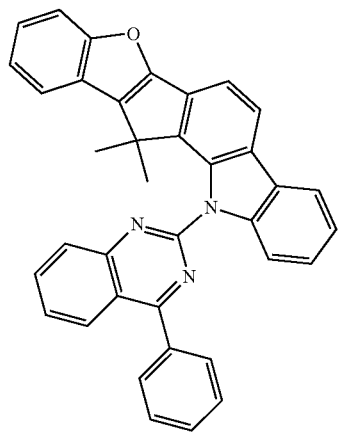
330
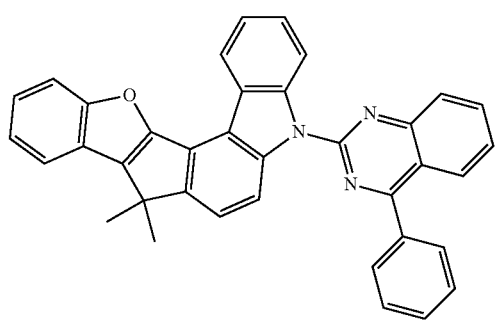
331
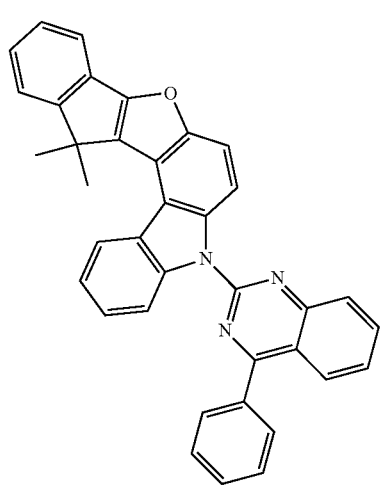

332
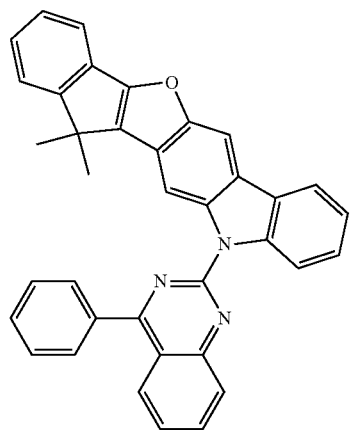
333
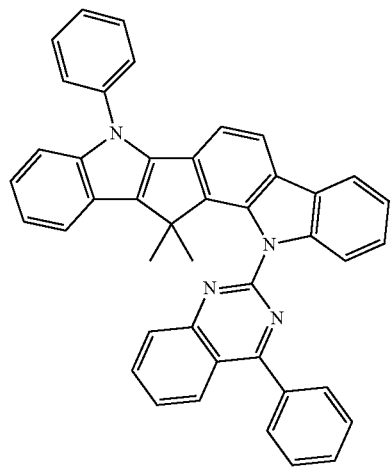
334
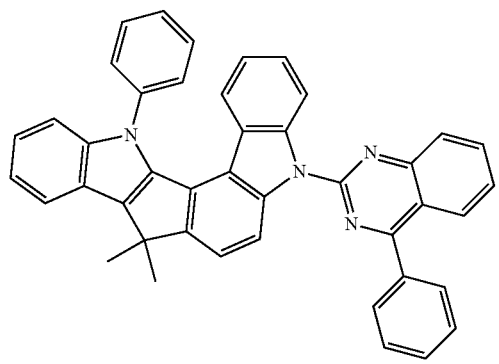
335
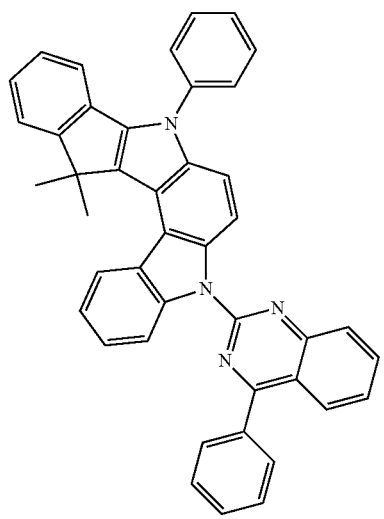
336
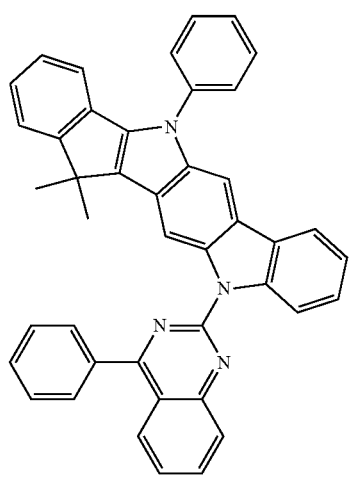
337
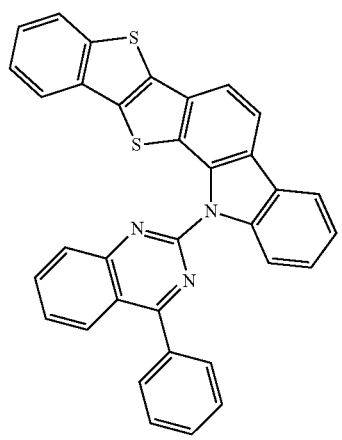

338
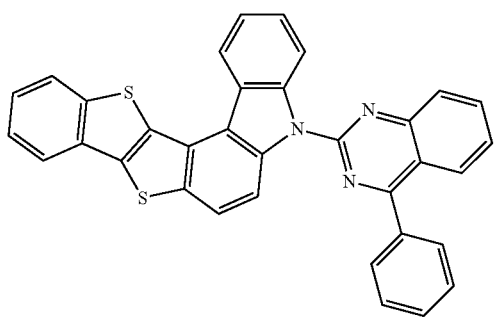
339
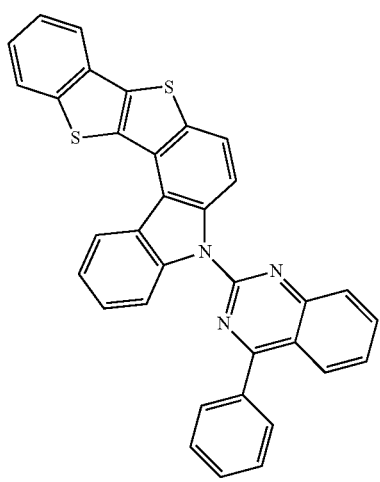
340
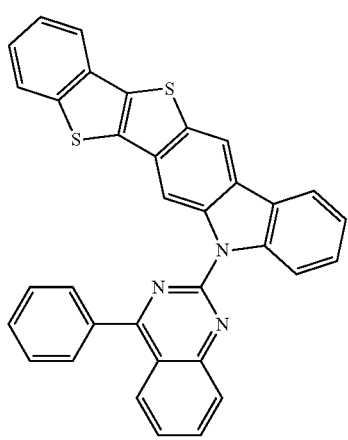
341
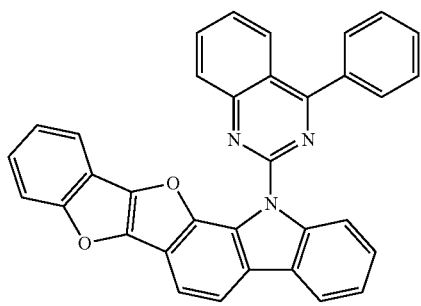
342
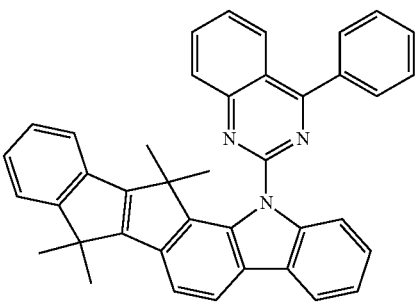
343
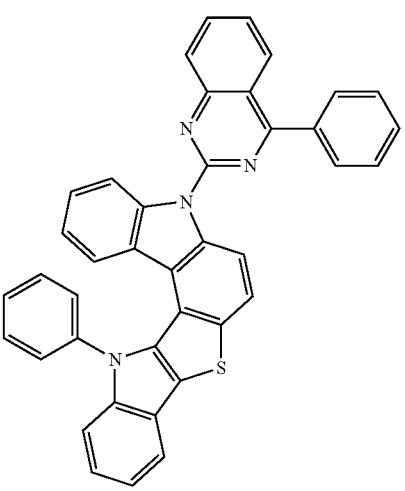
344
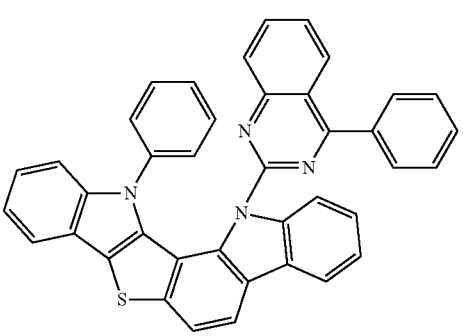
345
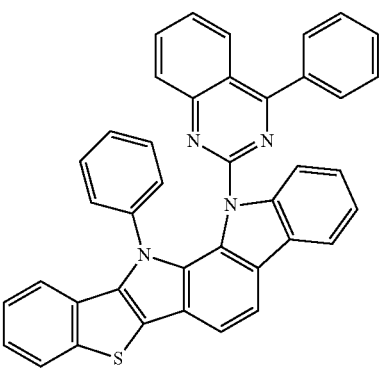

346
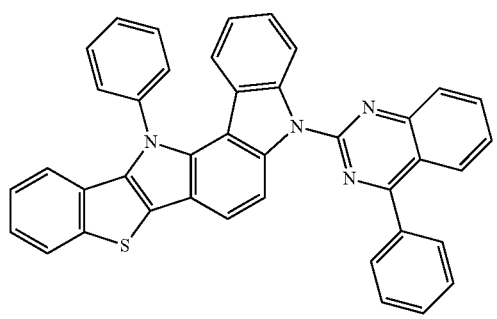
347
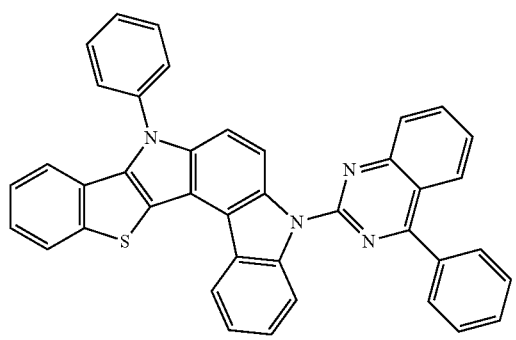
348
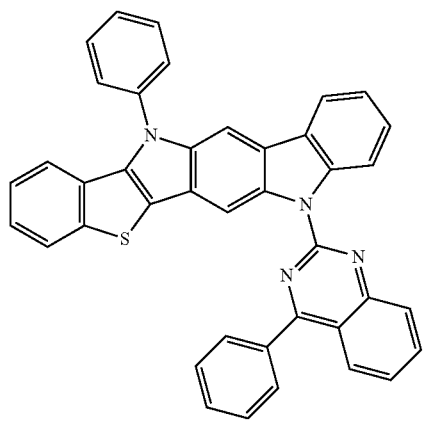
349
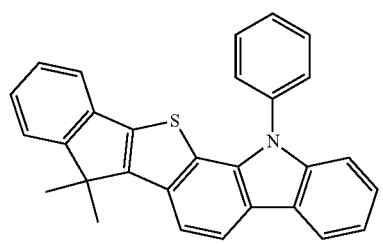
350
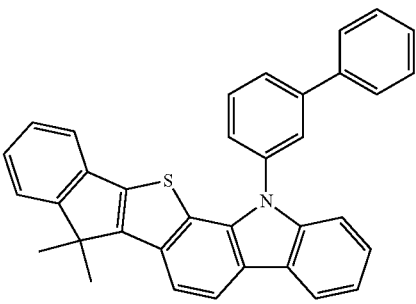
351
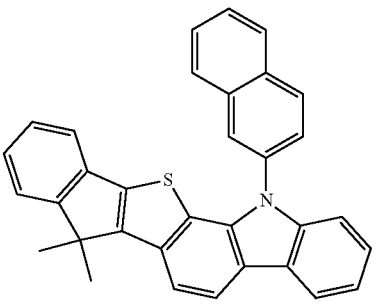
352
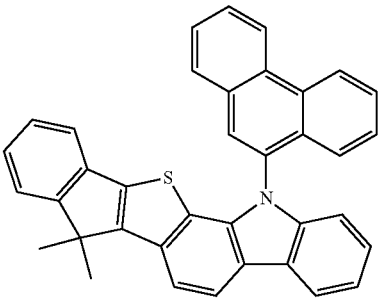
353
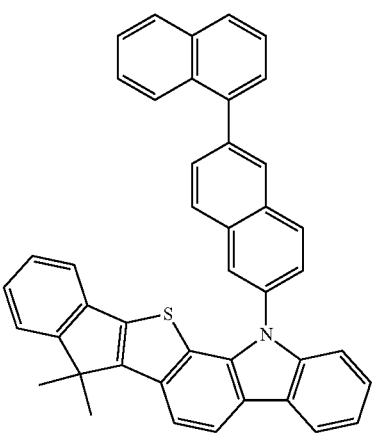

-continued
354
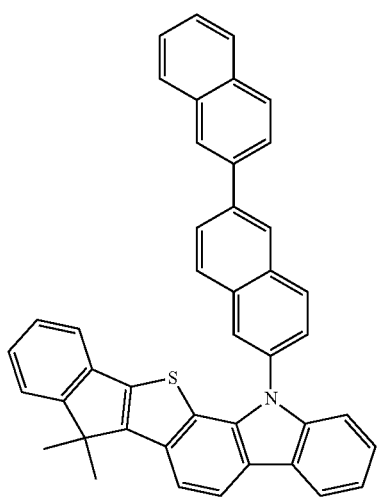
355
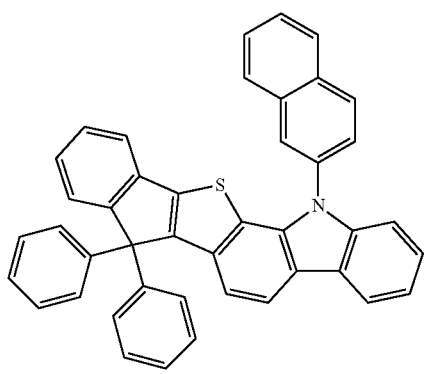
356
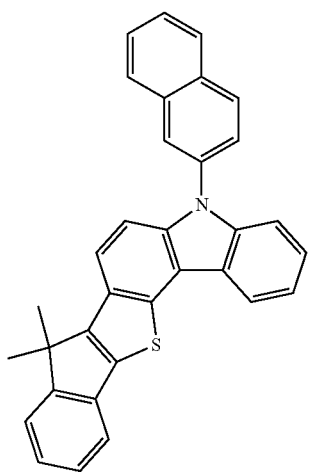
-continued
357
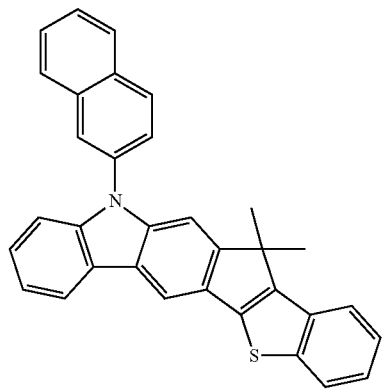
358
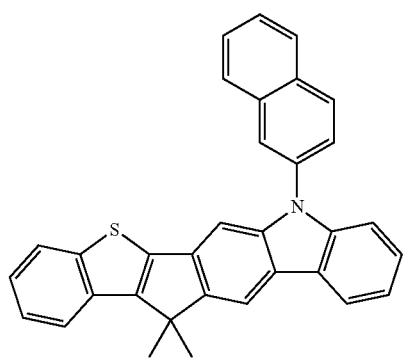
359
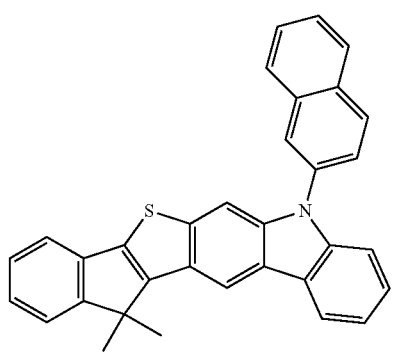
360
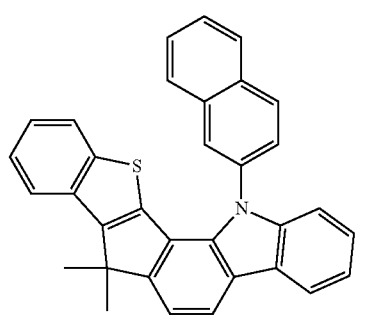

-continued
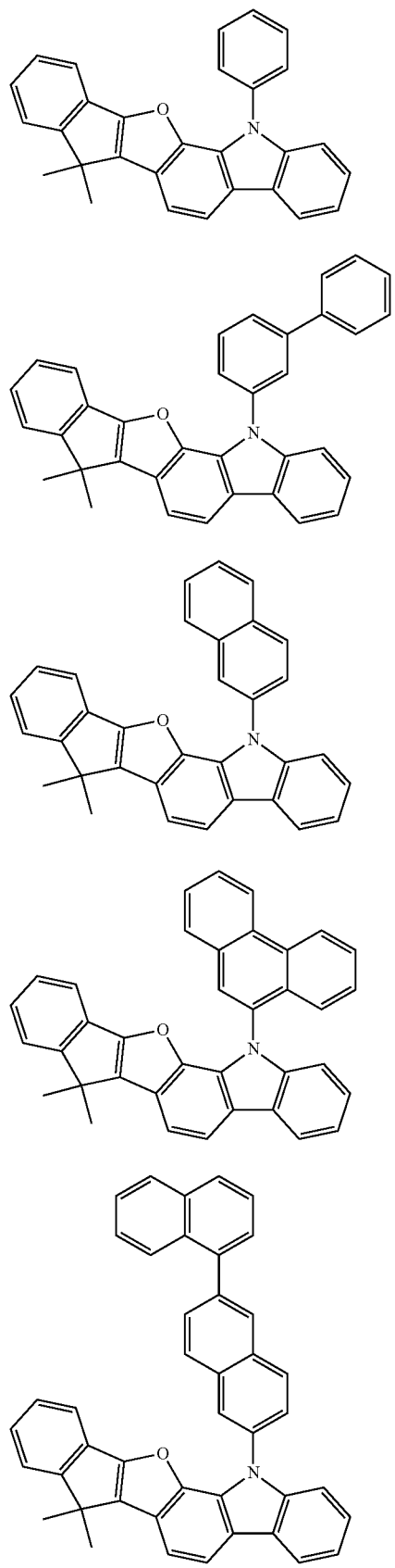
361
362
363
364
365
-continued
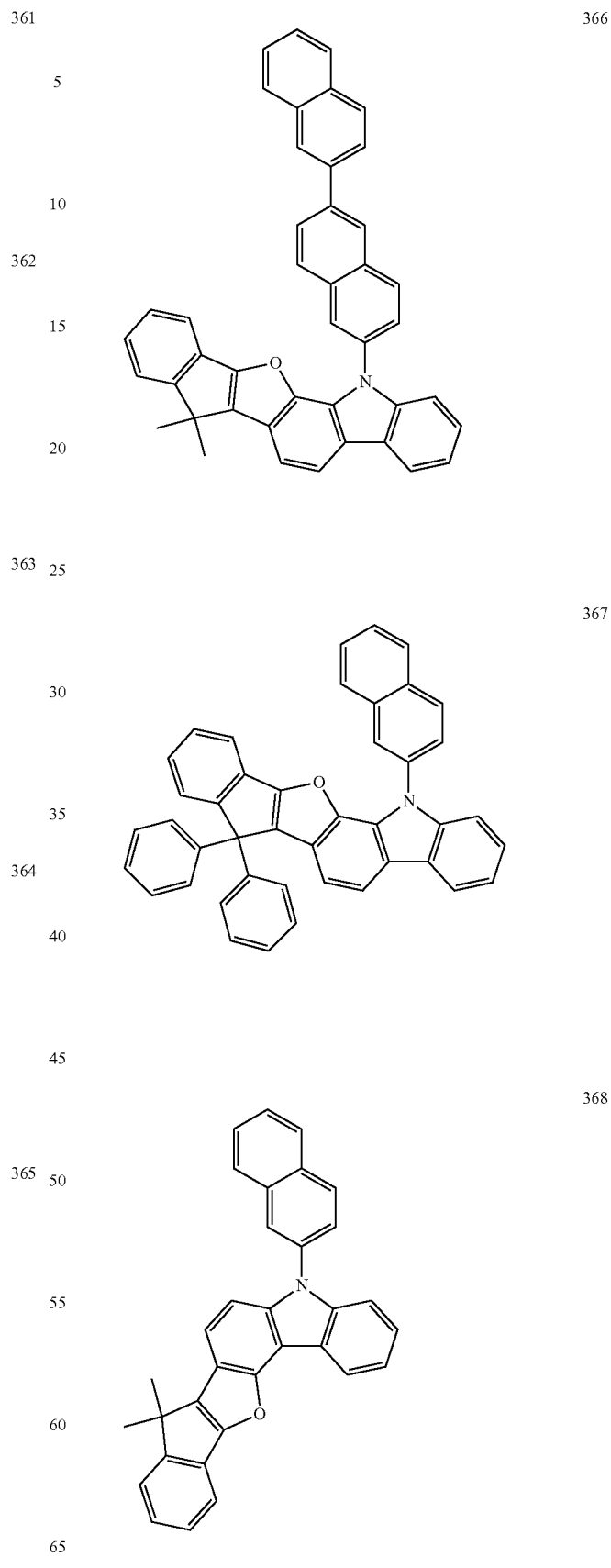
366
367
368

369
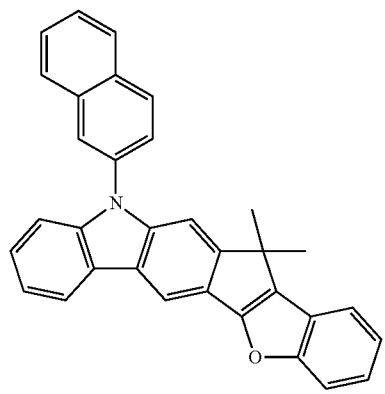
370
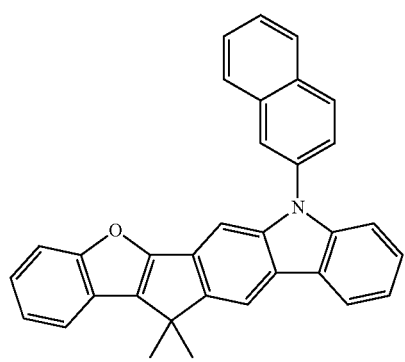
371
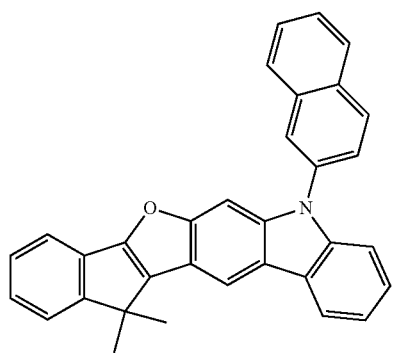
372
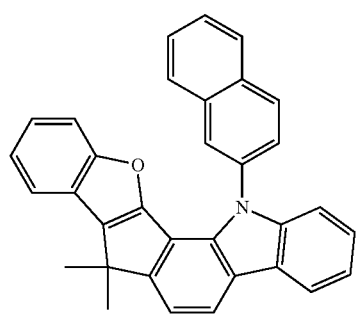
373
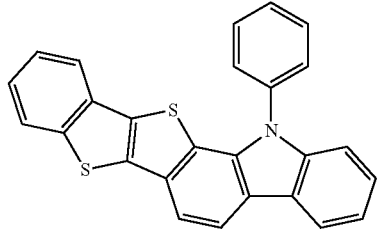
374
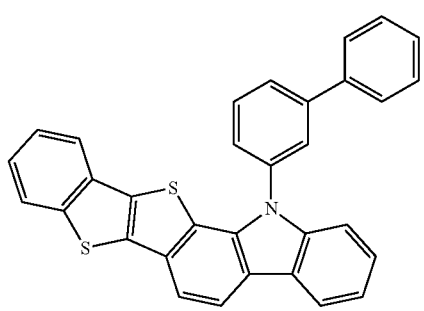
375
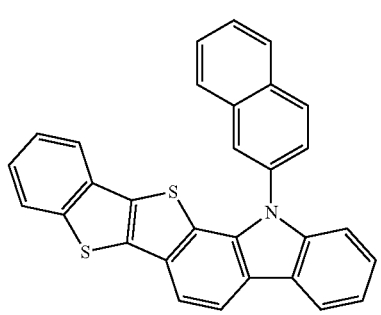
376
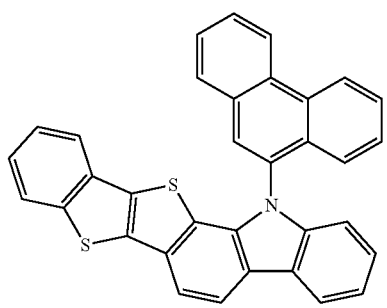
377
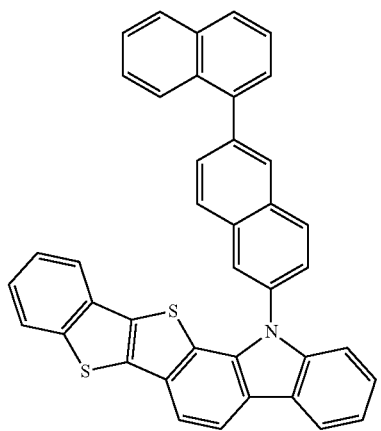

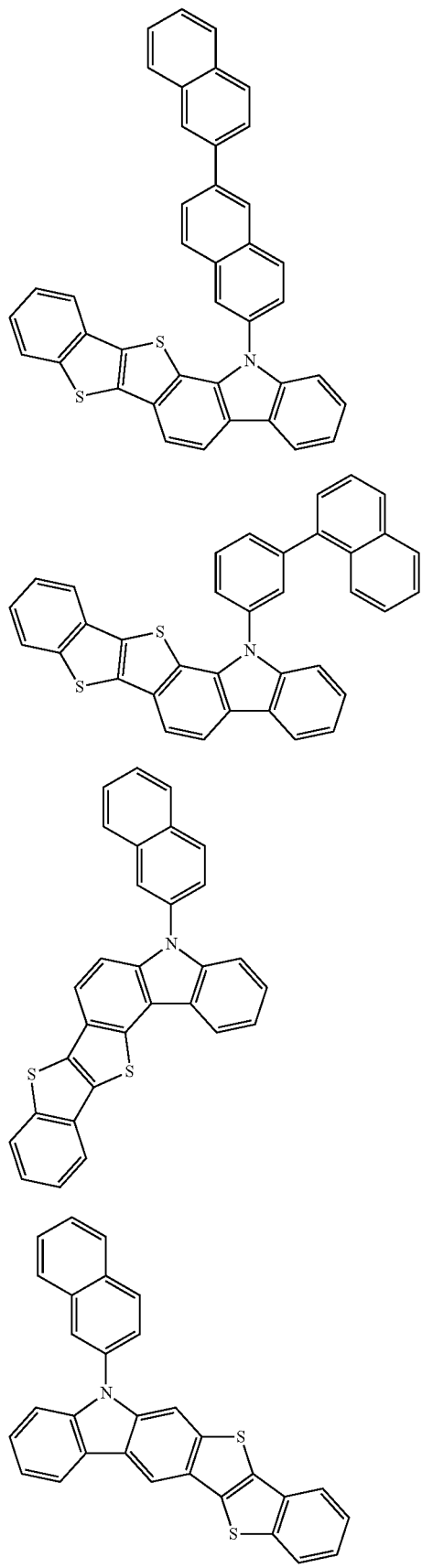
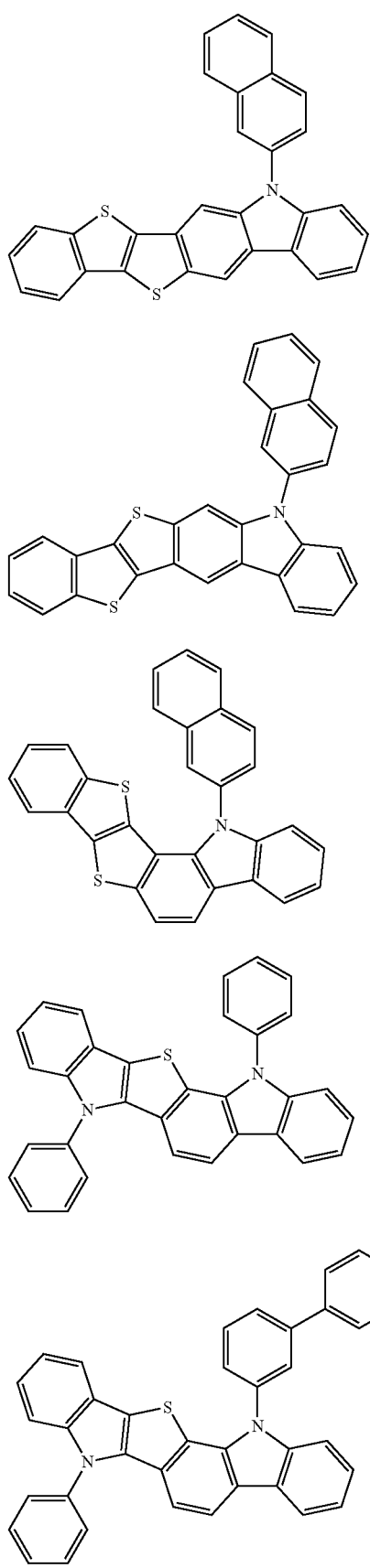

387
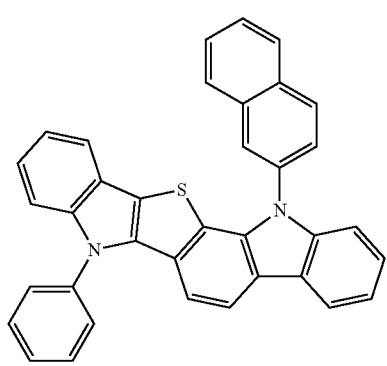
388
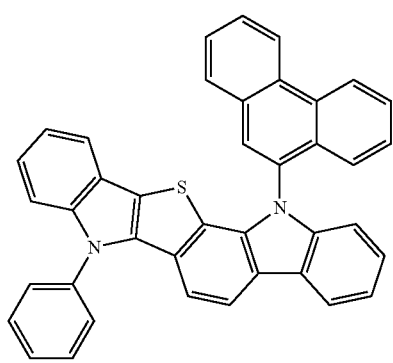
389
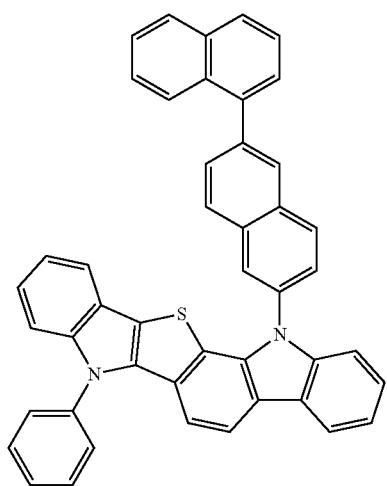
390
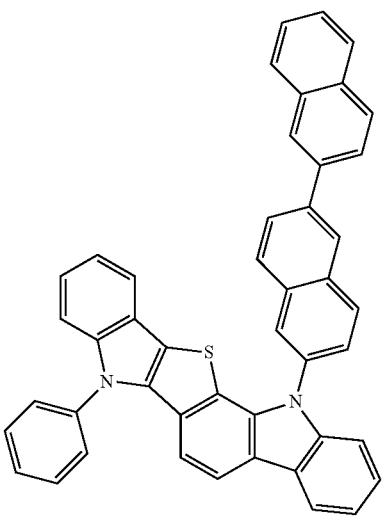
391
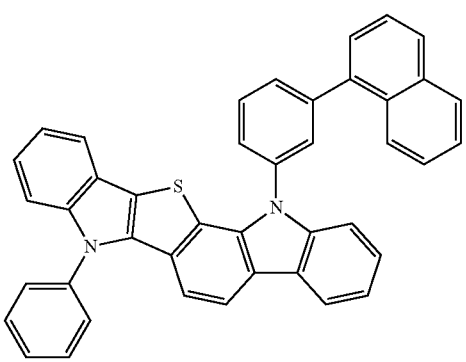
392
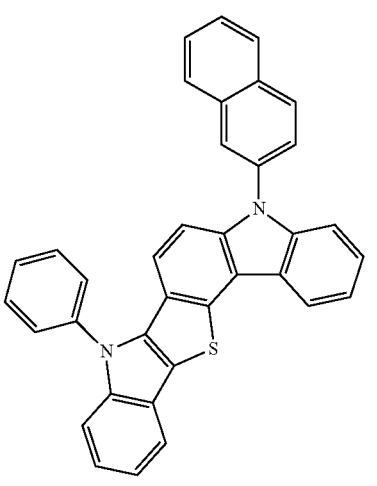

393 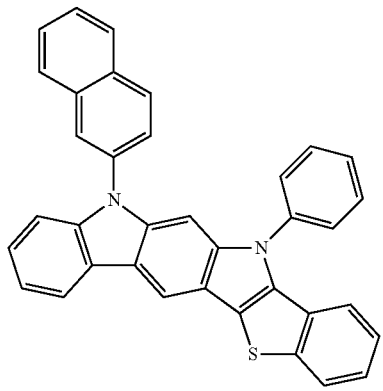
394 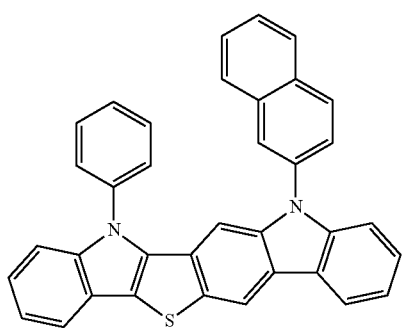
395 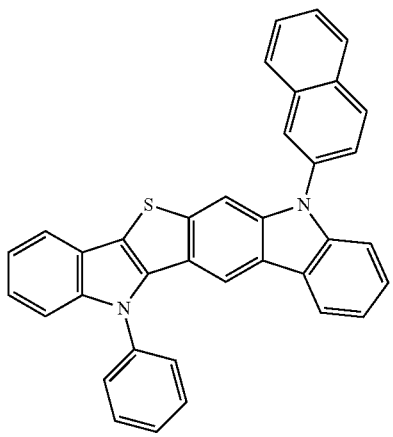
396 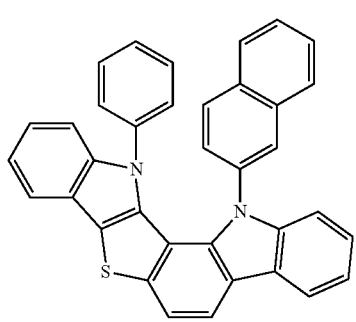
397 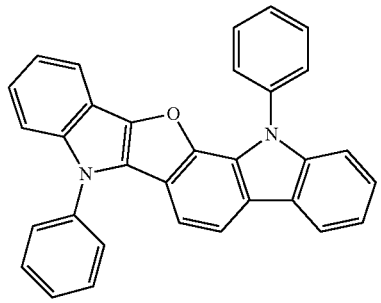
398 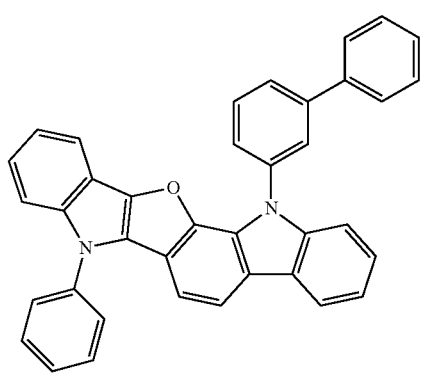
399 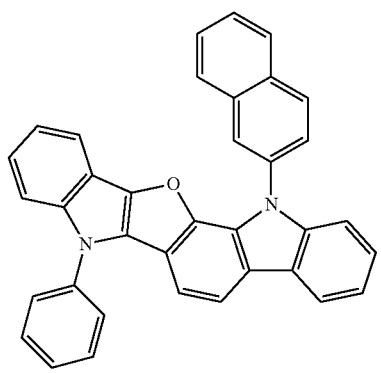
400 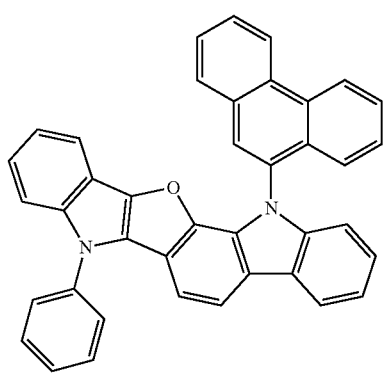

139
-continued
140
-continued
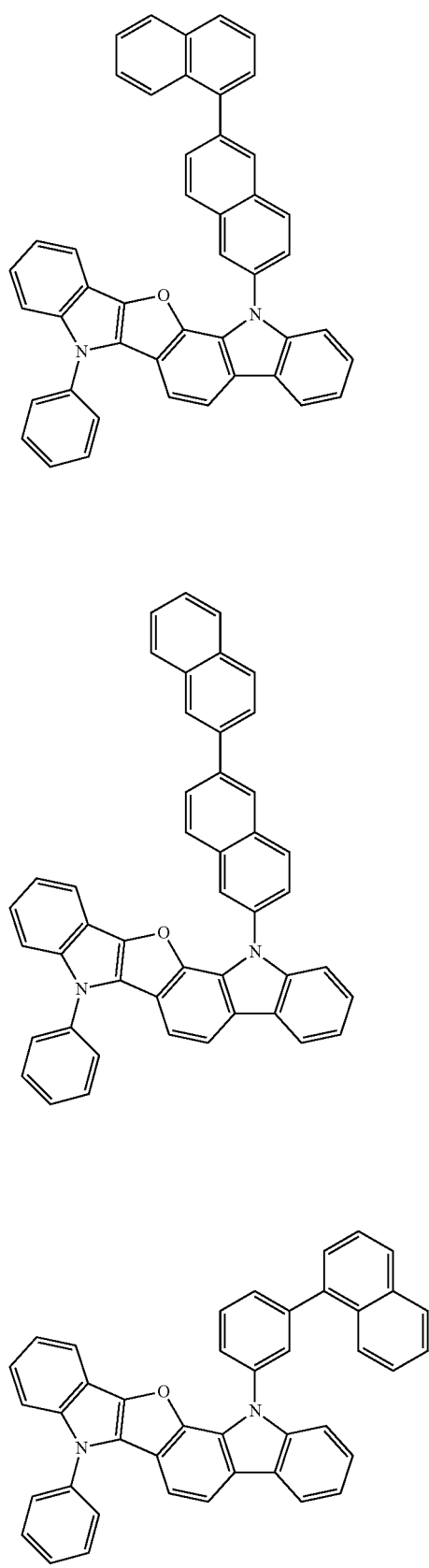
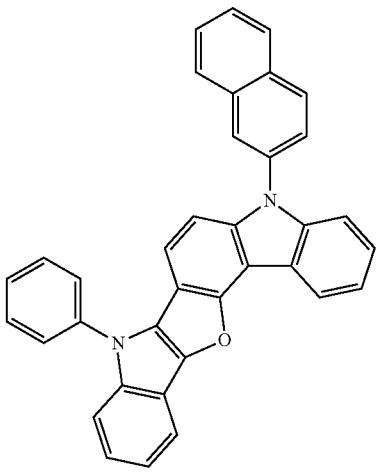
401
402
403
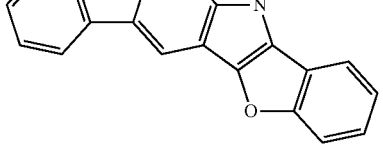
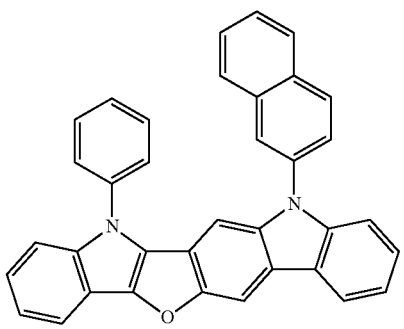
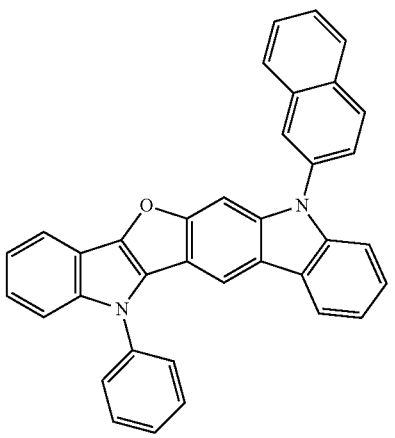
404
405
406
407

408
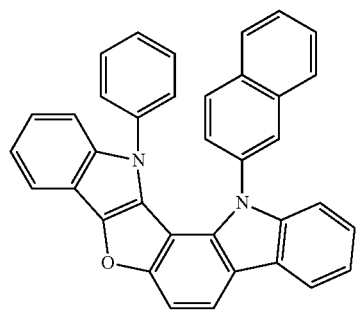
409
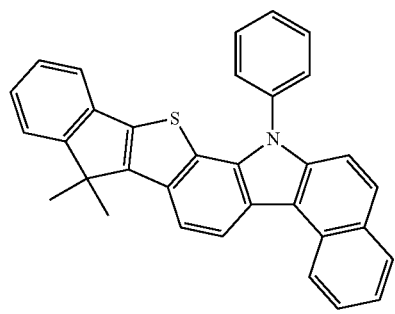
410
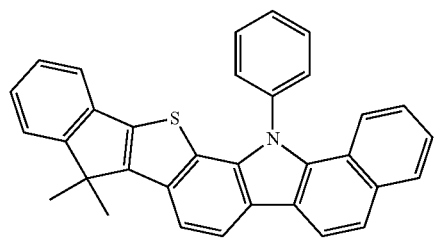
411
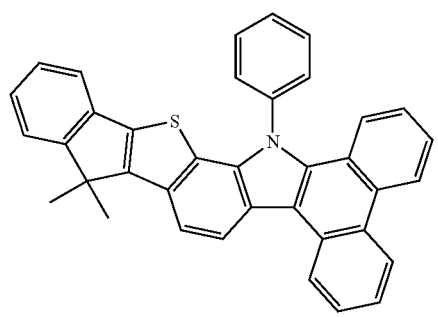
412
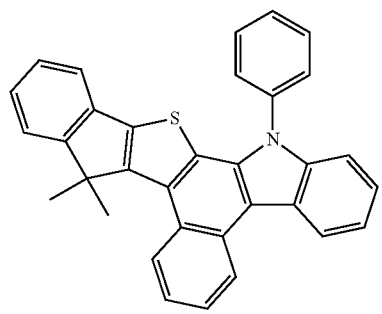
413
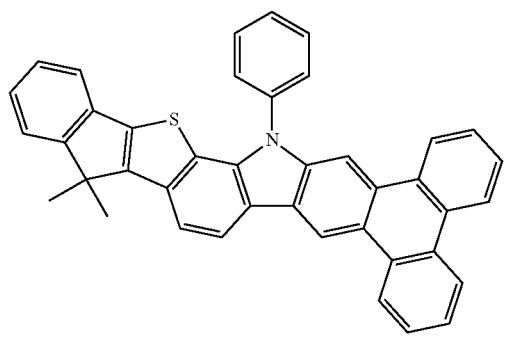
414
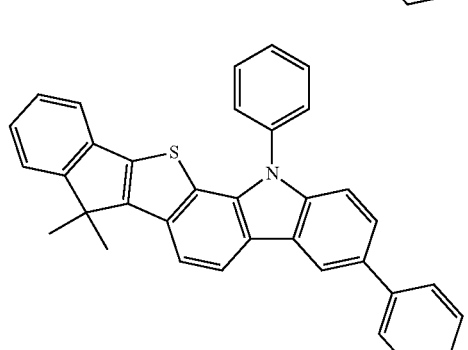
415
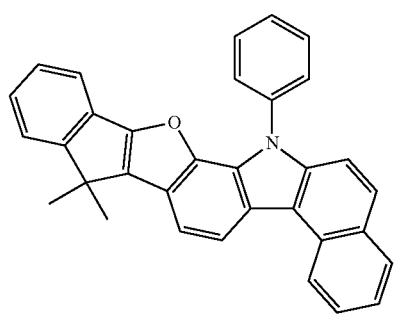
416
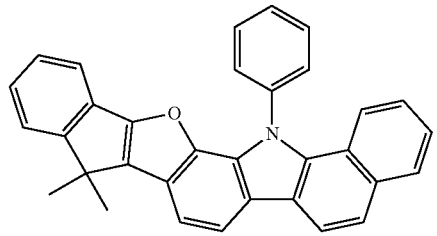
417
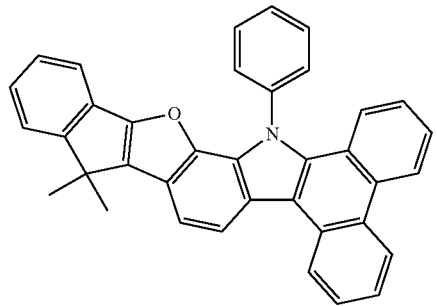

418
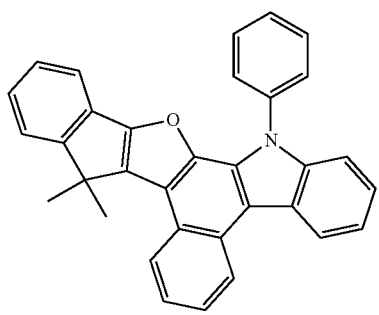
419
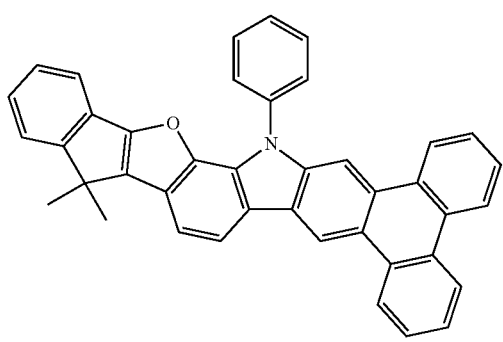
420
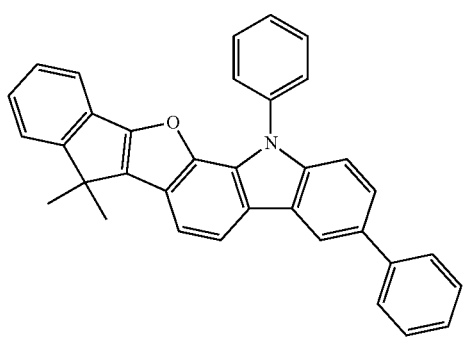
421
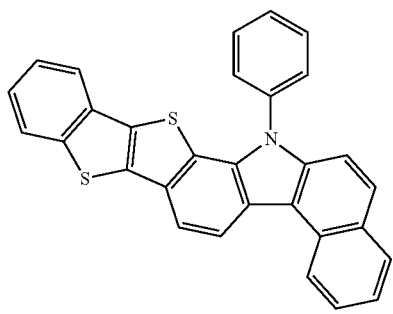
422
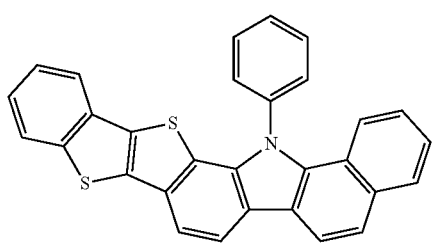
423
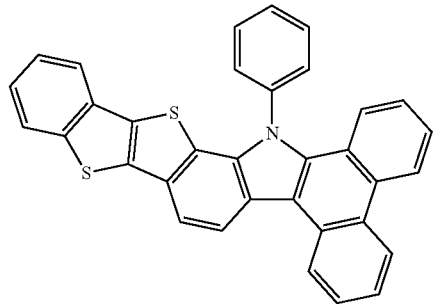
424
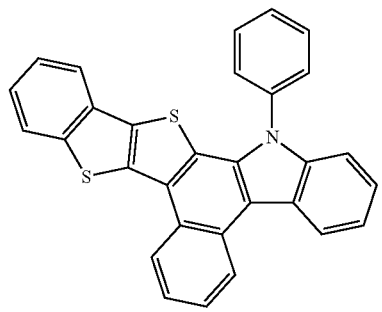
425
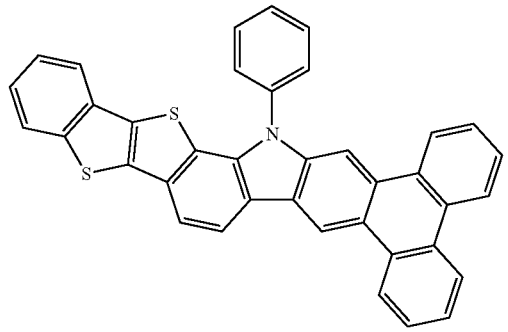
426
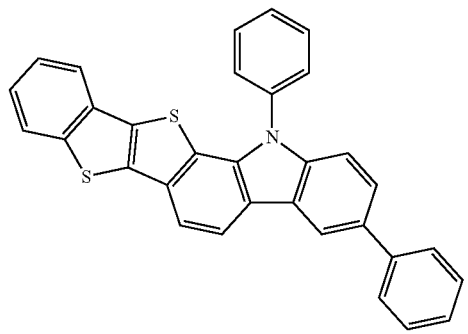
427
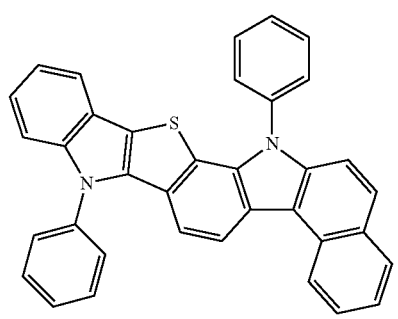

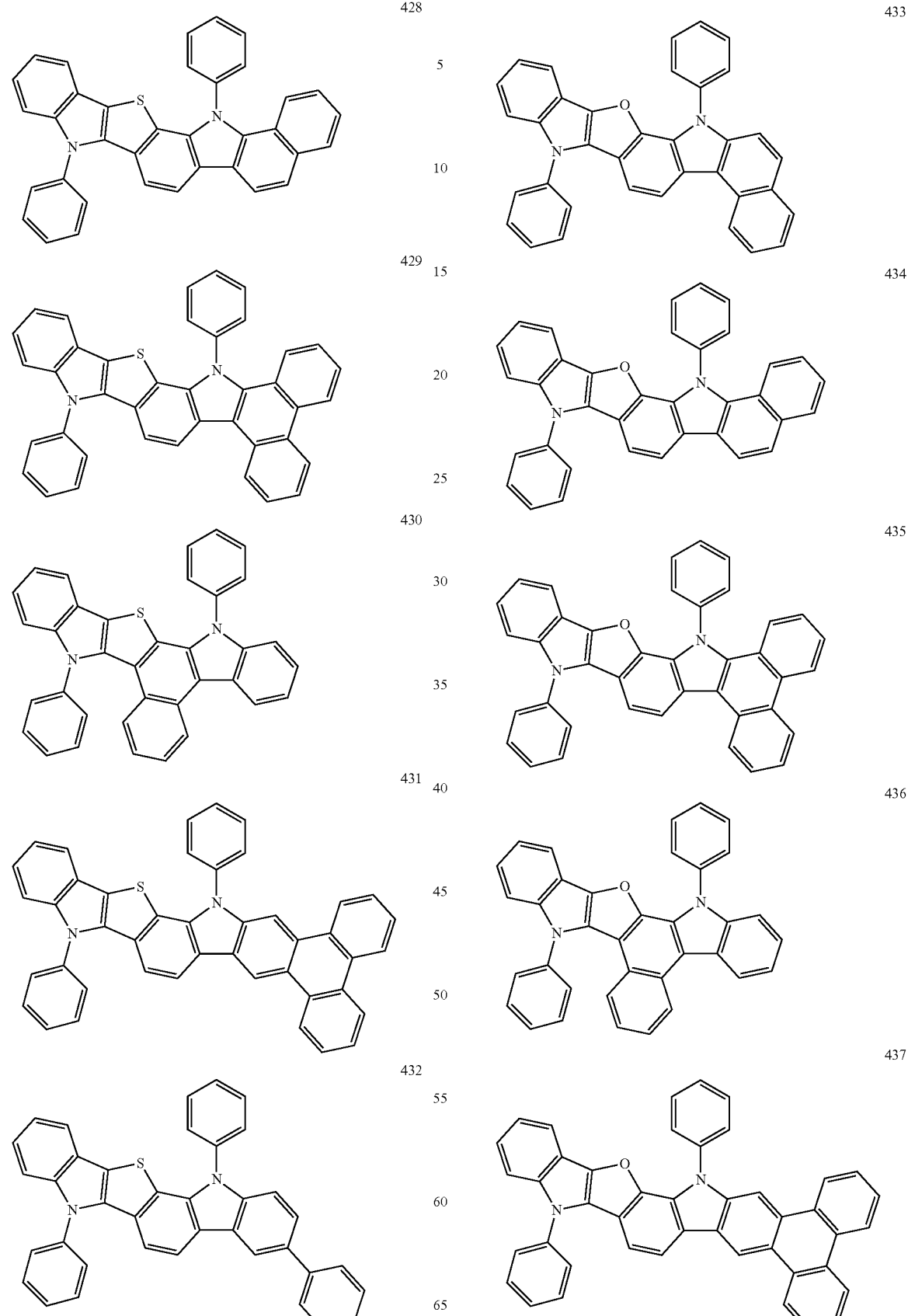

438
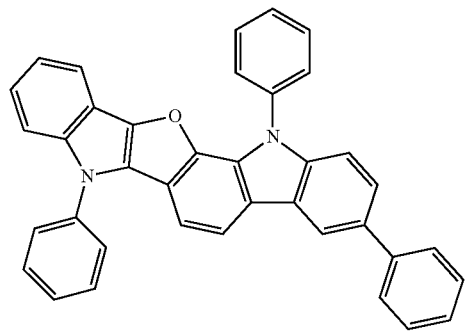
439
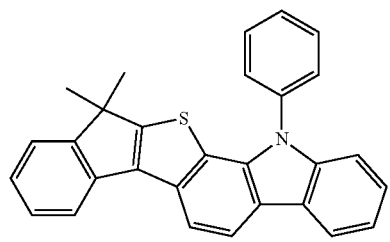
440
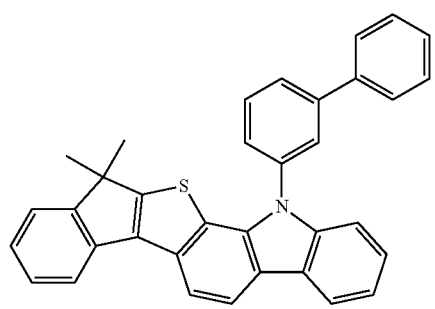
441
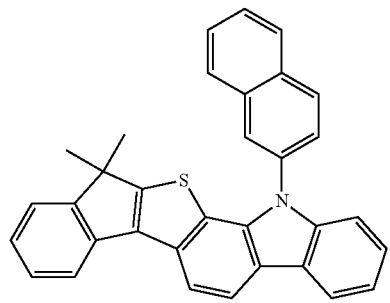
442
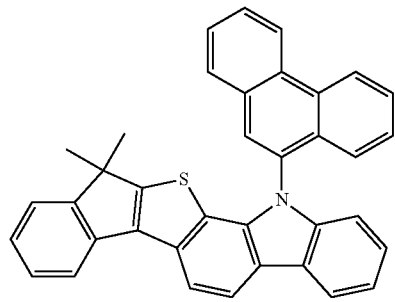
443
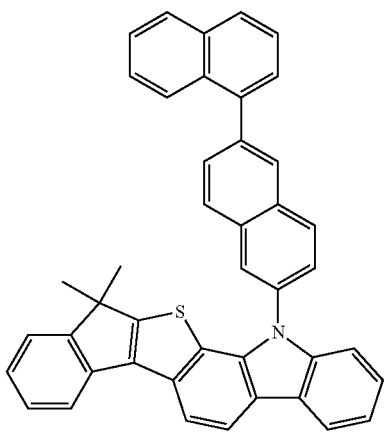
444
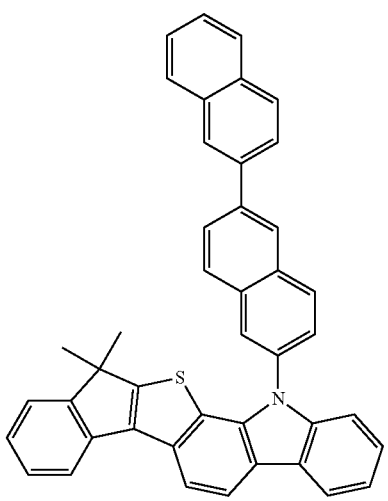
445
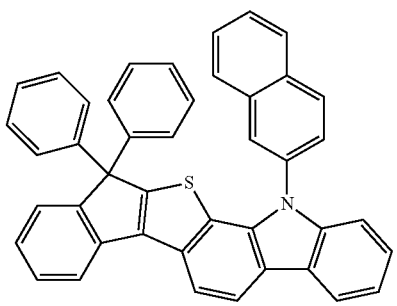

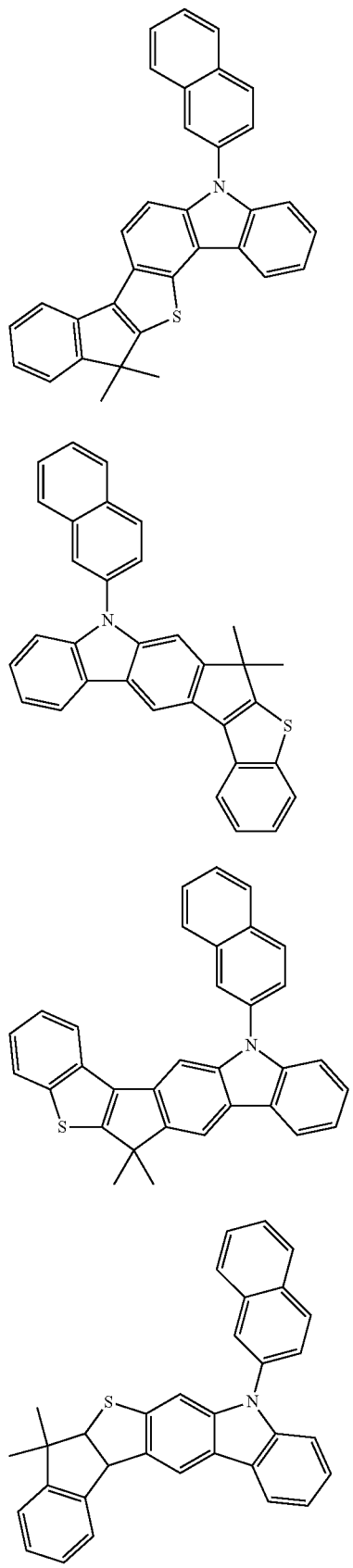
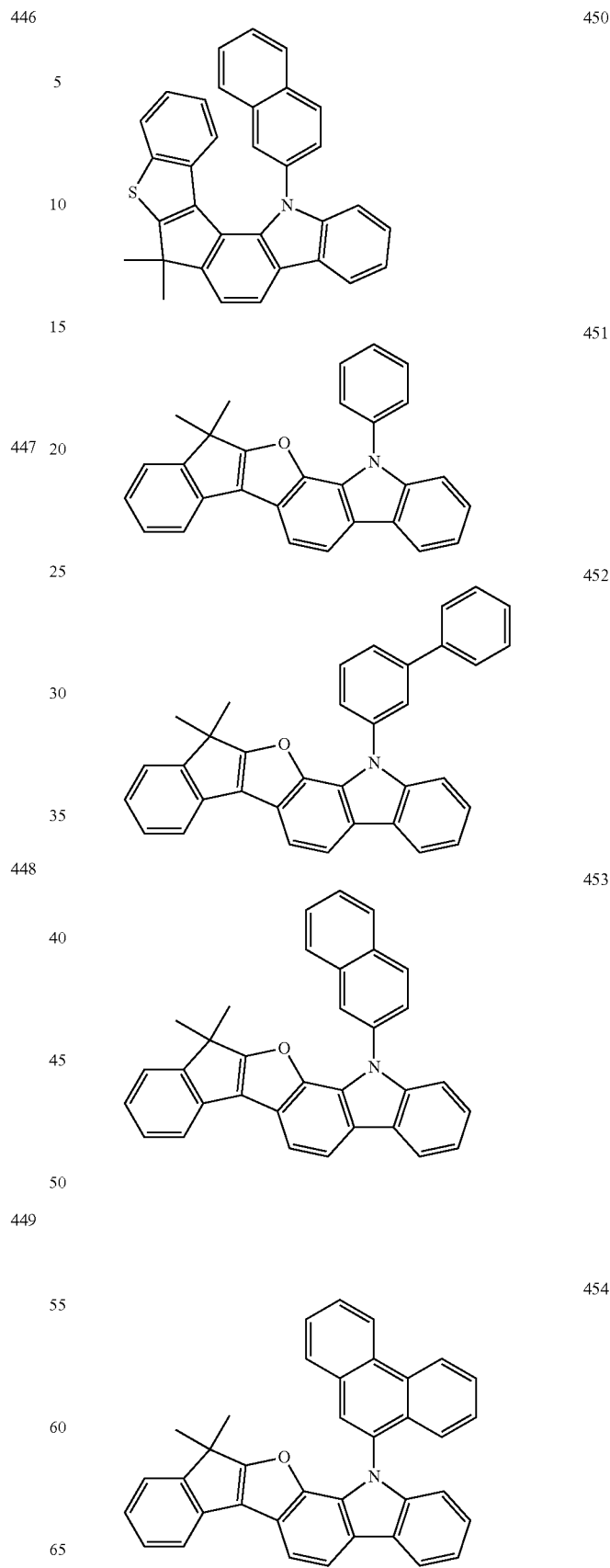

151
-continued
455
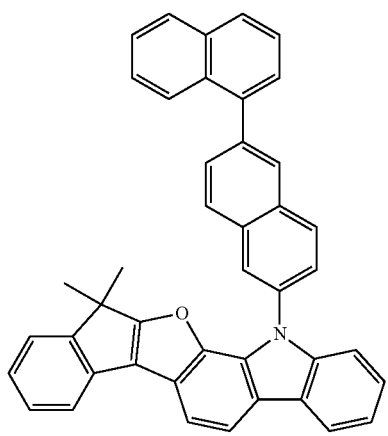
456
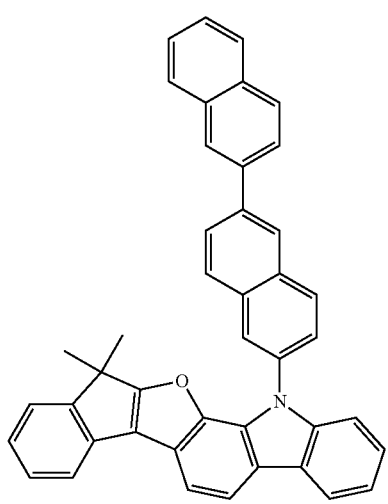
457
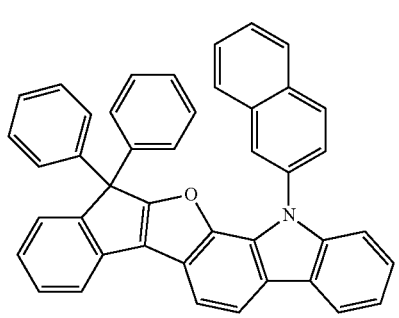
152
-continued
458
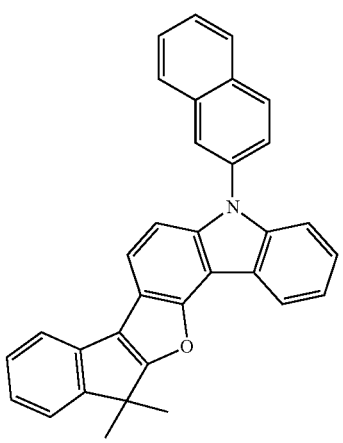
459
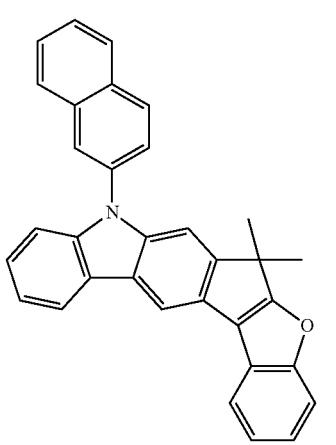
460
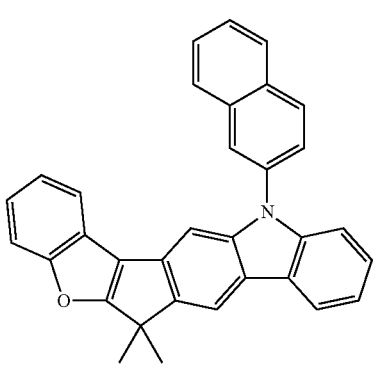
461
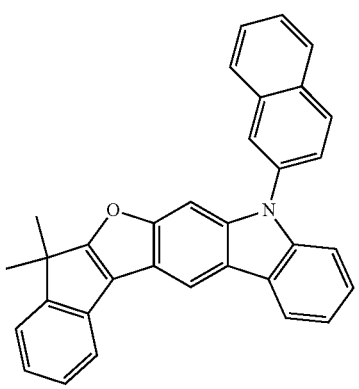

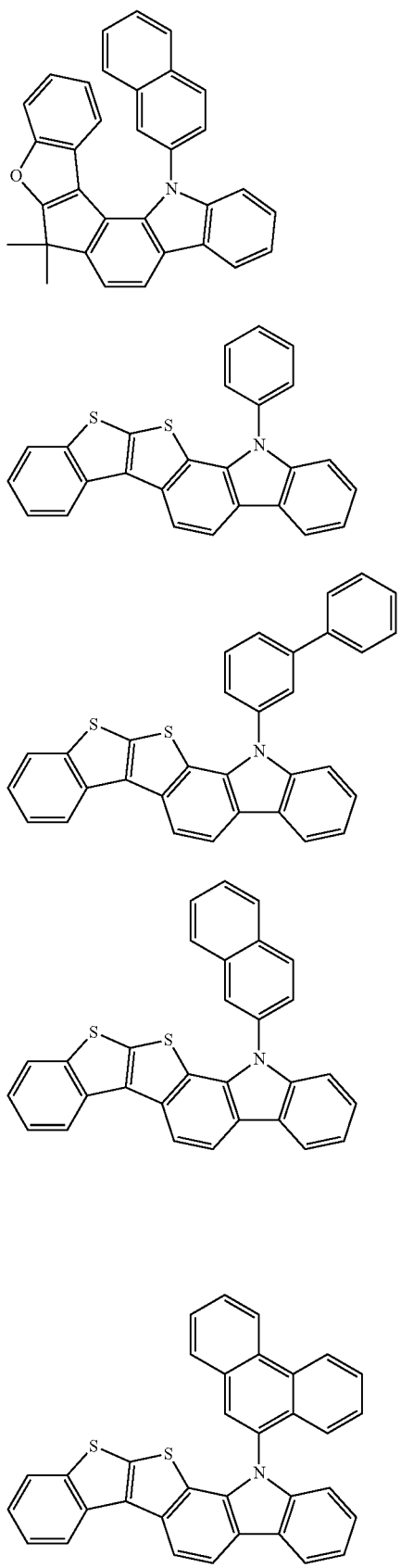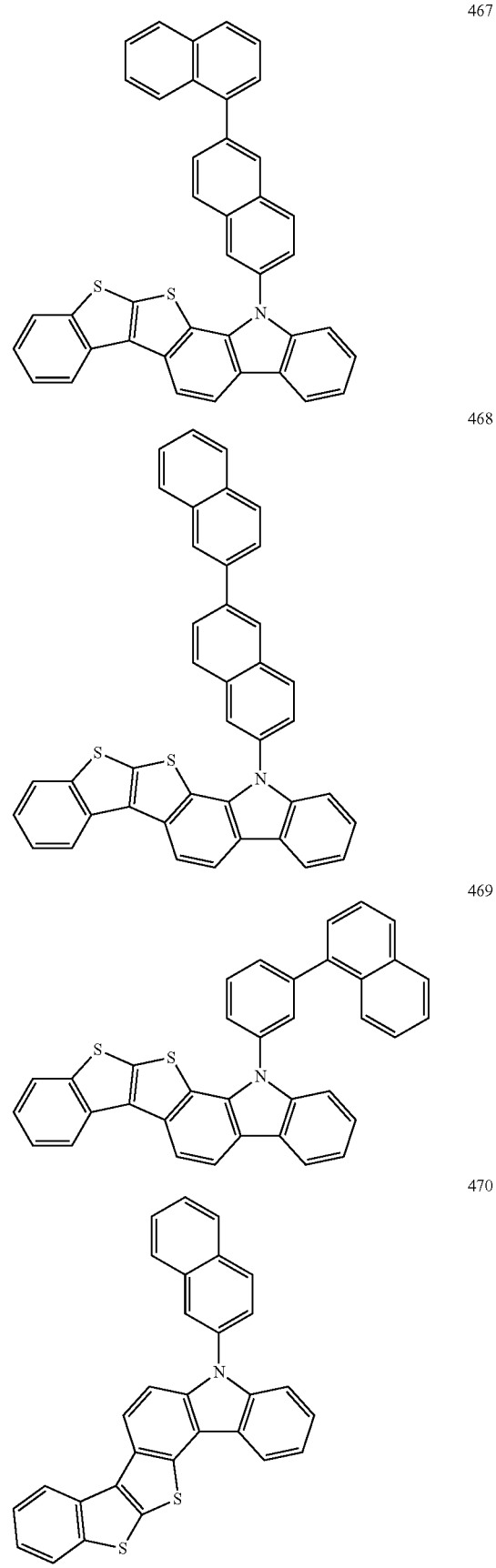

471
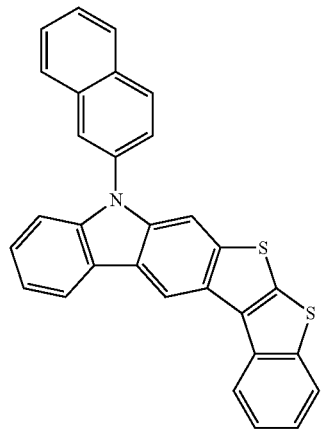
472
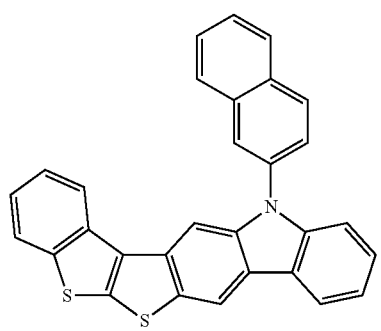
473
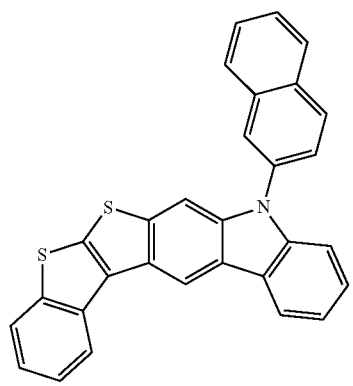
474
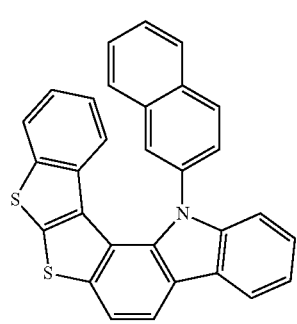
475
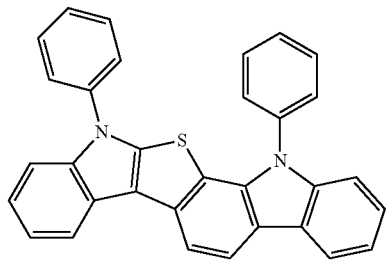
476
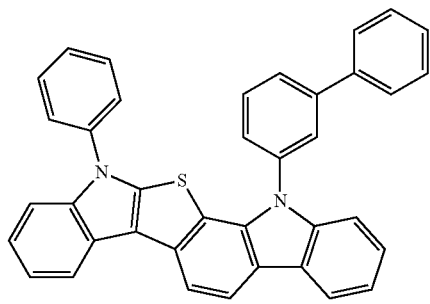
477
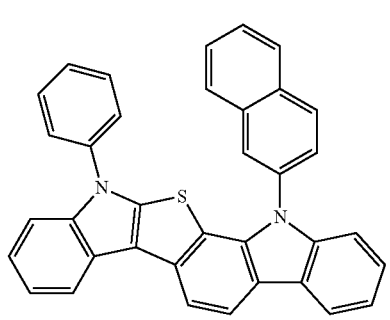
478
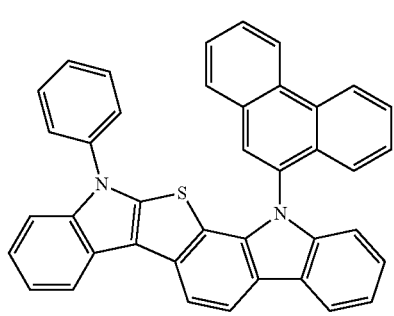
479

480
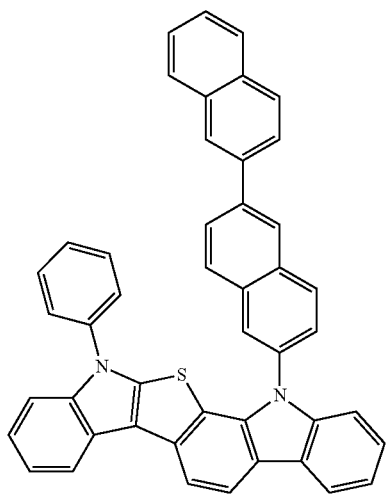
481
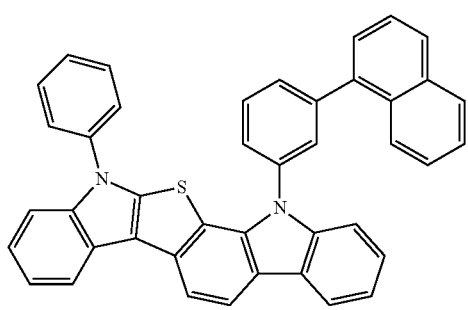
482
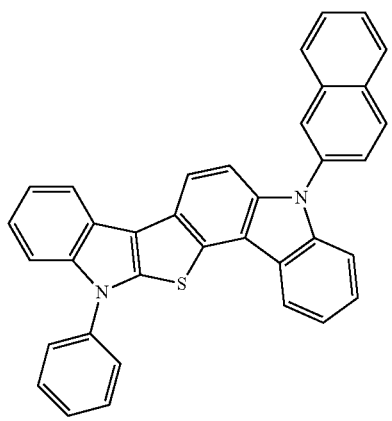
483
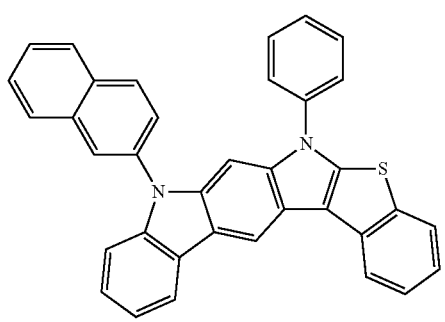
484
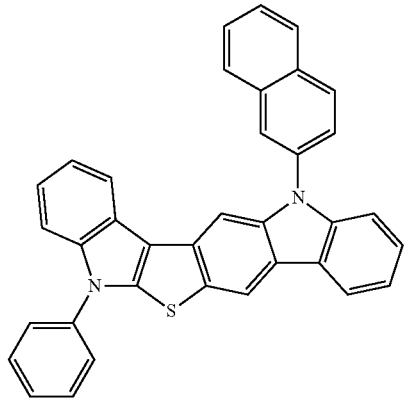
485
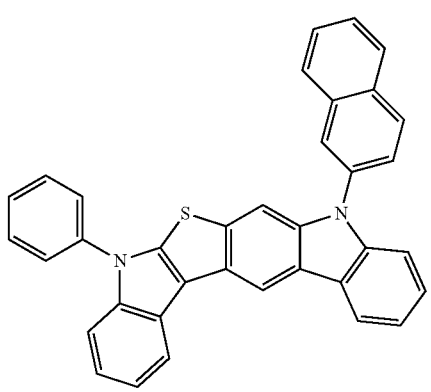
486
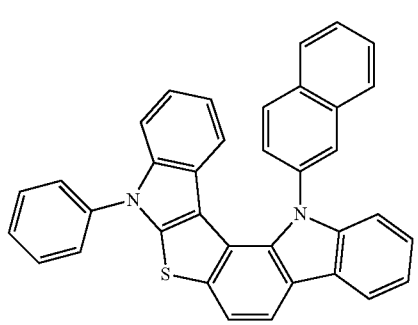
487
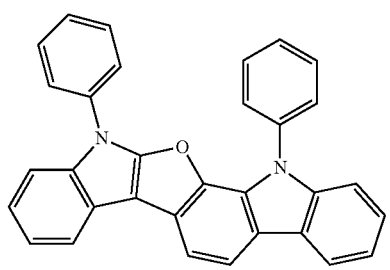

488
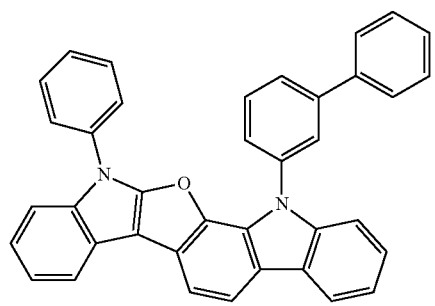
489
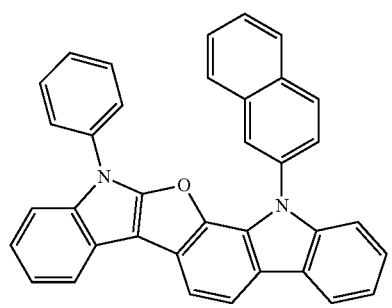
490
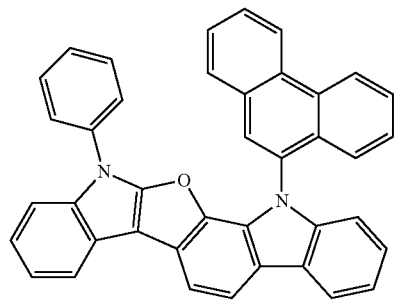
491
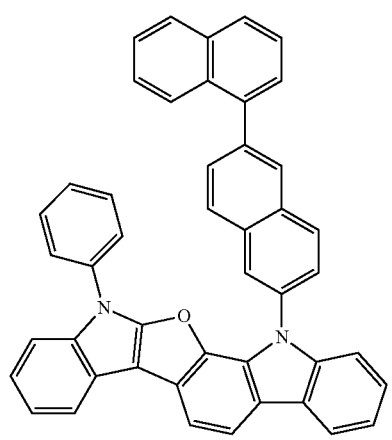
492
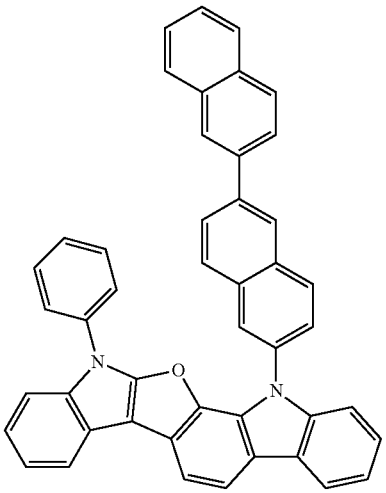
493
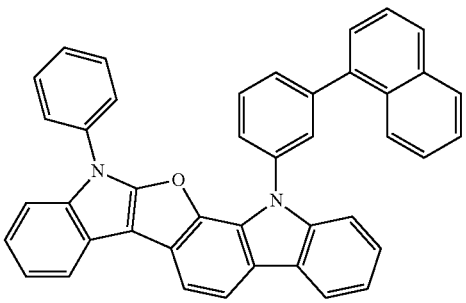
494
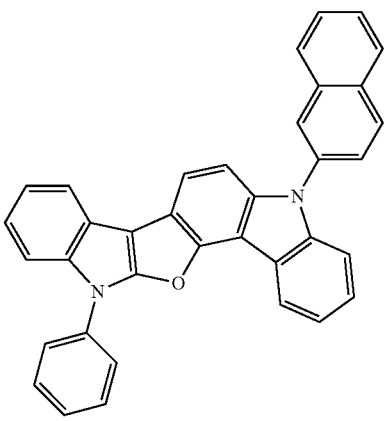
495
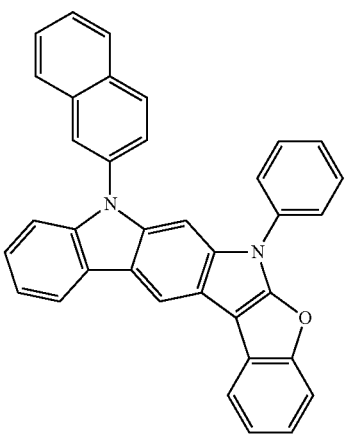

496
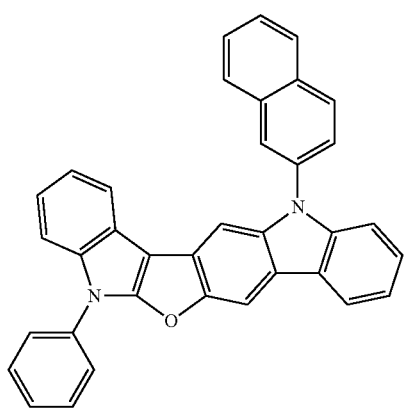
497
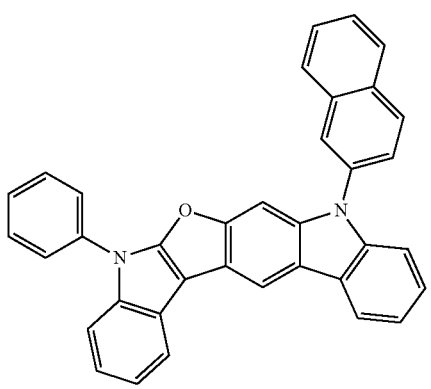
498
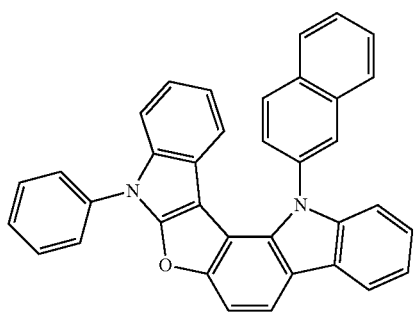
499
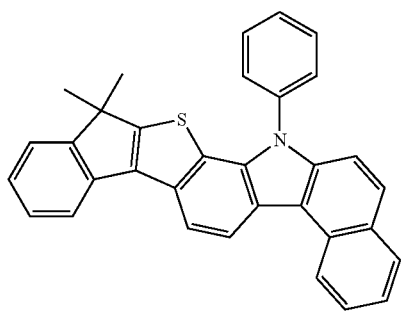
500
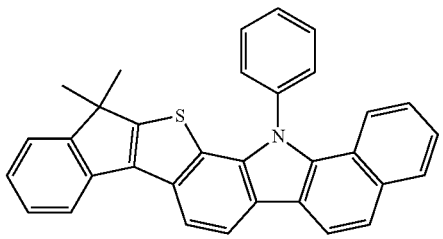
501
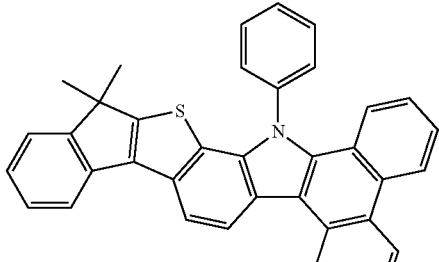
502
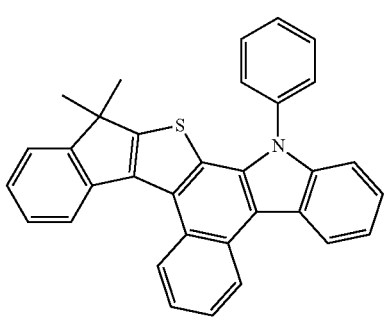
503
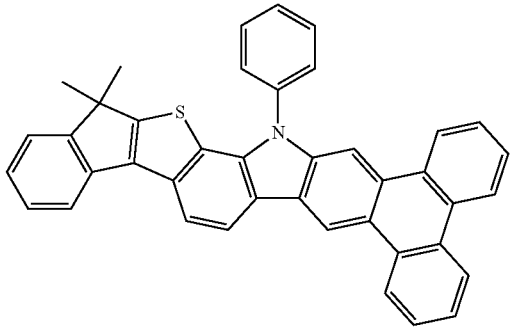
504
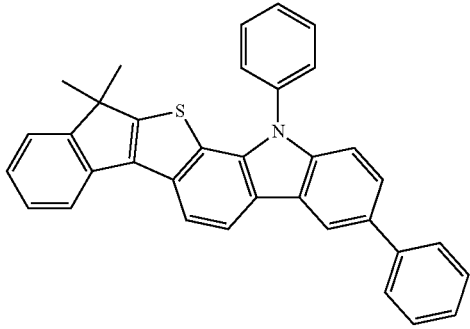

-continued
505
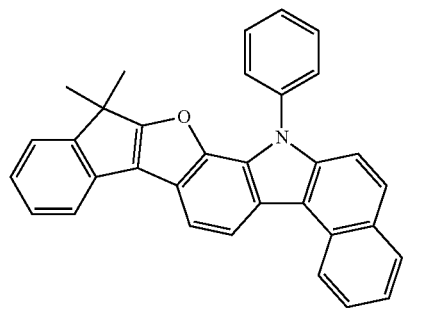
506
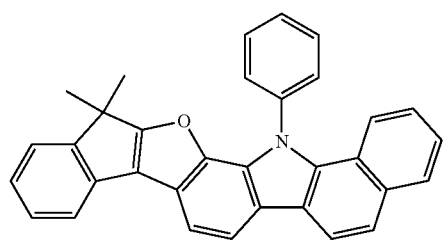
507
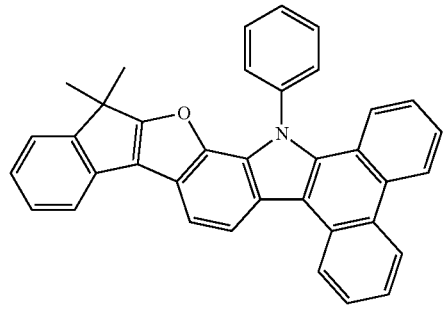
508
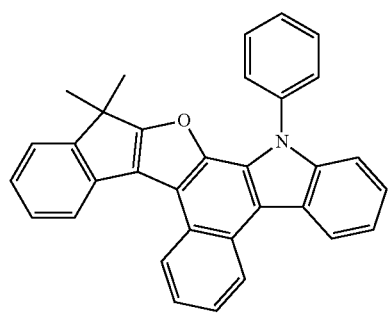
509
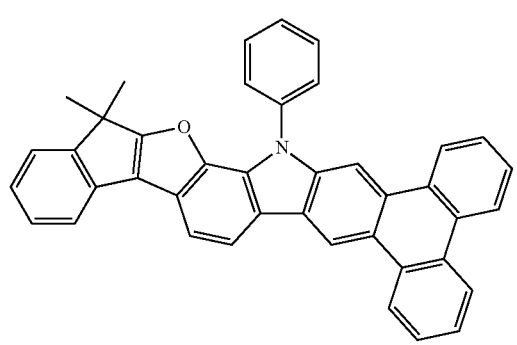
-continued
510
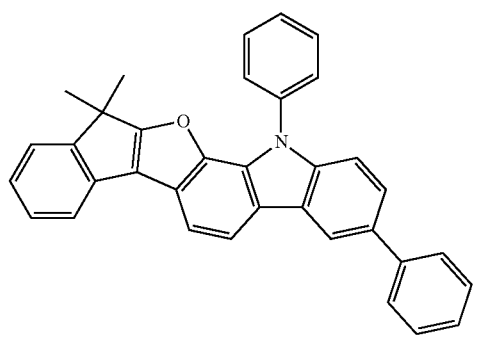
511
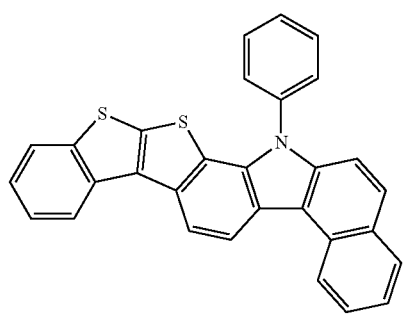
512
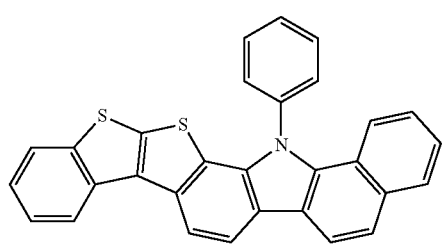
513
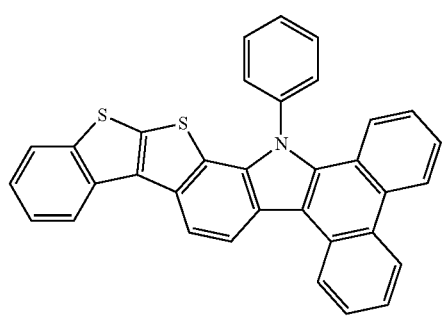
514
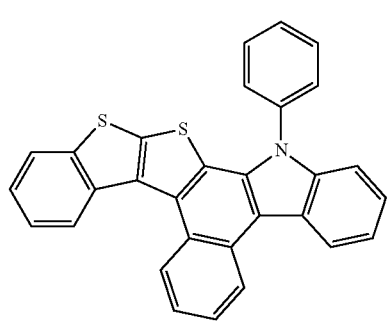

515
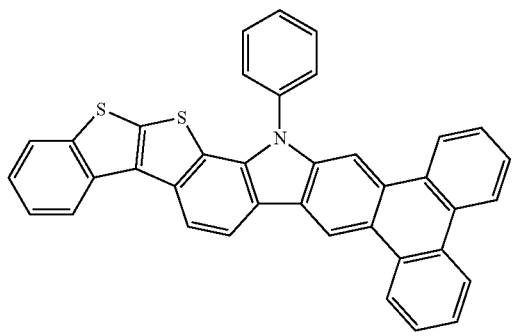
516
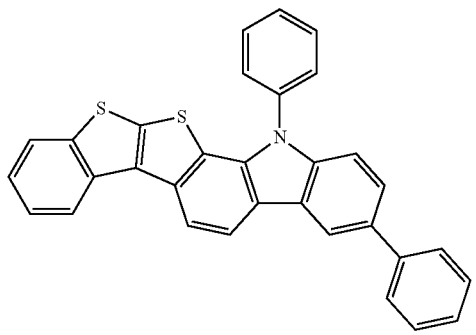
517
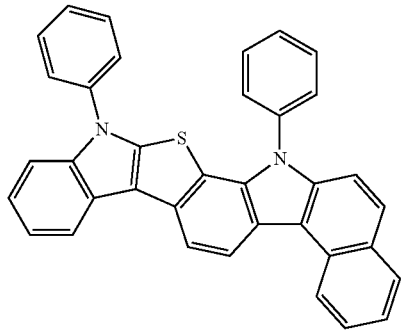
518
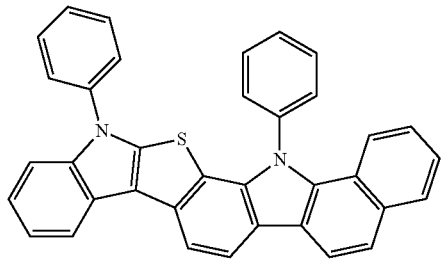
519
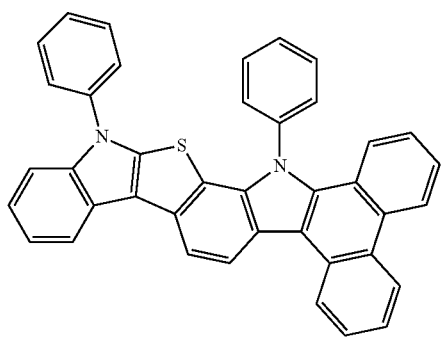
520
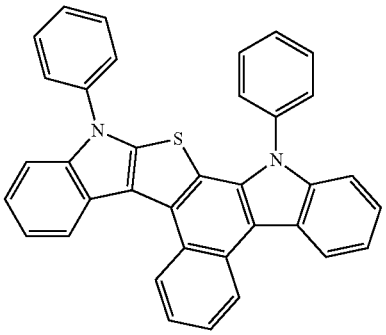
521
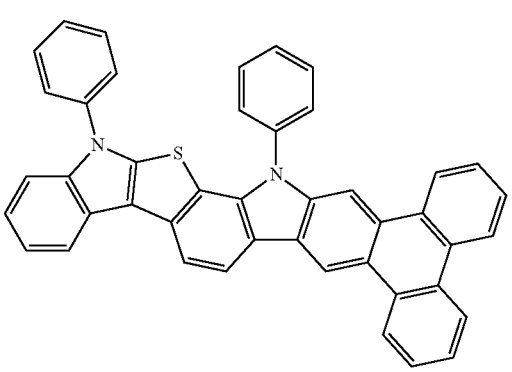
522
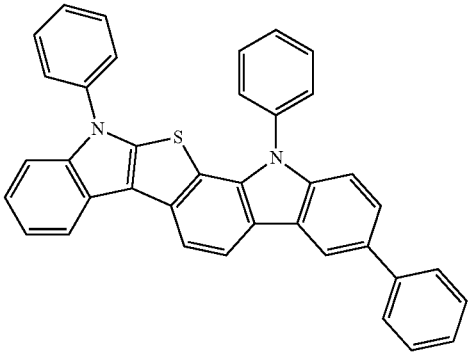
523
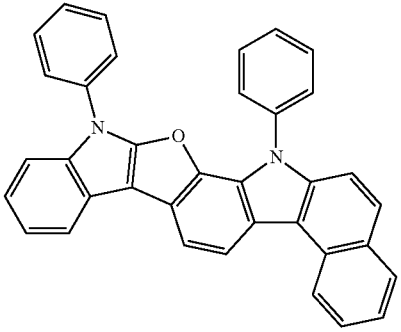

167
-continued
524
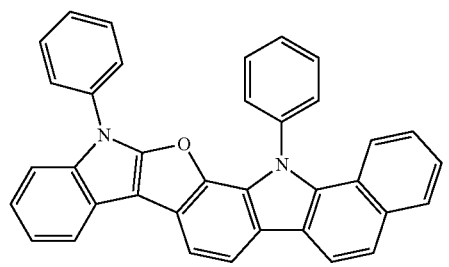
525
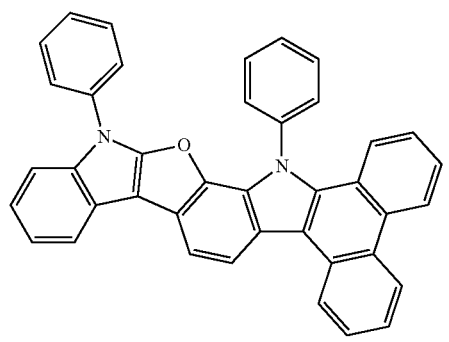
526
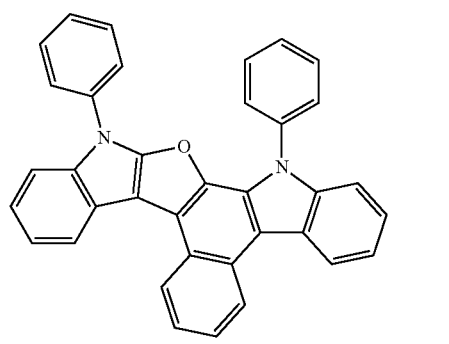
527
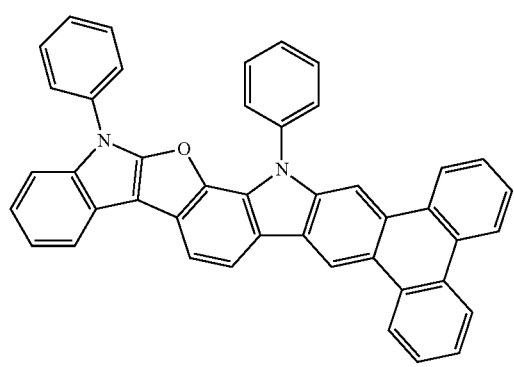
168
-continued
528
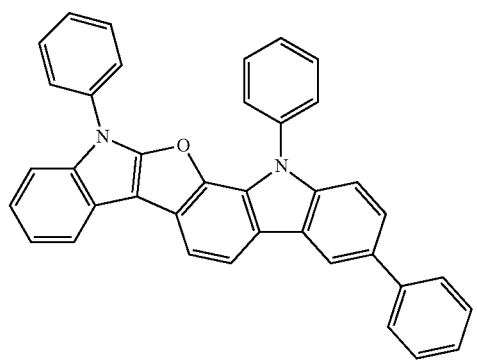
529
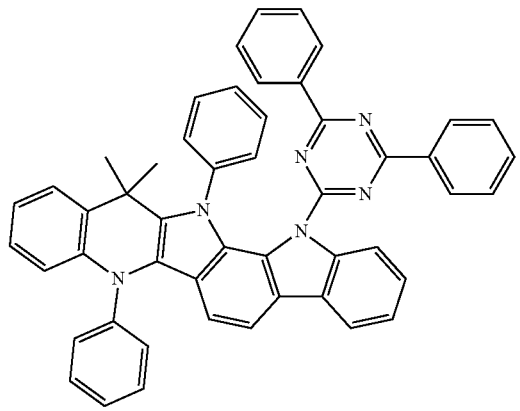
530
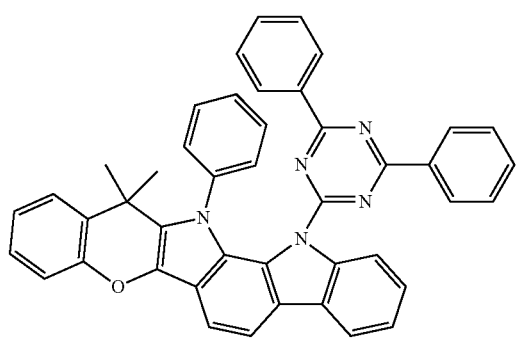
531
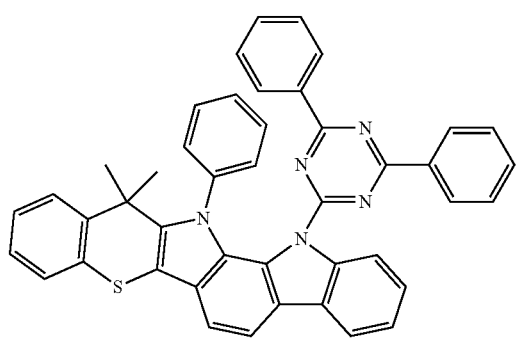

532
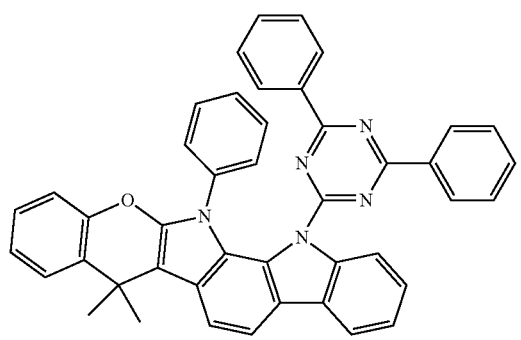
533
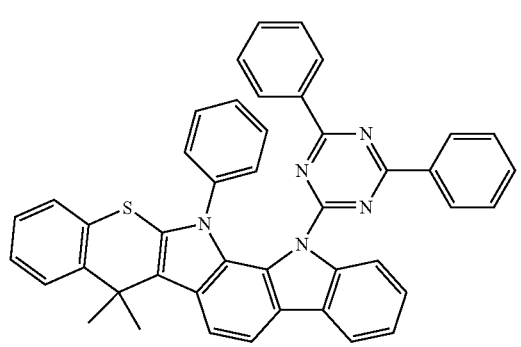
534
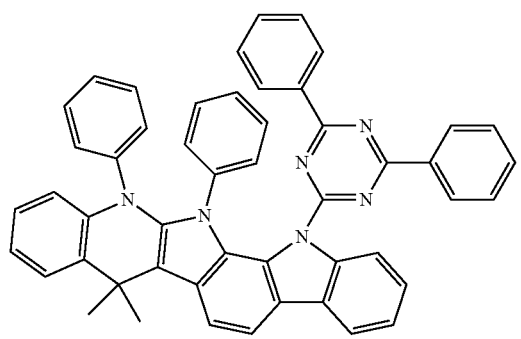
535
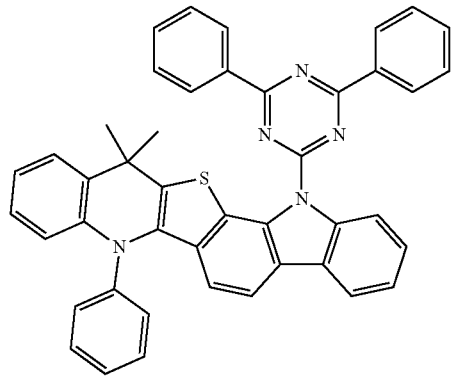
536
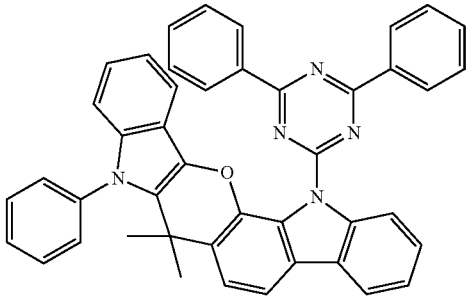
537
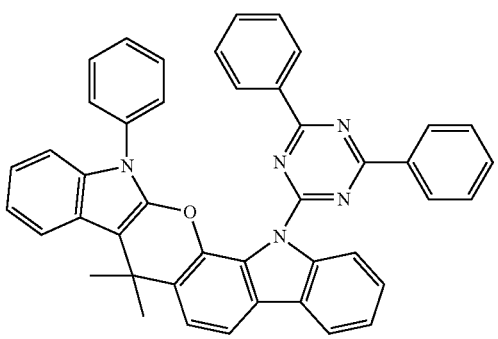
538
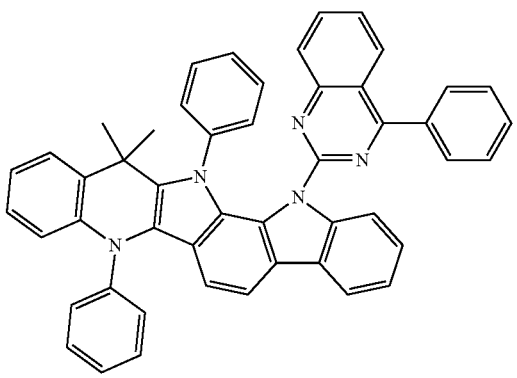
539
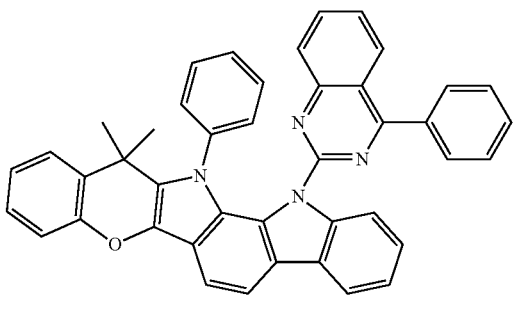

540
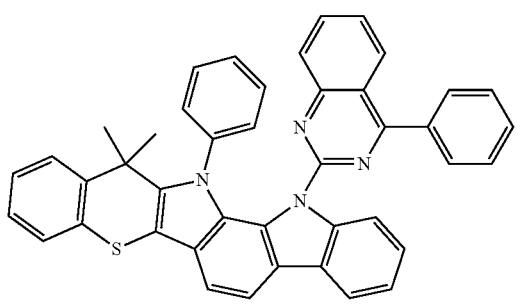
541
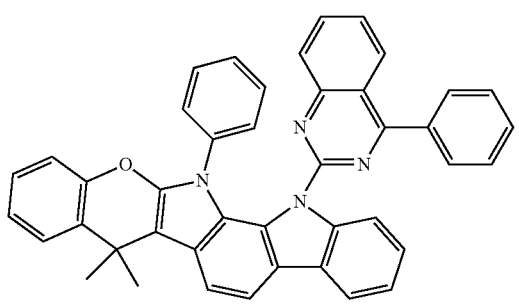
542
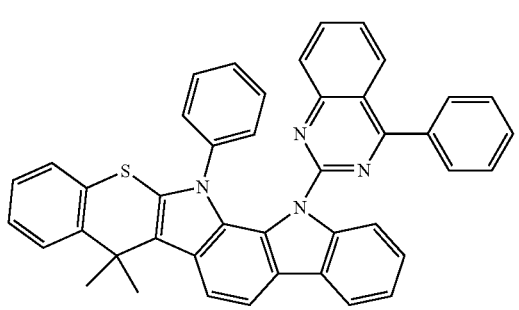
543
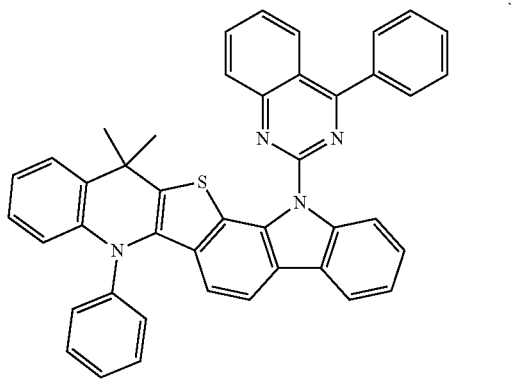
544
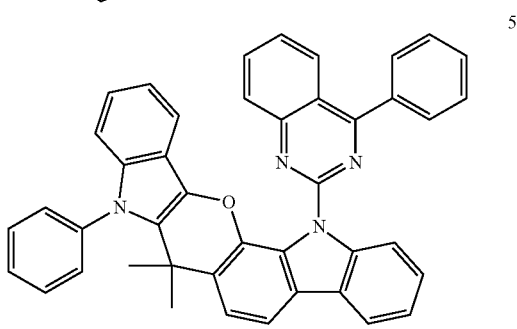
545
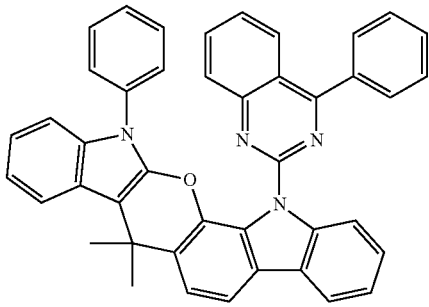
546
547
548
549
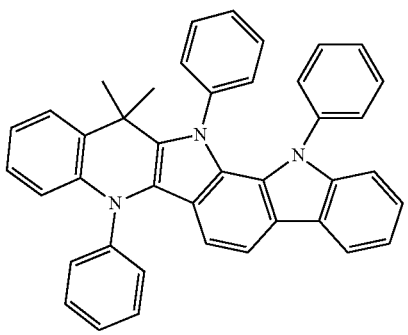

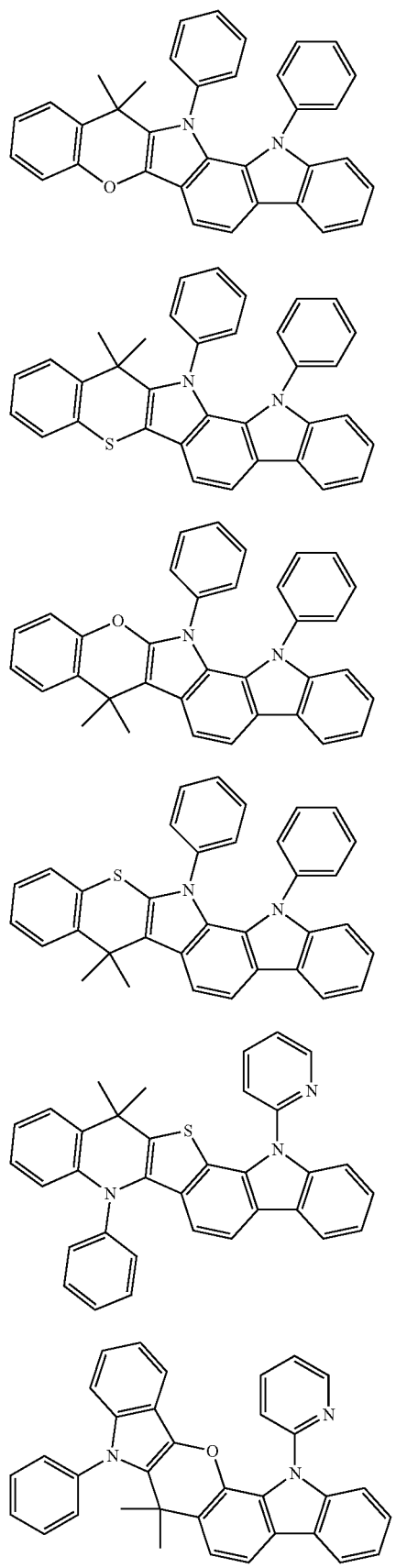
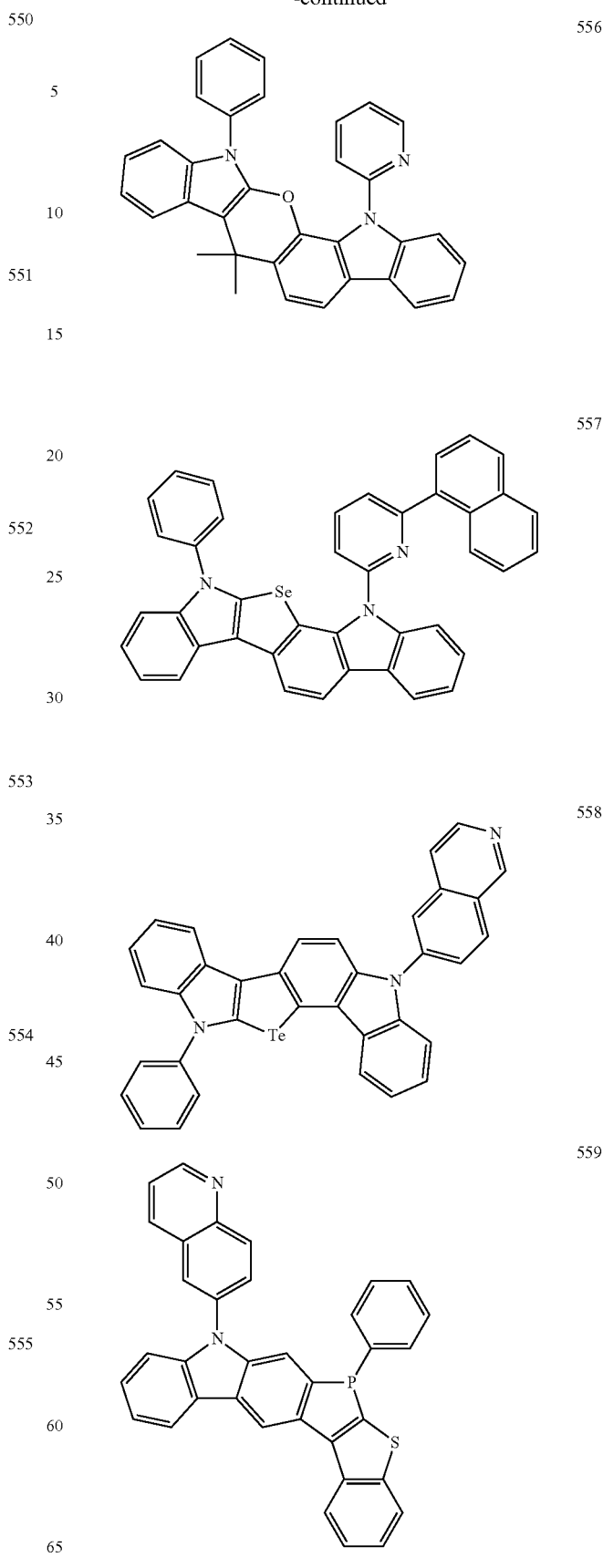

-continued
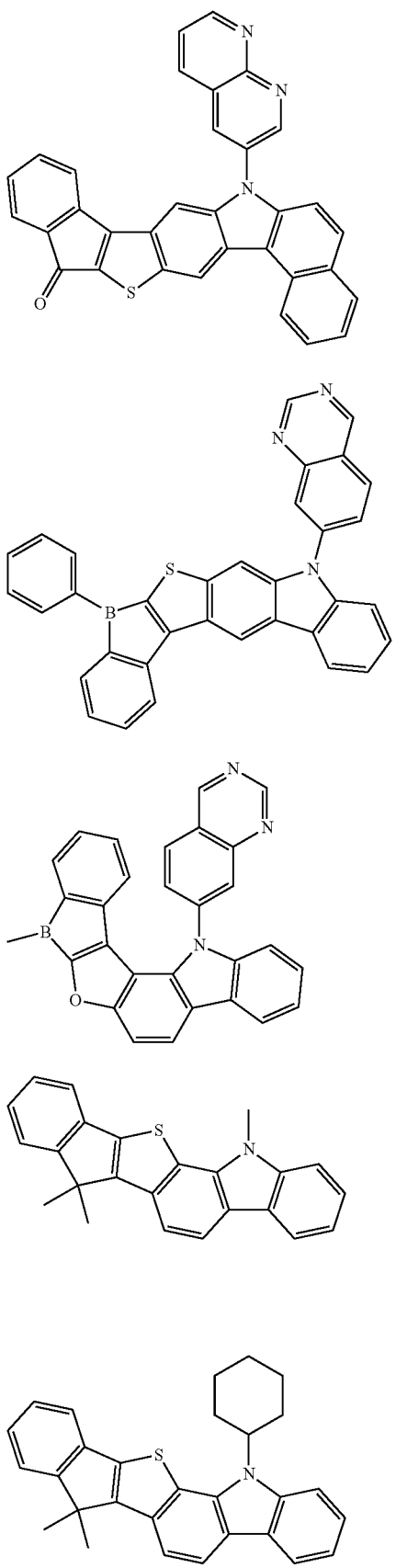
-continued
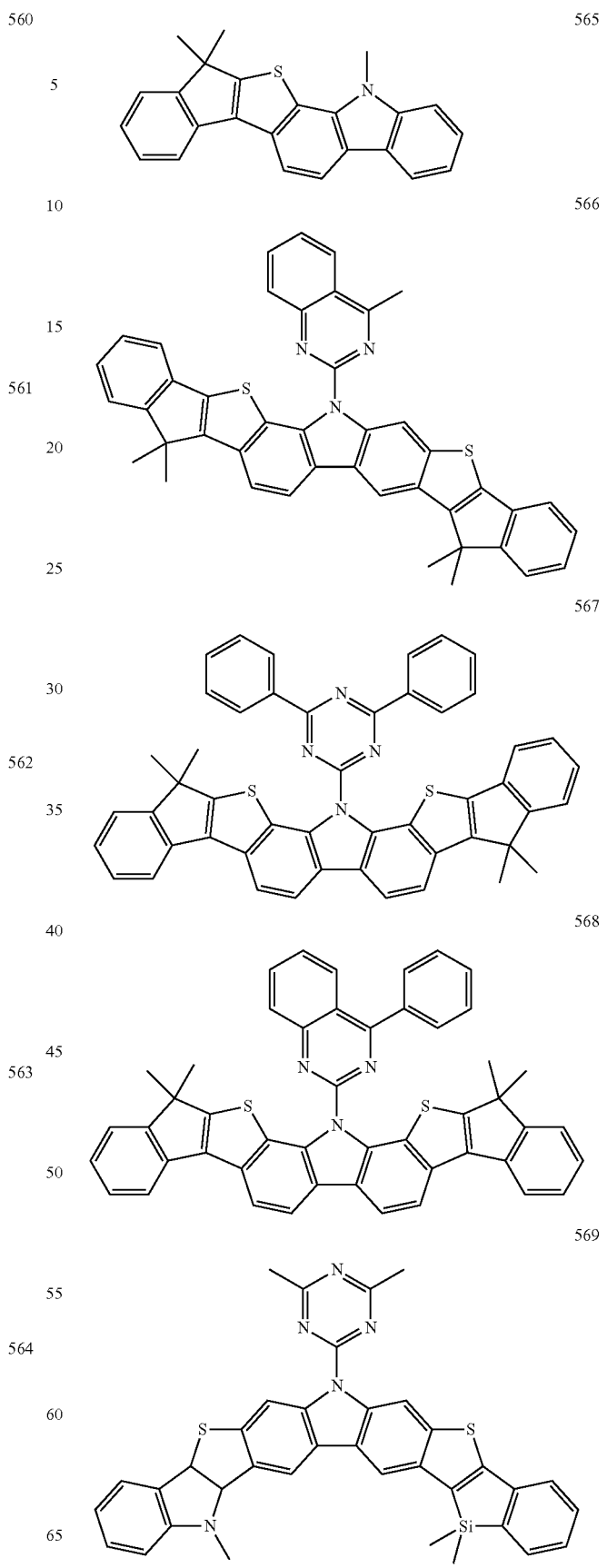

177
-continued
570
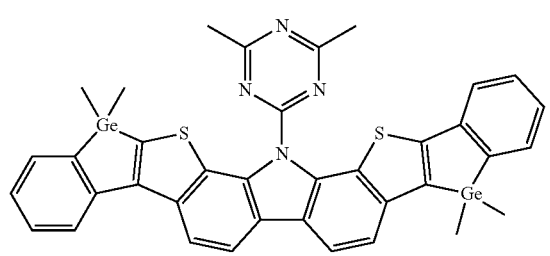
571
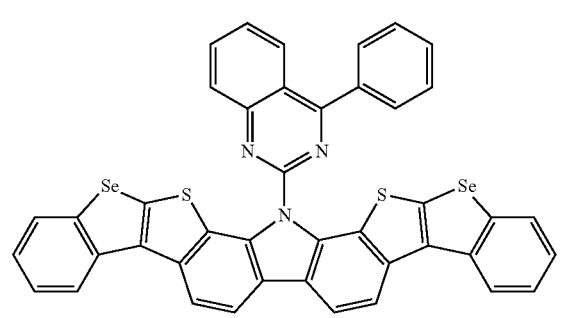
572
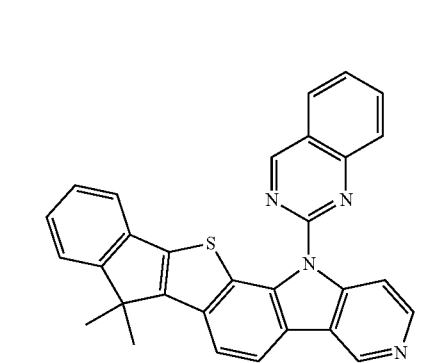
573
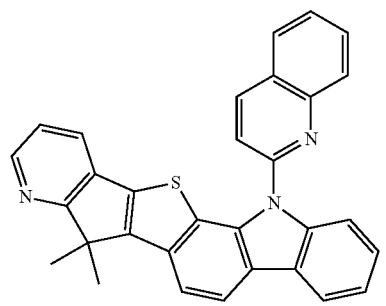
574
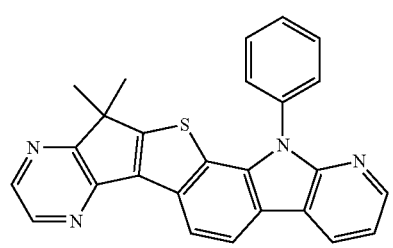
178
-continued
575
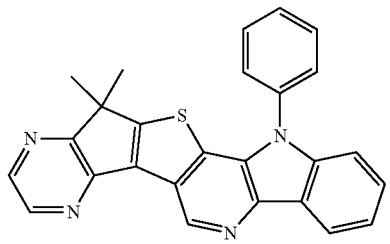
576
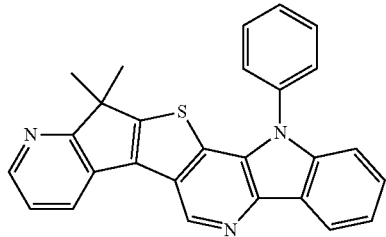
577
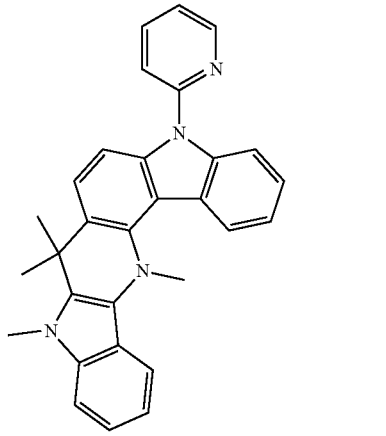
578
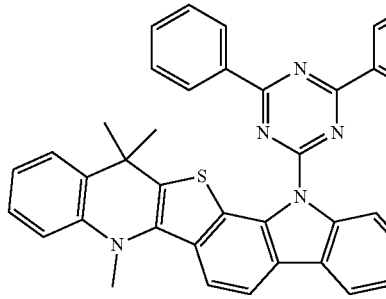
579
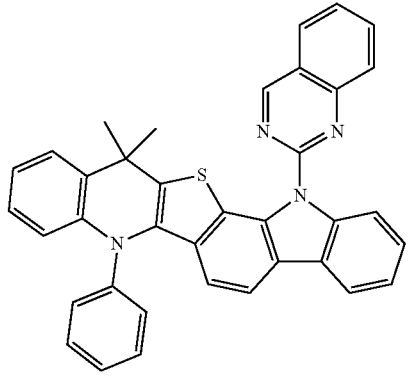

-continued

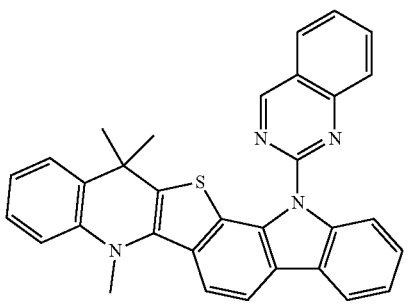

580

The heterocyclic compound of Formula 1 has a core structure of which free rotation is not easily allowed, and thus, in the case of forming a thin film according to a deposition method using the heterocyclic compound, the movement of electrons and/or holes may be facilitated. Accordingly, an organic light-emitting device including the heterocyclic compound may operate at a low driving voltage.

The heterocyclic compound of Formula 1 has a suitable triplet energy band gap for efficient phosphorescent emission, and accordingly, an organic light-emitting device including the heterocyclic compound may have high efficiency.

Aromatic rings are connected with each other (e.g., fused together) in the heterocyclic compound of Formula 1, and thus, charges may be widely distributed (upon a long conjugation length). In this regard, the heterocyclic compound may have excellent electrical stability, and accordingly, an organic light-emitting device including the heterocyclic compound may have a long lifespan.

Therefore, an organic light-emitting device including the heterocyclic compound of Formula 1 may have low driving voltage, high efficiency, and long lifespan characteristics.

The heterocyclic compound of Formula 1 may be synthesized according to synthesis methods generally available in the art. A method of synthesizing the heterocyclic compound may be understood by one of ordinary skill in the art by referring to Examples described below, but the present disclosure is not limited thereto.

The heterocyclic compound of Formula 1 may be used between a pair of electrodes of an organic light-emitting device. For example, the heterocyclic compound of Formula 1 may be included in an emission layer. Thus, in some embodiments, there is provided an organic light-emitting device including: a first electrode; a second electrode facing the first electrode; and an organic layer disposed between the first electrode and the second electrode and including an emission layer, wherein the organic layer includes at least one of the heterocyclic compounds of Formula 1.

As used herein, the expression "(an organic layer) includes the heterocyclic compound" may be construed as meaning (an organic layer) may include one of the heterocyclic compound in a range of Formula 1 or at least two different heterocyclic compounds in a range of Formula 1.

For example, the organic layer may include, as the heterocyclic compound, Compound 1 only. Here, Compound 1 may be included in the emission layer of the organic light-emitting device. Alternatively, the organic layer may include, as the heterocyclic compound, Compound 1 and Compound 2. Here, Compound 1 and Compound 2 may be both included in a same layer (for example, in some embodiments Compound 1 and Compound 2 are both included in the emission layer), or may be included in different layers from each other (for example, in some embodiments Compound 1 is included in the emission layer while Compound 2 is included in an electron transport layer).

The organic layer may further include at least one of: i) a hole transport region between the first electrode and the emission layer and including at least one of a hole injection layer, a hole transport layer, a buffer layer, and an electron blocking layer; and ii) an electron transport region between the emission layer and the second electrode and including at least one of a hole blocking layer, an electron transport layer, and an electron injection layer.

As used herein, the term "organic layer" refers to a single and/or a plurality of layers disposed between the first electrode and the second electrode in the organic light-emitting device. A material included in the "organic layer" is not limited to an organic material.

The accompanying drawing is a schematic cross-sectional view of a structure of an organic light-emitting device 10 according to an example embodiment of the present disclosure. The organic light-emitting device 10 includes a first electrode 110, an organic layer 150, and a second electrode 190.

Hereinafter, a structure of an organic light-emitting device according to an example embodiment and a method of manufacturing an organic light-emitting device according to an example embodiment will be described in connection with the accompanying drawing.

A substrate may be additionally disposed under the first electrode 110 or on the second electrode 190 in the organic light-emitting device 10. The substrate may be a glass substrate or transparent plastic substrate, each with excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for forming the first electrode 110 may be selected from materials having a high work function to facilitate hole injection. The first electrode 110 may be a reflective electrode, a semi-transmissive electrode, or a transmissive electrode. The material for forming the first electrode 110 may be an indium tin oxide (ITO), indium zinc oxide (IZO), tin oxide ($SnO_2$), or zinc oxide (ZnO), each having transparency and excellent conductivity. Alternatively, when the first electrode 110 is a semi-transmissive electrode or a reflective electrode, the material for forming the first electrode 110 may be at least one selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including two or more layers. For example, the first electrode 110 may have a triple-layer structure of ITO/Ag/ITO, but embodiments are not limited thereto.

The organic layer 150 is disposed on the first electrode 110. The organic layer 150 includes an emission layer.

The organic layer 150 may include a hole transport region that is disposed between the first electrode 110 and the emission layer. The organic layer 150 may further include an electron transport region that is disposed between the emission layer and the second electrode 190.

The hole transport region may include at least one of a hole injection layer (HIL), a hole transport layer (HTL), and an electron blocking layer (EBL), and the electron transport region may include at least one of a hole blocking layer (HBL), an electron transport layer (ETL), and an electron injection layer (EIL), but embodiments are not limited thereto.

The hole transport region may have a single-layer structure formed of a single material, a single-layer structure formed of a plurality of different materials, or a multi-layer structure having a plurality of layers formed of a plurality of different materials.

For example, the hole transport region may have a single-layer structure formed of a plurality of different materials, or a structure of HIL/HTL, a structure of HIL/HTL/buffer layer, a structure of HIL/buffer layer, a structure of HTL/buffer layer, or a structure of HIL/HTL/EBL, wherein layers of each of the structures are sequentially stacked from the first electrode 110 in this stated order, but embodiments are not limited thereto.

When the hole transport region includes an HIL, the HIL may be formed on the first electrode 110 by using various suitable methods, such as vacuum deposition, spin coating, casting, a Langmuir-Blodgett (LB) method, ink-jet printing, laser-printing, or laser-induced thermal imaging (LITI).

When the HIL is formed by vacuum deposition, the vacuum deposition may be performed at a deposition temperature in a range of about 100° C. to about 500° C., at a vacuum degree in a range of about $10^{-8}$ torr to about $10^{-3}$ torr, and at a deposition rate in a range of about 0.01 Å/sec to about 100 Å/sec, in consideration of a composition of a compound for forming the HIL and a structure of the suitable or desired HIL.

When the HIL is formed by spin coating, the spin coating may be performed at a coating rate in a range of about 2,000 rpm to about 5,000 rpm and at a temperature in a range of about 80° C. to about 200° C., in consideration of a composition of a compound for forming the HIL and a structure of the suitable or desired HIL.

When the hole transport region includes an HTL, the HTL may be formed on the first electrode 110 or on the HIL by using various suitable methods, such as vacuum deposition, spin coating, casting, a LB method, ink-jet printing, laser-printing, or LITI. When the HTL is formed by vacuum deposition or by spin coating, the deposition conditions or the coating conditions may be the same or substantially the same as (e.g., may be inferred based on) the deposition conditions or the coating conditions for forming the HIL.

The hole transport region may include, for example, at least one selected from m-MTDATA, TDATA, 2-TNATA, NPB, β-NPB, TPD, Spiro-TPD, Spiro-NPB, methylated-NPB, TAPC, HMTPD, DNTPD, 4,4',4''-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), a compound represented by Formula 201, and a compound represented by Formula 202:

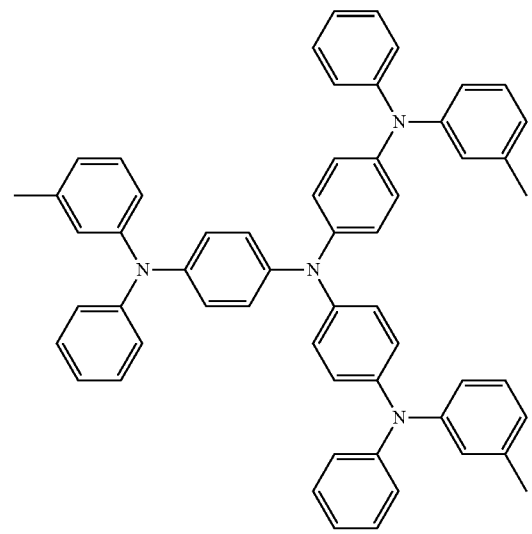

m-MTDATA

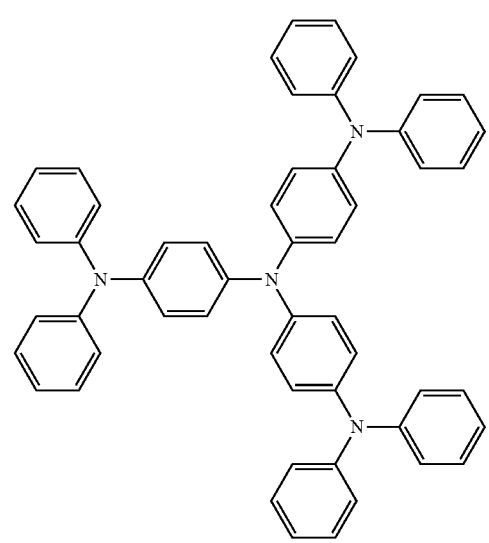

TDATA

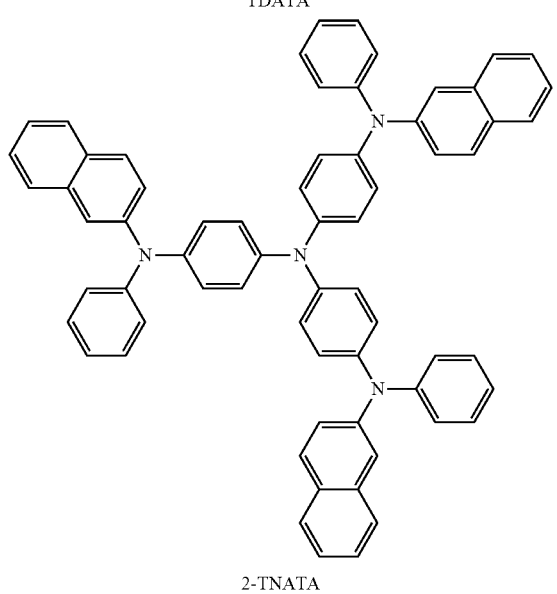

2-TNATA

-continued

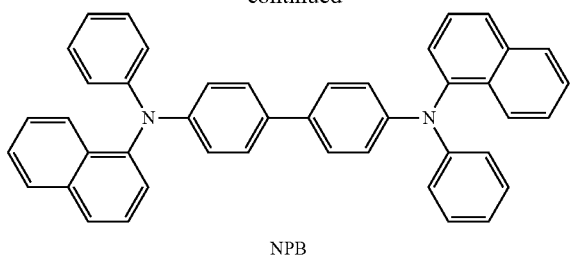

NPB

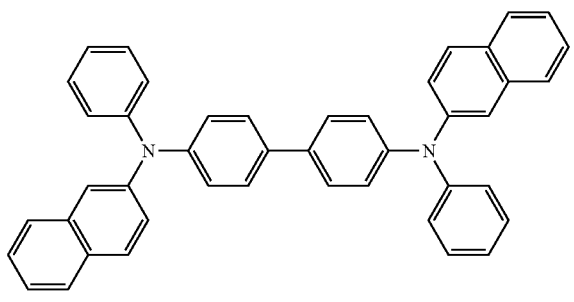

β-NPB


TPD


Spiro-TPD

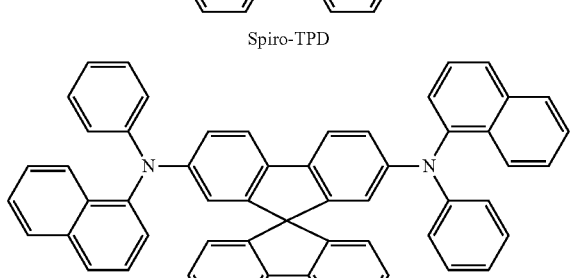

Spiro-NPB

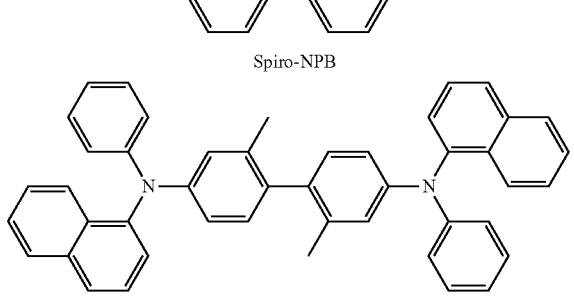

methylated NPB

-continued

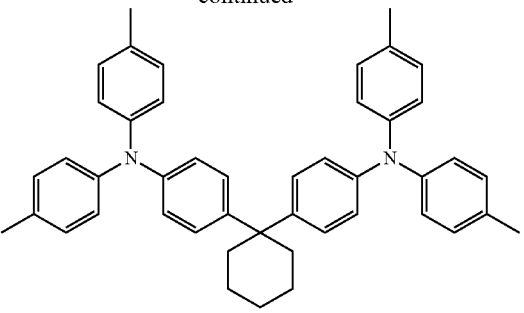

TAPC

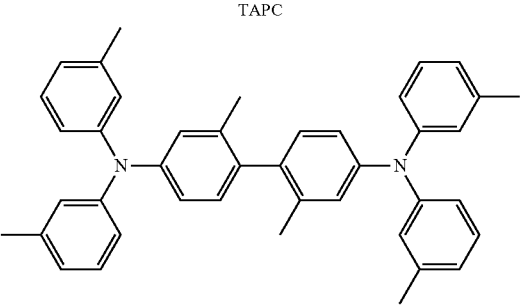

HMTPD

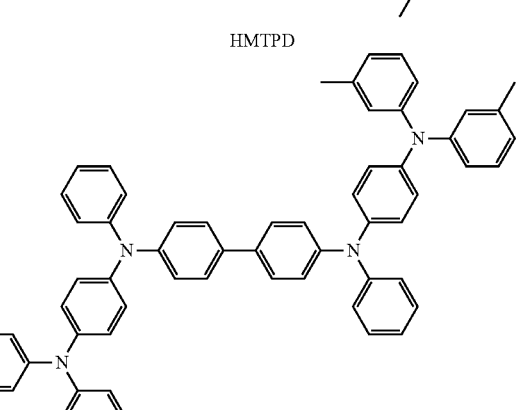

DNTPD

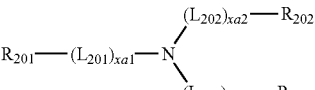

Formula 201

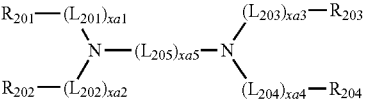

Formula 202

In Formulae 201 and 202, $L_{201}$ to $L_{205}$ may be each independently the same as defined in connection with $L_1$ in the present specification (e.g., $L_{201}$ to $L_{205}$ may each independently be the same or substantially the same as described with respect to $L_1$);

xa1 to xa4 may be each independently selected from 0, 1, 2, and 3;

xa5 may be selected from 1, 2, 3, 4, and 5; and $R_{201}$ to $R_{205}$ may be each independently the same as defined in connection with $R_1$ in the present specification (e.g., $R_{201}$ to $R_{205}$ may each independently be the same or substantially the same as described with respect to $R_1$).

For example, in Formulae 201 and 202, $L_{201}$ to $L_{205}$ may be each independently selected from:

a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthalenylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2 or 3; and $R_{201}$ to $R_{205}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments are not limited thereto.

The compound represented by Formula 201 may be represented by Formula 201A:

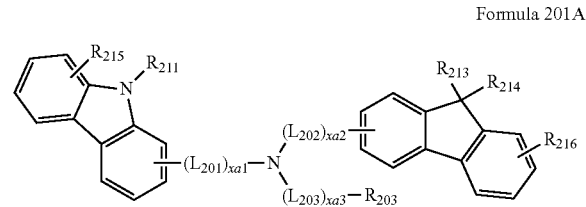

Formula 201A

For example, the compound represented by Formula 201 may be represented by Formula 201A-1, but embodiments are not limited thereto:

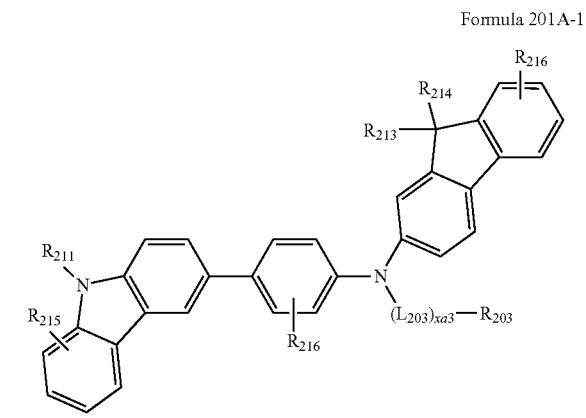

Formula 201A-1

The compound represented by Formula 202 may be represented by Formula 202A, but embodiments are not limited thereto:

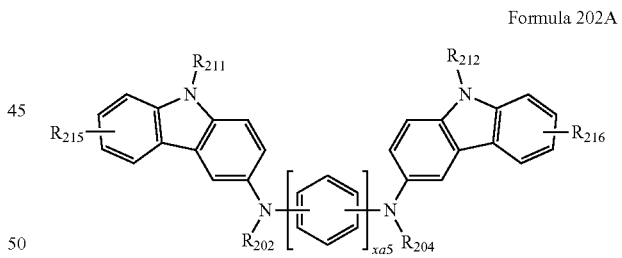

Formula 202A

In Formulae 201A, 201A-1, and 202A, $L_{201}$ to $L_{203}$, xa1 to xa3, xa5, and $R_{202}$ to $R_{204}$ are the same as defined in the present specification (e.g., $L_{201}$ to $L_{203}$, xa1 to xa3, xa5, and $R_{202}$ to $R_{204}$ may be the same or substantially the same as described with respect to Formulae 201 and 202), $R_{211}$ and $R_{212}$ are the same as defined in connection with $R_{203}$ (e.g., $R_{211}$ and $R_{212}$ may be the same or substantially the same as $R_{203}$ of Formulae 201 and 202), and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

For example, in Formulae 201A, 201A-1 and 202A, $L_{201}$ to $L_{203}$ may be each independently selected from a phenylene group, a naphthylenylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylenylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently 0 or 1;

$R_{203}$, $R_{211}$, and $R_{212}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may be 1 or 2.

In Formulae 201A and 201A-1, $R_{213}$ and $R_{214}$ may be fused to each other (e.g., fused together) and form a saturated or unsaturated ring.

The compound represented by Formula 201 and the compound represented by Formula 202 may include Compounds HT1 to HT20, but embodiments are not limited thereto.

HT1

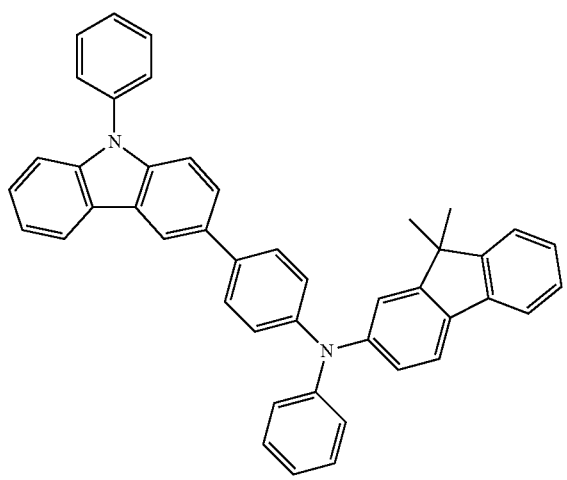

HT2

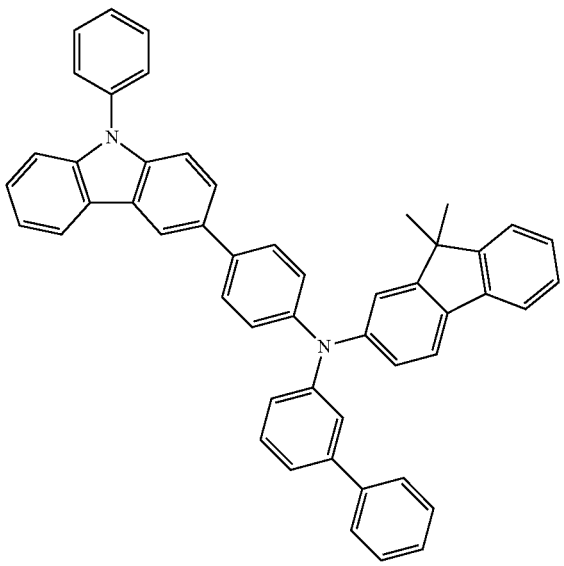

HT3

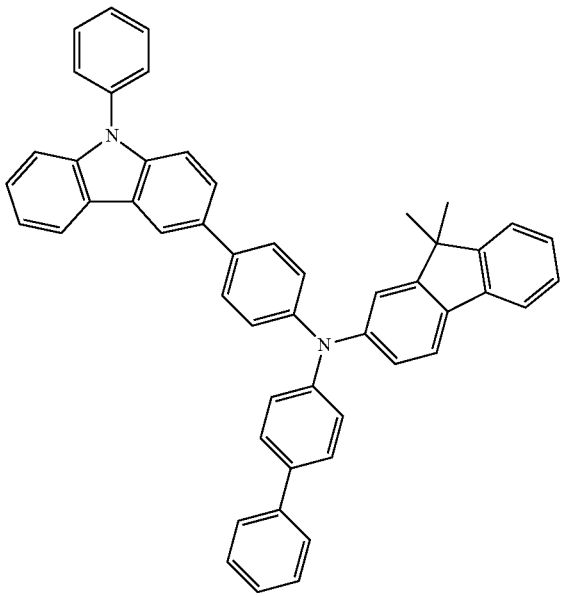

-continued
HT4
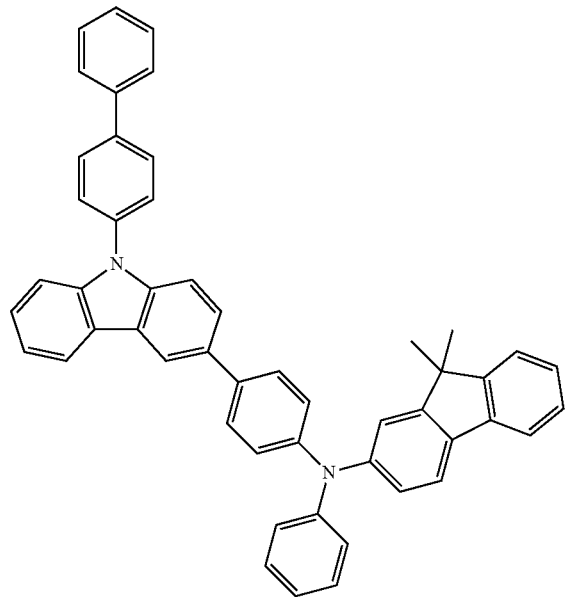
HT5
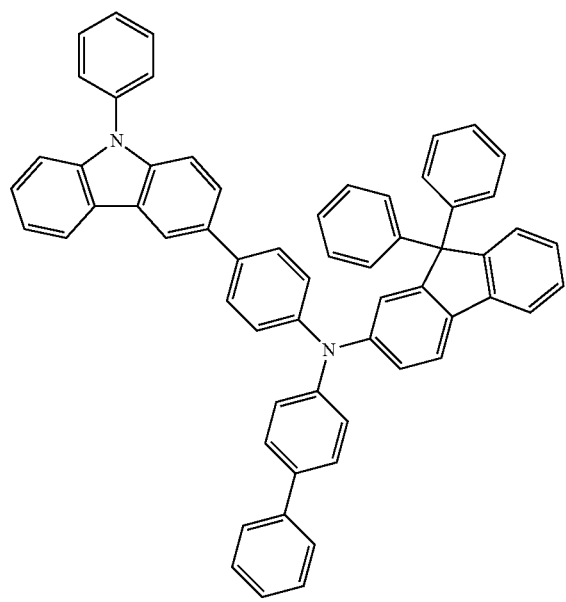
HT6
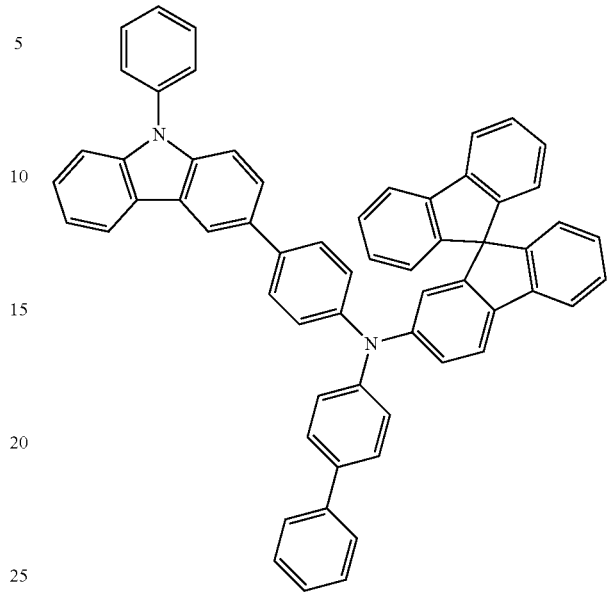
HT7
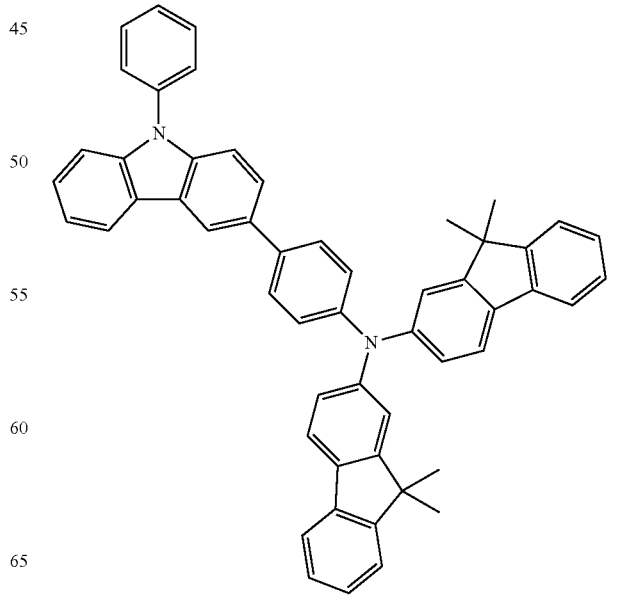

193
-continued
HT8
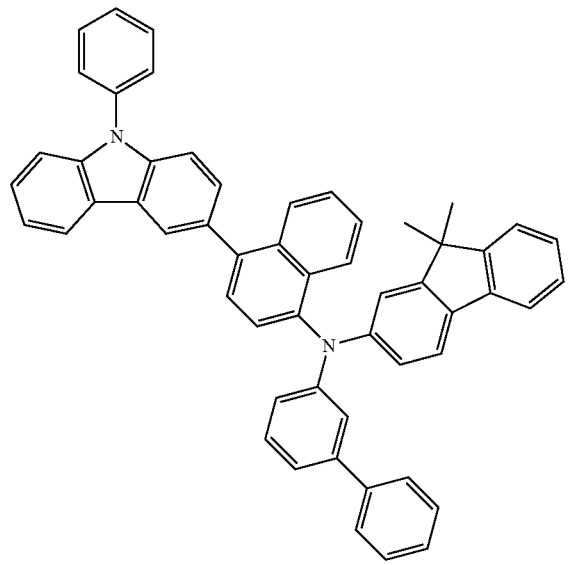
194
-continued
HT10
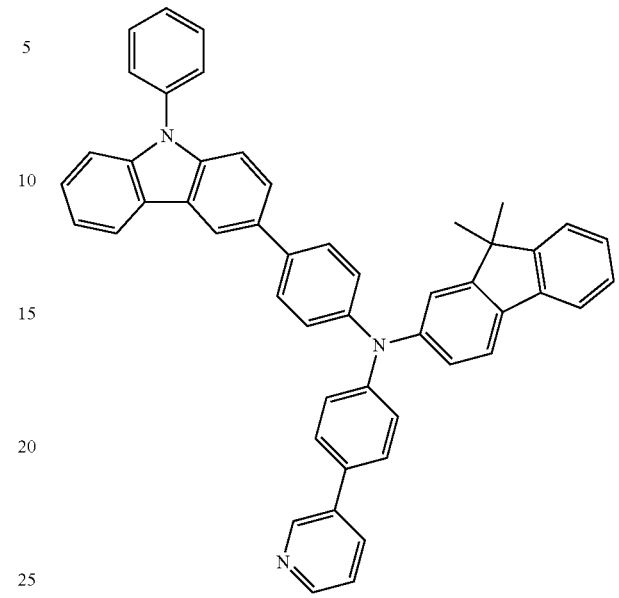
HT9
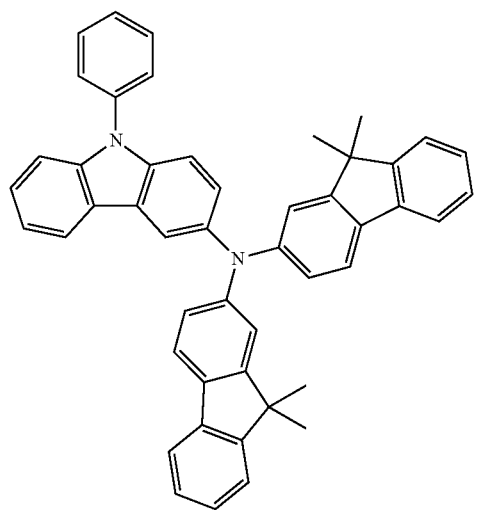
HT11
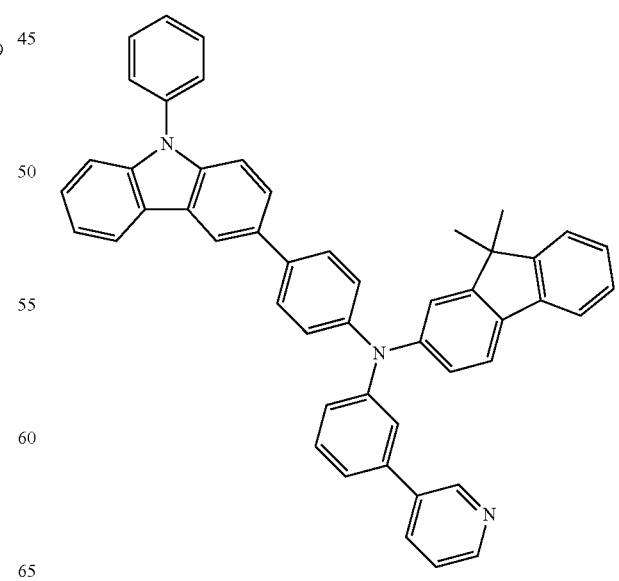

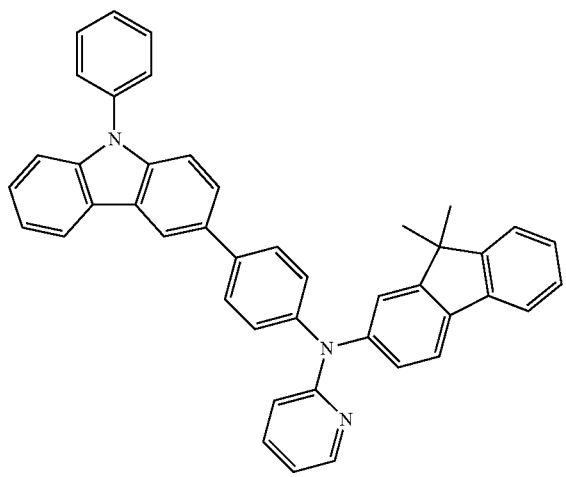
HT12
HT13
HT14
HT15
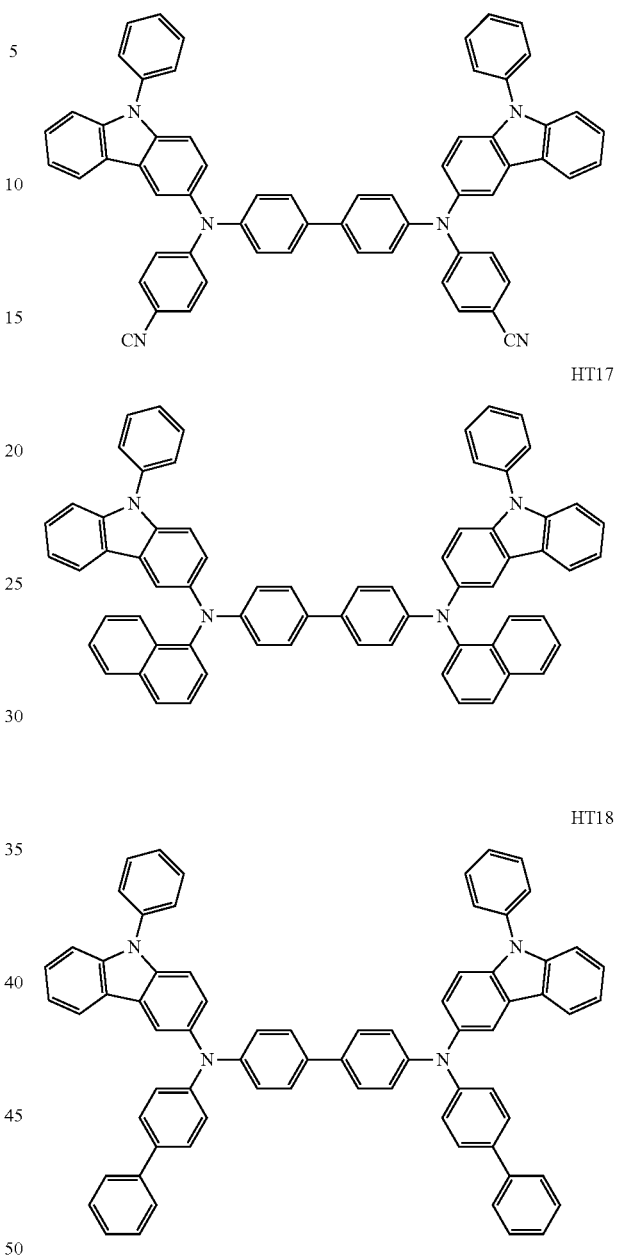
HT16
HT17
HT18
HT19

-continued

HT20

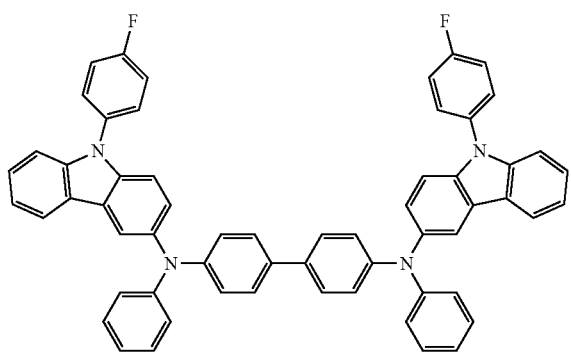

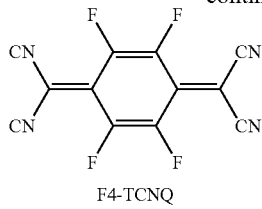

F4-TCNQ

A thickness of the hole transport region may be in a range of about 100 Å to about 10,000 Å, for example, about 100 Å to about 1,000 Å. When the hole transport region includes both an HIL and an HTL, a thickness of the HIL may be in a range of about 100 Å to about 10,000 Å, and, for example, about 100 Å to about 1,000 Å, and a thickness of the HTL may be in a range of about 50 Å to about 2,000 Å, and, for example, about 100 Å to about 1,500 Å. When thicknesses of the hole transport region, the HIL, and the HTL are within these ranges described above, hole transporting properties may be suitable or satisfactory without a substantial increase in a driving voltage.

The hole transport region may further include a charge-generating material to improve conductive properties in addition to the materials described above. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, but embodiments are not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below, but embodiments are not limited thereto.

The hole transport region may further include, in addition to the HIL and the HTL, at least one of a buffer layer and an EBL. The buffer layer may compensate for an optical resonance distance of light according to a wavelength of the light emitted from the emission layer, and thus, may improve light-emission efficiency. In this regard, a material that is included in the hole transport region may be used as a material that is included in the buffer layer. The EBL may serve as a layer that reduces or prevents electrons from being injected from the electron transport region.

The emission layer may be formed on the first electrode 110 or on the hole transport region by using various suitable methods, such as vacuum deposition, spin coating, casting, a LB method, ink-jet printing, laser-printing, or LITI. When the emission layer is formed by vacuum deposition or by spin coating, the deposition conditions or the coating conditions may be the same or substantially the same as (e.g., may be inferred based on) the deposition conditions or the coating conditions for forming the HIL.

When the organic light-emitting device 10 is a full-color organic light-emitting device, the emission layer may be patterned into a red emission layer, a green emission layer, and a blue emission layer, according to an individual sub-pixel. Alternatively, the emission layer may have a structure of a red emission layer, a green emission layer, and a blue emission layer, each of which layers are sequentially stacked in the stated order. In this regard, a material emitting red light, a material emitting green light, and a material emitting blue light may have a mixed structure without having division of layers, thereby emitting white light.

The emission layer may include a host and a dopant. The host may include at least one of the heterocyclic compounds of Formula 1.

The host may include, in addition to the heterocyclic compound of Formula 1, at least one of TPBi, TBADN, AND (also referred to as "DNA"), CBP, CDBP, and TCP:

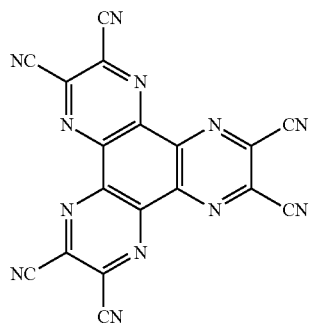

Compound HT-D1

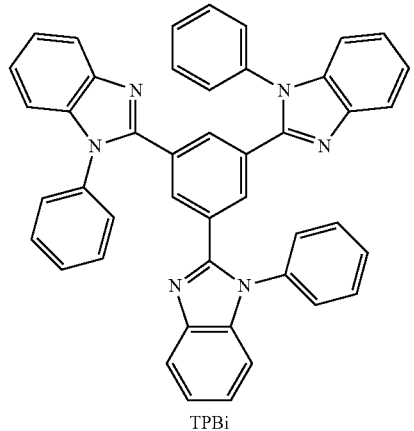

TPBi

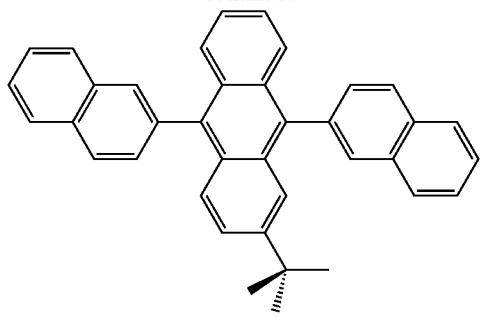

TBADN

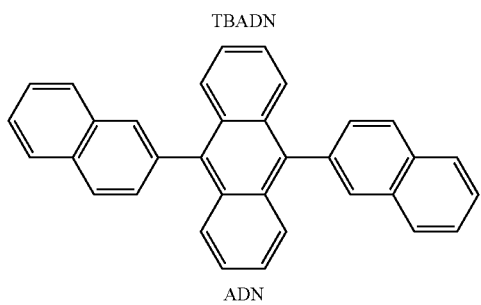

ADN

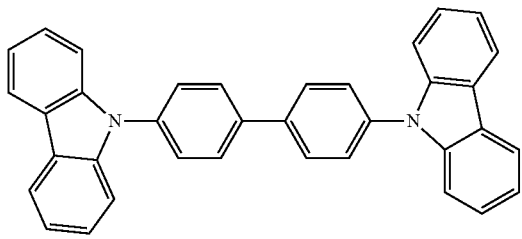

CBP

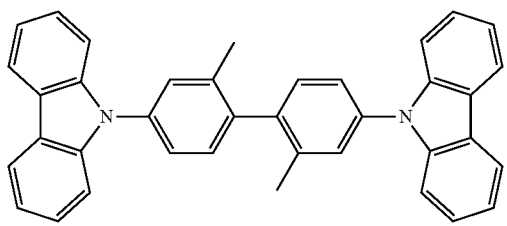

CDBP

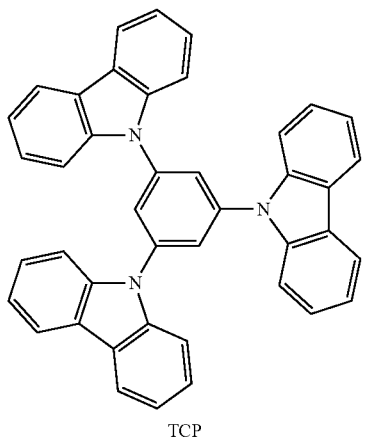

TCP

The dopant may include at least one of a fluorescent dopant and a phosphorescent dopant.

The phosphorescent dopant may include an organic metal complex represented by Formula 401:

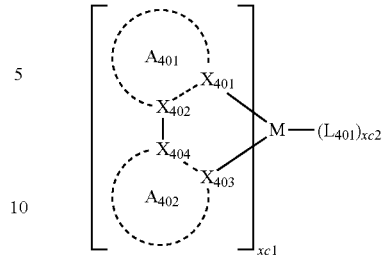

Formula 401

In Formula 401,

M may be selected from iridium (Ir), platinum (Pt), osmium (Os), titanium (Ti), zirconium (Zr), hafnium (Hf), europium (Eu), terbium (Tb), and thulium (TM);

$X_{401}$ to $X_{404}$ may be each independently N or C;

$A_{401}$ and $A_{402}$ rings may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene;

at least one of substituents of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isoxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzimidazole, the substituted benzofuran, the substituted benzothiophene, the substituted isobenzothiophene, the substituted benzoxazole, the substituted isobenzoxazole, the substituted triazole, the substituted oxadiazole, the substituted triazine, the substituted dibenzofuran, and the substituted dibenzothiophene may be selected from:

a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$aryloxy(aryloxy group, $C_6$-$C_{60}$arylthio(arylthio group, $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_1$-$C_{10}$heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{433}$)($Q_{434}$)($Q_{435}$), and —B($Q_{426}$)($Q_{427}$)

$L_{401}$ may be an organic ligand;

xc1 may be 1, 2, or 3; and xc2 may be 0, 1, 2, or 3, wherein $Q_{401}$ to $Q_{407}$, $Q_{411}$ to $Q_{417}$, and $Q_{421}$ to $Q_{427}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group.

In an example embodiment, $L_{401}$ may be a monovalent organic ligand, a divalent organic ligand, or a trivalent organic ligand. For example, $L_{401}$ may be selected from a halogen ligand (e.g., Cl or F), a diketone ligand (e.g., acetylacetonate, 1,3-diphenyl-1,3-propanedionate, 2,2,6,6-tetramethyl-3,5-heptanedionate, or hexafluoroacetonate, a carboxylic acid ligand (e.g., picolinate, dimethyl-3-pyrazolecarboxylate, or benzoate), a carbon monoxide ligand, an isonitrile ligand, a cyano ligand, and a phosphorus ligand (e.g., phosphine or phosphite), but is not limited thereto.

When $A_{401}$ in Formula 401 has 2 or more substituents, 2 or more substituents of $A_{401}$ may be bonded to each other to form a saturated ring or an unsaturated ring.

When $A_{402}$ in Formula 401 has 2 or more substituents, 2 or more substituents of $A_{402}$ may be bonded to each other to form a saturated ring or an unsaturated ring.

When xc1 in Formula 401 is 2 or more, a plurality of ligands

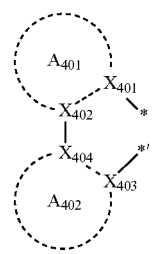

in Formula 401 may be identical to or different from each other. When xc1 in Formula 401 is 2 or more, $A_{401}$ and $A_{402}$ may be each independently bonded to $A_{401}$ and $A_{402}$ of other neighboring ligands, directly or via a linking group (e.g., a $C_1$-$C_5$ alkylene group, —N(R')— (wherein R' may be a $C_1$-$C_{10}$ alkyl group or a $C_6$-$C_{20}$ aryl group), or —C(=O)—).

The phosphorescent dopant may include at least one of Compounds PD1 to PD74, but is not limited thereto:

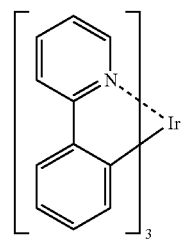

PD1

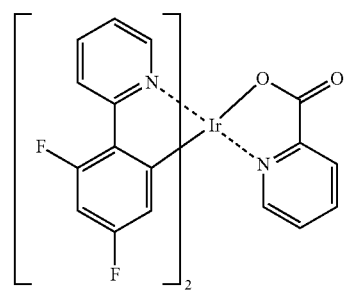

PD2

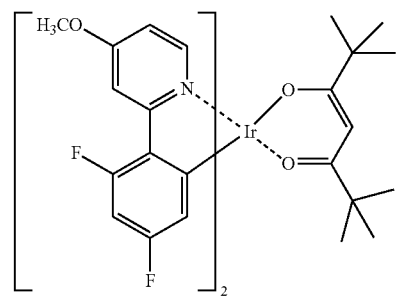

PD3

PD4
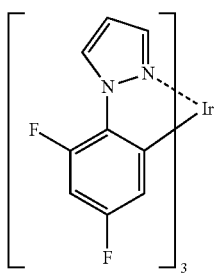
PD5
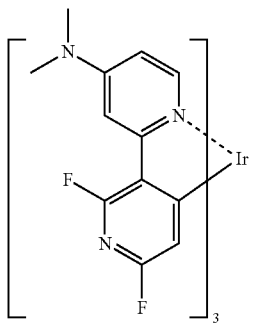
PD6
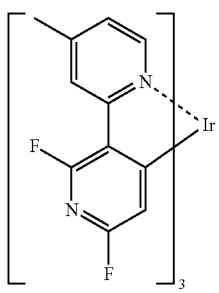
PD7
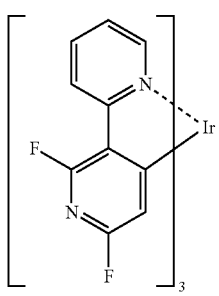
PD8
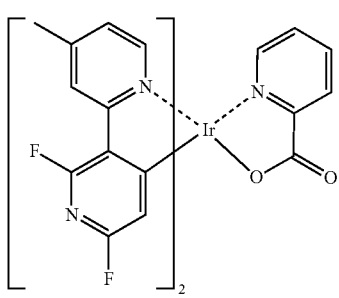
PD9
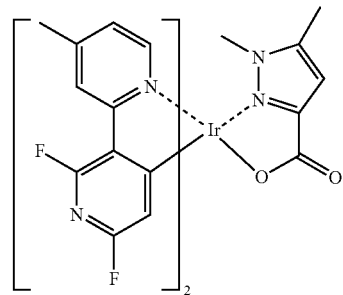
PD10
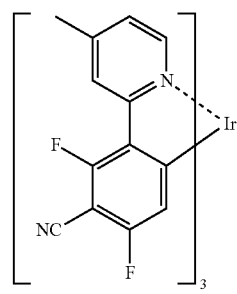
PD11
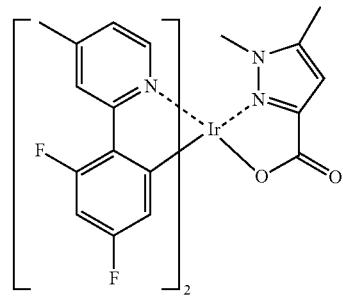
PD12
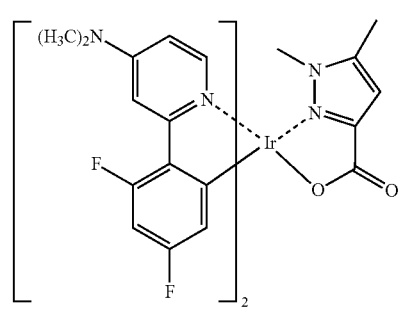
PD13
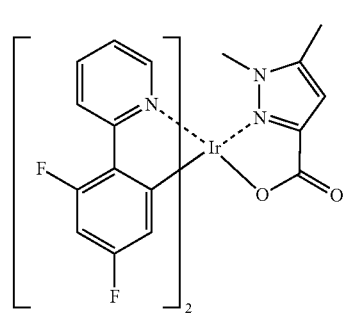

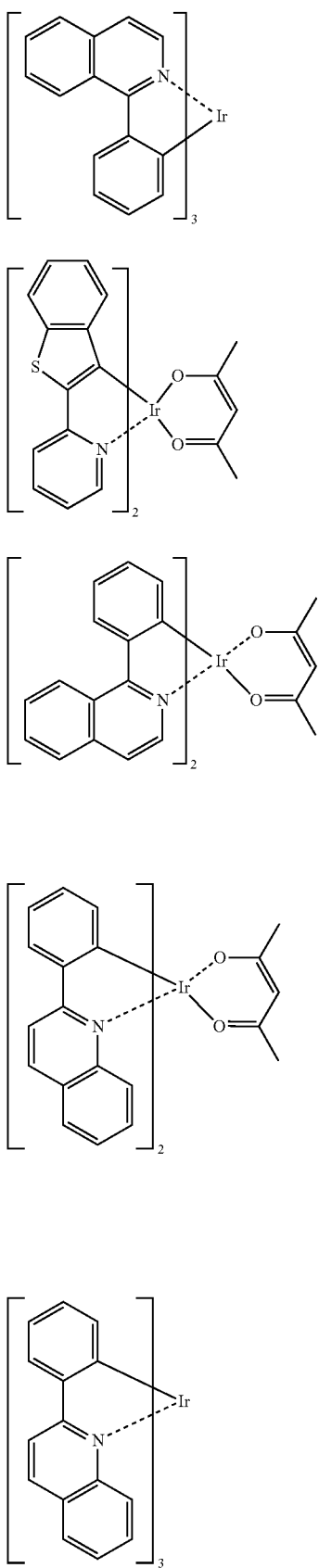
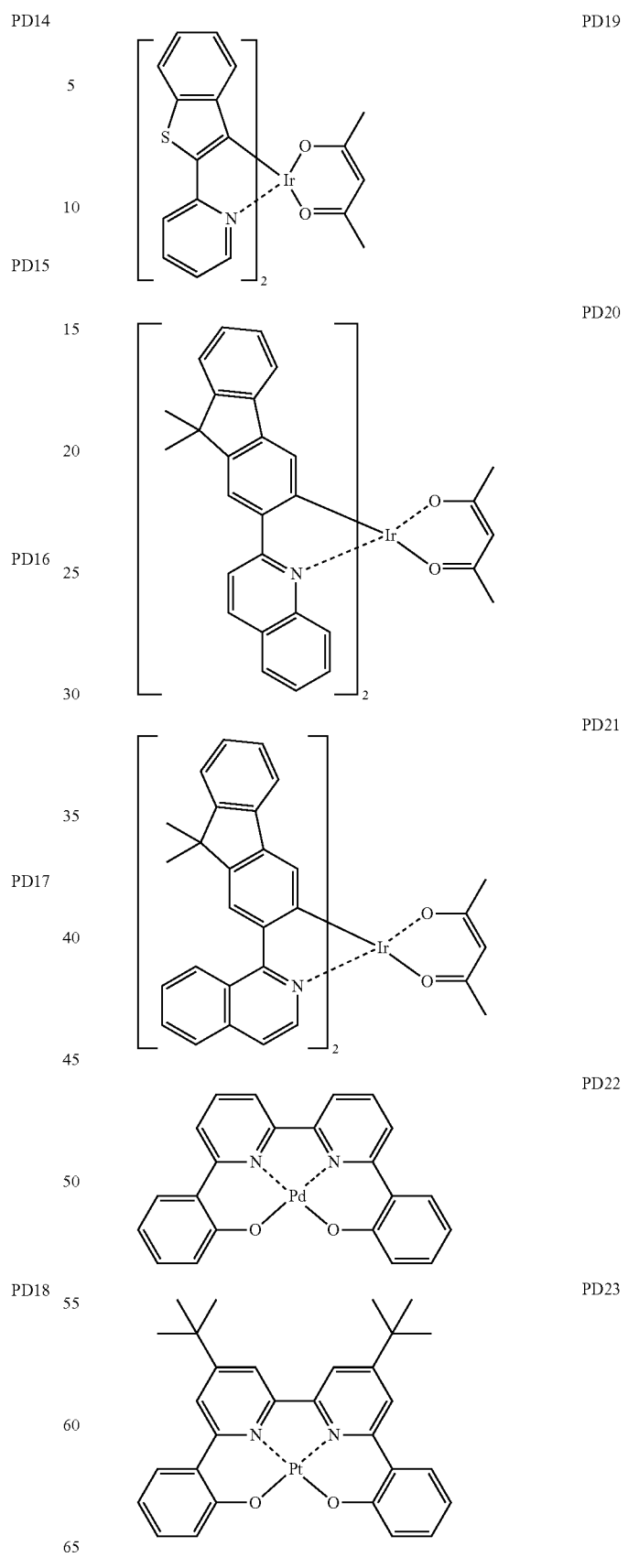

PD24 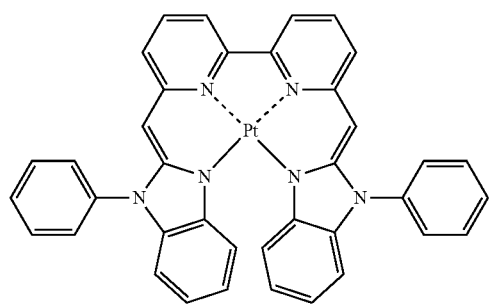
PD25 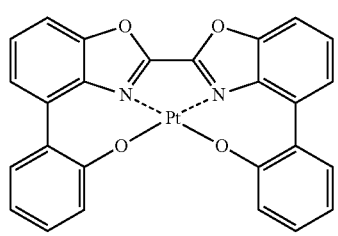
PD26 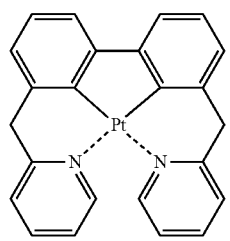
PD27 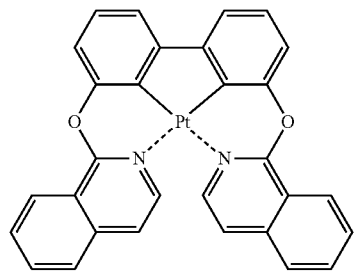
PD28 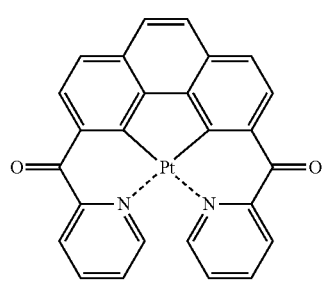
PD29 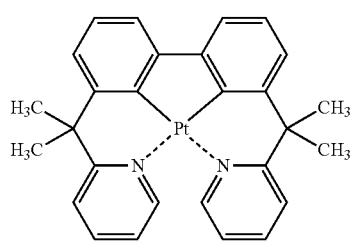
PD30 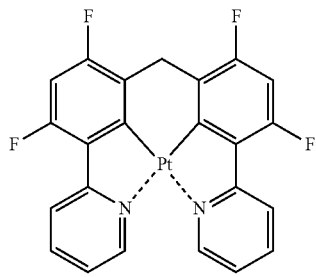
PD31 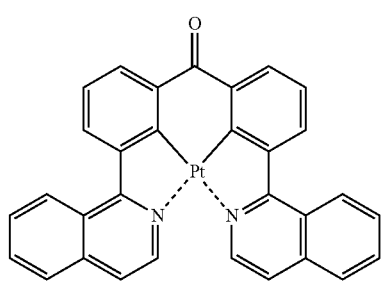
PD32 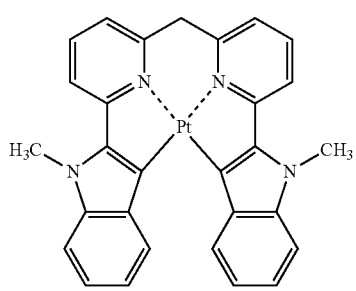
PD33 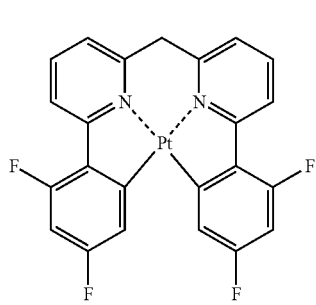
PD34 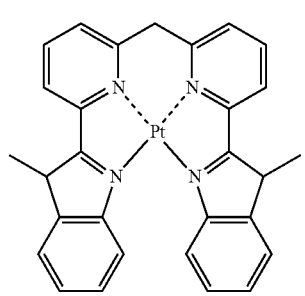

-continued
PD35 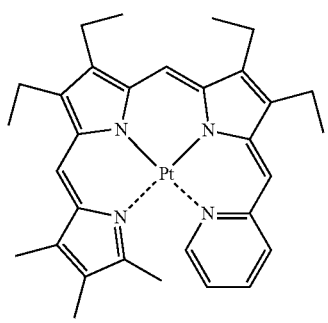
PD36 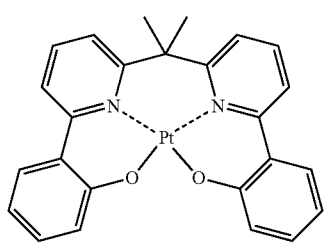
PD37 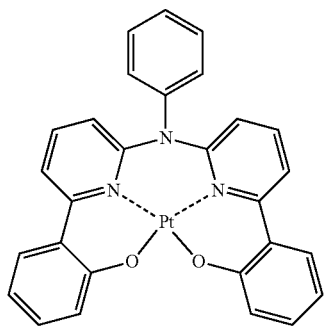
PD38 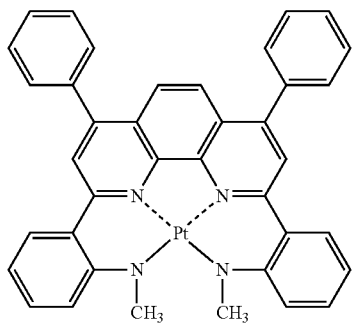
PD39 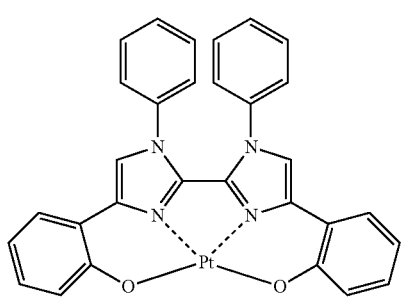
-continued
PD40 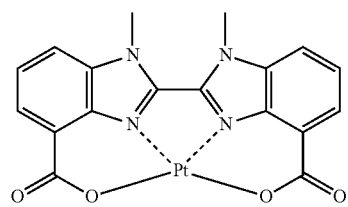
PD41 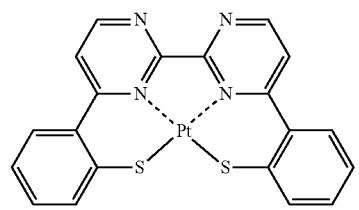
PD42 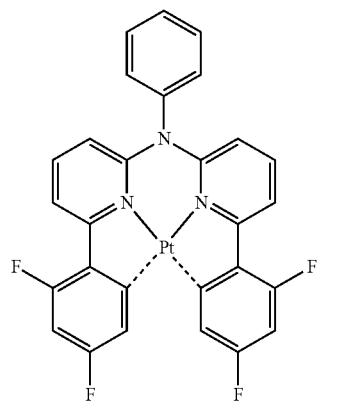
PD43 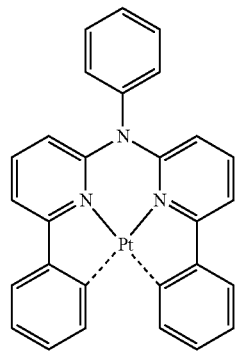
PD44 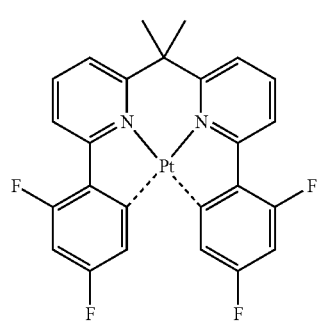

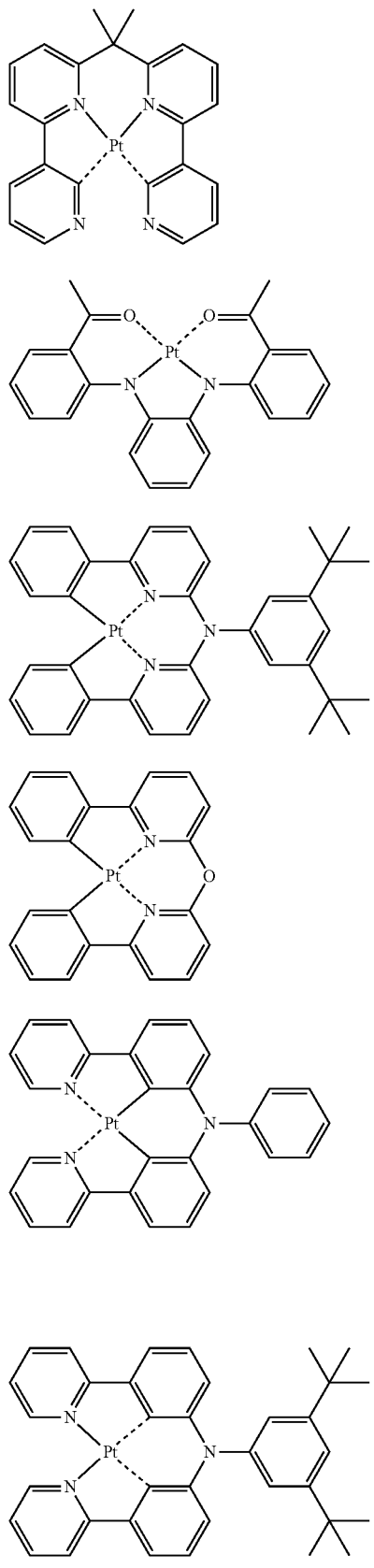
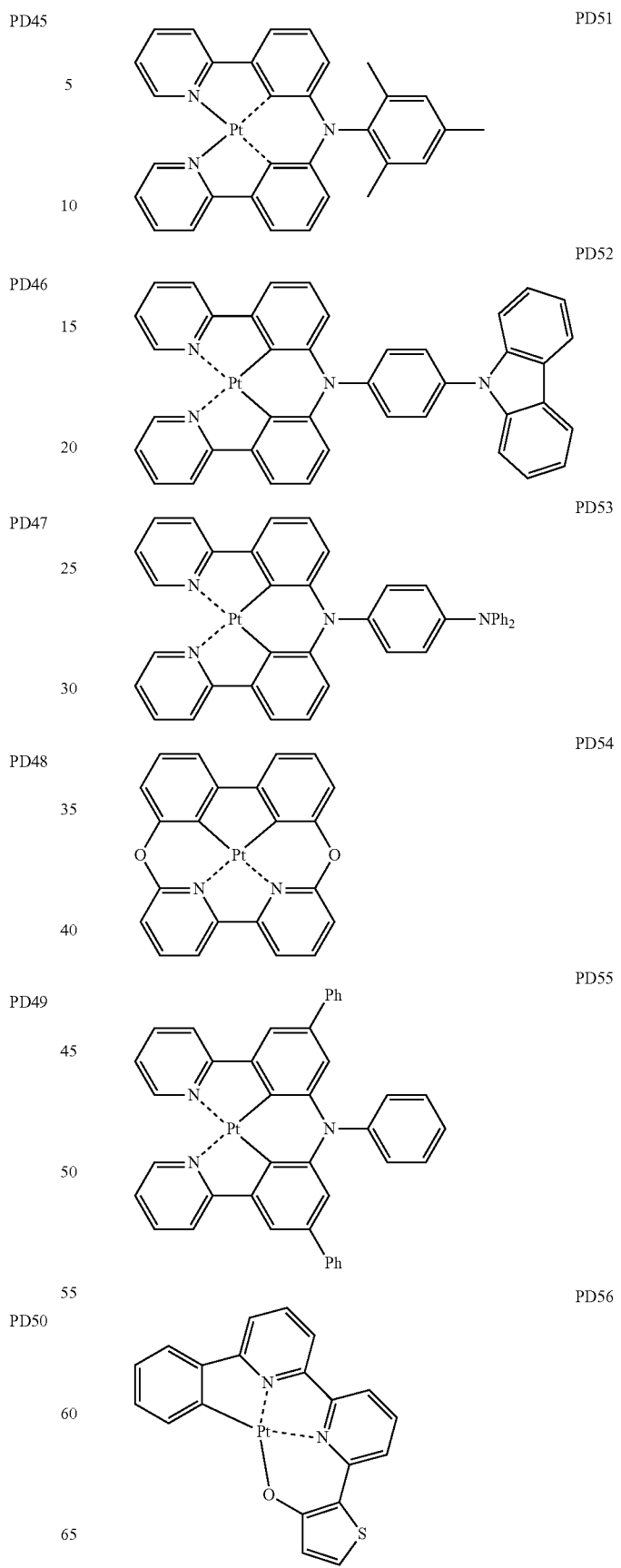

PD57
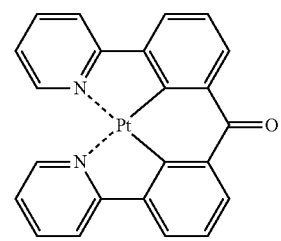
PD58
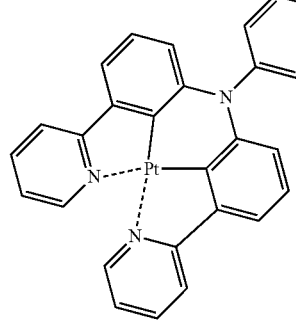
PD59
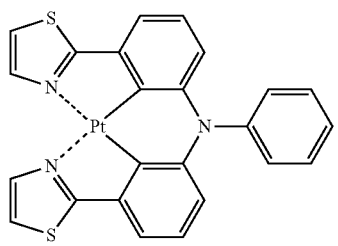
PD60
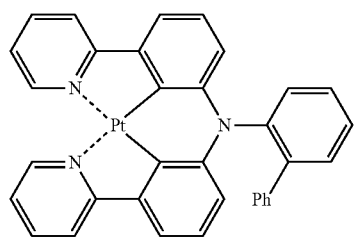
PD61
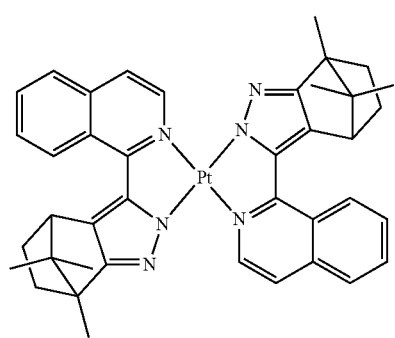
PD62
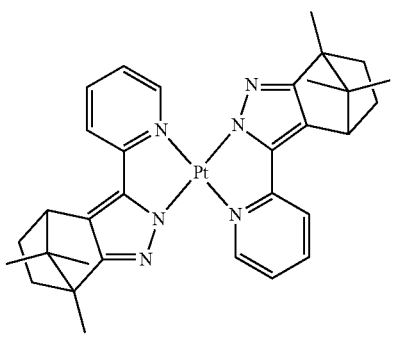
PD63
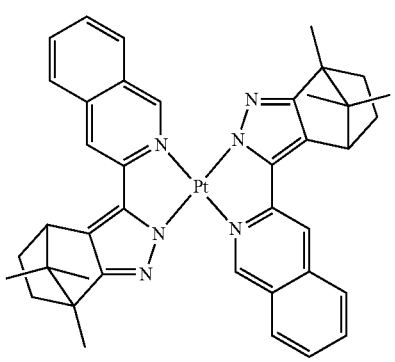
PD64
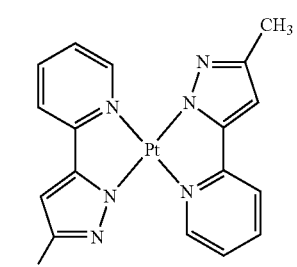
PD65
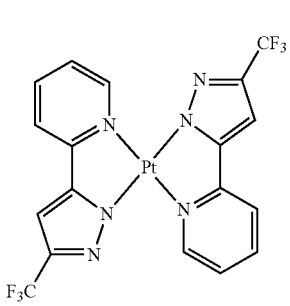
PD66
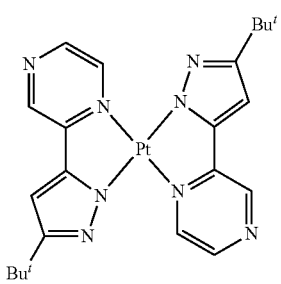

-continued

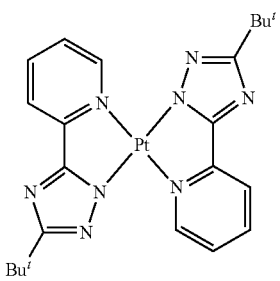
PD67

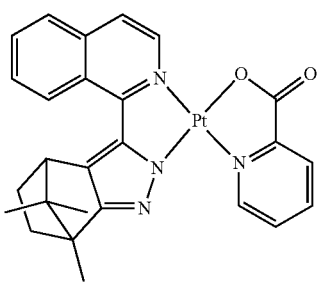
PD68

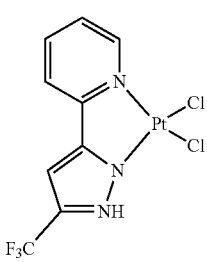
PD69

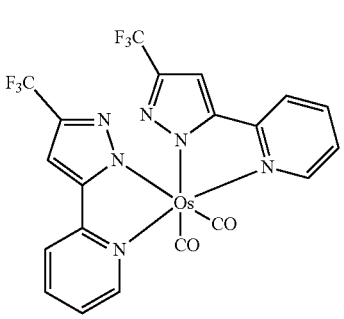
PD70

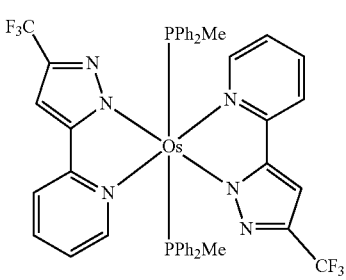
PD71

-continued

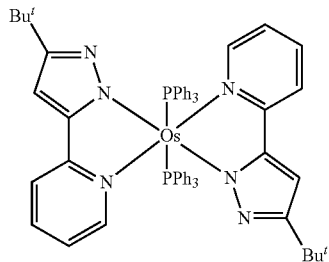
PD72

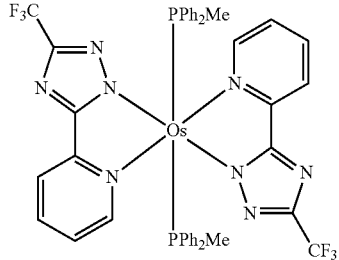
PD73

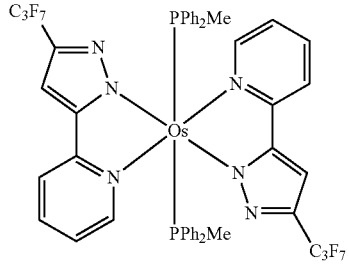
PD74

Alternatively, the phosphorescent dopant may include PtOEP:

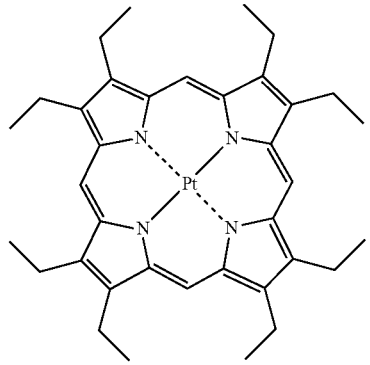
PtOEP

An amount of the dopant included in the emission layer may be from about 0.01 to about 15 parts by weight, based on 100 parts by weight of the host, but is not limited thereto.

A thickness of the emission layer may be from about 100 Å to about 1,000 Å, e.g., about 200 Å to about 600 Å. When the thickness of the emission layer is within these ranges, excellent emission characteristics may be obtained without a substantial increase in driving voltage.

Next, the electron transport region may be disposed on the emission layer.

The electron transport region may include at least one of an HBL, an ETL, and an EIL, but embodiments are not limited thereto.

For example, the electron transport region may have a structure of ETL/EIL or a structure of HBL/ETL/EIL, each of which layers are sequentially stacked in the stated order from the emission layer, but embodiments are not limited thereto.

The electron transport region may include an HBL. When the emission layer includes a phosphorescent dopant, the HBL may serve as a layer that reduces or prevents triplet excitons or holes from being diffused into the ETL.

When the electron transport region includes the HBL, the HBL may be formed on the emission layer by using various suitable methods, such as vacuum deposition, spin coating, casting, a LB method, ink-jet printing, laser-printing, or LITI. When the HBL is formed by vacuum deposition or by spin coating, the deposition conditions or the coating conditions may be the same or substantially the same as (e.g., may be inferred based on) the deposition conditions or the coating conditions for forming the HIL.

The HBL may include, for example, at least one of BCP and Bphen, but embodiments are not limited thereto.

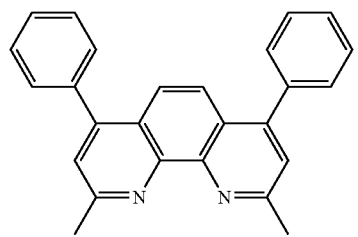

BCP

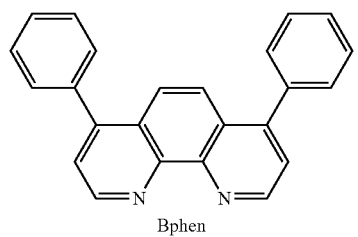

Bphen

A thickness of the HBL may be from about 20 Å to about 1,000 Å, e.g., about 30 Å to about 300 Å. When the thickness of the HBL is within these ranges, excellent hole blocking characteristics may be obtained without a substantial increase in driving voltage.

The electron transport region may include an ETL, and the ETL may be formed on the emission layer or on the HBL by using various suitable methods, such as vacuum deposition, spin coating, casting, a LB method, ink-jet printing, laser-printing, or LITI. When the ETL is formed by vacuum deposition or by spin coating, the deposition conditions or the coating conditions may be the same or substantially the same as (e.g., may be inferred based on) the deposition conditions or the coating conditions for forming the HIL.

The ETL may include at least one of BCP and Bphen above and Alq$_3$, Balq, TAZ, and NTAZ:

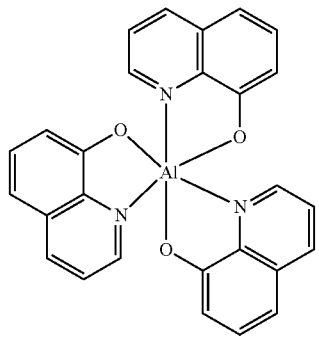

Alq3

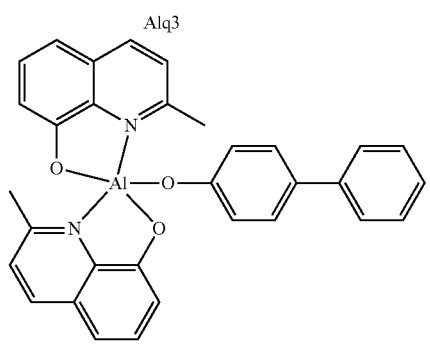

BAlq

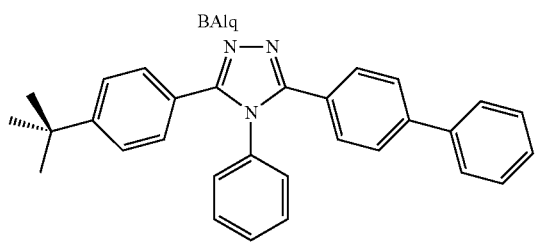

TAZ

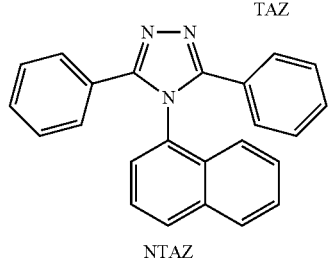

NTAZ

Alternatively, the ETL may include at least one of compounds represented by Formula 601:

$$Ar_{601}-[(L_{601})_{xe1}-E_{601}]_{xe2}$$  Formula 601

In Formula 601, $Ar_{601}$ may be the same as defined in connection with $Ar_{301}$ (e.g., $Ar_{601}$ may be the same or substantially the same as described with respect to $Ar_{301}$);

$L_{601}$ may be the same as defined in connection with $L_{201}$ (e.g., $L_{601}$ may be the same or substantially the same as described with respect to $L_{201}$);

$E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group;

xe1 may be selected from 0, 1, 2, and 3; and
xe2 may be selected from 1, 2, 3, and 4.

Alternatively, the ETL may include at least one of compounds represented by Formula 602:

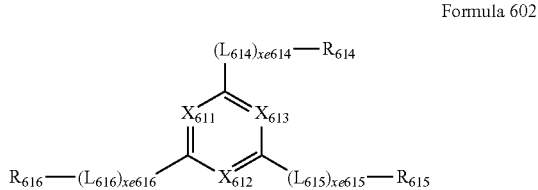

Formula 602

In Formula 602, $X_{611}$ may be N or C-$(L_{611})_{xe611}$-$R_{611}$; $X_{612}$ may be N or C-$(L_{612})_{xe612}$-$R_{612}$; $X_{613}$ may be N or C-$(L_{613})_{xe613}$-$R_{613}$, and at least one of $X_{611}$ to $X_{613}$ may be N;

$L_{611}$ to $L_{616}$ may be each independently the same as defined in connection with $L_{201}$ in the present specification (e.g., $L_{601}$ to $L_{616}$ may each independently be the same or substantially the same as described with respect to $L_{201}$);

$R_{611}$ to $R_{616}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from 0, 1, 2, and 3.

The compound represented by Formula 601 and the compound represented by 602 may include at least one of Compounds ET1 to ET16:

ET1
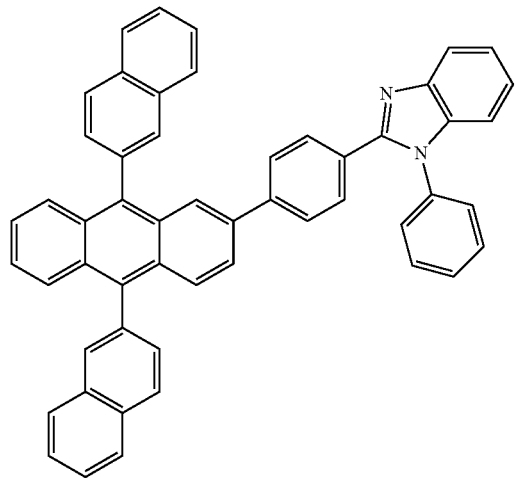
ET2
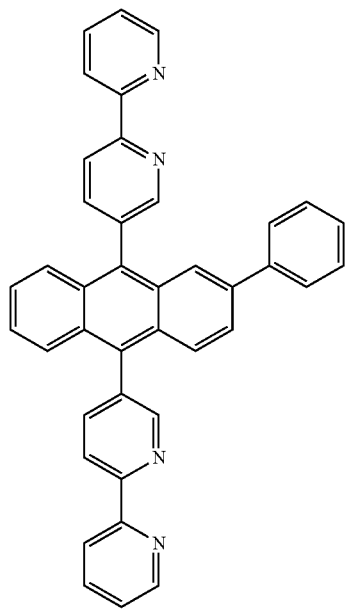
ET3
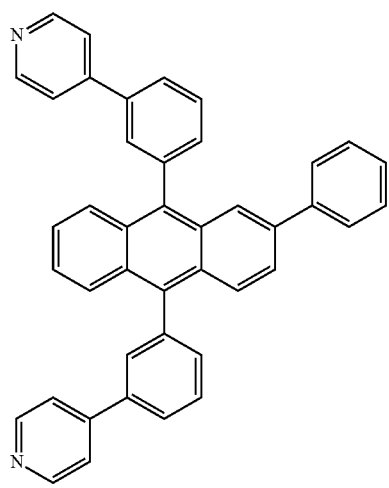
ET4
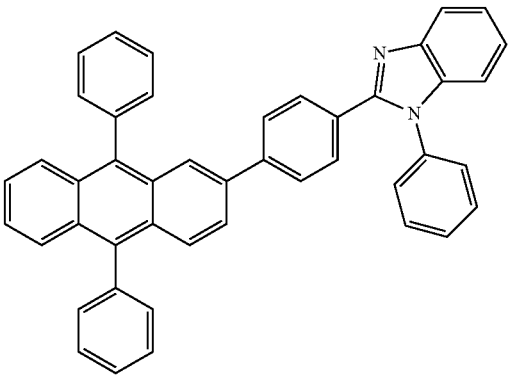
ET5
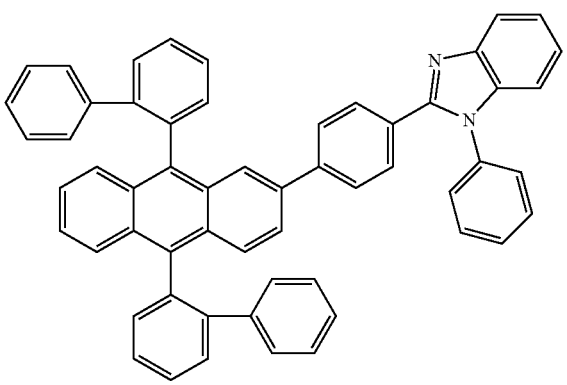
ET6
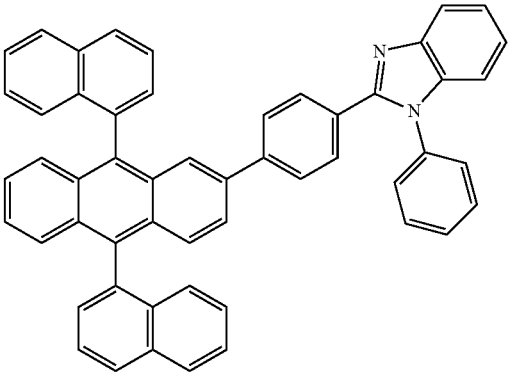

ET7
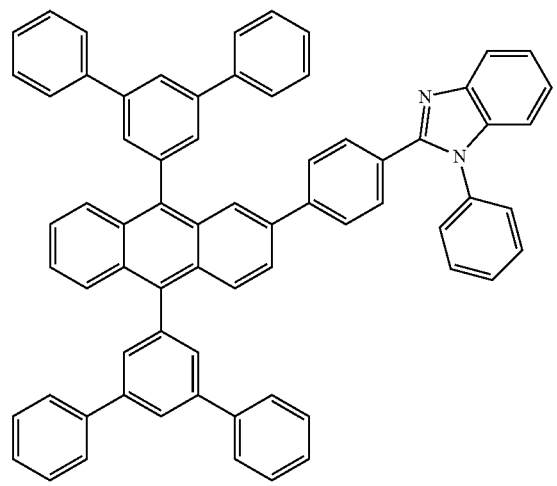
ET8
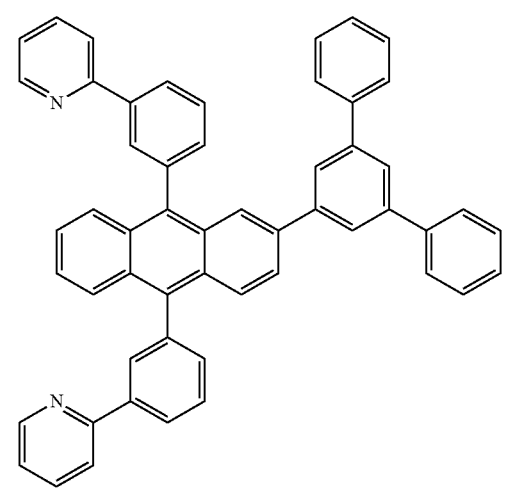
ET9
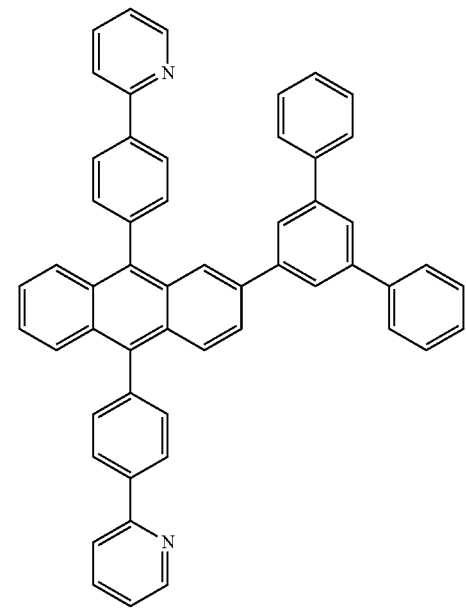
ET10
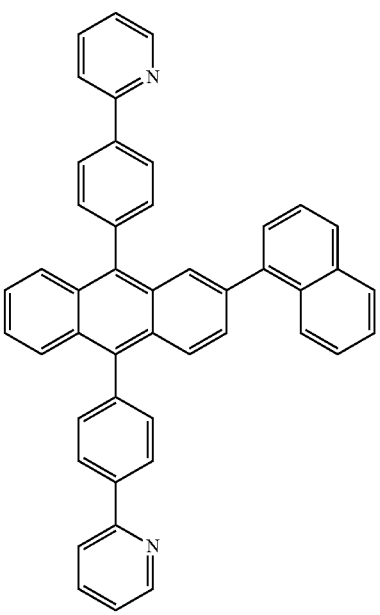
ET11
ET12
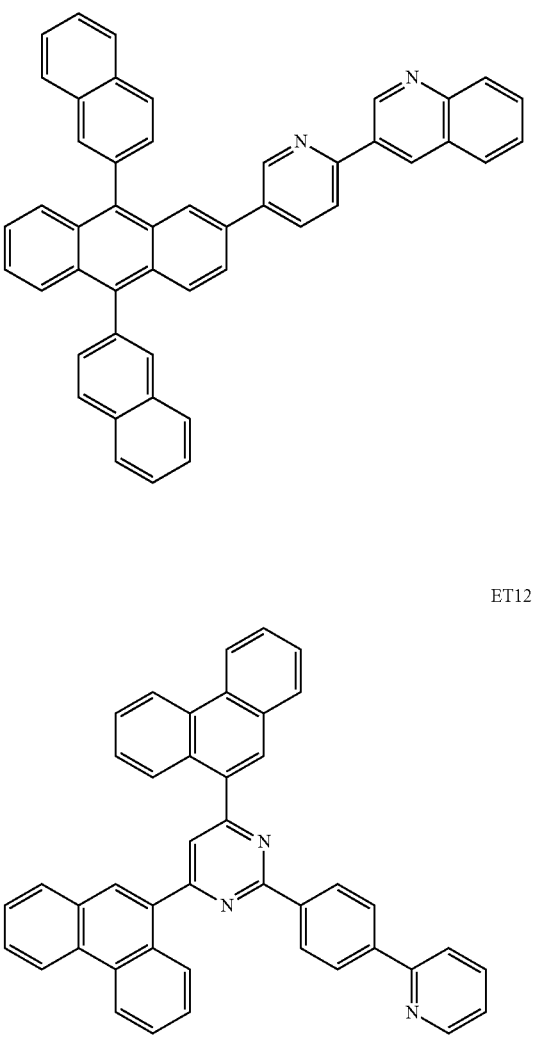

-continued

ET13
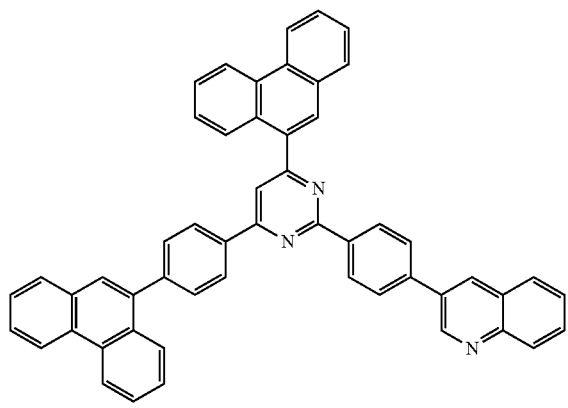

ET14
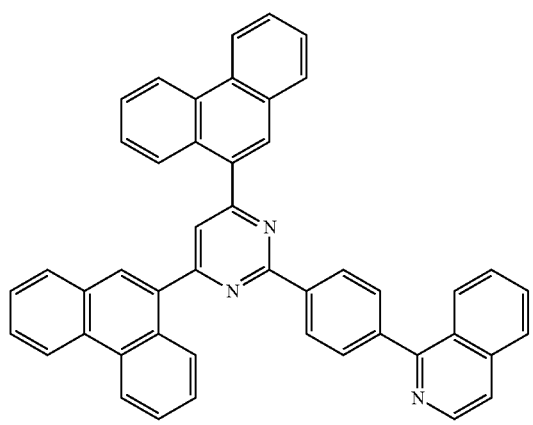

ET15
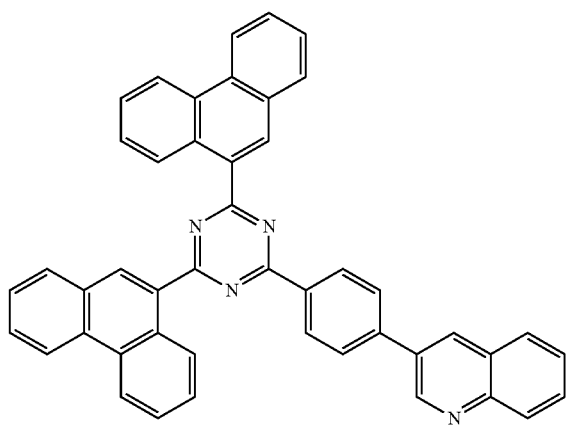

-continued

ET16
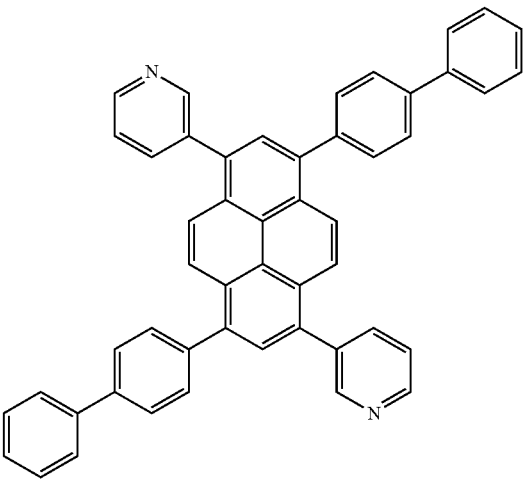

A thickness of the ETL may be from about 100 Å to about 1,000 Å, e.g., about 150 Å to about 500 Å. When the thickness of the ETL is within these ranges, excellent electron transporting characteristics may be obtained without a substantial increase in driving voltage.

The ETL may further include, in addition to the materials described above, a metal-containing material.

The metal-containing material may include a Li complex. The Li complex may include, for example, Compound ET-D1 (e.g., lithium quinolate (LiQ)) or ET-D2.

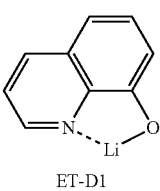
ET-D1

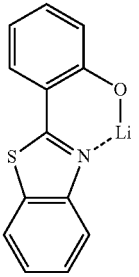
ET-D2

The electron transport region may include an EIL that facilitates electron injection from the second electrode 190.

The EIL may be formed on the ETL by using various suitable methods, such as vacuum deposition, spin coating, casting, a LB method, ink-jet printing, laser-printing, or LITI. When the EIL is formed by vacuum deposition or by spin coating, the deposition conditions or the coating conditions may be the same or substantially the same as (e.g., may be inferred based on) the deposition conditions or the coating conditions for forming the HIL.

The EIL may include at least one selected from LiF, NaCl, CsF, $Li_2O$, BaO, and LiQ.

A thickness of the EIL may be from about 1 Å to about 100 Å, e.g., about 3 Å to about 90 Å. When the thickness of the EIL is within these ranges, suitable or satisfactory electron injecting characteristics may be obtained without a substantial increase in driving voltage.

The second electrode 190 may be disposed on the organic layer 150. The second electrode 190 may be a cathode, which is an electron injection electrode. Here, a material for forming the second electrode 190 may be a material having a low work function, such as a metal, an alloy, an electrically conductive compound, or a mixture thereof. Detailed examples of the material for forming the second electrode 190 may include lithium (Li), magnesium (Mg), aluminum (Al), aluminum-lithium (Al—Li), calcium (Ca), magnesium-indium (Mg—In), and magnesium-silver (Mg—Ag). Alternatively, the material for forming the second electrode 190 may include ITO or IZO. The second electrode 190 may be a semi-transmissive electrode or a transmissive electrode.

Hereinbefore, the organic light-emitting device is described in connection with the accompanying drawing, but embodiments are not limited thereto.

A $C_1$-$C_{60}$ alkyl group as used herein refers to a linear or branched aliphatic hydrocarbon monovalent group having 1 to 60 carbon atoms, and detailed examples thereof include a methyl group, an ethyl group, a propyl group, an isobutyl group, a sec-butyl group, a ter-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group), and detailed examples thereof include a methoxy group, an ethoxy group, and an isopropyloxy group.

A $C_2$-$C_{60}$ alkenyl group as used herein refers to a hydrocarbon group formed by substituting at least one carbon double bond in a main chain (e.g., the middle) or terminal end of the $C_2$-$C_{60}$ alkyl group, and detailed examples thereof include an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group formed by substituting at least one carbon triple bond in a main chain (e.g., the middle) or terminal end of the $C_2$-$C_{60}$ alkyl group, and detailed examples thereof are an ethynyl group and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms, and detailed examples thereof include a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_1$-$C_{10}$ heterocycloalkyl group as used herein refers to a monovalent monocyclic group having at least one heteroatom selected from N, O, P, and S as a ring-forming atom and 1 to 10 carbon atoms, and detailed examples thereof include a tetrahydrofuranyl group and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof and does not have aromaticity (e.g., the ring is not aromatic), and detailed examples thereof include a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one heteroatom selected from N, O, P, and S as a ring-forming atom, 1 to 10 carbon atoms, and at least one double bond in its ring. Detailed examples of the $C_1$-$C_{10}$ heterocycloalkenyl group include a 2,3-hydrofuranyl group and a 2,3-hydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, these rings may be fused to each other (e.g., fused together).

A $C_1$-$C_{60}$ heteroaryl group as used herein refers to a monovalent group having a carbocyclic aromatic system that has at least one heteroatom selected from N, O, P, and S as a ring-forming atom, and 1 to 60 carbon atoms. A $C_1$-$C_{60}$ heteroarylene group as used herein refers to a divalent group having a carbocyclic aromatic system that has at least one heteroatom selected from N, O, P, and S as a ring-forming atom, and 1 to 60 carbon atoms. Detailed examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, these rings may be fused to each other (e.g., fused together).

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group as used herein indicates —$SA_{103}$ (wherein $A_{103}$ is the $C_6$-$C_{60}$ aryl group).

A monovalent non-aromatic condensed polycyclic group (e.g., a group having 8 to 60 carbon atoms) as used herein refers to a monovalent group that has two or more rings condensed to each other, has carbon atoms only as a ring-forming atom, and has non-aromaticity in the entire molecular structure (e.g., the entire molecular structure is not aromatic). A detailed example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group (e.g., a group having 1 to 60 carbon atoms) as used herein refers to a monovalent group that has two or more rings condensed to each other, has heteroatoms as a ring-forming atom selected from N, O, P, and S, in addition to C, and has non-aromaticity in the entire molecular structure (e.g., the entire molecular structure is not aromatic). A detailed example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

At least one of substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a —$C_{60}$ alkoxy group;

a $C_1$-$C_{60}$ alkyl group, a $C_2$-$C_{60}$ alkenyl group, a $C_2$-$C_{60}$ alkynyl group, and a —$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, wherein $Q_{11}$ to $Q_{17}$, $Q_{21}$ to $Q_{27}$, and $Q_{31}$ to $Q_{37}$ may be each independently selected from a hydrogen, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and a $C_1$-$C_{30}$ alkoxy group;

a $C_1$-$C_{30}$ alkyl group, a $C_2$-$C_{30}$ alkenyl group, a $C_2$-$C_{30}$ alkynyl group, and a $C_1$-$C_{30}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_1$-$C_{30}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenylene group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a cyclopentyl group, a cyclohexyl group, a cycloheptyl group, cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenylene group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a cyclopentyl group, a cyclohexyl group, a cycloheptyl group, cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group and a $C_1$-$C_{30}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_1$-$C_{30}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_{11}$ to $Q_{17}$ and $Q_{31}$ to $Q_{37}$ may be each independently from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenylene group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a hydrogen, a $C_1$-$C_{30}$ alkyl group, a $C_2$-$C_{30}$ alkenyl group, a $C_2$-$C_{30}$ alkynyl group, a $C_1$-$C_{30}$ alkoxy group, a cyclopentyl group, a cyclohexyl group, a cycloheptyl group, cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, but embodiments are not limited thereto.

Hereinafter, an organic light-emitting device according to an embodiment will be described in detail with reference to Synthesis Examples and Examples. The term "B was used instead of A" used in describing Synthesis Examples denotes that a molar equivalent of A was identical (or substantially the same) to a molar equivalent of B.

EXAMPLE

Synthesis Example 1: Synthesis of Compound 4

1) Reaction Scheme 1-1: Synthesis of Intermediate 1-a

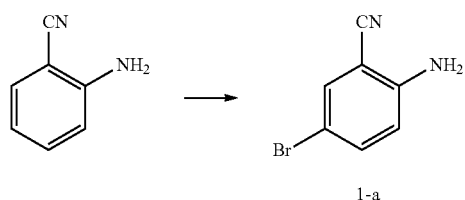 [SMILES: N#Cc1ccccc1N ; N#Cc1cc(Br)ccc1N]

1-a 35.1 g (297 mmol) of 2-aminobenzonitrile, 55.56 g (312 mmol) of N-bromosuccinimide, and 350 mL of dimethylformamide were placed in a 1 L reactor, and then, stirred for 4 hours. After distilled water was added thereto, solid residues obtained by filtering the reaction solution were separated-purified by chromatography, so as to obtain 54.2 g (yield: 92.6%) of Intermediate 1-a.

2) Reaction Scheme 1-2: Synthesis of Intermediate 1-b

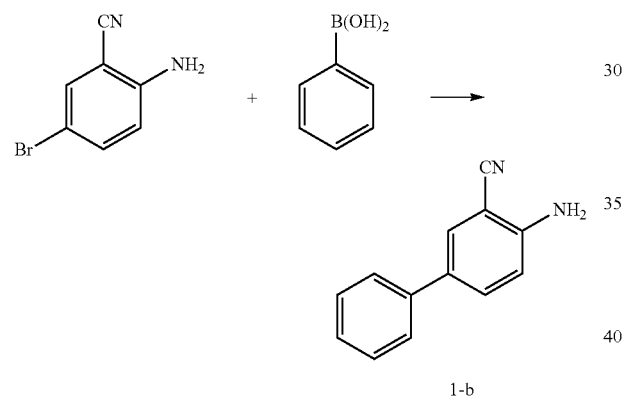

1-b 50 g (254 mmol) of Intermediate 1-a, 40.2 g (330 mmol) of phenylboronic acid, 13.3 g (12.0 mmol) of tetrakis(triphenylphosphine)palladium, 70.1 g (508 mmol) of potassium carbonate, 250 mL of 1,4-dioxane, 250 mL of toluene, and 100 mL of distilled water were placed in a 2 L reactor, and then, stirred at a temperature of 100° C. for 12 hours. The reaction solution was cooled to room temperature, and then, extracted using ethylacetate. An organic layer obtained therefrom was concentrated under reduced pressure and separated-purified by chromatography, so as to obtain 45 g (yield: 91%) of Intermediate 1-b.

3) Reaction Scheme 1-3: Synthesis of Intermediate 1-c

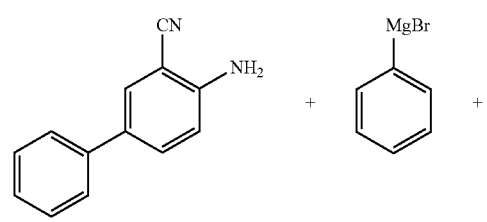

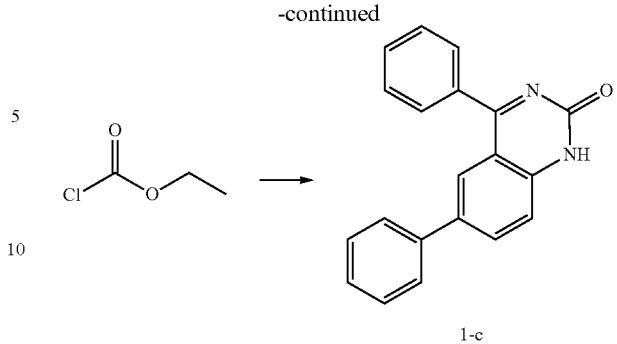

1-c 45.0 g (232 mmol) of Intermediate 1-b and 450 mL of tetrahydrofuran were placed in a 2 L reactor, and then, stirred. After the reaction solution was cooled to 0° C., 88.2 mL (487 mmol) of 3M phenylmagnesiumbromide was added dropwise thereto, and then, the mixed solution was refluxed for 3 hours. After the refluxed solution was cooled to 0° C., a solution in which 44.3 g (732 mmol) of ethylchloroformate was dissolved with 200 ml of tetrahydrofuran was added dropwise thereto, and then, the mixed solution was refluxed for 2 hours. After the refluxed solution was cooled to 0° C., a saturated ammonium chloride aqueous solution was added thereto, and then, extracted using ethylacetate and water. An organic layer obtained therefrom was concentrated under reduced pressure and separated-purified by chromatography, so as to obtain 46 g (yield: 80%) of Intermediate 1-c.

4) Reaction Scheme 1-4: Synthesis of Intermediate 1-d

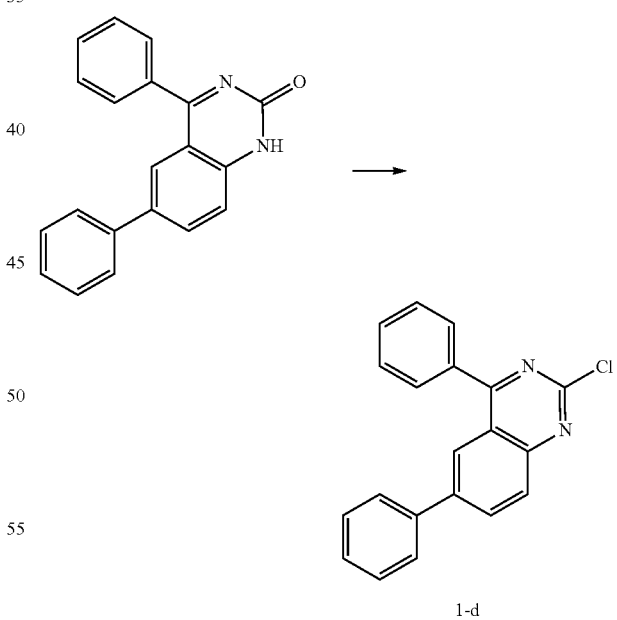

1-d 40 g (134 mmol) of Intermediate 1-c and 500 mL of phosphorus oxycloride were placed in a 2 L reactor, and then, refluxed for 5 hours. After the reaction solution was cooled to 0° C., distilled water was added dropwise thereto. Solid residues obtained by filtering the reaction solution were separated-purified by chromatography, so as to obtain 30.5 g (yield: 70.6%) of Intermediate 1-d.

5) Reaction Scheme 1-5: Synthesis of Intermediate 1-e

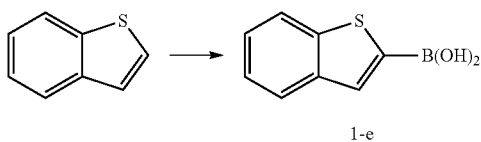 [SMILES: c1ccc2sccc2c1 ; OB(O)c1cc2ccccc2s1]

1-e 144 g (554 mmol) of benzothiophene and 1,000 mL of tetrahydrofuran were added in a 2 L reactor, and then, cooled to −78° C. 415 mL of n-butyllithium (1.6M hexane solution) was added dropwise thereto, and then, the mixed solution was stirred for 1 hour. After the reaction solution was stirred for 12 hours when warmed up to room temperature, the reaction solution was cooled to −78° C. again. 80.3 mL (664 mmol) of trimethylborate was added dropwise thereto, and then, the reaction solution was stirred for 2 hours when warmed up to room temperature. The reaction solution was cooled to 0° C. again, and then, 2N hydrochloric acid solution was added thereto. The mixed solution was extracted using ethylacetate and distilled water. An organic layer obtained therefrom was concentrated under reduced pressure and separated-purified by chromatography, so as to obtain 86 g (yield: 87.3%) of Intermediate 1-e.

6) Reaction Scheme 1-6: Synthesis of Intermediate 1-f

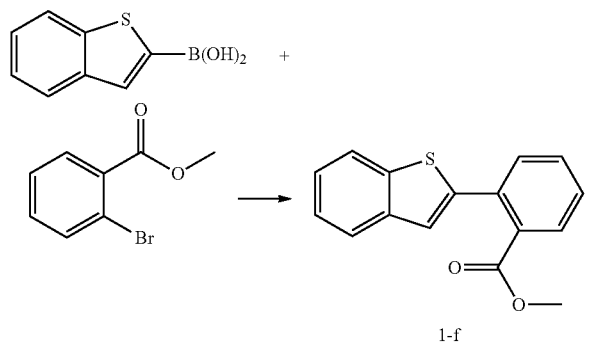

1-f 75 g (349 mmol) of 2-bromo methylbenzoate, 80.7 g (453 mmol) of Intermediate 1-e, 10.1 g (9 mmol) of tetrakis(triphenylphosphine)palladium, 120.5 g (872 mmol) of potassium carbonate, 370 mL of 1,4-dioxane, 370 mL of toluene, and 160 mL of distilled water were placed in a 2 L reactor, and then, stirred at a temperature of 100° C. for 12 hours. The reaction solution was cooled to room temperature, and then, extracted using ethylacetate. An organic layer obtained therefrom was concentrated under reduced pressure and separated-purified by chromatography, so as to obtain 80 g (yield: 85.9%) of Intermediate 1-f.

7) Reaction Scheme 1-7: Synthesis of Intermediate 1-g

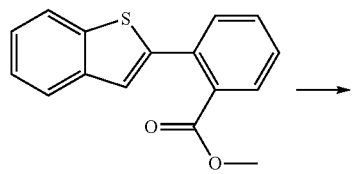

-continued

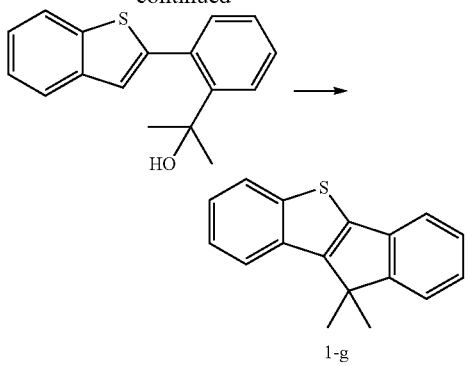

1-g 80 g (298 mmol) of Intermediate 1-f and 800 mL of tetrahydrofuran were placed in a 2 L reactor, and then, stirred. After the reaction solution was cooled to 0° C., 348 mL (1,043 mmol) of 3M methylmagnesiumbromide was added dropwise thereto, and then, the mixed solution was refluxed for 3 hours. A saturated ammonium chloride aqueous solution was added thereto, and then, the mixed solution was extracted using ethylacetate and water. After an organic layer obtained therefrom was concentrated under reduced pressure, 270 mL of phosphoric acid was added thereto, and then, stirred for 12 hours. The organic layer was extracted using methylene chloride and distilled water, concentrated under reduced pressure, and separated-purified by chromatography, so as to obtain 55 g (yield: 78.1%) of Intermediate 1-g.

8) Reaction Scheme 1-8: Synthesis of Intermediate 1-h

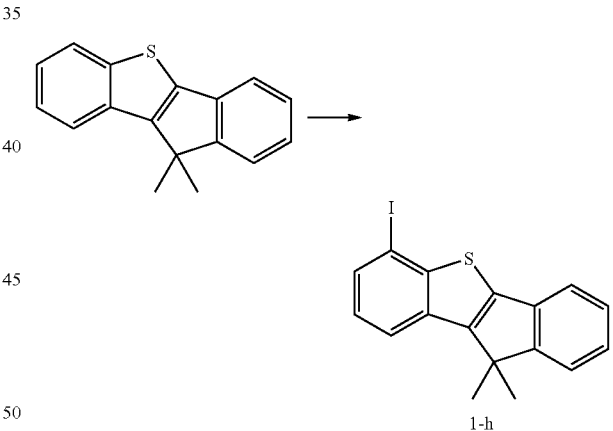

1-h 110 g (439 mmol) of Intermediate 1-g and 1,100 mL of tetrahydrofuran were placed in a 2 L reactor, and then, stirred. After the reaction solution was cooled to −78° C., 302 mL (483 mmol) of n-butyllithium (1.6M hexane solution) was added dropwise thereto, and then, the mixed solution was stirred for 1 hour when warmed up to room temperature. 134 g (530 mmol) of iodine was added thereto, and then, the mixed solution was stirred for 2 hours when warmed up to room temperature. A sodium thiosulfate aqueous solution was added thereto, and the mixed solution was extracted using ethylacetate and distilled water. An organic layer obtained therefrom was concentrated under reduced pressure and separated-purified by chromatography, so as to obtain 127 g (yield: 76.9%) of Intermediate 1-h.

9) Reaction Scheme 1-9: Synthesis of Intermediate 1-i

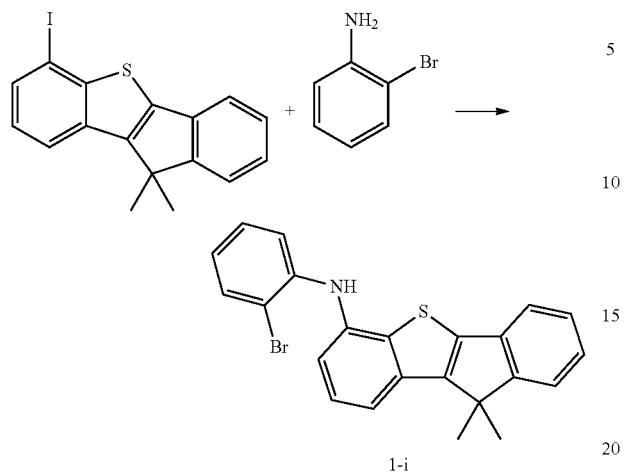

1-i 127 g (338 mmol) of Intermediate 1-h, 70 g (407 mmol) of 2-bromoaniline, 0.9 g (4 mmol) of dipalladium acetate, 7.1 g (12 mmol) of xantphos, 154 g (472 mmol) of cesium carbonate, and 1,000 mL of toluene were placed in a 2 L reactor, and then, stirred for 12 hours. After the reaction solution was filtered at a high temperature, residues obtained therefrom were concentrated under reduced pressure and separated-purified by chromatography, so as to obtain 100 g (yield: 70%) of Intermediate 1-i.

10) Reaction Scheme 1-10: Synthesis of Intermediate 1-j

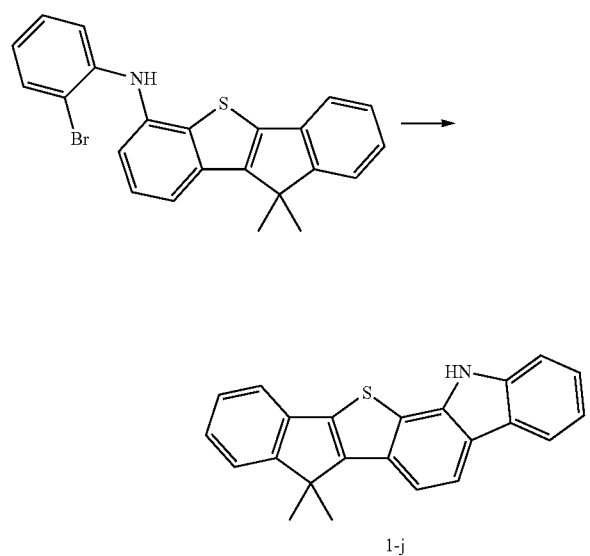

1-j 75 g (178 mmol) of Intermediate 1-l, 1.3 g (4 mmol) of tricyclohexylphosphine tetrafluoroborate, 0.4 g (2 mmol) of dipalladium acetate, 49.3 g (357 mmol) of potassium carbonate, and 1,000 mL of toluene were placed in a 2 L reactor, and then, refluxed for 12 hours. After the reaction solution was filtered at a high temperature, residues obtained therefrom were concentrated under reduced pressure and separated-purified by chromatography, so as to obtain 50 g (yield: 82.6%) of Intermediate 1-j.

11) Reaction Scheme 1-11: Synthesis of Compound 4

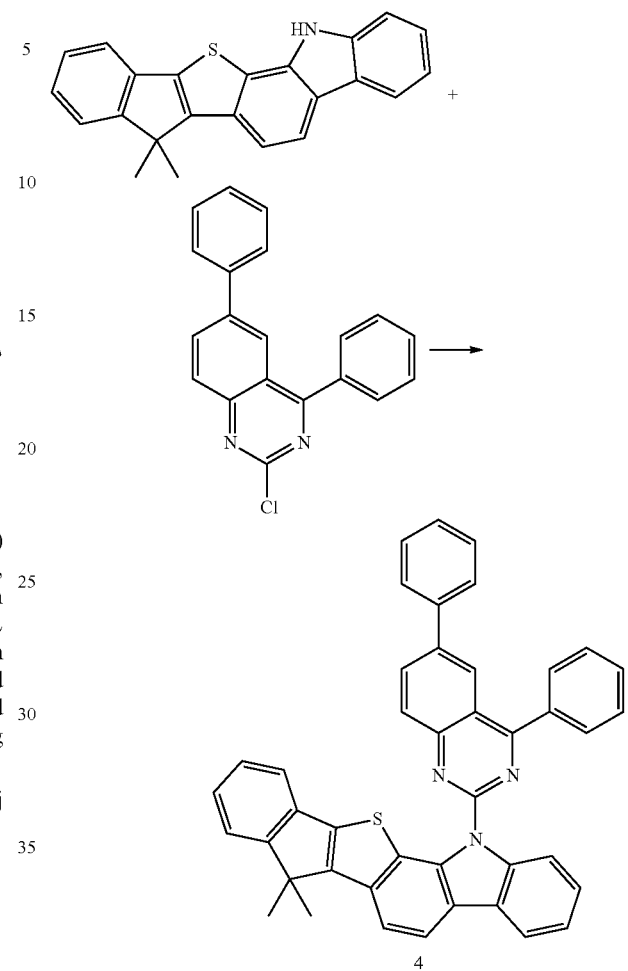

4

10 g (29 mmol) of Intermediate 1-j, 12.1 g (33 mmol) of Intermediate 1-d, 0.5 g (0.6 mmol) of tris(dibenzylideneacetone)dipalladium, 0.9 g (3 mmol) of tri-tert-butylphosphonium tetrafluoroborate, 5.7 g (60 mmol) of sodium tert-butoxide, and 70 mL of xylene were placed in a 300 mL reactor, and then, refluxed for 12 hours. After the mixed solution was filtered at a high temperature, residues obtained therefrom were concentrated under reduced pressure and separated-purified by chromatography, so as to obtain 7 g (yield: 38.3%) of Compound 4.

MS [M]+: 620

Synthesis Example 2: Synthesis of Compound 7

1) Reaction Scheme 2-1: Synthesis of Intermediate 2-a

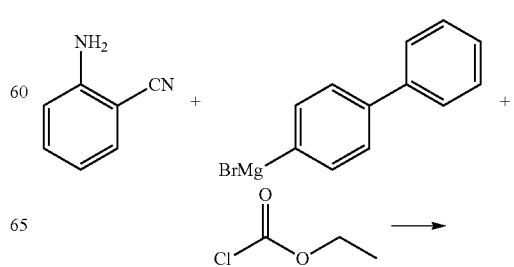

-continued

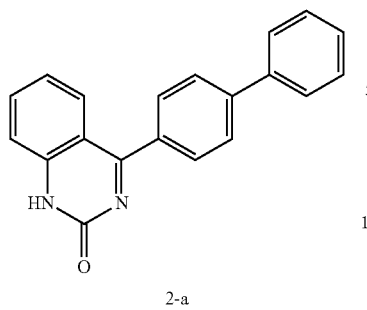
2-a 43.7 g (yield: 77.6%) of Intermediate 2-a was obtained in the same manner as in Synthesis Example 1, except that 2-aminobenzonitrile was used instead of Intermediate 1-b of Reaction Scheme 1-3 in Synthesis Example 1 and 4-biphenylmagnesiumbromide was used instead of 3M phenylmagnesiumbromide.

2) Reaction Scheme 2-2: Synthesis of Intermediate 2-b

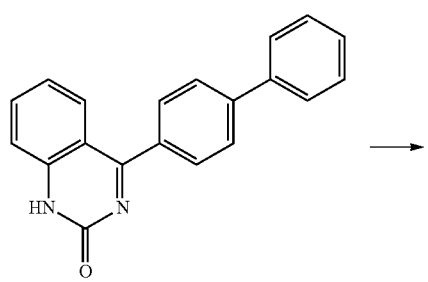
2-b 29.7 g (yield: 80.2%) of Intermediate 2-b was obtained in the same manner as in Synthesis Example 1, except that Intermediate 2-a was used instead of Intermediate 1-c of Reaction Scheme 1-4 in Synthesis Example 1.

3) Reaction Scheme 2-3: Synthesis of Compound 7

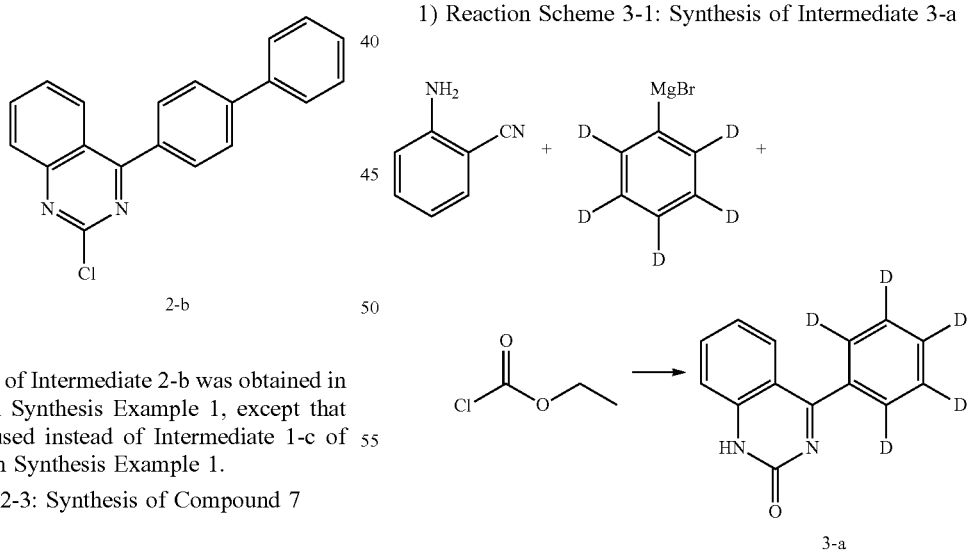

6.7 g (yield: 36.7%) of Compound 7 was obtained in the same manner as in Synthesis Example 1, except that Intermediate 2-b was used instead of Intermediate 1-d of Reaction Scheme 1-11 in Synthesis Example 1.

MS [M]$^+$: 620

Synthesis Example 3: Synthesis of Compound 12

1) Reaction Scheme 3-1: Synthesis of Intermediate 3-a

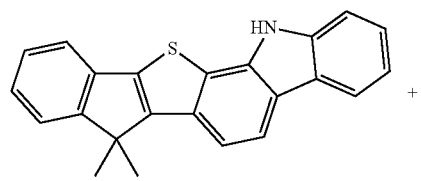
3-a 51 g (yield: 78.3%) of Intermediate 3-a was obtained in the same manner as in Synthesis Example 1, except that 2-aminobenzonitrile was used instead of Intermediate 1-b of Reaction Scheme 1-3 in Synthesis Example 1 and phenyl-d5-magnesiumbromide was used instead of 3M phenylmagnesiumbromide.

2) Reaction Scheme 3-2: Synthesis of Intermediate 3-b

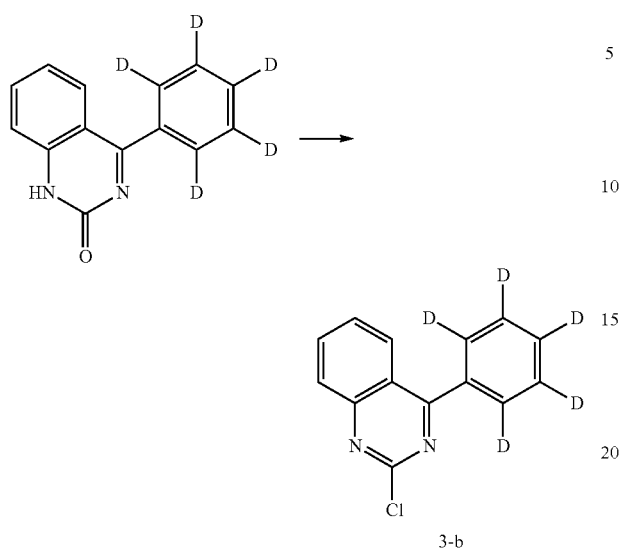

3-b 31 g (yield: 57.8%) of Intermediate 3-b was obtained in the same manner as in Synthesis Example 1, except that Intermediate 3-a was used instead of Intermediate 1-c of Reaction Scheme 1-4 in Synthesis Example 1.

3) Reaction Scheme 3-3: Synthesis of Compound 12

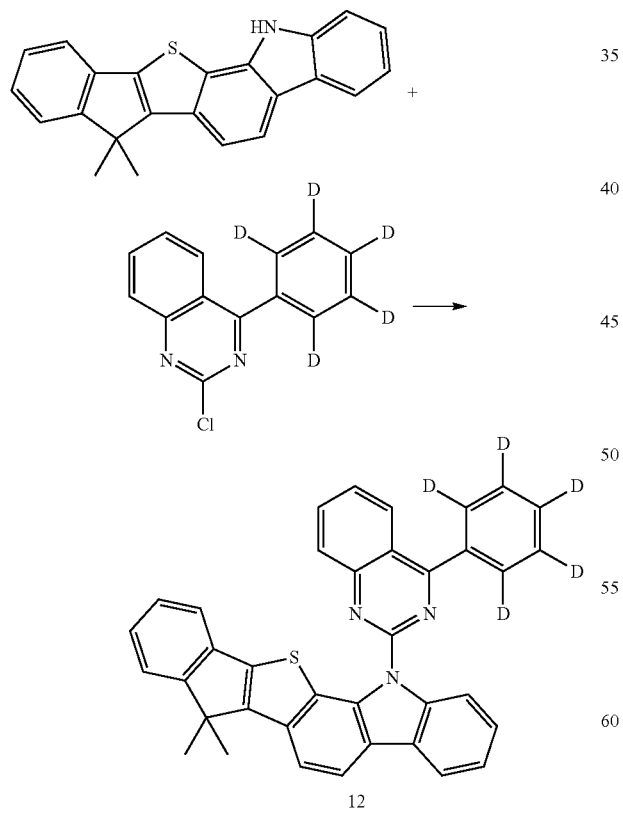

12

8.4 g (yield: 31.7%) of Compound 12 was obtained in the same manner as in Synthesis Example 1, except that Intermediate 3-b was used instead of Intermediate 1-d of Reaction Scheme 1-11 in Synthesis Example 1.

MS [M]$^+$: 549

Synthesis Example 4: Synthesis of Compound 15

1) Reaction Scheme 4-1: Synthesis of Intermediate 4-a

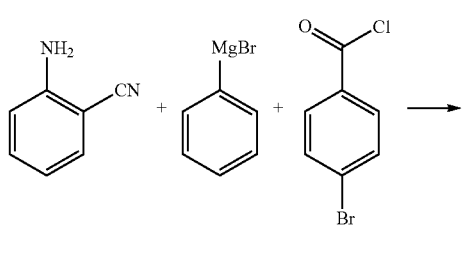

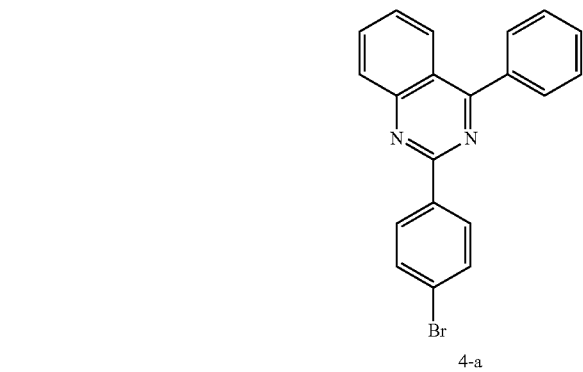

4-a 20.0 g (169 mmol) of 2-aminobenzonitrile and 200 mL of tetrahydrofuran were placed in a 1 L reactor, and 113 mL (339 mmol) 3M phenylmagnesiumbromide was slowly added dropwise thereto. The mixed solution was refluxed for 3 hours. After it was confirmed that 2-aminobenzonitrile was removed from the reactor, the reaction solution was cooled to 0° C., and a solution in which 44.58 g (0.203 mmol) of 4-bromobenzoyl chloride was dissolved with 200 mL of tetrahydrofuran was slowly added dropwise thereto. The mixed solution was refluxed for 2 hours. An ammonium-chloride aqueous solution was added to the reactor, and the reaction solution was extracted using ethylacetate and water. An organic layer obtained therefrom was concentrated under reduced pressure and separated-purified by chromatography, so as to obtain 25 g (yield: 40.8%) of Intermediate 4-a.

2) Reaction Scheme 4-2: Synthesis of Compound 15

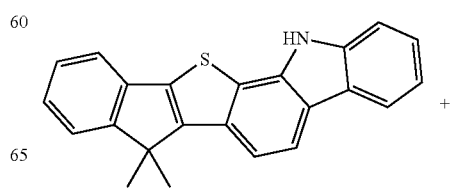

3-bromobenzoyl chloride was used instead of 4-bromobenzoyl chloride of Reaction Scheme 4-1 in Synthesis Example 4.

2) Reaction Scheme 5-2: Synthesis of Compound 16

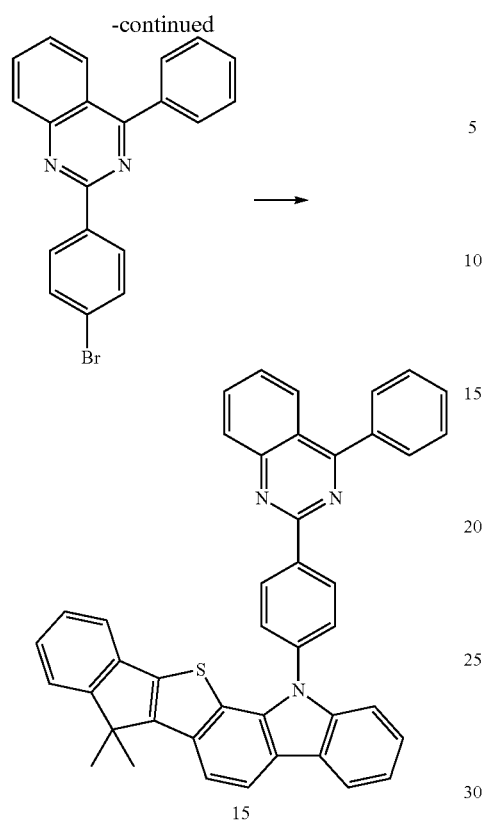

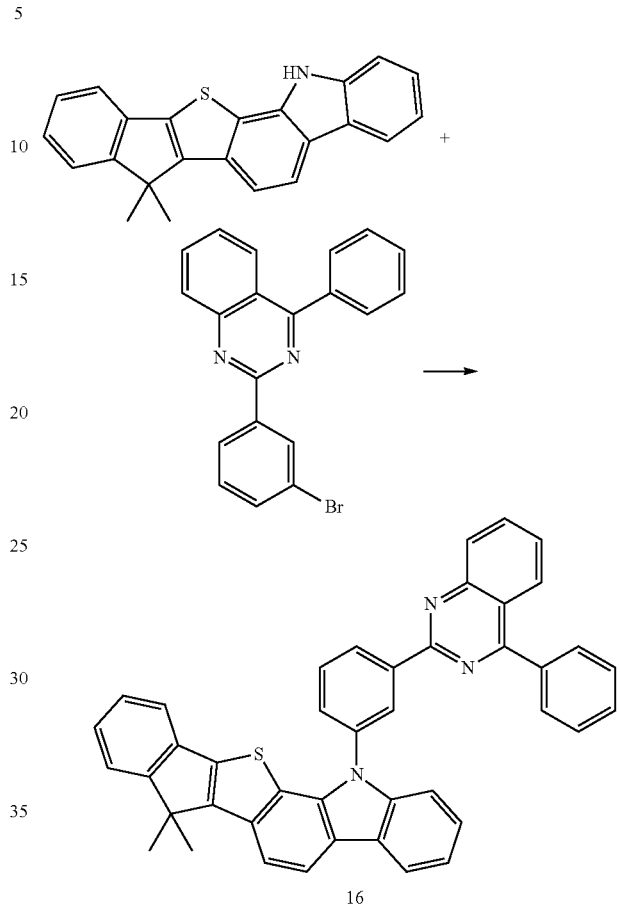

5.2 g (yield: 27.6%) of Compound 15 was obtained in the same manner as in Synthesis Example 1, except that Intermediate 4-a was used instead of Intermediate 1-d of Reaction Scheme 1-11 in Synthesis Example 1.

MS [M]$^+$: 620

Synthesis Example 5: Synthesis of Compound 16

1) Reaction Scheme 5-1: Synthesis of Intermediate 5-a

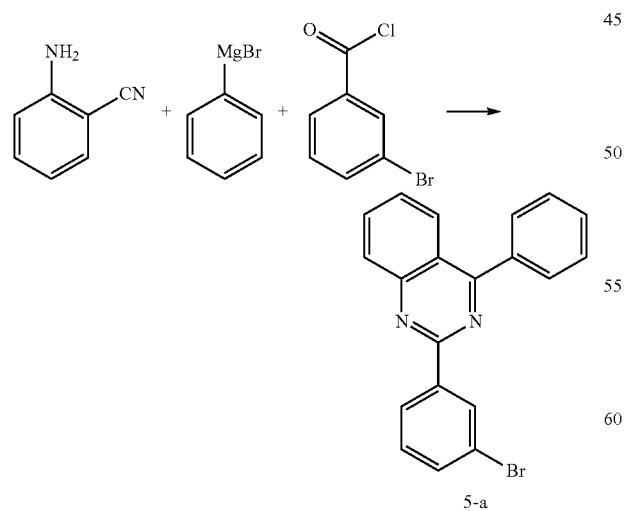

37 g (yield: 60.3%) of Intermediate 5-a was obtained in the same manner as in Synthesis Example 1, except that 8.4 g (yield: 31.8%) of Compound 16 was obtained in the same manner as in Synthesis Example 1, except that Intermediate 5-a was used instead of Intermediate 1-d of Reaction Scheme 1-11 in Synthesis Example 1.

MS [M]$^+$: 620

Synthesis Example 6: Synthesis of Compound 24

1) Reaction Scheme 6-1: Synthesis of Intermediate 6-a

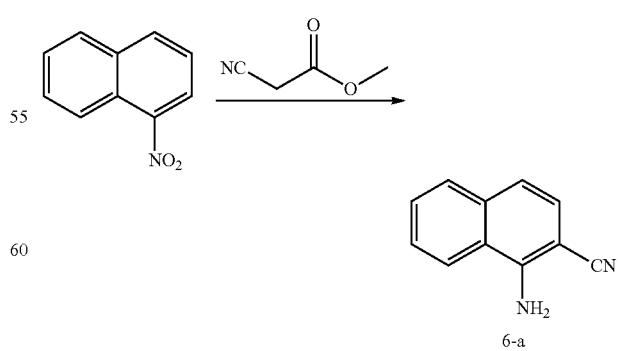

139.8 g (1.236 mol) of ethyl cyanoacetate, 29.5 g (0.453 mol) of potassium cyanide, 46.2 g (0.824 mol) of potassium hydroxide, and 920 mL of dimethylformamide were placed in a 2 L reactor, and then, stirred at a temperature of 10° C. for 20 minutes. 92 g (412 mol) of 1-nitronaphthalene was added thereto, and the mixed solution was stirred at a temperature of 60° C. for 4 hours. After a solvent was concentrated in the reactor, 600 mL of a 10% sodium hydroxide aqueous solution was added thereto. The mixed solution was stirred under reflux for 1 hour. Solid residues obtained by filtering the reaction solution were separated-purified by chromatography using methylene chloride and heptane, so as to obtain 50 g (yield: 60%) of Formula 6-a.

2) Reaction Scheme 6-2: Synthesis of Intermediate 6-b

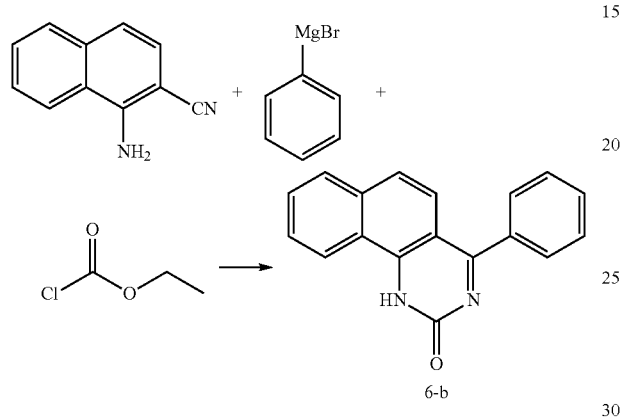

50 g (yield: 60%) of Intermediate 6-a was obtained in the same manner as in Synthesis Example 1, except that Intermediate 6-1 of Reaction Scheme 6-1 was used instead of Intermediate 1-b of Reaction Scheme 1-3.

3) Reaction Scheme 6-3: Synthesis of Intermediate 6-c

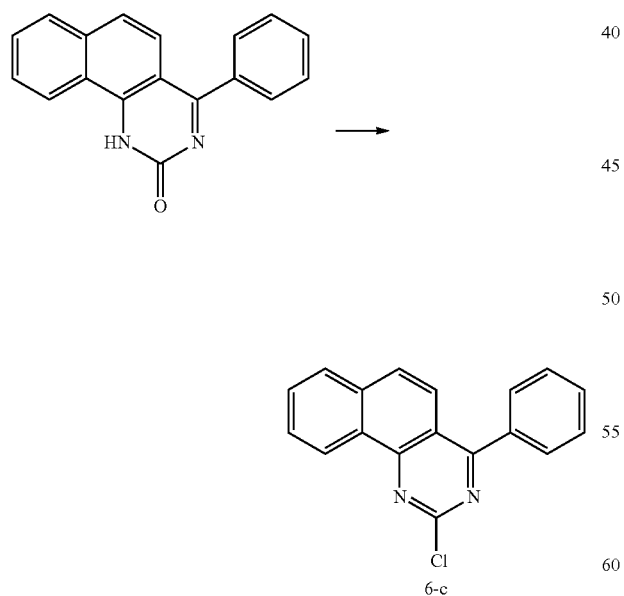

30.5 g (yield: 70.6%) of Intermediate 6-c was obtained in the same manner as in Synthesis Example 1, except that Intermediate 6-b was used instead of Intermediate 1-c of Reaction Scheme 1-4 in Synthesis Example 1.

4) Reaction Scheme 6-4: Synthesis of Compound 24

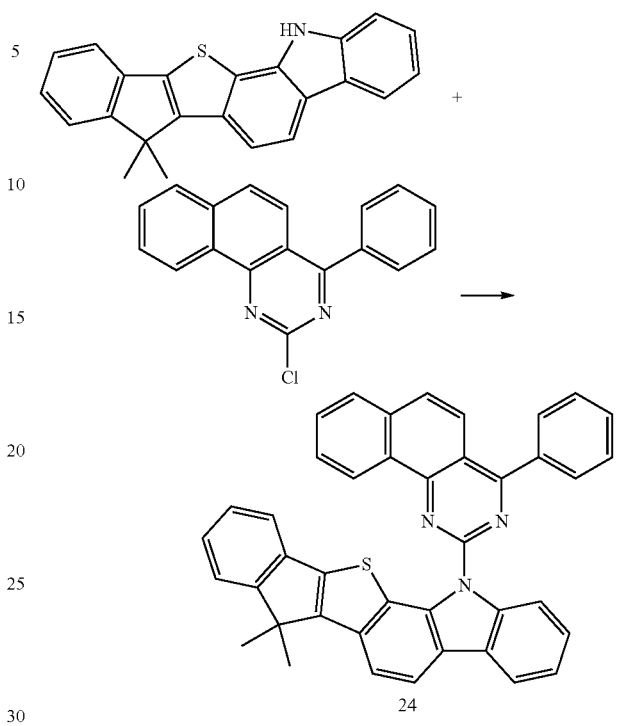

6.8 g (yield: 35.1%) of Compound 24 was obtained in the same manner as in Synthesis Example 1, except that Intermediate 6-c was used instead of Intermediate 1-d of Reaction Scheme 1-11 in Synthesis Example 1.

MS [M]$^+$: 594

Synthesis Example 7: Synthesis of Compound 26

1) Reaction Scheme 7-1: Synthesis of Intermediate 7-a

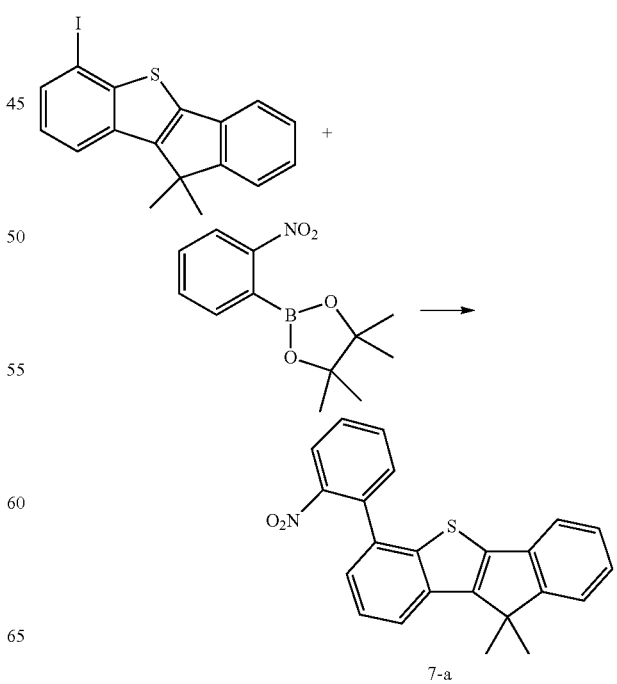

28 g (74 mmol) of Intermediate 1-h, 24.1 g (97 mmol) of 2-nitrophenylborate, 2.2 g (0.19 mmol) of tetrakis(triphenylphosphine)palladium, 25.7 g (186 mmol) of potassium carbonate, 140 mL of 1,4-dioxane, 140 mL of toluene, and 50 mL of distilled water were placed in a reactor, and then, stirred at a temperature of 100° C. for 12 hours. After the completion of the reaction, the reaction solution was cooled to room temperature, and then, extracted using ethylacetate. An organic layer obtained therefrom was concentrated under reduced pressure and separated-purified by chromatography, so as to obtain 20.7 g (yield: 74.9%) of Intermediate 7-a.

2) Reaction Scheme 7-2: Synthesis of Intermediate 7-b

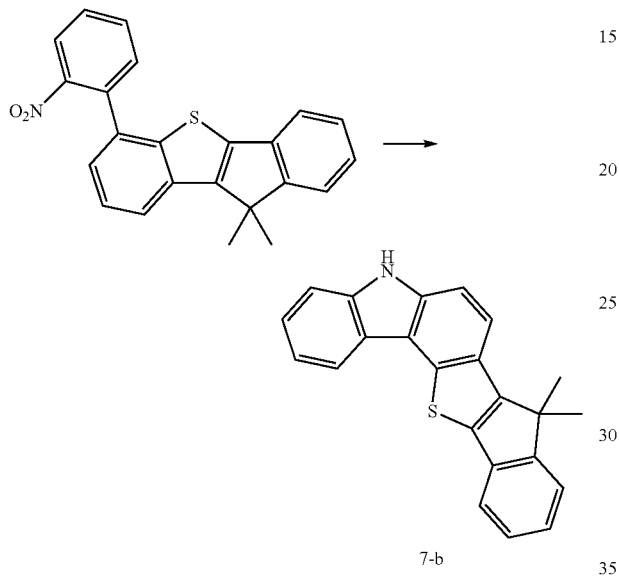

7-b 20.7 g (27 mmol) of Intermediate 7-a, 21.2 g (81 mmol) of triphenylphosphine, and 200 mL of dichlorobenzene were placed in a reactor, and then, refluxed for 12 hours. After the completion of the reaction, the reaction solution, which was in a hot condition, was filtered under reduced pressure. The filtered solution was dried under reduced pressure, and then, separated-purified by chromatography, so as to obtain 12.9 g (yield: 68.2%) of Intermediate 1-l.

3) Reaction Scheme 7-3: Synthesis of Compound 26

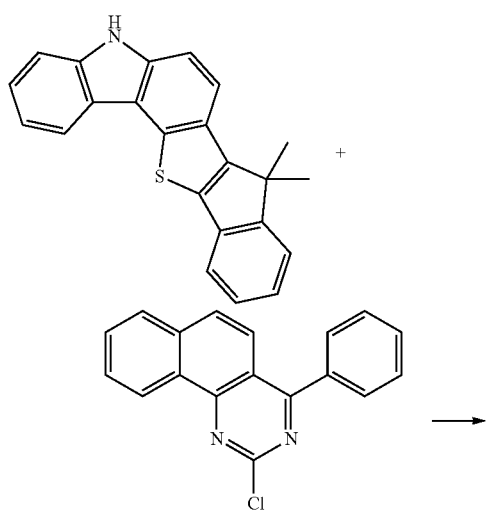

-continued

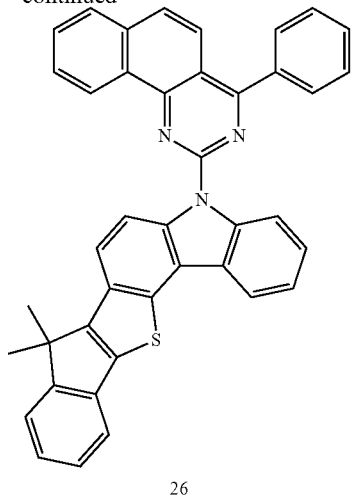

26

26 9.3 g (yield: 34.8%) of Compound 26 was obtained in the same manner as in Synthesis Example 1, except that Intermediate 7-b and Intermediate 6-c were used instead of Intermediate 1-j and Intermediate 1-d of Reaction Scheme 1-11 in Synthesis Example 1, respectively.

MS [M]$^+$: 594

Synthesis Example 8: Synthesis of Compound 33

1) Reaction Scheme 8-1: Synthesis of Intermediate 8-a

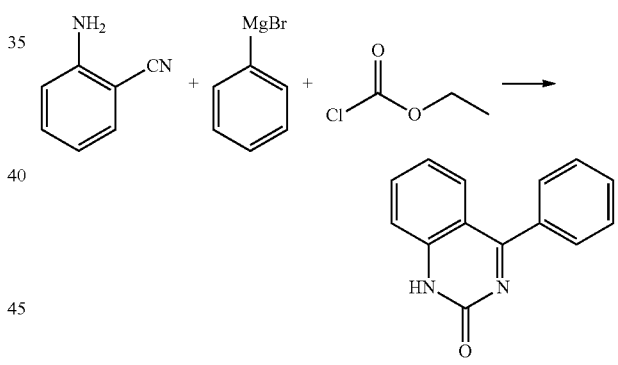

8-a 48.2 g (yield: 75.7%) of Intermediate 8-a was obtained in the same manner as in Synthesis Example 1, except that 2-aminobenzonitrile was used instead of Intermediate 1-b of Reaction Scheme 1-3 in Synthesis Example 1.

2) Reaction Scheme 8-2: Synthesis of Intermediate 8-b

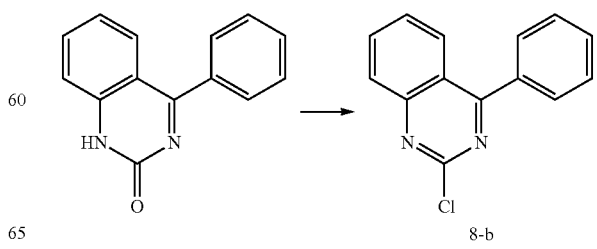

8-b 32.1 g (yield: 68.4%) of Intermediate 8-b was obtained in the same manner as in Synthesis Example 1, except that Intermediate 8-a was used instead of Intermediate 1-c of Reaction Scheme 1-4 in Synthesis Example 1.

3) Reaction Scheme 8-3: Synthesis of Intermediate 8-c

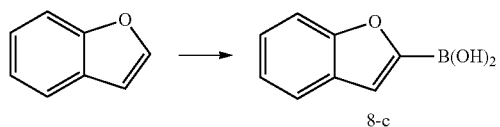 [SMILES: c1ccc2occc2c1 ; OB(O)c1cc2ccccc2o1]

123.4 g (yield: 87.4%) of Intermediate 8-c was obtained in the same manner as in Synthesis Example 1, except that benzofuran was used instead of benzothiophene of Reaction Scheme 1-5 in Synthesis Example 1.

4) Reaction Scheme 8-4: Synthesis of Intermediate 8-d

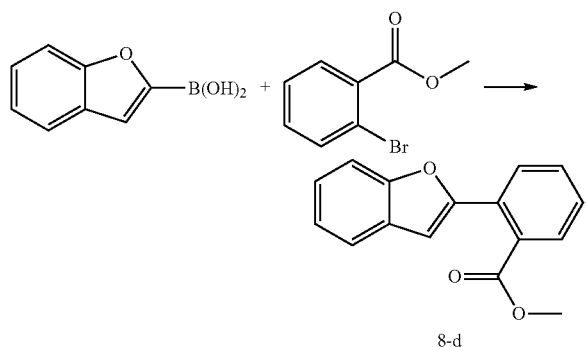

106.2 g (yield: 79.3%) of Intermediate 8-d was obtained in the same manner as in Synthesis Example 1, except that Intermediate 8-c was used instead of Intermediate 1-e of Reaction Scheme 1-6 in Synthesis Example 1.

5) Reaction Scheme 8-5: Synthesis of Intermediate 8-e

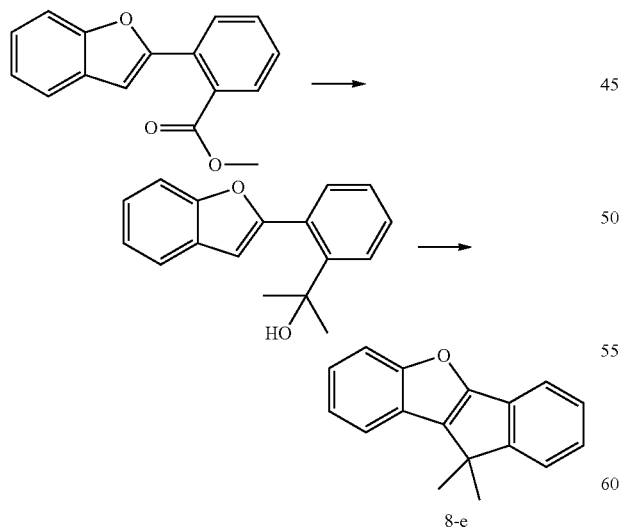

84.3 g (yield: 75.5%) of Intermediate 8-e was obtained in the same manner as in Synthesis Example 1, except that Intermediate 8-d was used instead of Intermediate 1-f of Reaction Scheme 1-7 in Synthesis Example 1.

6) Reaction Scheme 8-6: Synthesis of Intermediate 8-f

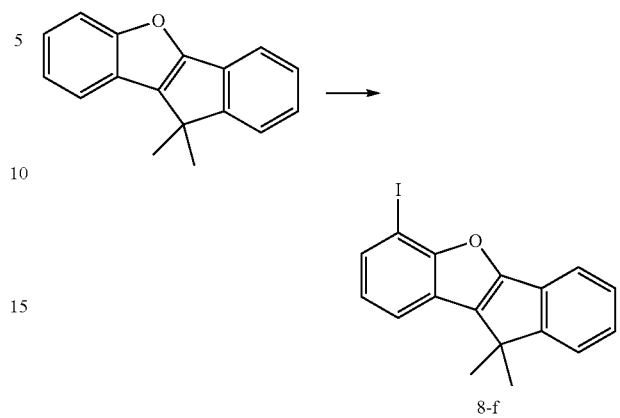

110.6 g (yield: 80.9%) of Intermediate 8-f was obtained in the same manner as in Synthesis Example 1, except that Intermediate 8-d was used instead of Intermediate 1-g of Reaction Scheme 1-8 in Synthesis Example 1.

7) Reaction Scheme 8-7: Synthesis of Intermediate 8-g

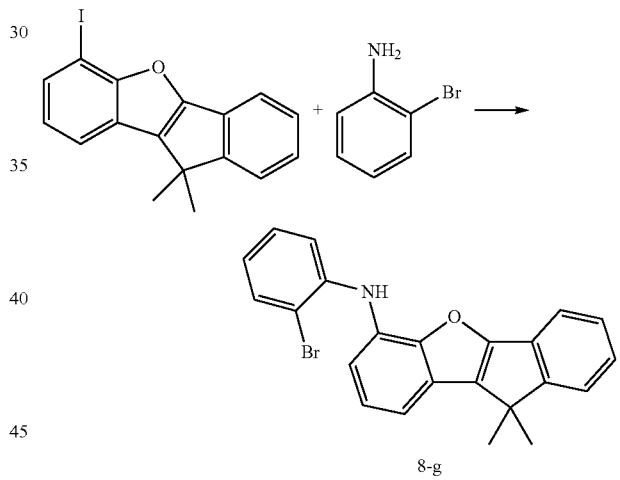

85.3 g (yield: 74.5%) of Intermediate 8-g was obtained in the same manner as in Synthesis Example 1, except that Intermediate 8-f was used instead of Intermediate 1-h of Reaction Scheme 1-9 in Synthesis Example 1.

8) Reaction Scheme 8-8: Synthesis of Intermediate 8-h

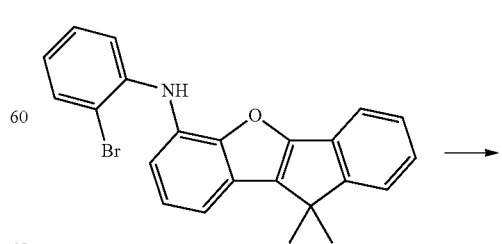

-continued

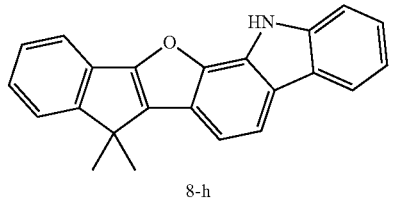

8-h 31.5 g (yield: 74.2%) of Intermediate 8-h was obtained in the same manner as in Synthesis Example 1, except that Intermediate 8-g was used instead of Intermediate 1-i of Reaction Scheme 1-10 in Synthesis Example 1.

9) Reaction Scheme 8-9: Synthesis of Compound 33

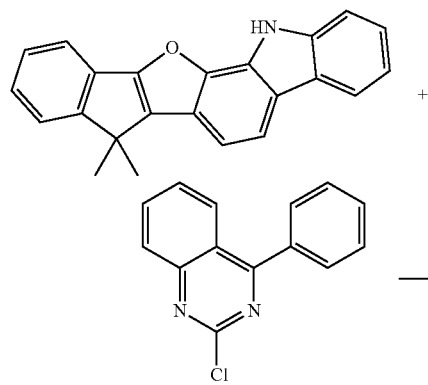

+

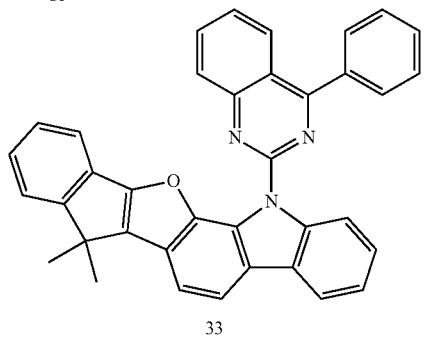

33

6.2 g (yield: 31.8%) of Compound 33 was obtained in the same manner as in Synthesis Example 1, except that Intermediate 8-b and Intermediate 8-h were used instead of Intermediate 1-d and Intermediate 1-j of Reaction Scheme 1-11 in Synthesis Example 1, respectively.

MS [M]$^+$: 528

Synthesis Example 9: Synthesis of Compound 34

1) Reaction Scheme 9-1: Synthesis of Compound 34

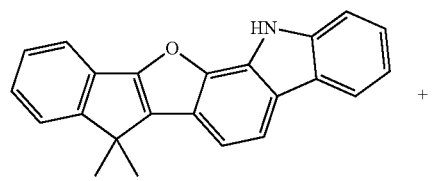

+

-continued

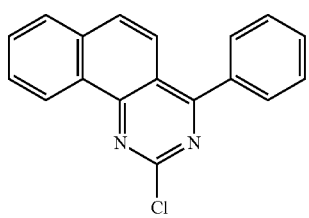

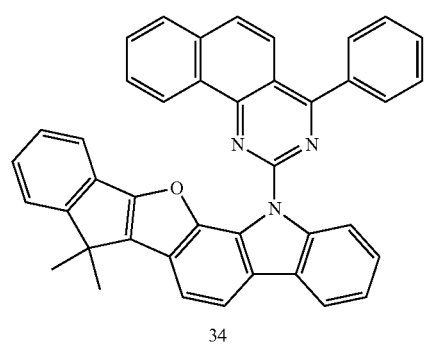

34

8.6 g (yield: 29.7%) of was obtained in the same manner as in Synthesis Example 1, except that Intermediate 6-c was used instead of Intermediate 1-d of Reaction Scheme 1-11 in Synthesis Example 1.

MS [M]$^+$: 578

Synthesis Example 10: Synthesis of Compound 35

1) Reaction Scheme 10-1: Synthesis of Compound 35

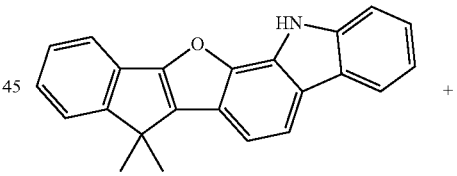

+

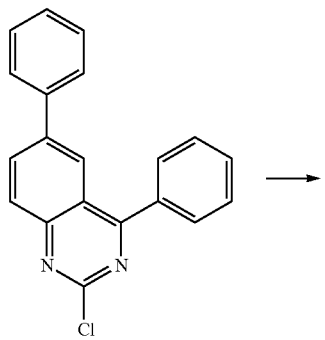

253
-continued

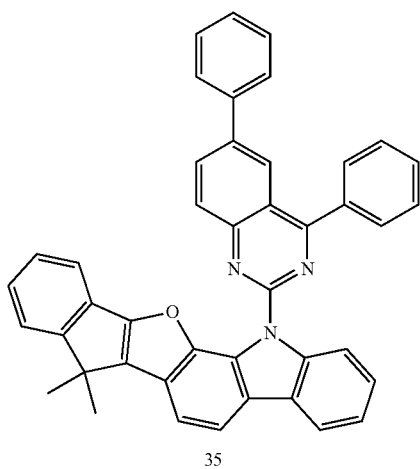

35

7.2 g (yield: 28.5%) of Compound 35 was obtained in the same manner as in Synthesis Example 1, except that Intermediate 8-h was used instead of Intermediate 1-j of Reaction Scheme 1-11 in Synthesis Example 1.

MS [M]+: 578

Synthesis Example 11: Synthesis of Compound 44

1) Reaction Scheme 11-1: Synthesis of Intermediate 11-a

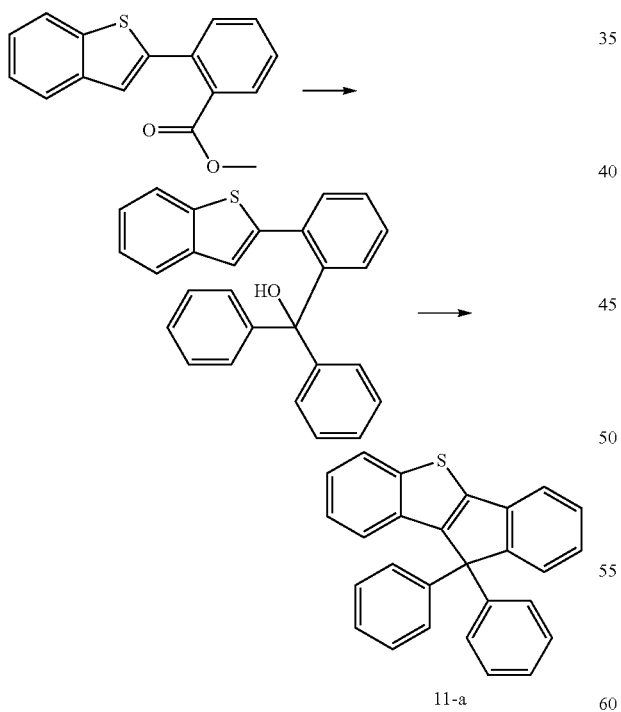

11-a 42.7 g (yield: 80.6%) of Intermediate 11-a was obtained in the same manner as in Synthesis Example 1, except that 3M phenylmagnesiumbromide was used instead of 3M methylmagnesiumbromide of Reaction Scheme 1-7 in Synthesis Example 1.

2) Reaction Scheme 11-2: Synthesis of Intermediate 11-b

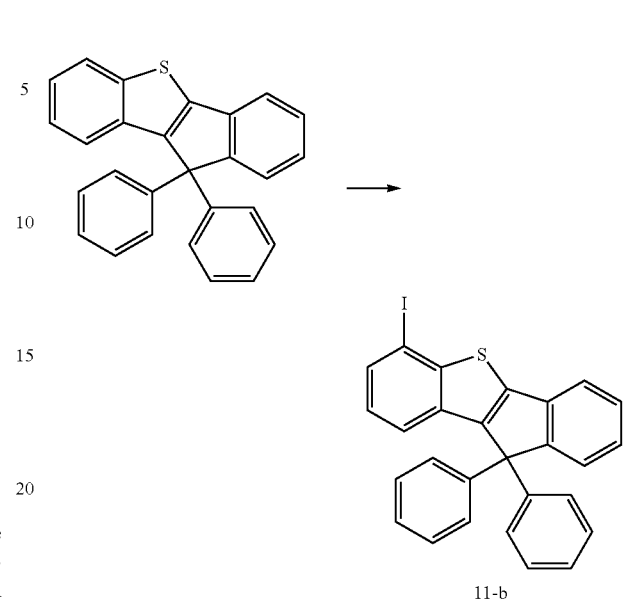

11-b 49.3 g (yield: 76.4%) of Intermediate 11-b was obtained in the same manner as in Synthesis Example 1, except that Intermediate 11-a was used instead of Intermediate 1-g of Reaction Scheme 1-8 in Synthesis Example 1.

31 Reaction Scheme 11-3: Synthesis of Intermediate 11-c

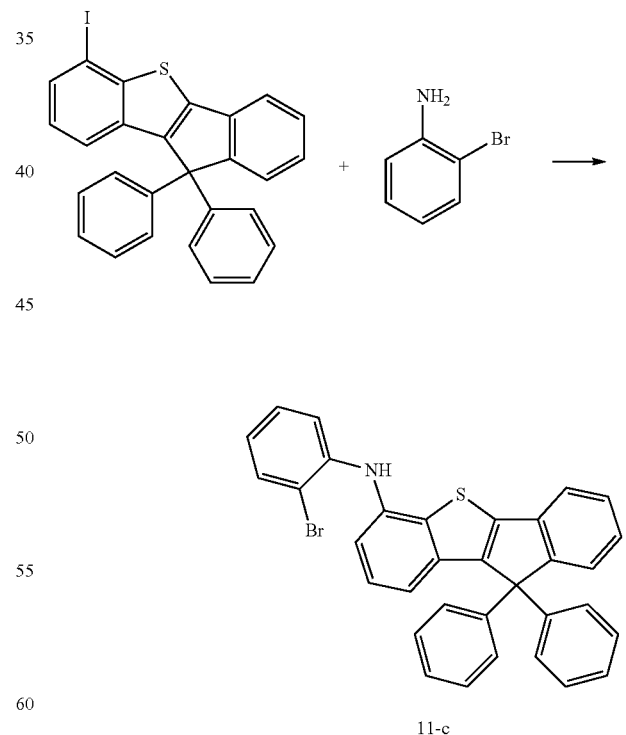

11-c 37.2 g (yield: 69.7%) of Intermediate 11-c was obtained in the same manner as in Synthesis Example 1, except that Intermediate 11-b was used instead of Intermediate 1-h of Reaction Scheme 1-9 in Synthesis Example 1.

4) Reaction Scheme 11-4: Synthesis of Intermediate 11-d

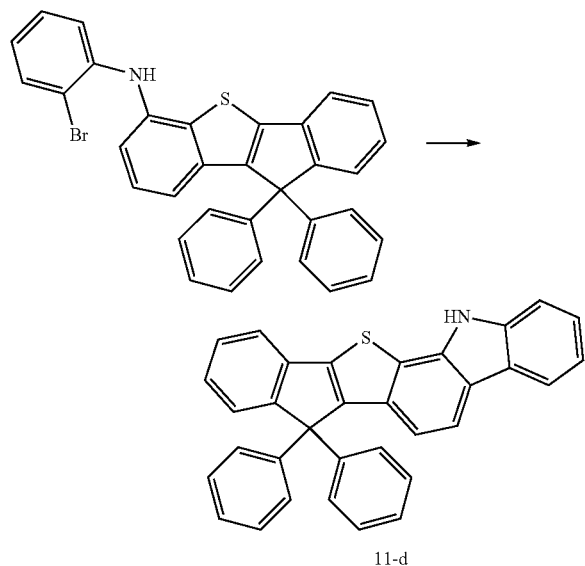

11-d 27.3 g (yield: 70.4%) of Intermediate 11-d was obtained in the same manner as in Synthesis Example 1, except that Intermediate 11-c was used instead of Intermediate 1-i of Reaction Scheme 1-10 in Synthesis Example 1.

5) Reaction Scheme 11-5: Synthesis of Compound 44

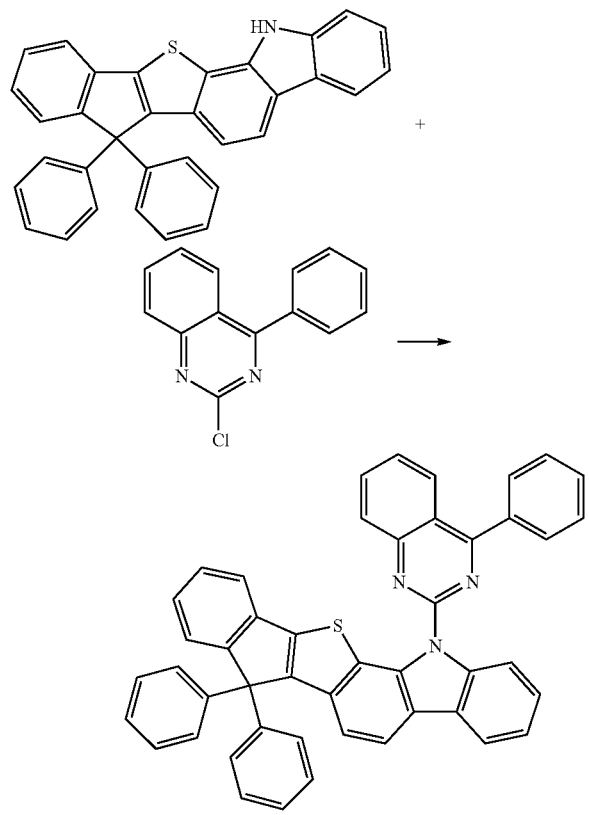

44

6.7 g (yield: 37.4%) of Compound 44 was obtained in the same manner as in Synthesis Example 1, except that Intermediate 11-d was used instead of Intermediate 1-j of Reaction Scheme 1-11 in Synthesis Example 1.

MS [M]$^+$: 668

Synthesis Example 12: Synthesis of Compound 47

1) Reaction Scheme 12-1: Synthesis of Intermediate 12-a

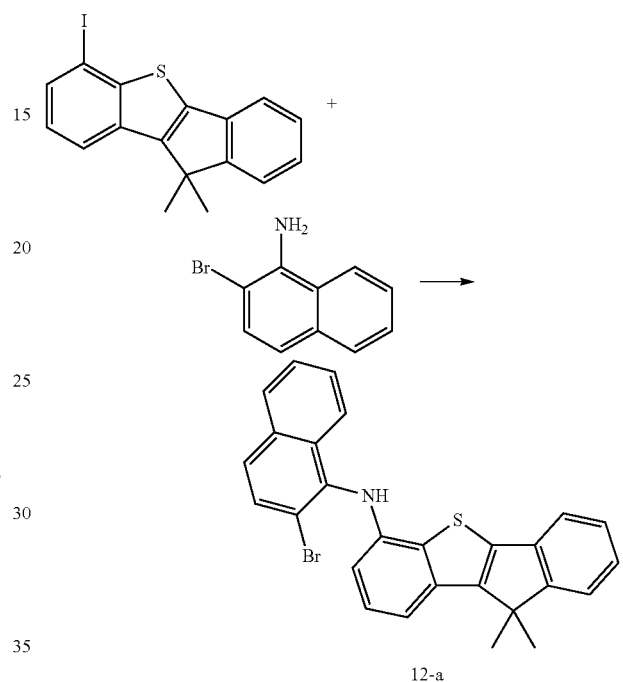

12-a 35.7 g (yield: 73.1%) of Intermediate 12-a was obtained in the same manner as in Synthesis Example 1, except that 2-bromo-1-naphthaleneamine was used instead of 2-bromoaniline of Reaction Scheme 1-9 in Synthesis Example 1.

2) Reaction Scheme 12-2: Synthesis of Intermediate 12-b

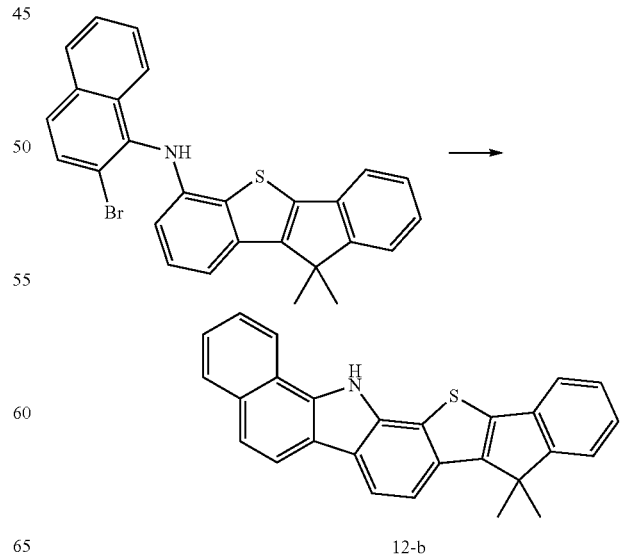

12-b 29.5 g (yield: 68.4%) of Intermediate 12-b was obtained in the same manner as in Synthesis Example 1, except that Intermediate 12-a was used instead of Intermediate 1-i of Reaction Scheme 1-10 in Synthesis Example 1.

3) Reaction Scheme 12-3: Synthesis of Compound 47

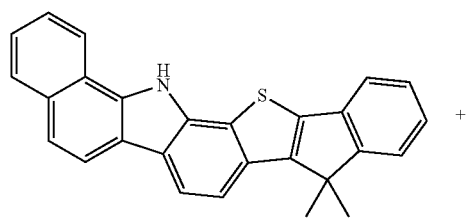
+
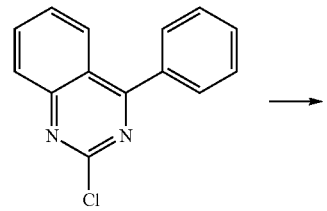
→
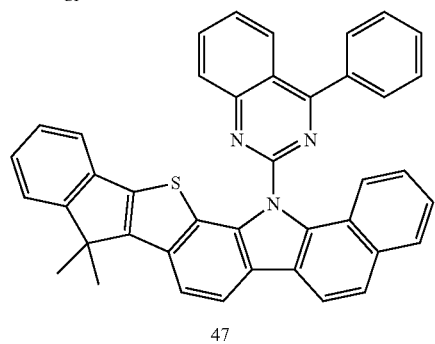

47

4.8 g (yield: 41.9%) of Compound 47 was obtained in the same manner as in Synthesis Example 1, except that Intermediate 12-b was used instead of Intermediate 1-j of Reaction Scheme 1-11 in Synthesis Example 1.

MS [M]⁺: 594

Synthesis Example 13: Synthesis of Compound 123

1) Reaction Scheme 13-1: Synthesis of Intermediate 13-a

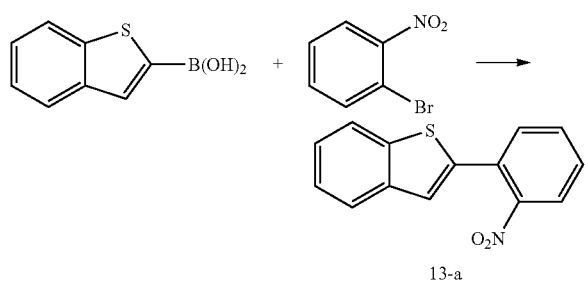

13-a 65 g (yield: 64.3%) of Intermediate 13-a was obtained in the same manner as in Synthesis Example 1, except that 1-bromo-2-nitrobenzene was used instead of 2-bromo methylbenzoate of Reaction Scheme 1-6 in Synthesis Example 1.

2) Reaction Scheme 13-2: Synthesis of Intermediate 13-b

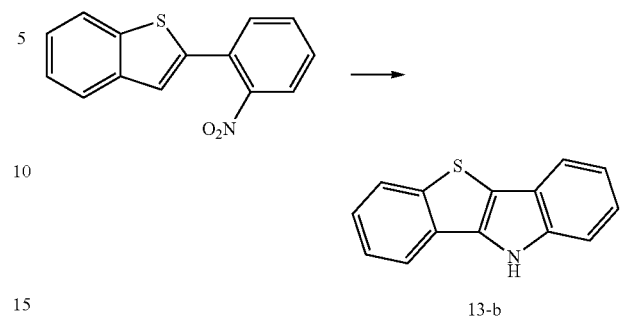

13-b 47 g (yield: 82.7%) of Intermediate 13-b was obtained in the same manner as in Synthesis Example 1, except that Intermediate 13-a was used instead of Intermediate 7-a of Reaction Scheme 7-2 in Synthesis Example 7.

3) Reaction Scheme 13-3: Synthesis of Intermediate 13-c

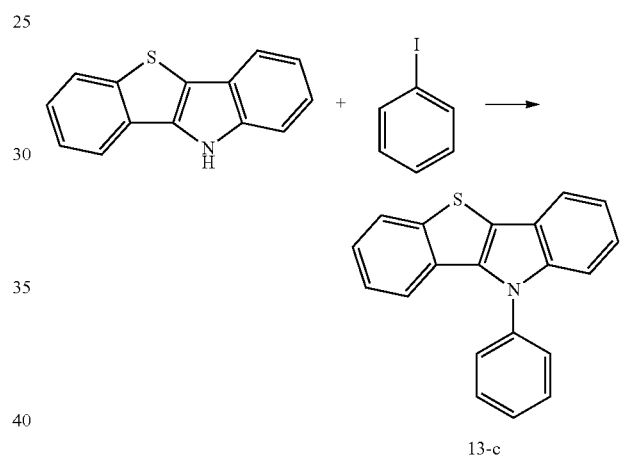

13-c 43.1 g (193 mmol) of Intermediate 13-b, 47.3 g (232 mmol) of iodobenzene, 1.8 g (10 mmol) of iodinecopper, 86.1 g of potassium phosphate, 46.3 g (405 mmol) of 1,2-cyclohexyldiamine, and 430 mL of 1,4-dioxane were placed in a 1 L reactor, and then, stirred at a temperature of 100° C. for 12 hours. After the reaction solution was filtered at a high temperature, residues obtained therefrom were concentrated under reduced pressure and separated-purified by chromatography, so as to obtain 56 g (yield: 96.9%) of Intermediate 11-c.

4) Reaction Scheme 13-4: Synthesis of Intermediate 13-d

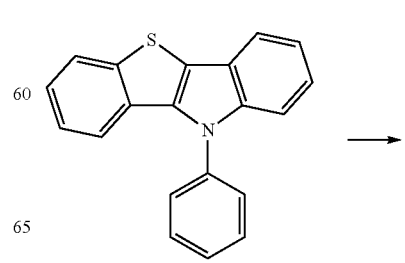

-continued

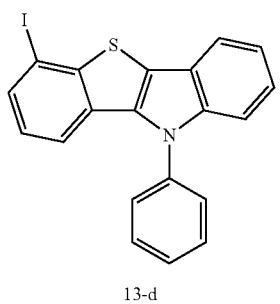

13-d 64.2 g (yield: 76.8%) of Intermediate 13-d was obtained in the same manner as in Synthesis Example 1, except that Intermediate 13-c was used instead of Intermediate 1-g of Reaction Scheme 1-8 in Synthesis Example 1.

5) Reaction Scheme 13-5: Synthesis of Intermediate 13-e

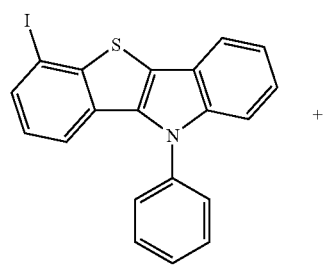

+

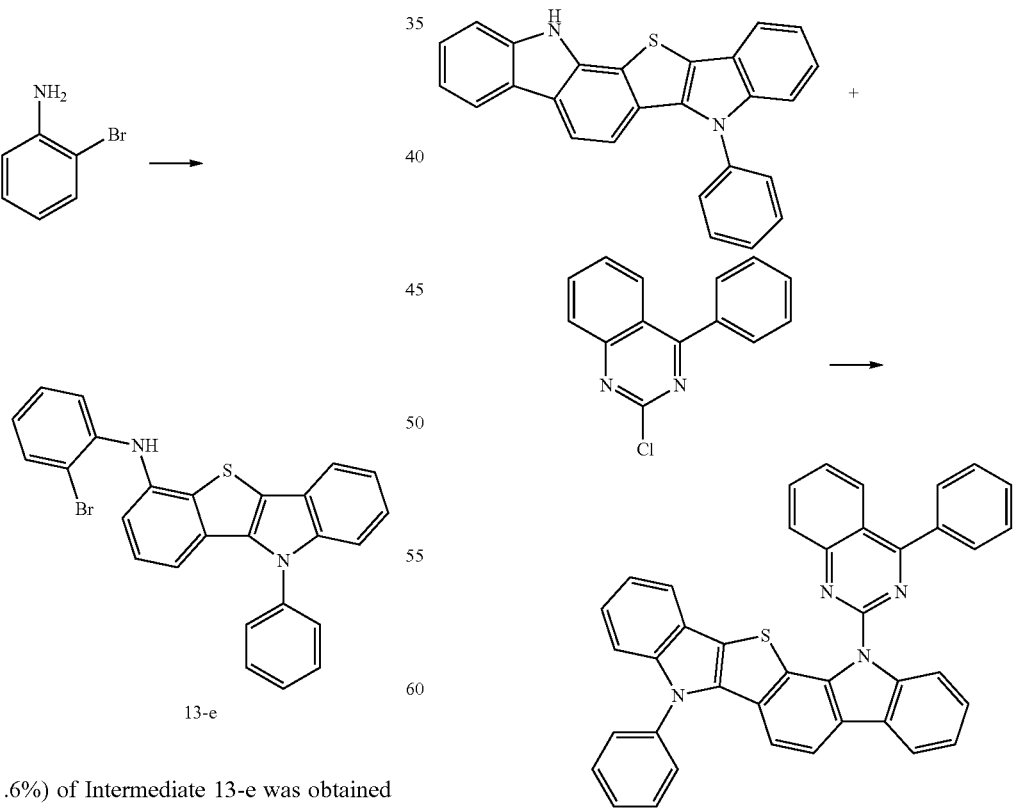

13-e 28.1 g (yield: 71.6%) of Intermediate 13-e was obtained in the same manner as in Synthesis Example 1, except that Intermediate 13-d was used instead of Intermediate 1-h of Reaction Scheme 1-9 in Synthesis Example 1.

6) Reaction Scheme 13-6: Synthesis of Intermediate 13-f

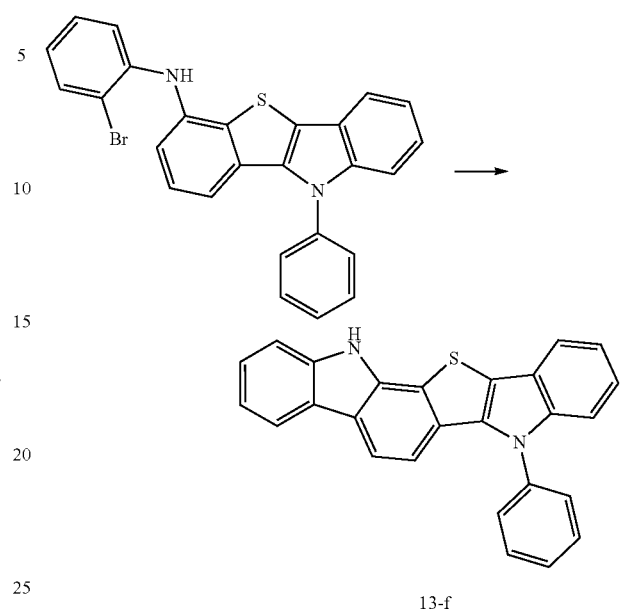

13-f 18.9 g (yield: 69.4%) of Intermediate 13-f was obtained in the same manner as in Synthesis Example 1, except that Intermediate 13-e was used instead of Intermediate 1-i of Reaction Scheme 1-10 in Synthesis Example 1.

7) Reaction Scheme 13-7: Synthesis of Compound 123

123

4.3 g (yield: 42.9%) of Compound 123 was obtained in the same manner as in Synthesis Example 1, except that Intermediate 13-f was used instead of Intermediate 1-j of Reaction Scheme 1-11 in Synthesis Example 1.

MS [M]+: 593

Synthesis Example 14: Synthesis of Compound 165

1) Reaction Scheme 14-1: Synthesis of Intermediate 14-a

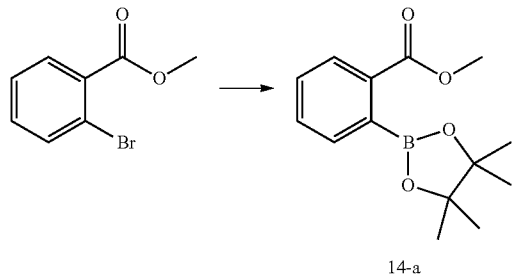 [SMILES: COC(=O)c1ccccc1Br ; COC(=O)c1ccccc1B1OC(C)(C)C(C)(C)O1]

14-a 100 g (465 mmol) of 2-bromoethylacetate, 177.1 g (698 mmol) of bis(pinacolato)diboron, 10.2 g (14 mmol) of [1,1'-bis(diphenylphosphino)ferrocene]dichloropalladium, 136.9 g (1395 mmol) of potassium acetate, and 1,000 mL of toluene were placed in a 2 L reactor, and then, refluxed for 12 hours. After the reaction solution was filtered at a high temperature, residues obtained therefrom were concentrated under reduced pressure and separated-purified by chromatography, so as to obtain 96 g (yield: 78.8%) of Intermediate 14-a.

2) Reaction Scheme 14-2: Synthesis of Intermediate 14-b

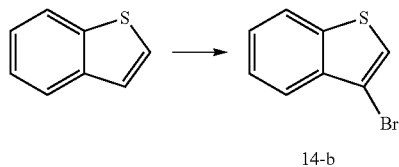 [SMILES: c1ccc2sccc2c1 ; Brc1csc2ccccc12]

14-b 35 g (261 mmol) of benzothiophene and 350 mL of tetrahydrofuran were placed in a 1 L reactor, and then, stirred. After the reaction solution was cooled to 0° C., 55.7 g (313 mmol) of N-bromosuccinimide was added thereto, and then, stirred for 1 hour. After the reaction solution was stirred for 12 hours when warmed up to room temperature, a sodium thiosulfite aqueous solution was added thereto. The mixed solution was extracted using ethylacetate and distilled water, and then, an organic layer was obtained therefrom was separated. The organic layer was concentrated under reduced pressure, so as to obtain 43 g (yield: 63.4%) of Intermediate 14-b.

3) Reaction Scheme 14-3: Synthesis of Intermediate 14-c

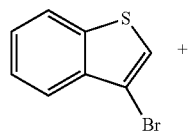

+

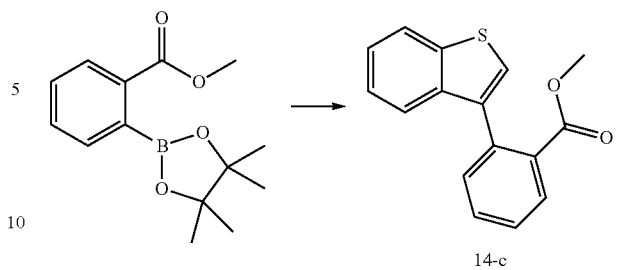

14-c 33 g (yield: 65.3%) of Intermediate 14-c was obtained in the same manner as in Synthesis Example 1, except that Intermediate 14-b and Intermediate 14-a were used instead of 2-bromo methylbenzoate and Intermediate 1-e of Reaction Scheme 1-6 in Synthesis Example 1, respectively.

4) Reaction Scheme 14-4: Synthesis of Intermediate 14-d

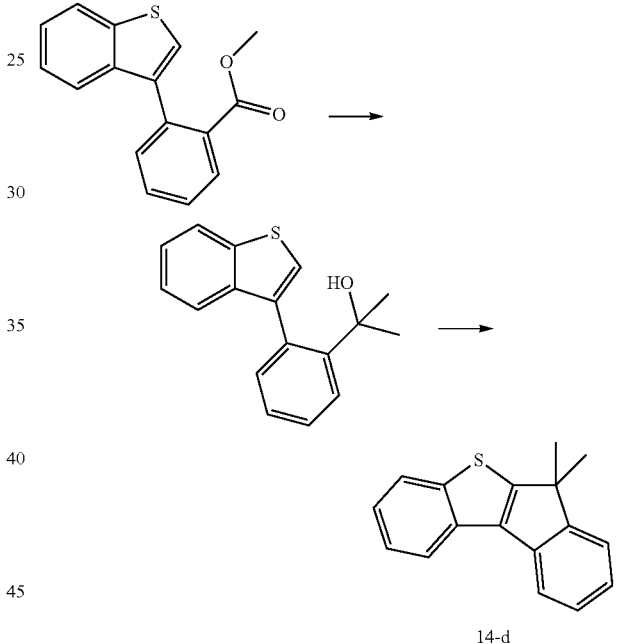

14-d 42 g (yield: 73.8%) of Intermediate 14-d was obtained in the same manner as in Synthesis Example 1, except that Intermediate 14-c was used instead of Intermediate 1-g of Reaction Scheme 1-8 in Synthesis Example 1.

5) Reaction Scheme 14-5: Synthesis of Intermediate 14-e

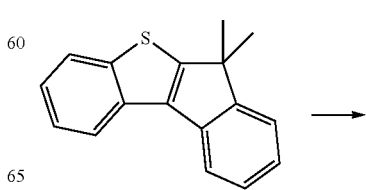

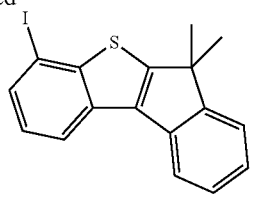

14-e 50 g (yield: 75.3%) of Intermediate 14-e was obtained in the same manner as in Synthesis Example 1, except that Intermediate 14-d was used instead of Intermediate 1-g of Reaction Scheme 1-8 in Synthesis Example 1.

6) Reaction Scheme 14-6: Synthesis of Intermediate 14-f

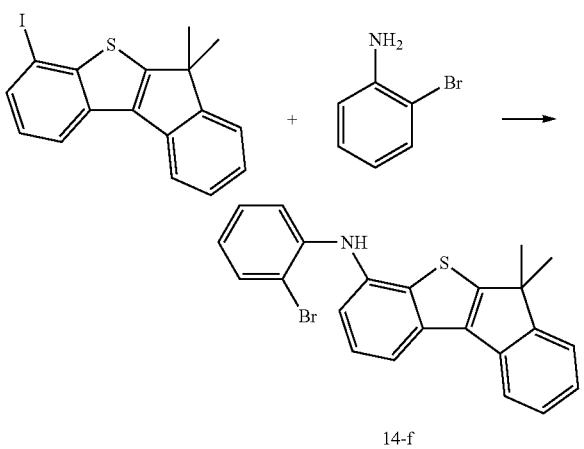

14-f 45 g (yield: 76.2%) of Intermediate 14-f was obtained in the same manner as in Synthesis Example 1, except that Intermediate 14-e was used instead of Intermediate 1-h of Reaction Scheme 1-9 in Synthesis Example 1.

7) Reaction Scheme 14-7: Synthesis of Intermediate 14-g

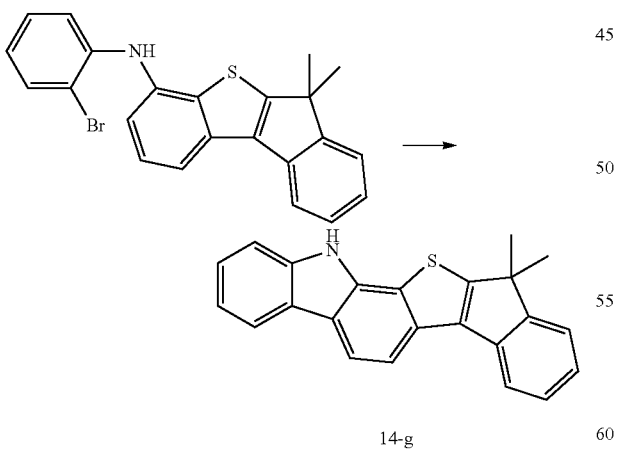

14-g 25 g (yield: 67.1%) of Intermediate 14-g was obtained in the same manner as in Synthesis Example 1, except that Intermediate 14-f was used instead of Intermediate 1-i of Reaction Scheme 1-10 in Synthesis Example 1.

8) Reaction Scheme 14-8: Synthesis of Compound 165

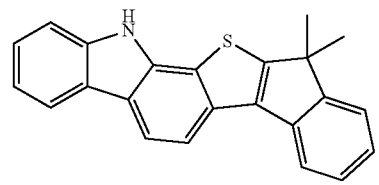

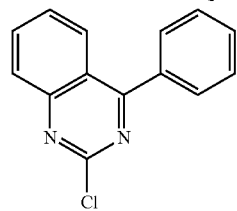

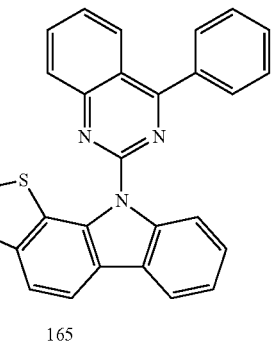

165

6.3 g (yield: 43.8%) of Compound 165 was obtained in the same manner as in Synthesis Example 1, except that Intermediate 13-g was used instead of Intermediate 1-j of Reaction Scheme 1-11 in Synthesis Example 1.

MS [M]$^+$: 544

Synthesis Example 15: Synthesis of Compound 351

1) Reaction Scheme 15-1: Synthesis of Compound 351

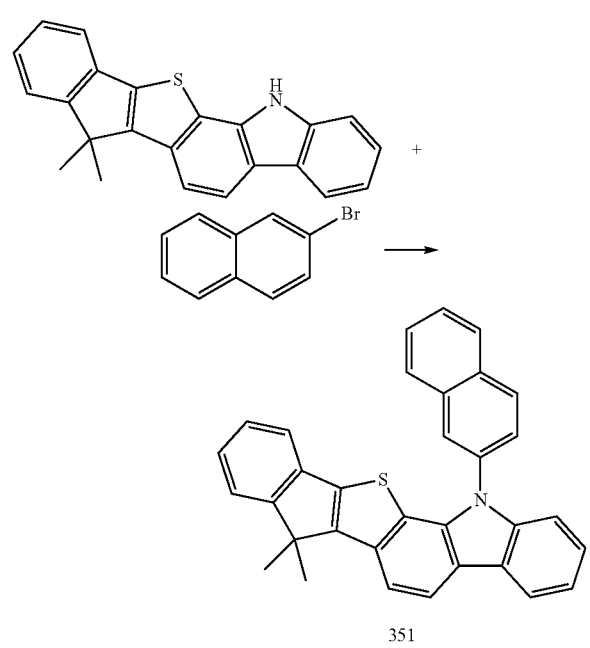

351

5.4 g (yield: 46.7%) of Compound 351 was obtained in the same manner as in Synthesis Example 1, except that 2-bromonaphthalene was used instead of Intermediate 1-d of Reaction Scheme 1-11 in Synthesis Example 1.

MS [M]$^+$: 466

Example 1

An ITO glass substrate was patterned to have a light-emitting area cut into a size of 2 mm×2 mm, and then, cleaned. After the ITO glass substrate was mounted on a vacuum chamber base that is set to have a base pressure of $1\times10^{-6}$ torr, DNTPD (700 Å), NPB (300 Å), Compound 3:RD-1 (at a weight ratio of 90:10) (300 Å), Compound ET16:Liq (at a weight ratio of 1:1) (250 Å), Liq (10 Å), and Al (1,000 Å) were sequentially cast on the ITO glass substrate in the stated order, thereby manufacturing an organic light-emitting device on the ITO glass substrate.

The structures of DNTPD, NPB, RD-1, Compound ET16, and Liq are as follows:

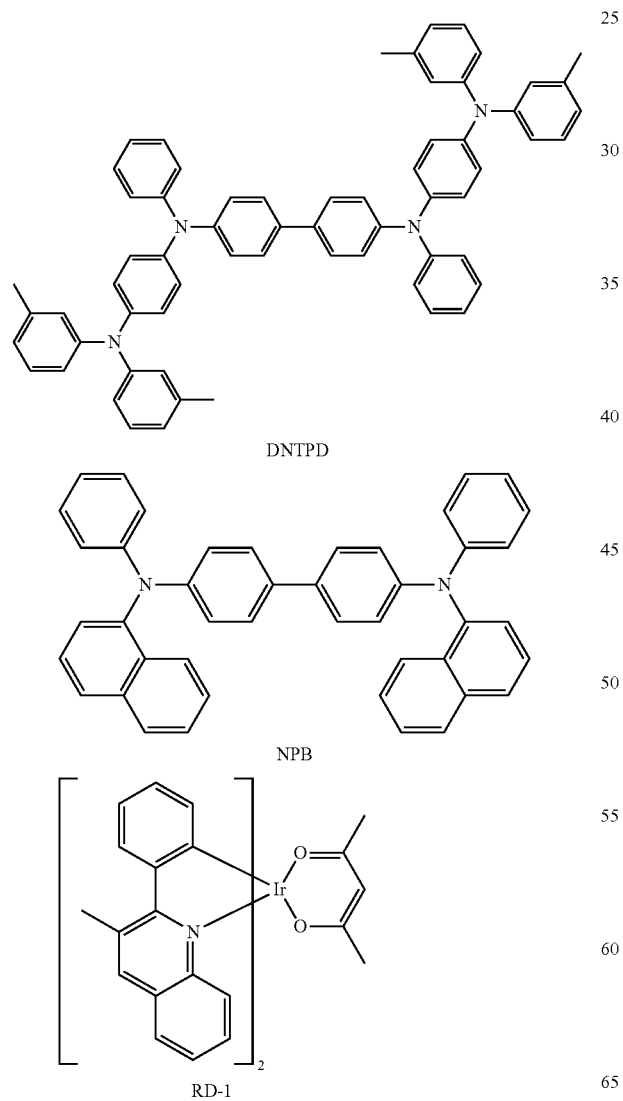

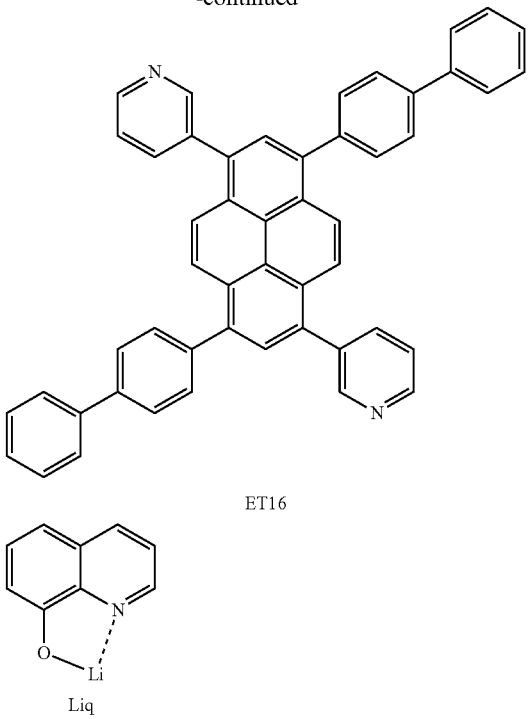

Example 2

An organic light-emitting device was manufactured in the same manner as in Example 1, except that Compound 4 was used instead of Compound 3 in the formation of the emission layer.

Example 3

An organic light-emitting device was manufactured in the same manner as in Example 1, except that Compound 7 was used instead of Compound 3 in the formation of the emission layer.

Example 4

An organic light-emitting device was manufactured in the same manner as in Example 1, except that Compound 9 was used instead of Compound 3 in the formation of the emission layer.

Example 5

An organic light-emitting device was manufactured in the same manner as in Example 1, except that Compound 10 was used instead of Compound 3 in the formation of the emission layer.

Example 6

An organic light-emitting device was manufactured in the same manner as in Example 1, except that Compound 15 was used instead of Compound 3 in the formation of the emission layer.

Example 7

An organic light-emitting device was manufactured in the same manner as in Example 1, except that Compound 16 was used instead of Compound 3 in the formation of the emission layer.

Example 8

An organic light-emitting device was manufactured in the same manner as in Example 1, except that Compound 24 was used instead of Compound 3 in the formation of the emission layer.

Example 9

An organic light-emitting device was manufactured in the same manner as in Example 1, except that Compound 33 was used instead of Compound 3 in the formation of the emission layer.

Example 10

An organic light-emitting device was manufactured in the same manner as in Example 1, except that Compound 165 was used instead of Compound 3 in the formation of the emission layer.

Comparative Example 1

An organic light-emitting device was manufactured in the same manner as in Example 1, except that BAlq was used instead of Compound 3 in the formation of the emission layer emission layer.

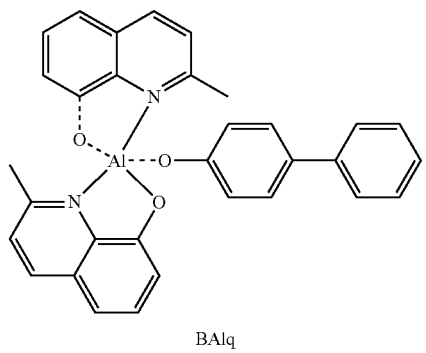

BAlq

Evaluation Example 1

Driving voltages, luminance, color coordinates, and lifespans (T95) of the organic light-emitting devices prepared in Examples 1 to 10 and Comparative Example 1 were evaluated, and the results are shown in Table 1 below. The expression "T95" as used herein refers to time required to reach 95% of luminance when initial luminance is considered as 100% (with respect to a current density of 3,000 $cd/m^2$).

TABLE 1

| Division | Host | Driving voltage (V) | Luminance $(Cd/m^2)$ | Efficiency (Cd/A) | CIEx | CIEy | T95 (hour) |
| --- | --- | --- | --- | --- | --- | --- | --- |
| Comparative Example 1 | BAlq | 6.2 | 1470 | 14.7 | 0.665 | 0.334 | 40 |
| Example 1 | Compound 3 | 4.3 | 2500 | 25.0 | 0.665 | 0.334 | 540 |
| Example 2 | Compound 4 | 4.1 | 2010 | 20.1 | 0.665 | 0.334 | 500 |
| Example 3 | Compound 7 | 4.1 | 2290 | 22.9 | 0.665 | 0.334 | 400 |
| Example 4 | Compound 9 | 4.7 | 2500 | 25.0 | 0.666 | 0.333 | 500 |
| Example 5 | Compound 10 | 4.4 | 2510 | 25.1 | 0.665 | 0.334 | 540 |
| Example 6 | Compound 15 | 4.2 | 2430 | 24.3 | 0.664 | 0.335 | 380 |
| Example 7 | Compound 16 | 3.7 | 2120 | 21.2 | 0.665 | 0.334 | 370 |
| Example 8 | Compound 24 | 4.3 | 2470 | 24.7 | 0.665 | 0.334 | 400 |
| Example 9 | Compound 33 | 4.1 | 2130 | 21.3 | 0.665 | 0.335 | 320 |
| Example 10 | Compound 165 | 4.1 | 2000 | 20.0 | 0.665 | 0.335 | 400 |

Referring to Table 1, it was confirmed that the organic light-emitting devices of Examples 1 to 10 had excellent driving voltages, luminance, and lifespan than compared to those of the organic light-emitting device of Comparative Example 1.

As described above, according to one or more of the above example embodiments, an organic light-emitting device including a heterocyclic compound may provide low driving voltage, high luminance, high efficiency, and long lifespan characteristics.

It should be understood that example embodiments described herein should be considered in a descriptive sense only and not for purposes of limitation. Descriptions of features or aspects within each example embodiment should typically be considered as available for other similar features or aspects in other example embodiments.

While one or more example embodiments have been described with reference to the accompanying drawing, it will be understood by those of ordinary skill in the art that various changes in form and details may be made therein without departing from the spirit and scope as defined by the following claims.

What is claimed is:

1. A heterocyclic compound represented by Formula 1 or selected from Compounds 189, 190, 192, 325, 326, 329, 330, 333, 334, 357, 358, 360, 369, 370, 372, 447, 448, 450, 459, 460, 462, 536, 537, 544, 545, 547, 548, 555 to 559, 572, and 573:

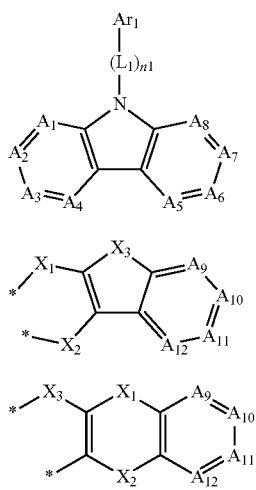

wherein, in the Formulae 1, 1a, and 1 b, $A_1$ is selected from $CR_1$ and nitrogen (N), $A_2$ is selected from $CR_2$ and N, $A_3$ is selected from $CR_3$ and N, $A_4$ is selected from $CR_4$ and N, $A_5$ is selected from $CR_5$ and N, $A_6$ is selected from $CR_6$ and N, $A_7$ is selected from $CR_7$ and N, $A_8$ is selected from $CR_8$ and N, $A_9$ is selected from $CR_9$ and N, $A_{10}$ is selected from $CR_{10}$ and N, $A_{11}$ is selected from $CR_{11}$ and N, and $A_{12}$ is selected from $CR_{12}$ and N;

two adjacent groups among the $A_1$ to the $A_8$ are each independently connected with a respective * of the Formula 1a or the Formula 1b to form a ring, wherein each * is a carbon atom of Formula 1;

$L_1$ is selected from a substituted or unsubstituted $C_3$-$C_{10}$ cycloalkylene, a substituted or unsubstituted $C_1$-$C_{10}$ heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{60}$ heteroarylene, a substituted or unsubstituted divalent non-aromatic condensed polycyclic group, and a substituted or unsubstituted divalent non-aromatic condensed heteropolycyclic group;

n1 is selected from 0, 1, 2, 3, and 4;

i) in Formula 1a, $X_1$ is selected from a single bond, O, and S;

$X_2$ is selected from a single bond, O, and S;

$X_3$ is selected from $C(R_{17})(R_{18})$, $N(R_{17})$, O, S, Se, Te, Po, $Si(R_{17})(R_{18})$, $Ge(R_{17})(R_{18})$, $P(R_{17})$, $P(R_{17})(=O)$, $C=O$, and $B(R_{17})$, at least one of $X_1$ and $X_2$ is selected from O and S, provided that when $X_1$ is a single bond, $X_3$ is selected from $N(R_{17})$, O, S, Se, Te, Po, $Si(R_{17})(R_{18})$, $Ge(R_{17})(R_{18})$, $P(R_{17})$, $P(R_{17})(=O)$, $C=O$, and $B(R_{17})$; and ii) in Formulae 1b, $X_1$ is selected from a single bond, $C(R_{13})(R_{14})$, $N(R_{13})$, O, S, Se, Te, Po, $Si(R_{13})(R_{14})$, $Ge(R_{13})(R_{14})$, $P(R_{13})$, $P(R_{13})(=O)$, $C=O$, and $B(R_{13})$; $X_2$ is selected from a single bond, $C(R_{15})(R_{16})$, $N(R_{15})$, O, S, Se, Te, Po, $Si(R_{15})(R_{16})$, $Ge(R_{15})(R_{16})$, $P(R_{15})$, $P(R_{15})(=O)$, $C=O$, and $B(R_{15})$; $X_3$ is selected from $C(R_{17})(R_{18})$, $N(R_{17})$, O, S, Se, Te, Po, $Si(R_{17})(R_{18})$, $Ge(R_{17})(R_{18})$, $P(R_{17})$, $P(R_{17})(=O)$, $C=O$, and $B(R_{17})$, provided that when $X_1$ is a single bond and $X_2$ is $C(R_{15})(R_{16})$, $X_3$ is selected from Te, Po, $Si(R_{17})(R_{18})$, $Ge(R_{17})(R_{18})$, $P(R_{17})$, $P(R_{17})(=O)$, $C=O$, and $B(R_{17})$;

$Ar_1$, $R_1$ to $R_{16}$ and $R_{18}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$R_{17}$ is selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{10}$ aryloxy group, a substituted or unsubstituted $C_6$-$C_{60}$ arylthio group, a substituted or unsubstituted $C_1$-$C_{10}$ heteroaryl group, a substituted or unsubstituted monovalent non-aromatic condensed polycyclic group, and a substituted or unsubstituted monovalent non-aromatic condensed heteropolycyclic group;

two adjacent groups among the $R_1$ to $R_{18}$ are optionally connected with each other to form a ring;

at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_{11}$ to $Q_{17}$, $Q_{21}$ to $Q_{27}$ and $Q_{31}$ to $Q_{37}$ are each independently selected from a hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group;

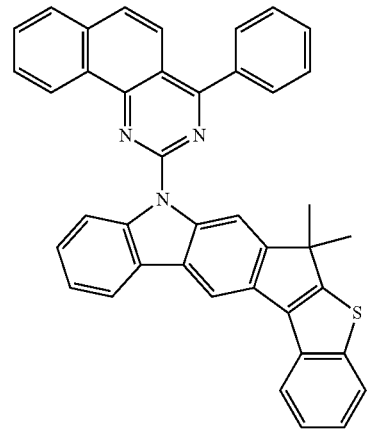

189

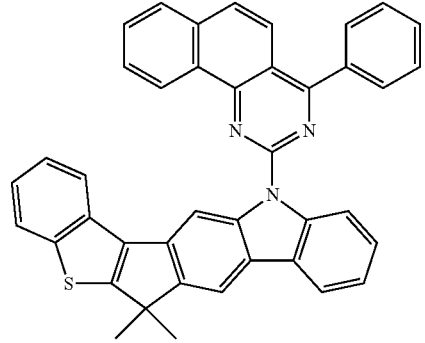

190

273
-continued
192
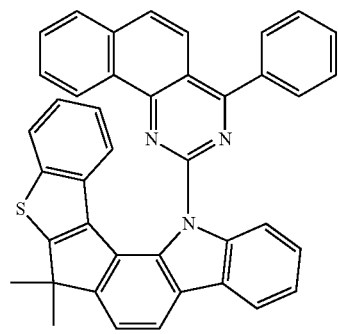
325
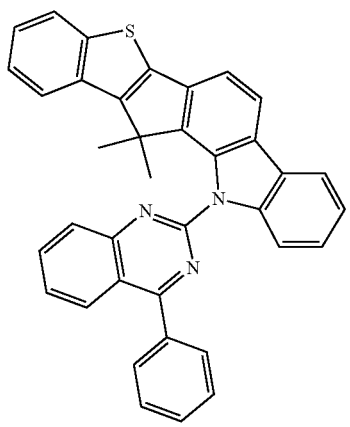
326
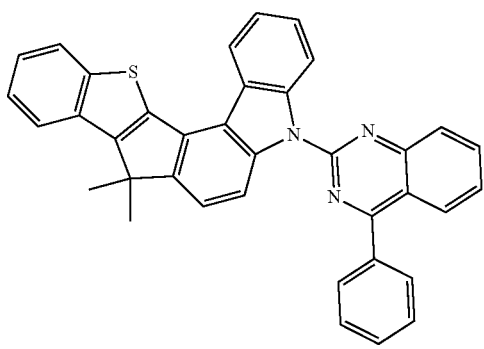
329
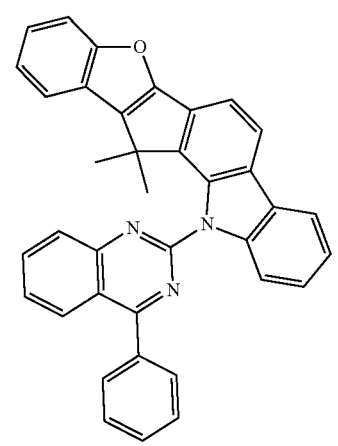
274
-continued
330
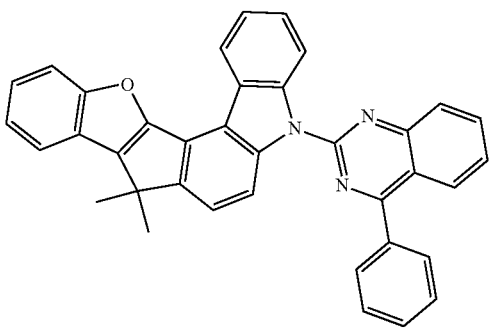
333
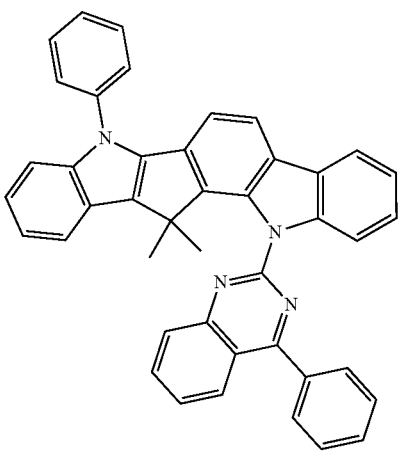
334
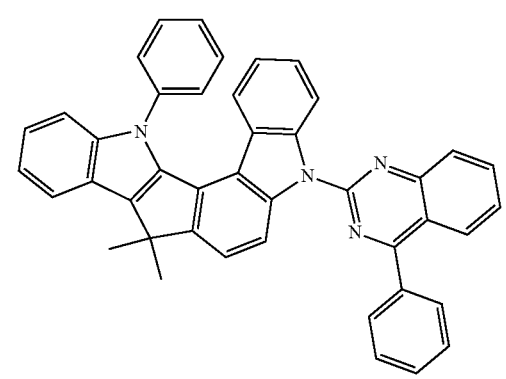
357
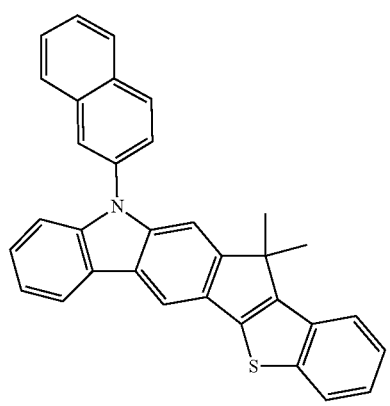

358
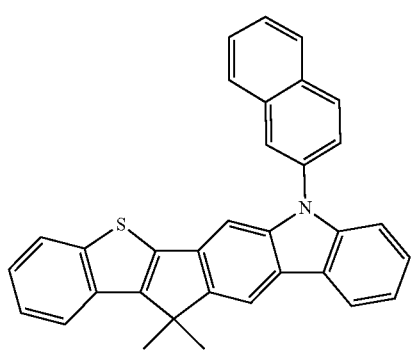
360
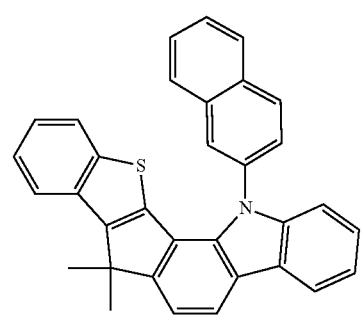
369
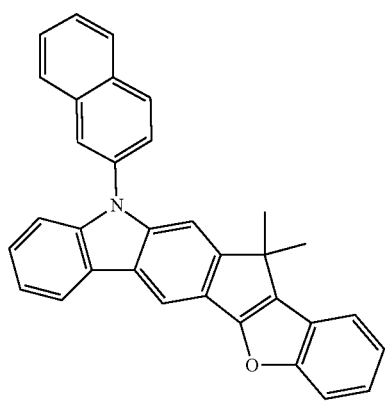
370
372
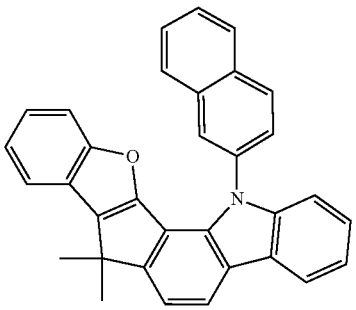
447
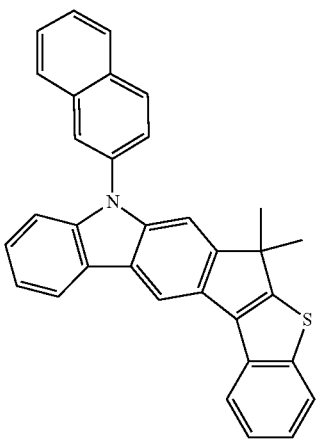
448
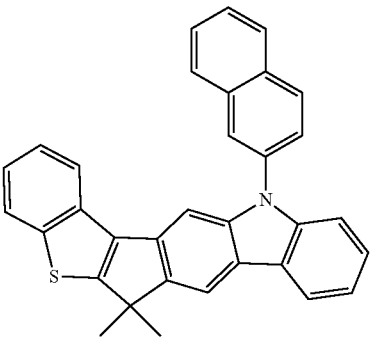
450
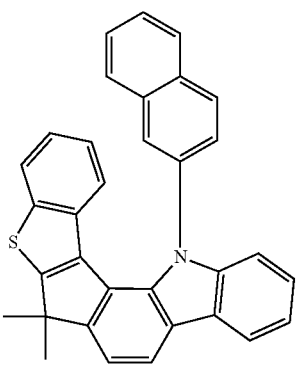

277
-continued
459
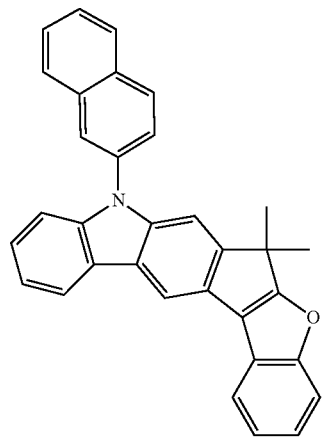
460
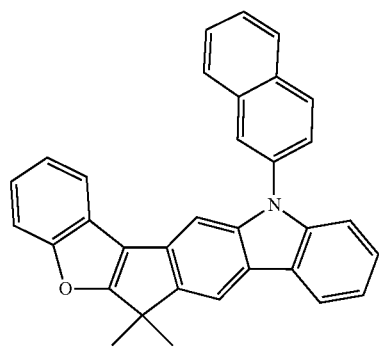
462
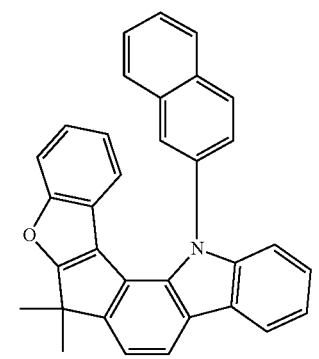
536
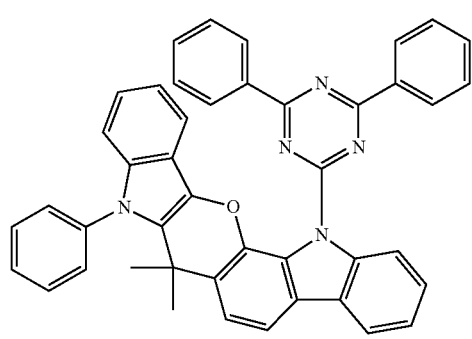
278
-continued
537
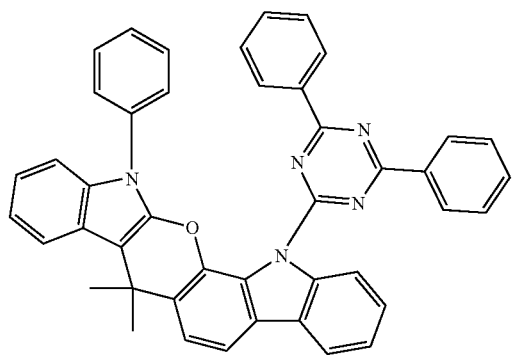
544
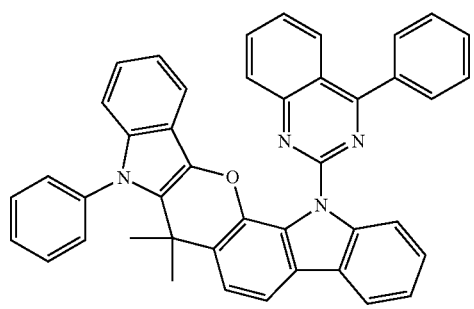
545
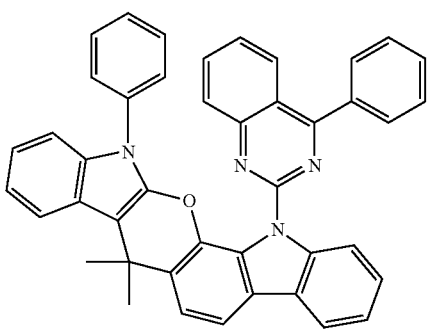
547
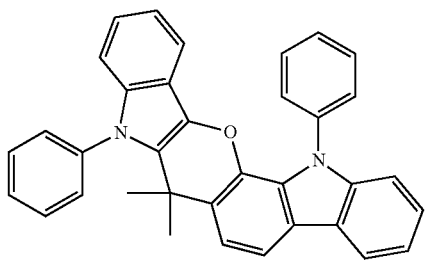
548
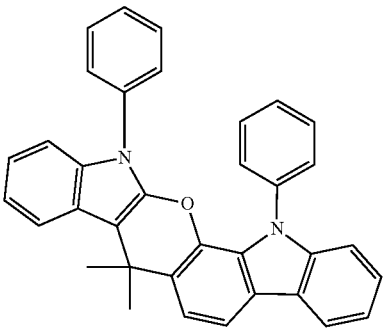

555
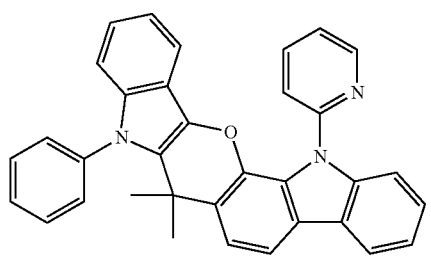

556
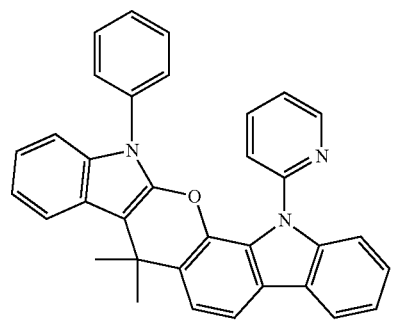

557
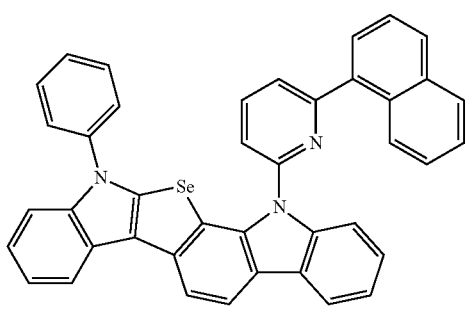

558
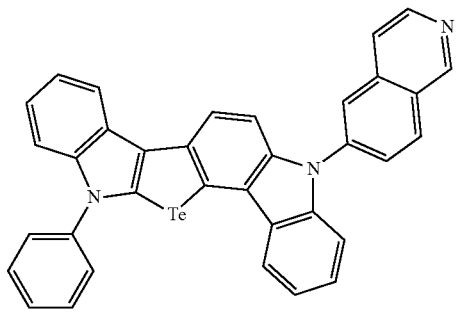

559
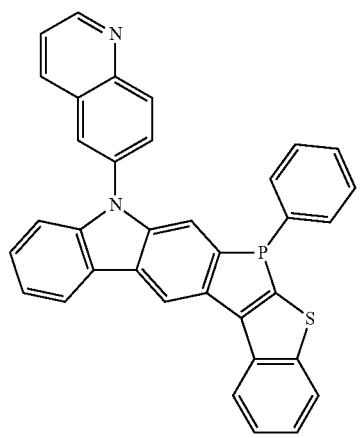

572
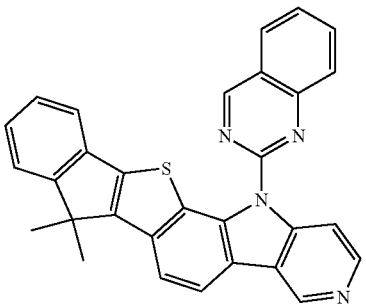

573
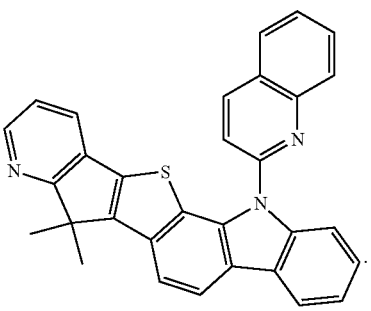

2. The heterocyclic compound of claim 1, wherein the $L_1$ is selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a benzoquinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a benzoquinazolinylene group, a cinnolinylene group, a carbazolylene group, a phenanthridinylene group, an acridinylene group, a phenanthrolinylene group, a phenazinylene group, a benzimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{60}$ aryloxy group, a $C_6$-$C_6$ arylthio group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group.

3. The heterocyclic compound of claim 1, wherein the $L_1$ is selected from:

a phenylene group, a naphthylene group, a pyridinylene group, a pyrimidinylene group, a quinolinylene group, an isoquinolinylene group, a benzoquinolinylene group, a quinoxalinylene group, a quinazolinylene group, a benzoquinazolinylene group and a triazinylene group; and a naphthylene group, a pyridinylene group, a pyrimidinylene group, a quinolinylene group, an isoquinolinylene group, a benzoquinolinylene group, a quinoxalinylene group, a quinazolinylene group, a benzoquinazolinylene group and a triazinylene group, each substituted with at least one of a deuterium, —F, —Cl, —Br, —I, a methyl group, an ethyl group, a tert-butyl group, a methoxy group, an ethoxy group, a tert-butoxy group, a phenoxy group, a phenylthio group, a phenyl group, a naphthyl group, a pyridinyl group, and a pyrimidinyl group.

4. The heterocyclic compound of claim 1, wherein the $L_1$ is selected from groups represented by Formulae 3-1 to 3-22:

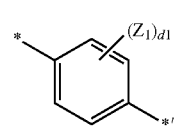
3-1

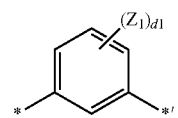
3-2

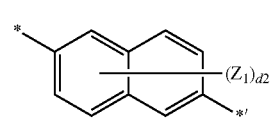
3-3

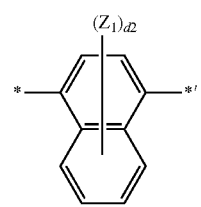
3-4

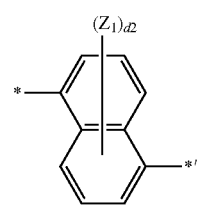
3-5

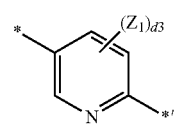
3-6

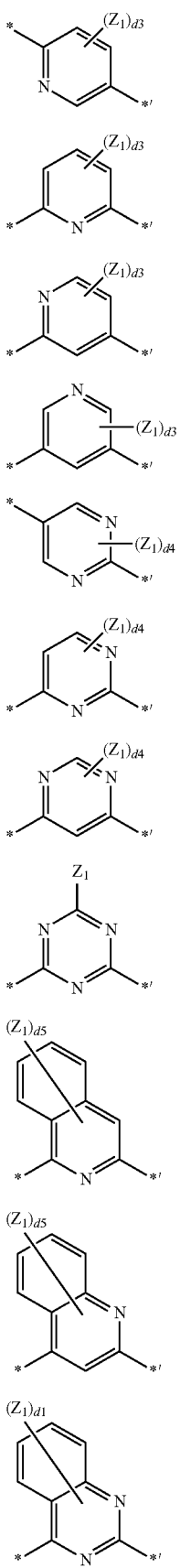
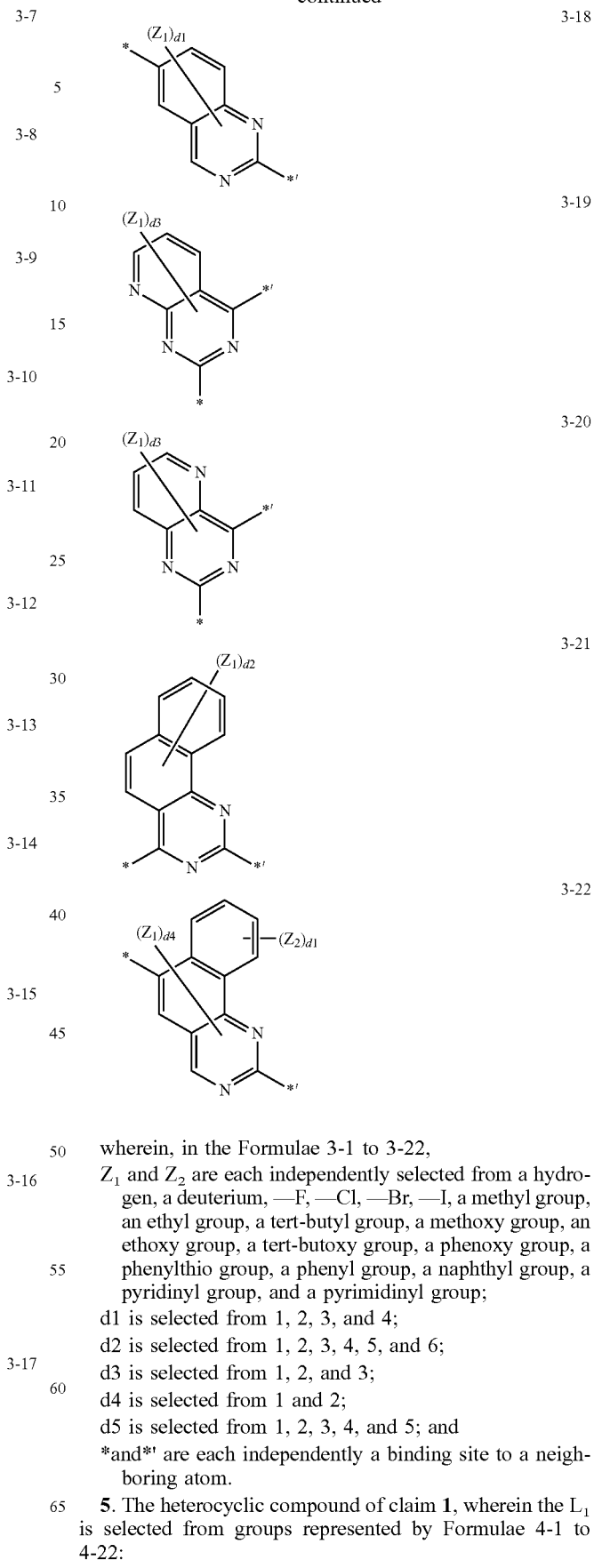

wherein, in the Formulae 3-1 to 3-22, $Z_1$ and $Z_2$ are each independently selected from a hydrogen, a deuterium, —F, —Cl, —Br, —I, a methyl group, an ethyl group, a tert-butyl group, a methoxy group, an ethoxy group, a tert-butoxy group, a phenoxy group, a phenylthio group, a phenyl group, a naphthyl group, a pyridinyl group, and a pyrimidinyl group;

d1 is selected from 1, 2, 3, and 4;
d2 is selected from 1, 2, 3, 4, 5, and 6;
d3 is selected from 1, 2, and 3;
d4 is selected from 1 and 2;
d5 is selected from 1, 2, 3, 4, and 5; and
*and*' are each independently a binding site to a neighboring atom.

5. The heterocyclic compound of claim 1, wherein the $L_1$ is selected from groups represented by Formulae 4-1 to 4-22:

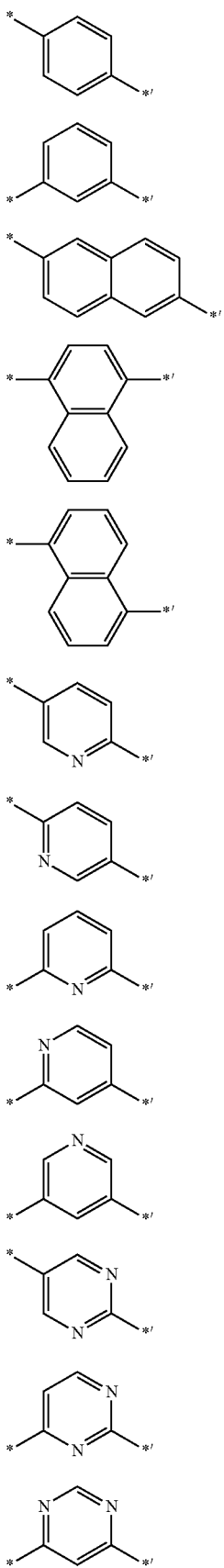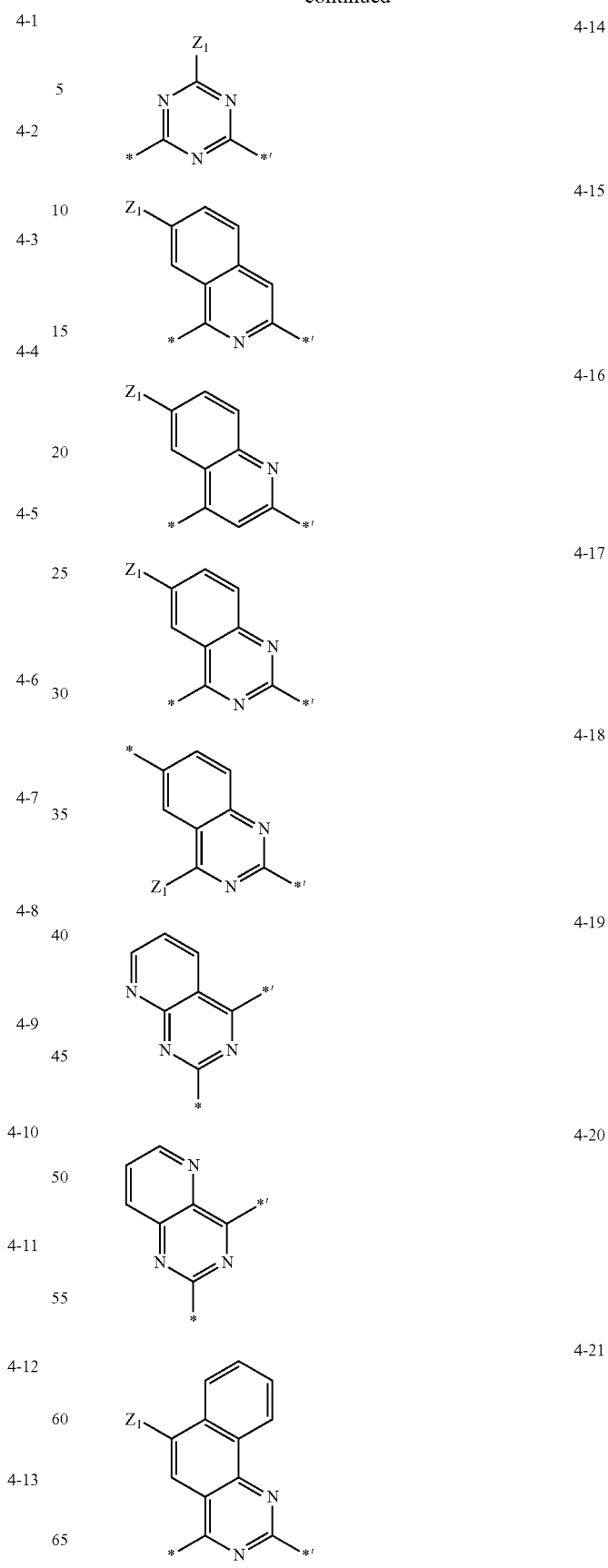

-continued 4-22

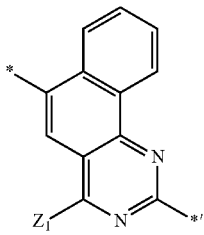

wherein, in the Formulae 4-1 to 4-22,
$Z_1$ is selected from a hydrogen, a deuterium, a methyl group, an ethyl group, a tert-butyl group, a methoxy group, an ethoxy group, a tert-butoxy group, a phenoxy group, a phenylthio group, a phenyl group, a naphthyl group, and a pyridinyl group;
*and*' are each independently a binding site to a neighboring atom.

6. The heterocyclic compound of claim 1, wherein n1 is selected from 0, 1, and 2.

7. The heterocyclic compound of claim 1, wherein the $X_1$ and $X_2$ are each independently selected from oxygen (O) and Sulfur (S).

8. The heterocyclic compound of claim 1, wherein the $X_3$ is selected from $C(R_{17})(R_{18})$ and $N(R_{17})$.

9. The heterocyclic compound of claim 1, wherein the $Ar_1$ is selected from:
a methyl group, an ethyl group, an n-propyl group, an iso-propyl group, a cyclopentyl group, a cyclohexyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovaleny group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a pyridoindolyl group, a benzoquinolinyl group, a phthalazinyl group, a naphthyridinyl group, a quinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, and a dibenzocarbazolyl group; and
a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a pyridoindolyl group, a benzoquinolinyl group, a phthalazinyl group, a naphthyridinyl group, a quinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, and a dibenzocarbazolyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{60}$ aryloxy group, a $C_6$-$C_{60}$ arylthio group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a carbazolyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group.

10. The heterocyclic compound of claim 1, wherein the $Ar_1$ is selected from:
a methyl group, a phenyl group, a naphthyl group, a pyridinyl group, a pyrimidinyl group, a quinolinyl group, an isoquinolinyl group, a carbazolyl group, a pyridoindolyl group, a quinoxalinyl group, a quinazolinyl group, a benzoquinazolinyl group, a benzimidazolyl group, and a triazinyl group; and a phenyl group, a naphthyl group, a pyridinyl group, a pyrimidinyl group, a quinolinyl group, an isoquinolinyl group, a carbazolyl group, a pyridoindolyl group, a quinoxalinyl group, a quinazolinyl group, a benzoquinazolinyl group, a benzimidazolyl group, and a triazinyl group, each substituted with at least one of a deuterium, —F, a methyl group, an ethyl group, an n-propyl group, an iso-propyl group, a tert-butyl group, a methoxy group, an ethoxy group, a tert-butoxy group, a phenoxy group, a phenylthio group, a phenyl group, a naphthyl group, and a pyridinyl group.

11. The heterocyclic compound of claim 1, wherein the $Ar_1$ is selected from groups represented by Formulae 5-1 to 5-48:

5-1
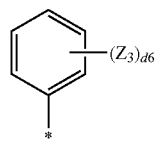

5-2
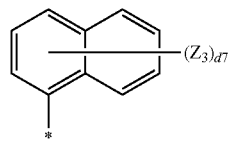

5-3
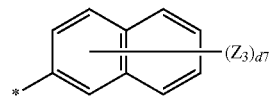

5-4
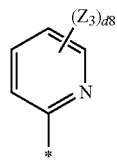

5-5
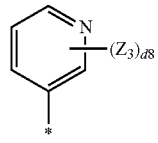

5-6
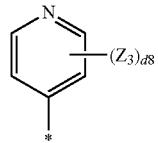

5-7
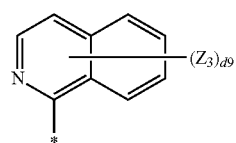

5-8
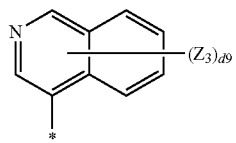

5-9
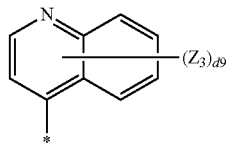

5-10
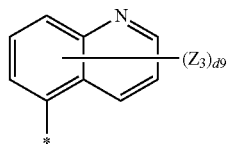

5-11
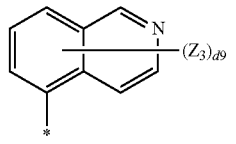

5-12
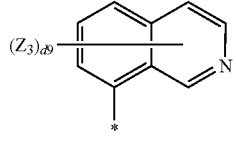

5-13
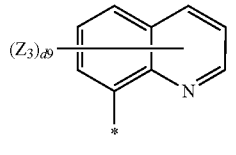

5-14
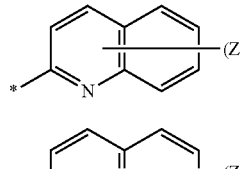

5-15
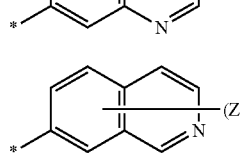

5-16
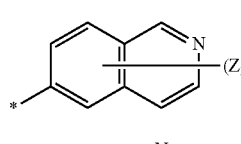

5-17
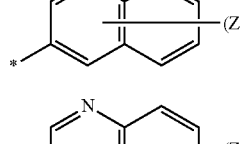

5-18
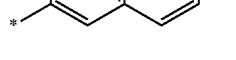

5-19

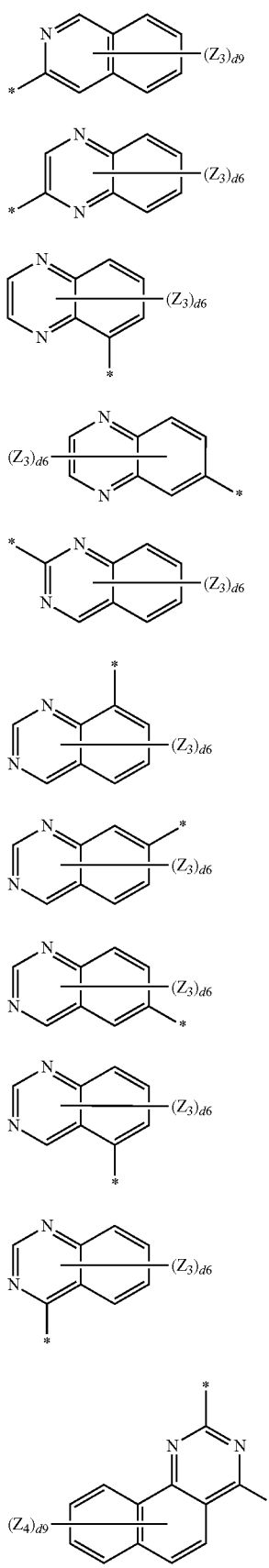
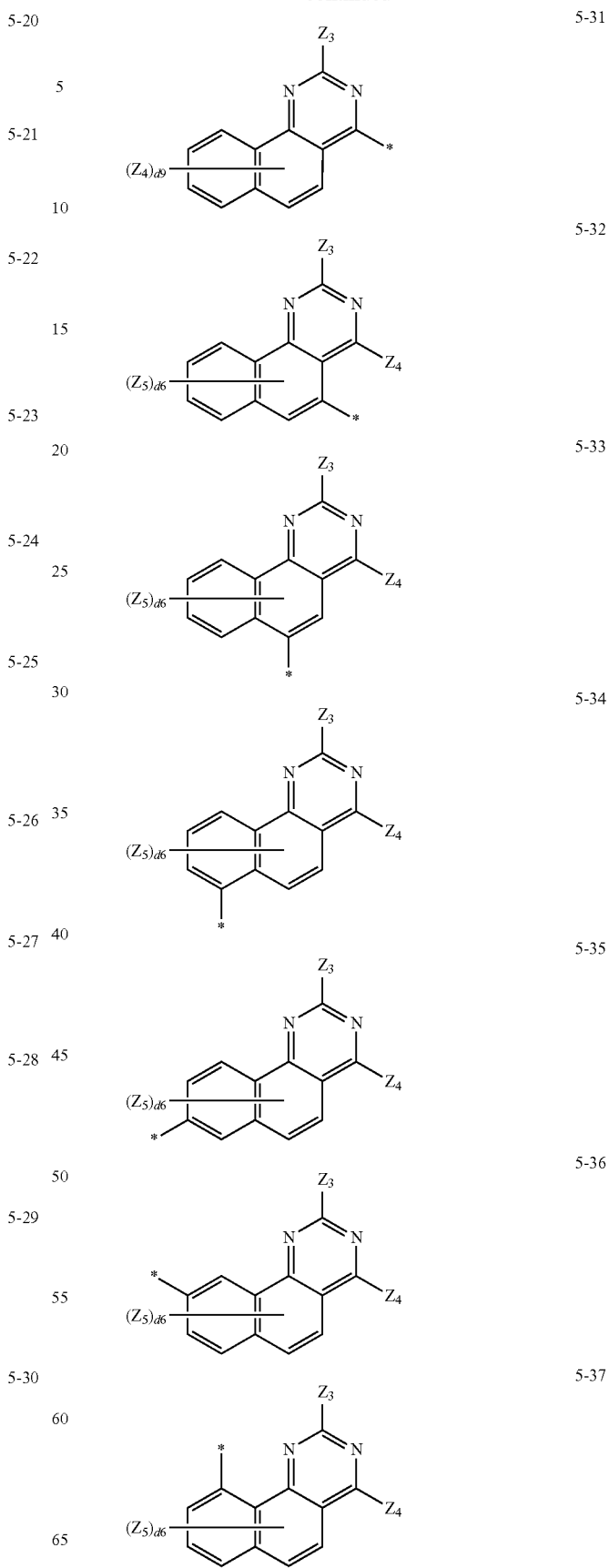

5-38 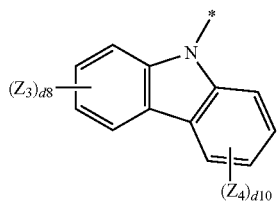

5-39 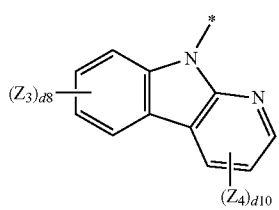

5-40 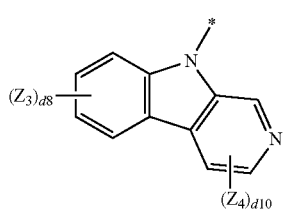

5-41 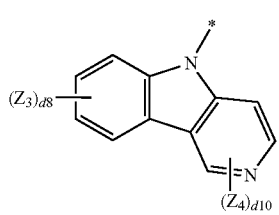

5-42 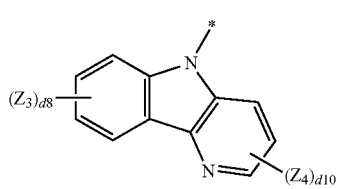

5-43 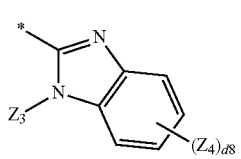

5-44 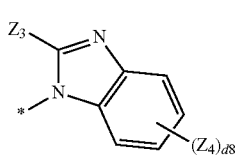

5-45 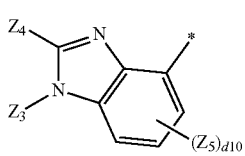

5-46 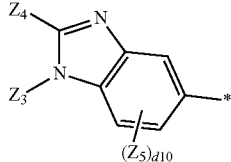

5-47 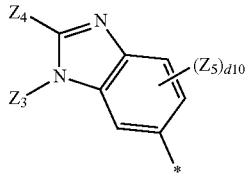

5-48 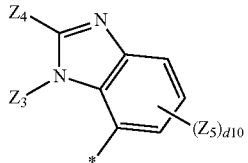

wherein, in the Formulae 5-1 to 5-48, $Z_3$ to $Z_5$ are each independently selected from a hydrogen, a deuterium, —F, a methyl group, an ethyl group, an n-propyl group, an iso-propyl group, a tert-butyl group, a methoxy group, an ethoxy group, a tert-butoxy group, a phenoxy group, a phenylthio group, a phenyl group, a naphthyl group, and a pyridinyl group;

d6 is selected from 1, 2, 3, 4, and 5;

d7 is selected from 1, 2, 3, 4, 5, 6, and 7;

d8 is selected from 1, 2, 3, and 4;

d9 is selected from 1, 2, 3, 4, 5, and 6; and

* is a binding site to a neighboring atom.

12. The heterocyclic compound of claim 1, wherein the $R_1$ to $R_{18}$ are each independently selected from:

a hydrogen, a deuterium, a methyl group, an ethyl group, an n-propyl group, an iso-propyl group, a phenyl group, a naphthyl group, and a pyridinyl group; and a phenyl group, a naphthyl group, and a pyridinyl group, each substituted with at least one of a phenyl group, a naphthyl group, and a pyridinyl group.

13. The heterocyclic compound of claim 1, wherein the $R_1$ to $R_{18}$ are each independently selected from:

a hydrogen, a methyl group, an iso-propyl group, a phenyl group, a naphthyl group, and a pyridinyl group; and a phenyl group substituted with a phenyl group.

14. The heterocyclic compound of claim 1, wherein the heterocyclic compound is represented by one of Formulae 1-1, 1-2, 1-5 to 1-12:

1-1

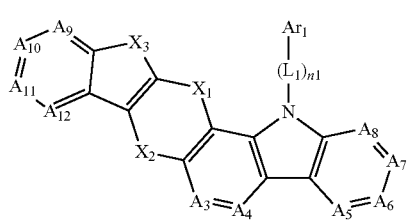

1-2
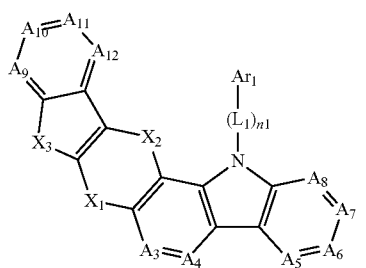
1-5
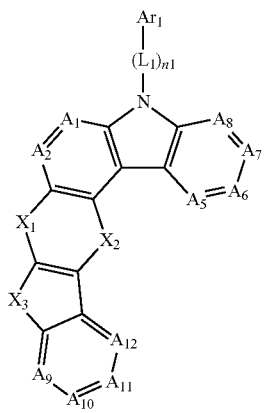
1-6
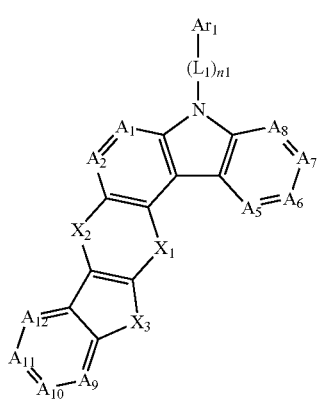
1-7
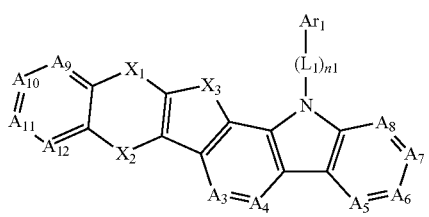
1-8
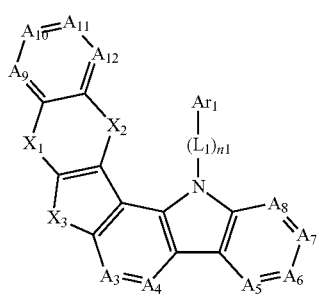
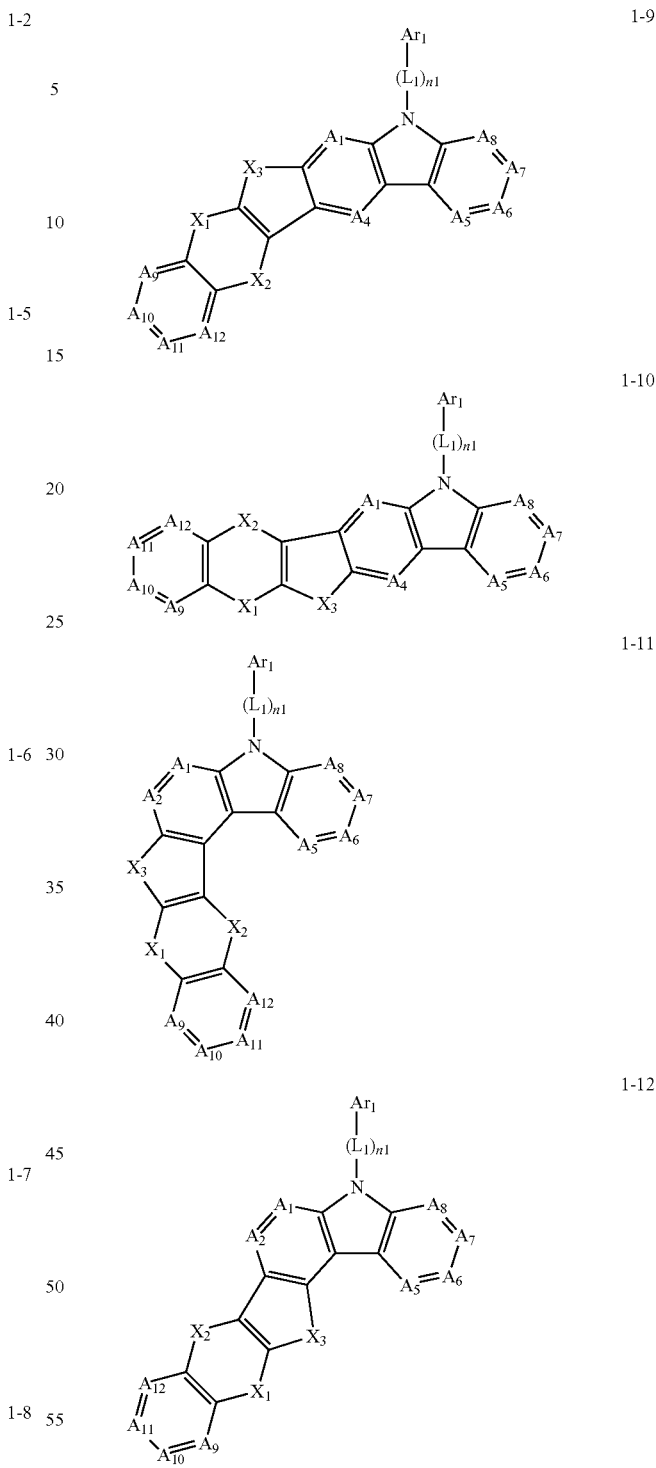
wherein, in Formulae 1-1 to 1-6, $X_1$ to $X_3$ are the same as defined in connection with Formula 1a, and in Formulae 1-7 to 1-12, $X_1$ to $X_3$ are the same as defined in connection with Formula 1b.
15. The heterocyclic compound of claim 1, wherein the heterocyclic compound is represented by Formulae 1-1 to 1-12:

1-1
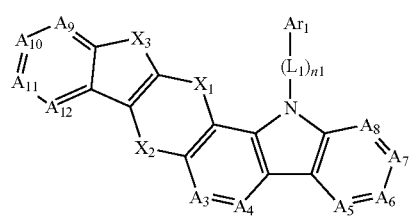
1-2
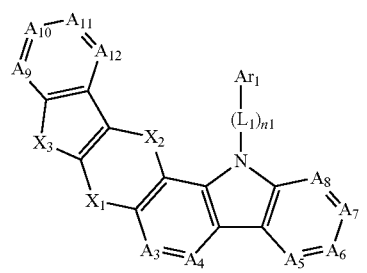
1-3
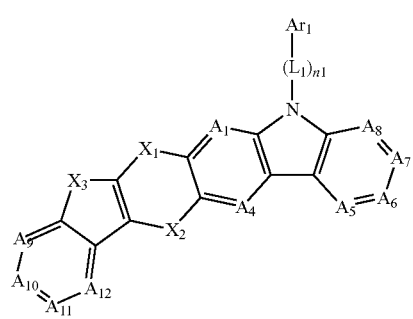
1-4
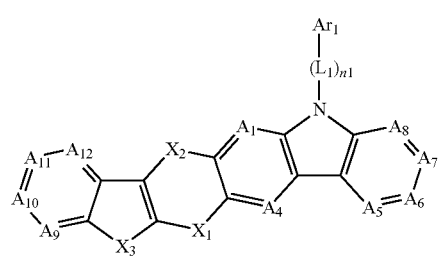
1-5
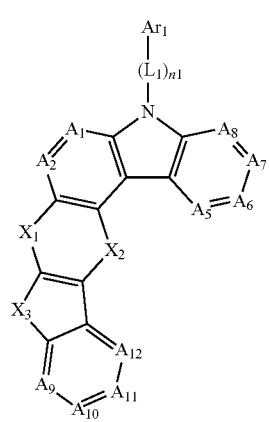
1-6
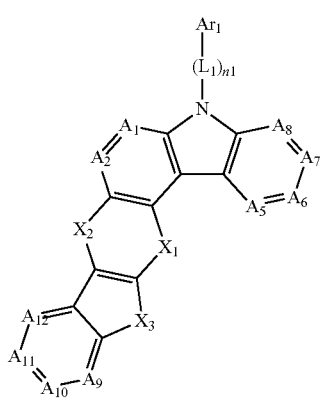
1-7
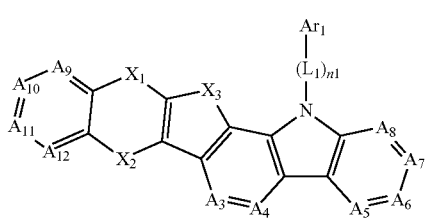
1-8
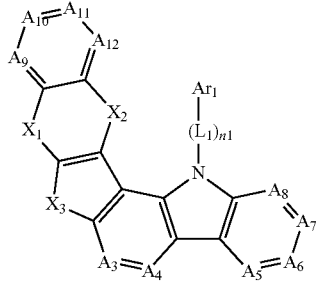
1-9
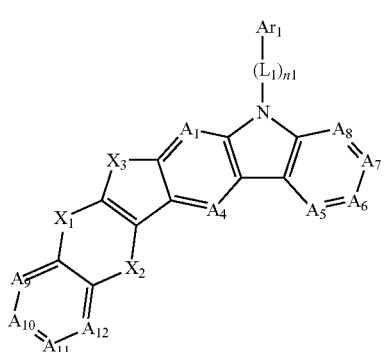
1-10
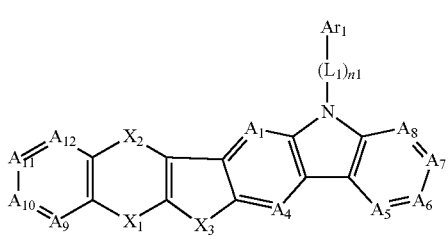

-continued

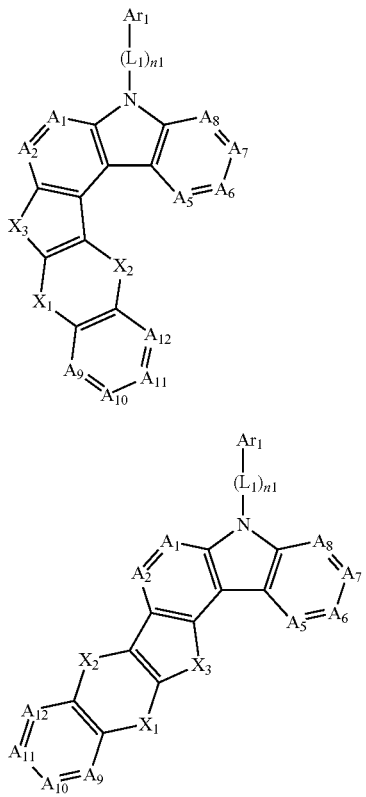

1-11

1-12 wherein, in the Formulae 1-1 to 1-12, $A_1$ is selected from $CR_1$ and N, $A_2$ is selected from $CR_2$ and N, $A_3$ is selected from $CR_3$ and N, $A_4$ is selected from $CR_4$ and N, $A_5$ is selected from $CR_5$ and N, $A_6$ is selected from $CR_6$ and N, $A_7$ is selected from $CR_7$ and N, $A_8$ is selected from $CR_8$ and N, $A_9$ is selected from $CR_9$ and N, $A_{10}$ is selected from $CR_{10}$ and N, $A_{11}$ is selected from $CR_{11}$ and N, and $A_{12}$ is selected from $CR_{12}$ and N;

$L_1$ is selected from a substituted or unsubstituted $C_3$-$C_{10}$ cycloalkylene, a substituted or unsubstituted $C_1$-$C_{10}$ heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{60}$ heteroarylene, a substituted or unsubstituted divalent non-aromatic condensed polycyclic group, and a substituted or unsubstituted divalent non-aromatic condensed heteropolycyclic group;

n1 is selected from 0, 1, and 2;

$X_1$ and $X_2$ are each independently selected from O and S;

$X_3$ is selected from $C(R_{17})(R_{18})$ and $N(R_{17})$;

$Ar_1$ and $R_1$ to $R_{12}$, $R_{17}$, and $R_{18}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

two adjacent groups among the $R_1$ to $R_{12}$, $R_{17}$, and $R_{18}$ are optionally connected with each other to form a ring;

at least one substituent of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_{11}$ to $Q_{17}$, $Q_{21}$ to $Q_{27}$ and $Q_{31}$ to $Q_{37}$ are each independently selected from a hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

16. The heterocyclic compound of claim 1, wherein the heterocyclic compound is represented by one of Formulae 1-21 to 1-32:

1-21

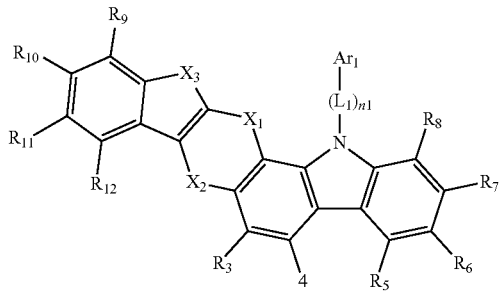

1-22

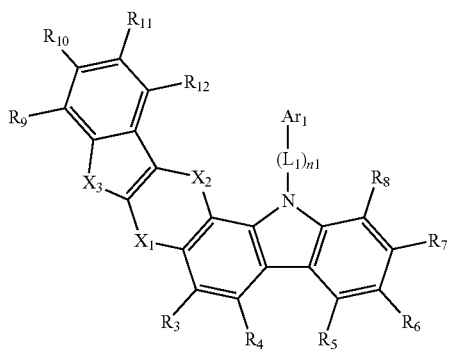

1-23

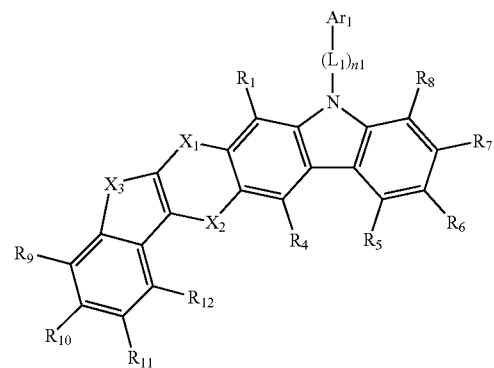

1-24

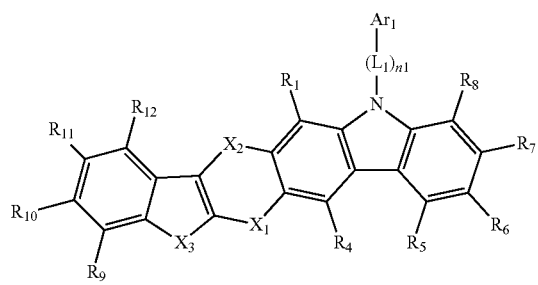

1-25

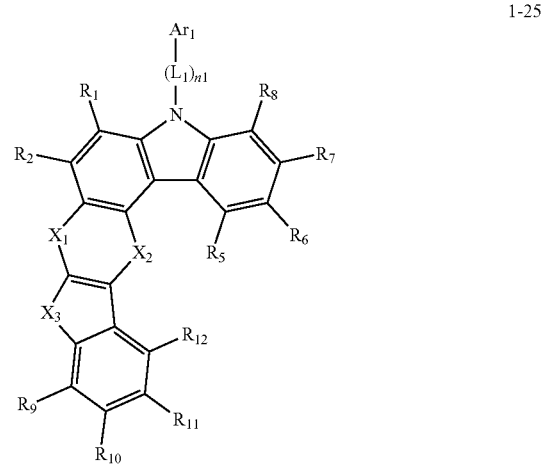

1-26

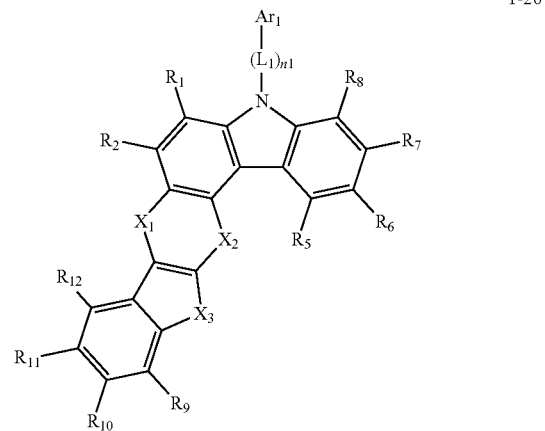

1-27
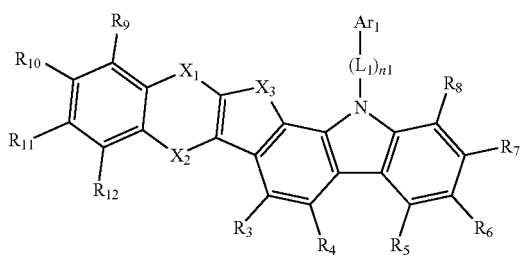
1-28
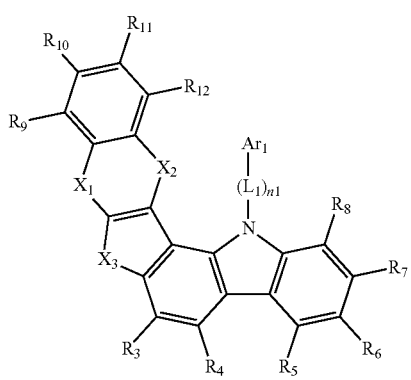
1-29
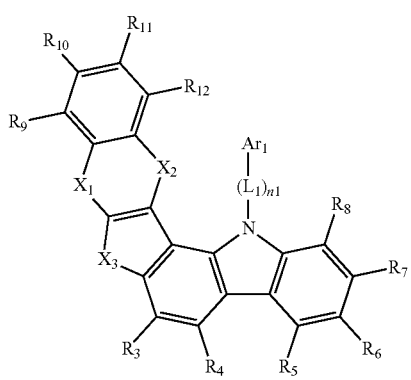
1-30
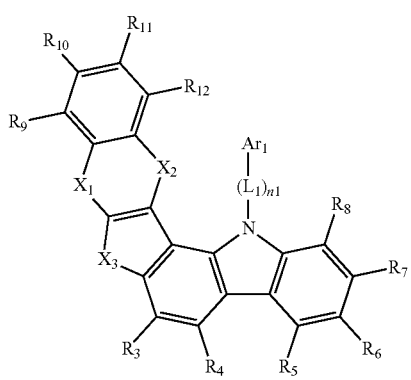
1-31
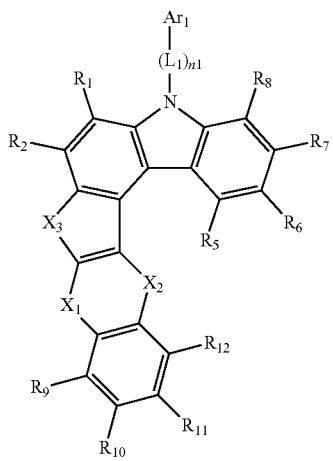
1-32
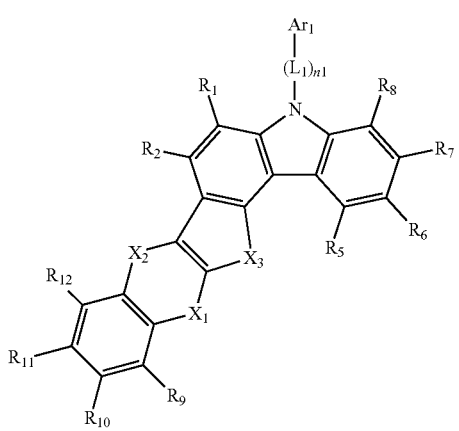
wherein, in the Formulae 1-21 to 1-32,
L₁ is selected from groups represented by Formulae 4-1 to 4-18;
4-1
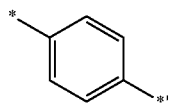
4-2
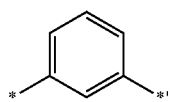
4-3
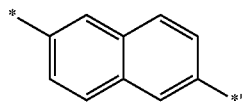
4-4
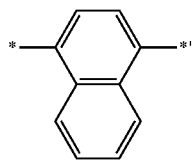

-continued

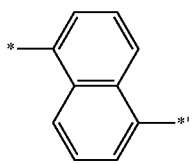 4-5

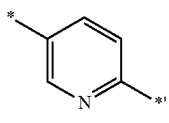 4-6

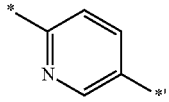 4-7

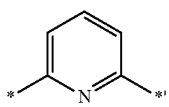 4-8

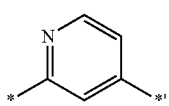 4-9

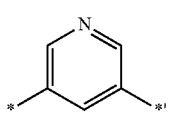 4-10

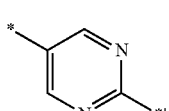 4-11

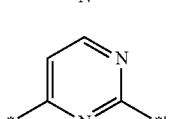 4-12

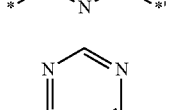 4-13

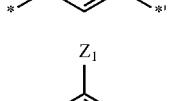 4-14

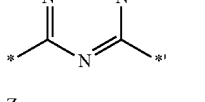 4-15

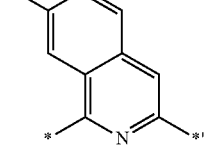 4-16

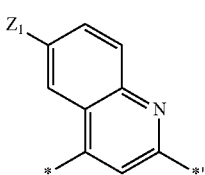

-continued

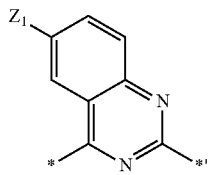 4-17

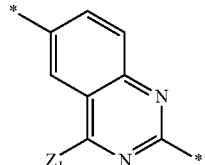 4-18

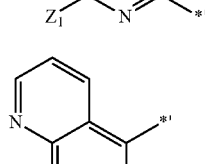 4-19

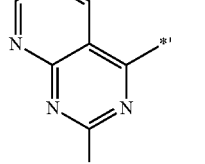 4-20

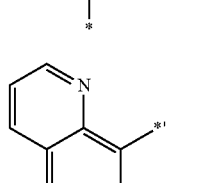 4-21

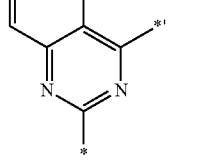 4-22 wherein, in the Formulae 4-1 to 4-22, $Z_1$ is selected from a hydrogen, a deuterium, a methyl group, an ethyl group, a tert-butyl group, a methoxy group, an ethoxy group, a tert-butoxy group, a phenoxy group, a phenylthio group, a phenyl group, a naphthyl group, and a pyridinyl group;

*and*' are each independently a binding site to a neighboring atom;

n1 is selected from 0, 1, and 2;

$X_1$ and $X_2$ are each independently selected from O and S;

$X_3$ is selected from $C(R_{17})(R_{18})$ and $N(R_{17})$;

$Ar_1$ is selected from:

a methyl group, a phenyl group, a naphthyl group, a pyridinyl group, a pyrimidinyl group, a quinolinyl group, an isoquinolinyl group, a carbazolyl group, a pyridoindolyl group, a quinoxalinyl group, a quinazolinyl group, a benzoquinazolinyl group, a benzimidazolyl group, and a triazinyl group; and a phenyl group, a naphthyl group, a pyridinyl group, a pyrimidinyl group, a quinolinyl group, an isoquinolinyl group, a carbazolyl group, a pyridoindolyl group, a quinoxalinyl group, a quinazolinyl group, a benzoquinazolinyl group, a benzimidazolyl group, and a triazinyl group, each substituted with at least one of a deuterium, —F, a methyl group, an ethyl group, an n-propyl group, an iso-propyl group, a tert-butyl group, a methoxy group, an ethoxy group, a tert-butoxy group, a phenoxy group, a phenylthio group, a phenyl group, a naphthyl group, and a pyridinyl group;

$R_1$ to $R_{12}$, $R_{17}$, and $R_{18}$ are each independently selected from:

a hydrogen, a deuterium, a methyl group, an ethyl group, an n-propyl group, an iso-propyl group, a phenyl group, a naphthyl group, and a pyridinyl group; and a phenyl group, a naphthyl group, and a pyridinyl group, each substituted with at least one of a phenyl group, a naphthyl group, and a pyridinyl group.

17. A heterocyclic compound, wherein the heterocyclic compound is any one of Compounds 27, 28, 30, 73, 85 to 188, 191, 193 to 324, 337 to 341, 343 to 348, 373 to 408, 421 to 446, 449, 451 to 458, 461, 463 to 535, 538 to 543, 546, 549 to 554, 560 to 562, 565, 567 to 571, and 574 to 580:

27
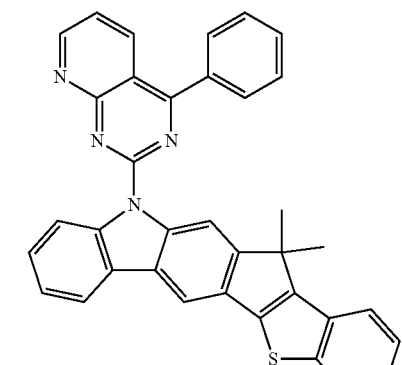

28
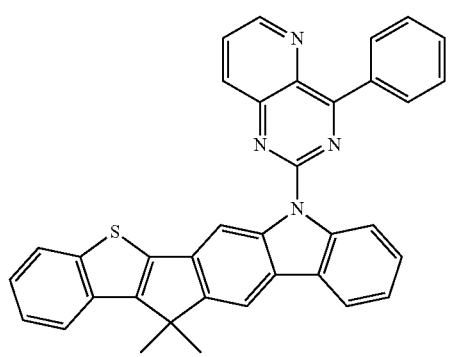

30
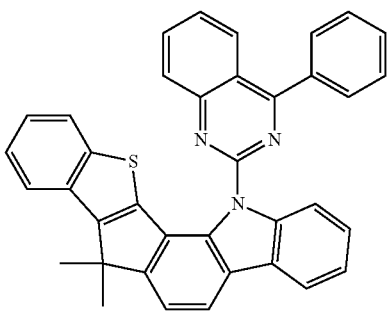

73
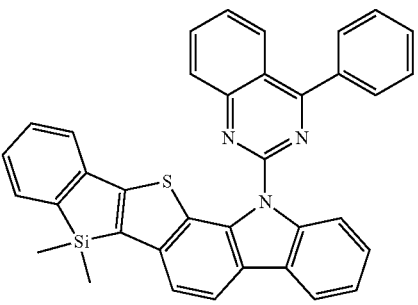

85
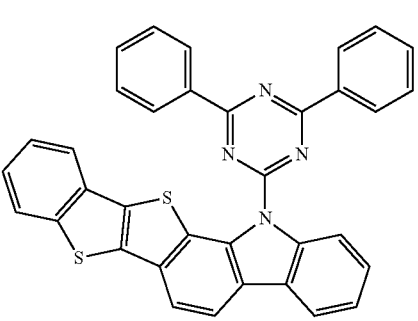

86
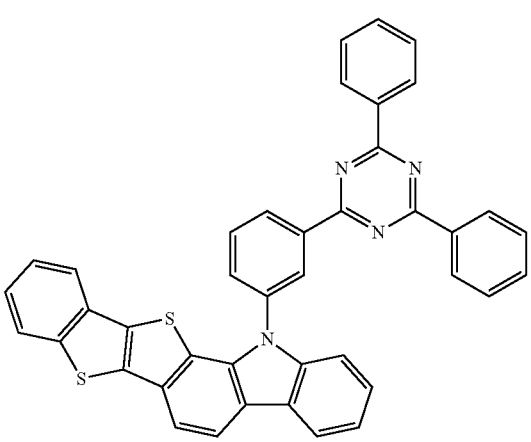

309
-continued
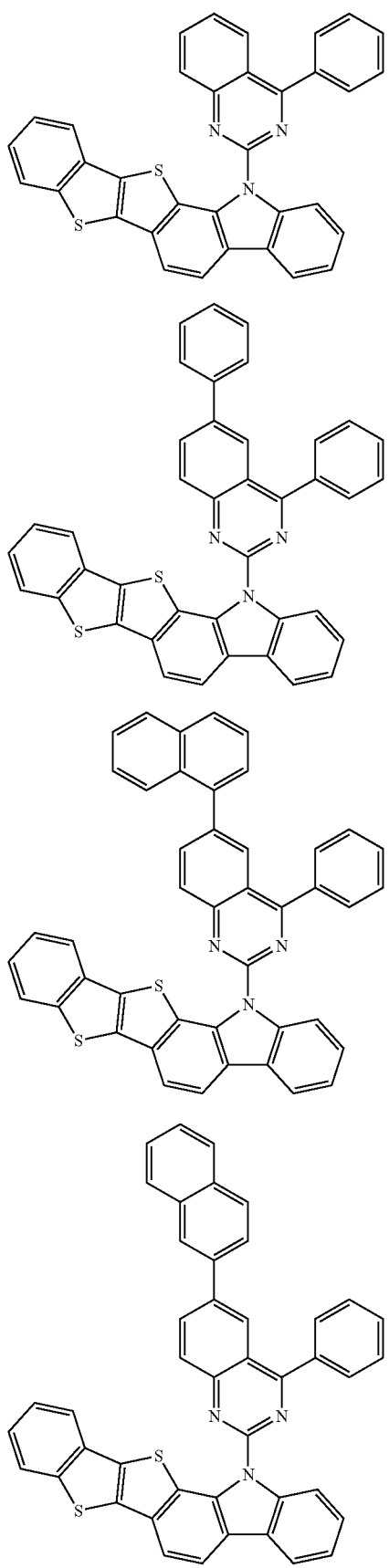
310
-continued
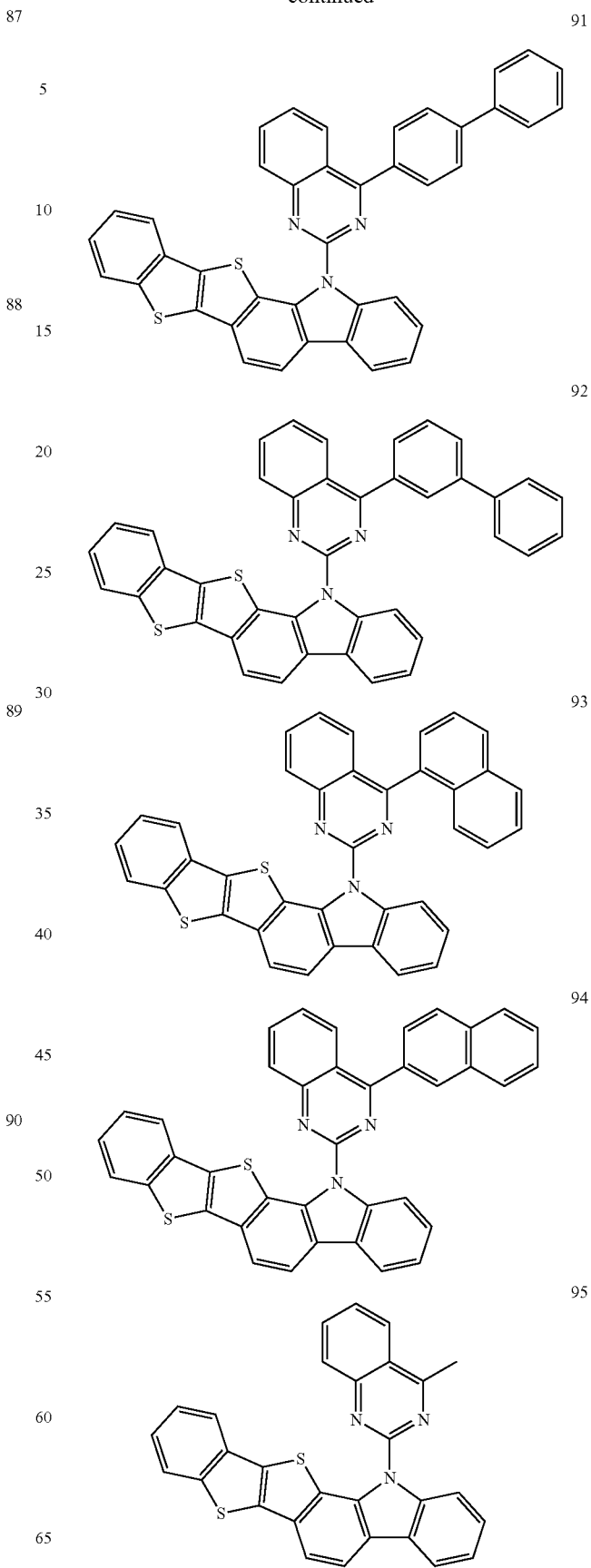

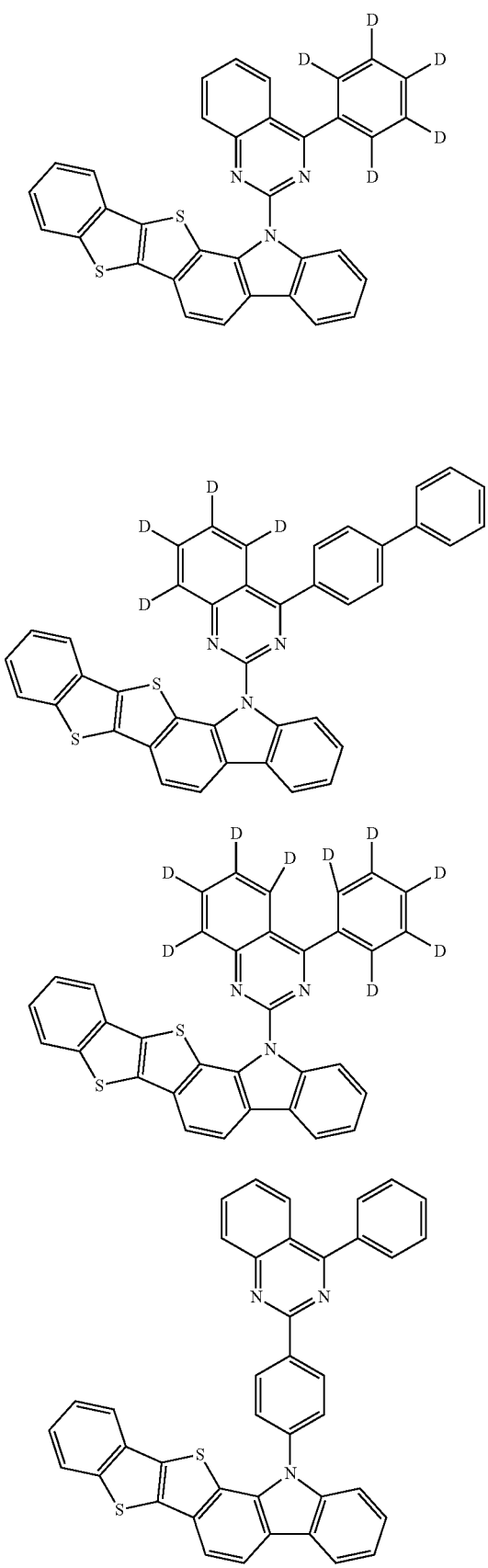

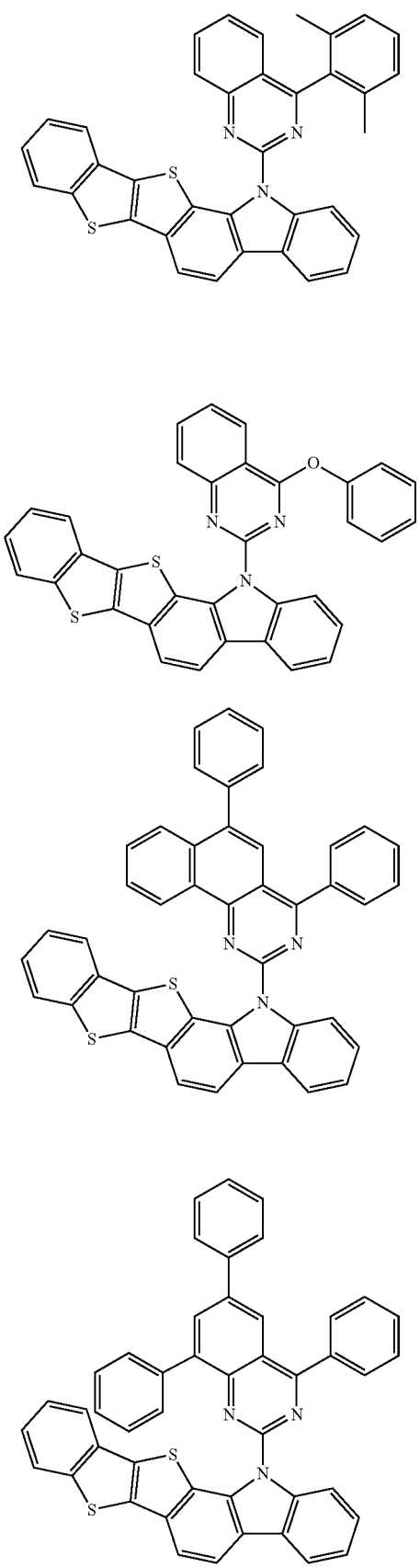
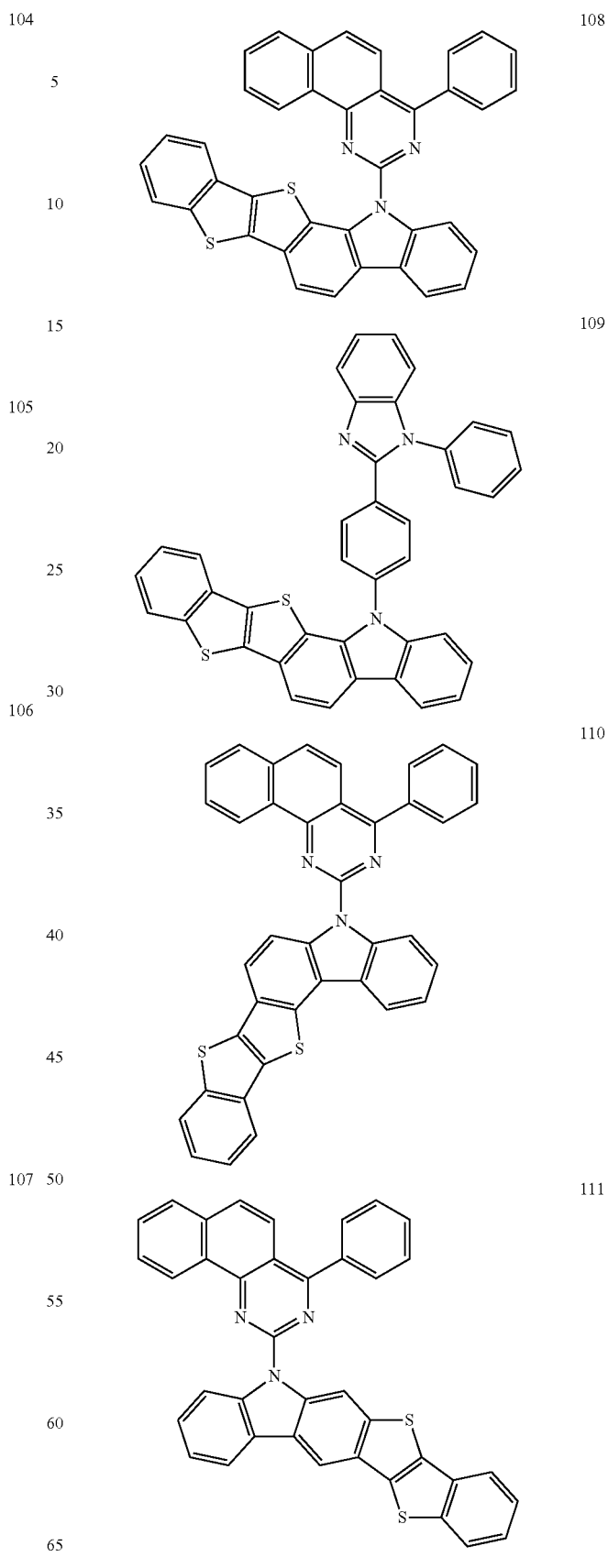

315
-continued
112
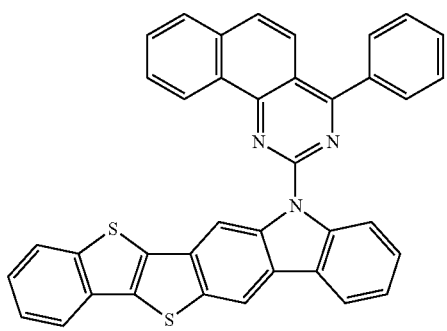
113
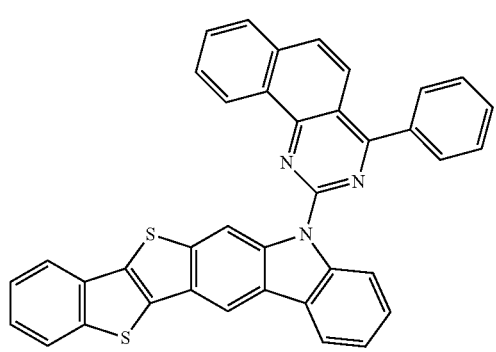
114
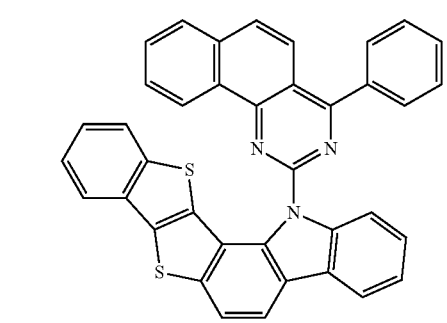
115
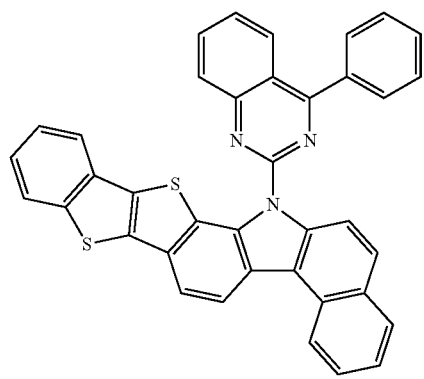
316
-continued
116
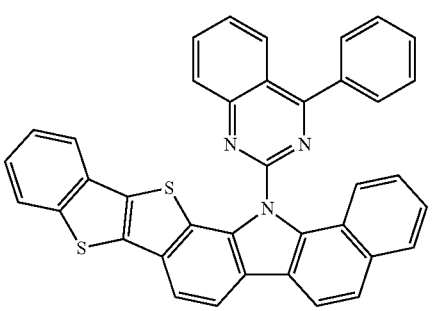
117
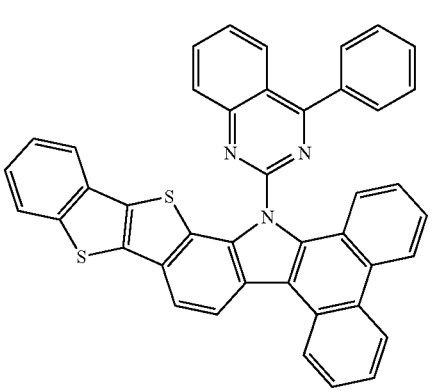
118
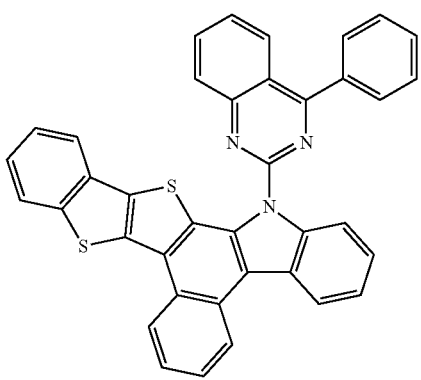
119
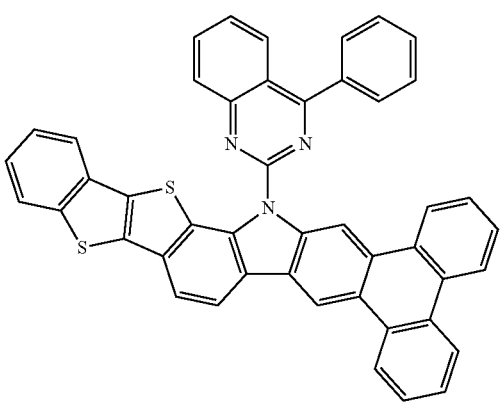

317
-continued
318
-continued
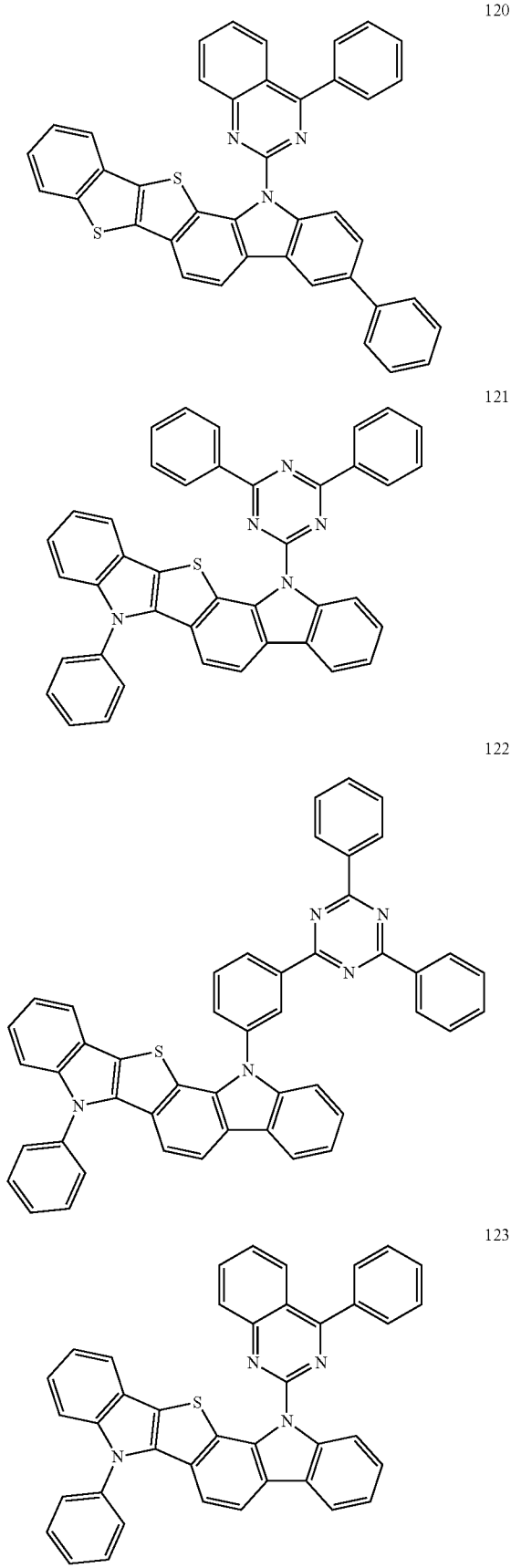
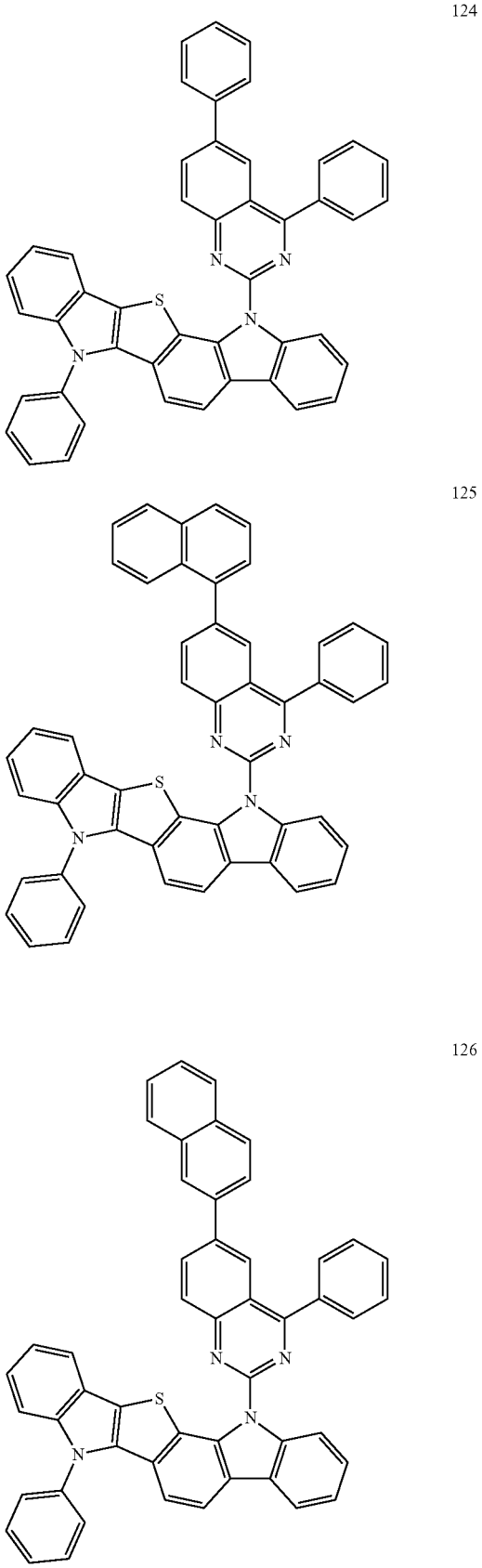

127
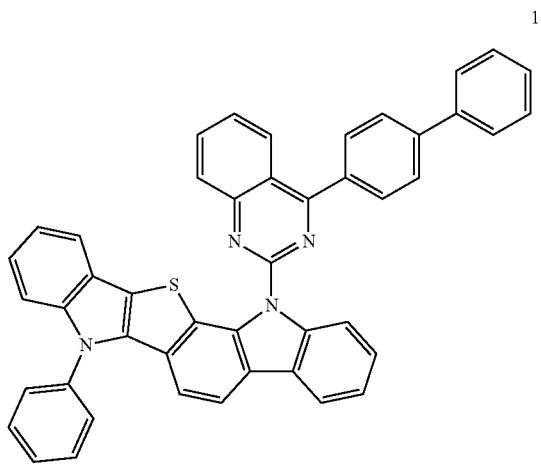
128
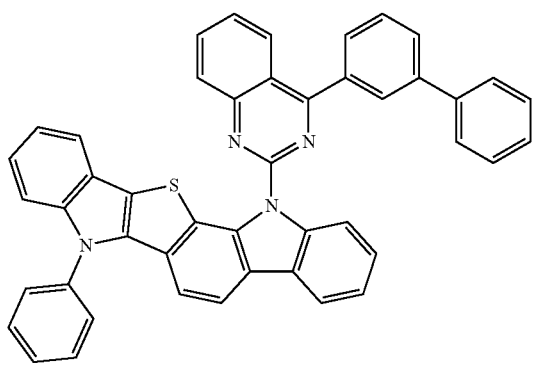
129
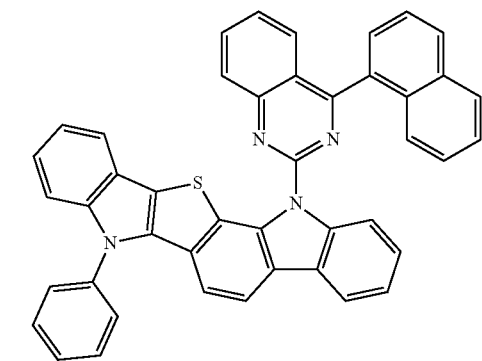
130
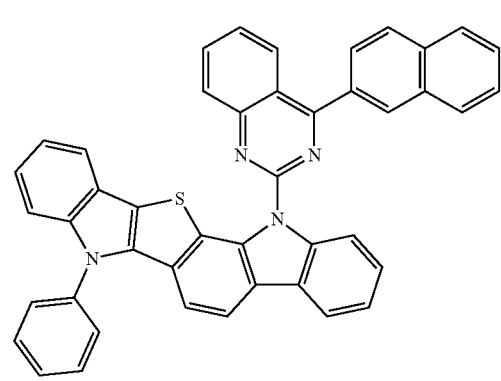
131
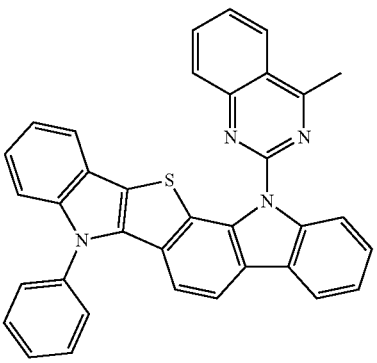
132
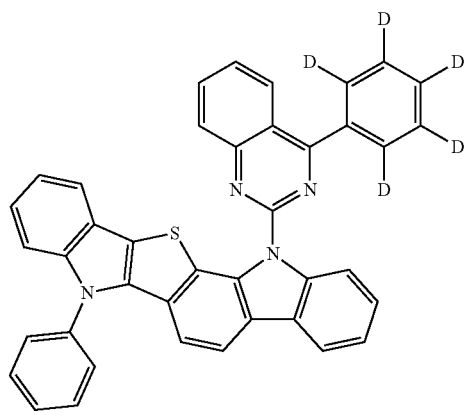
133
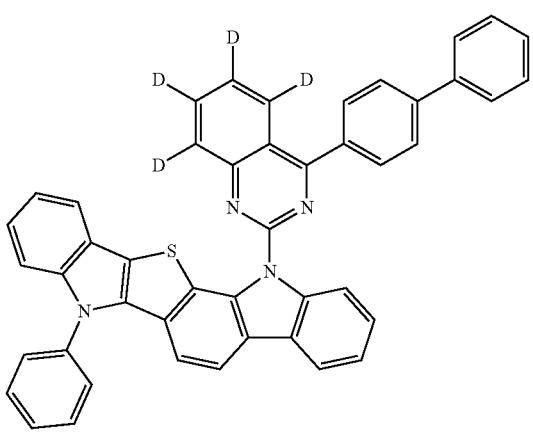
134
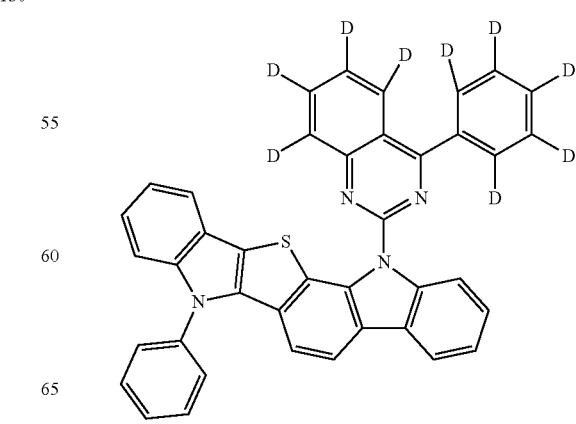

321
-continued
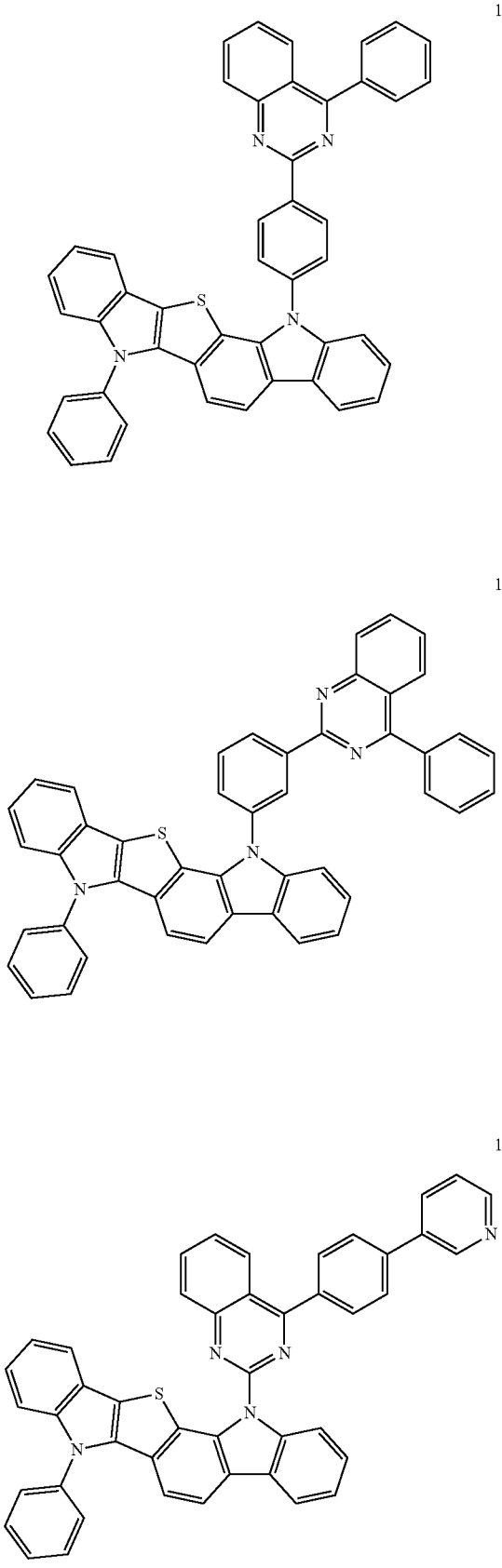
322
-continued
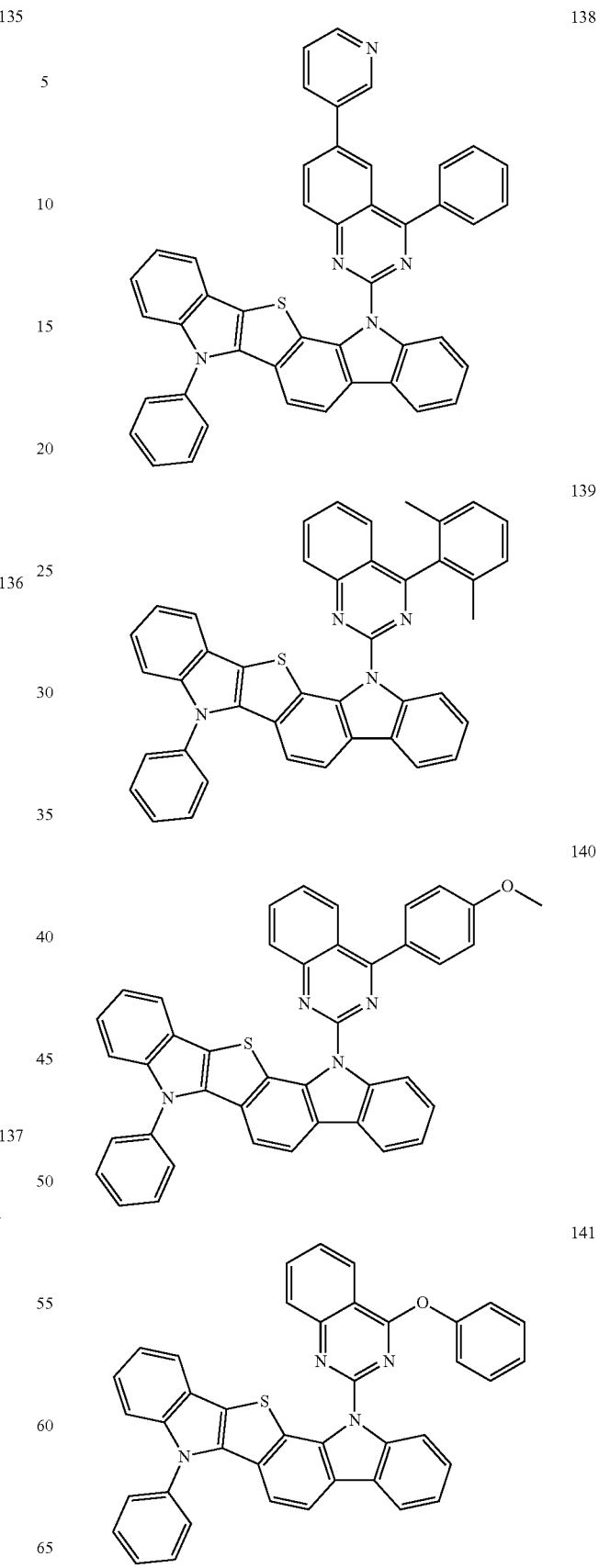

323
-continued
142
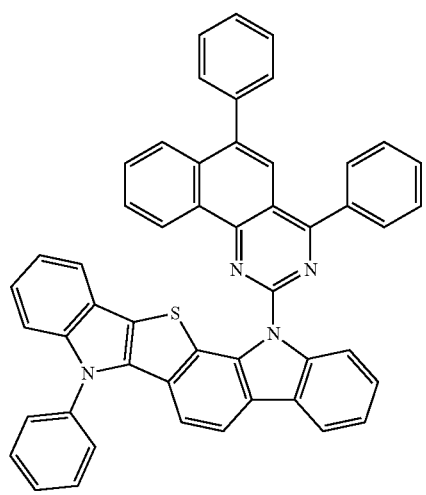
143
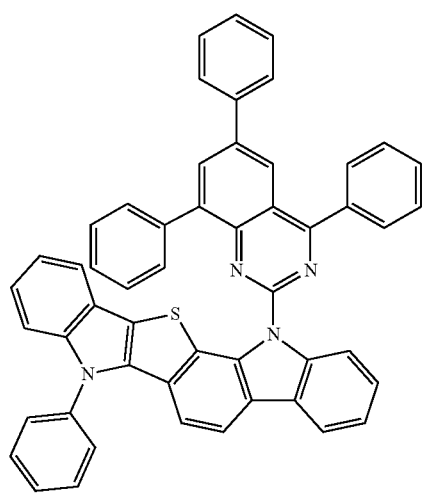
144
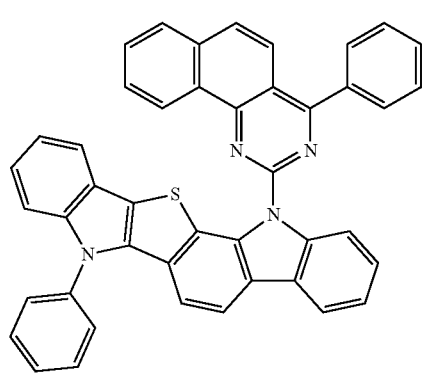
324
-continued
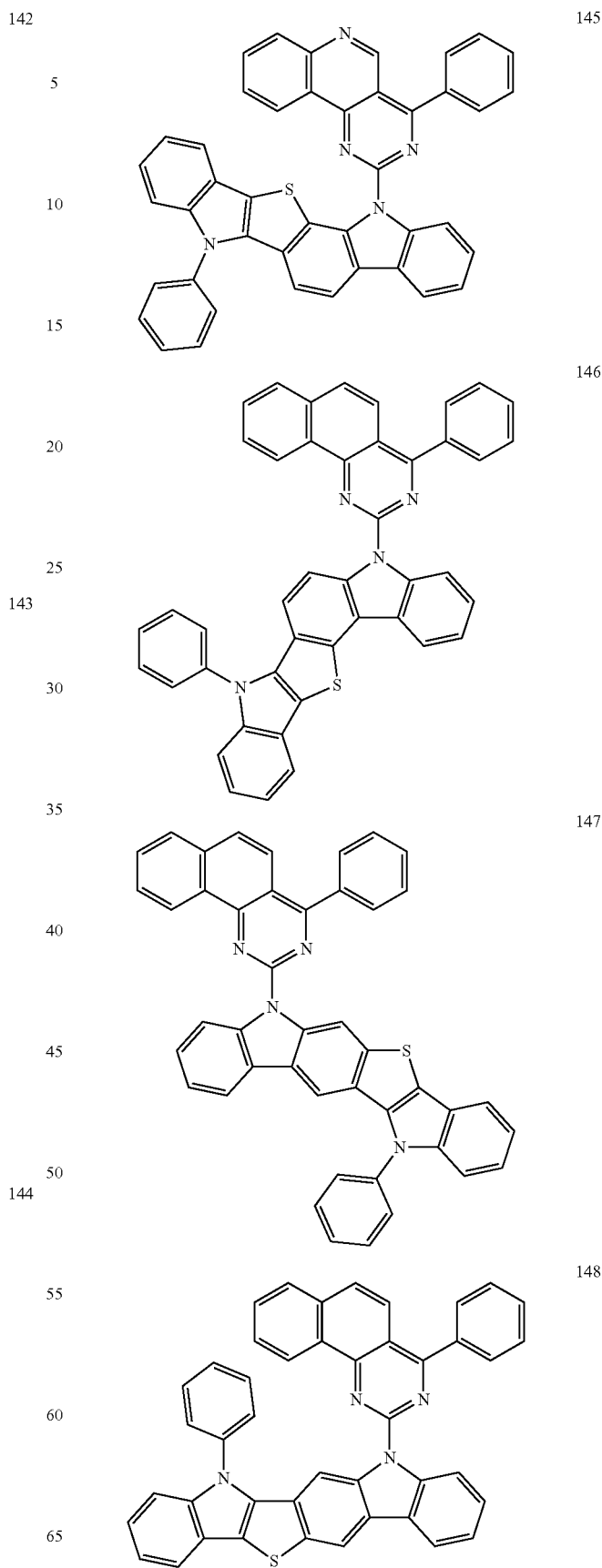

US 10,749,118 B2
325
-continued
149
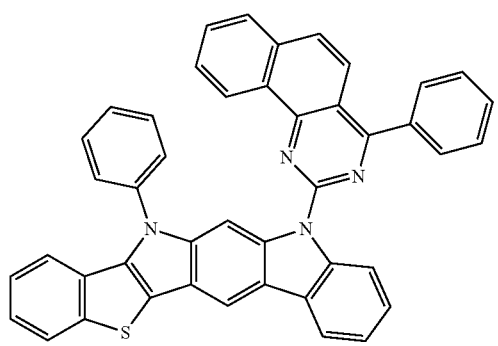
150
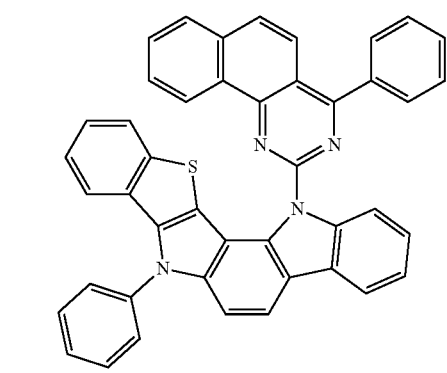
151
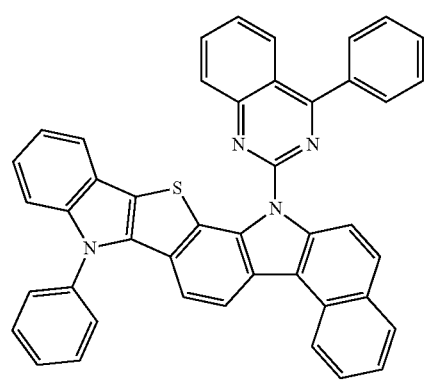
152
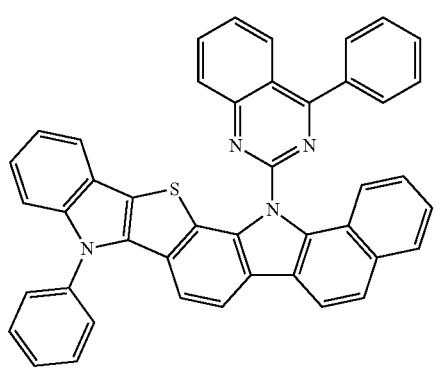
326
-continued
153
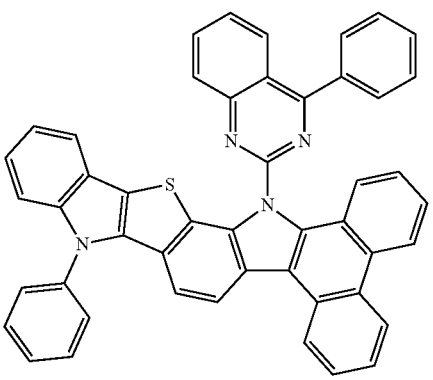
154
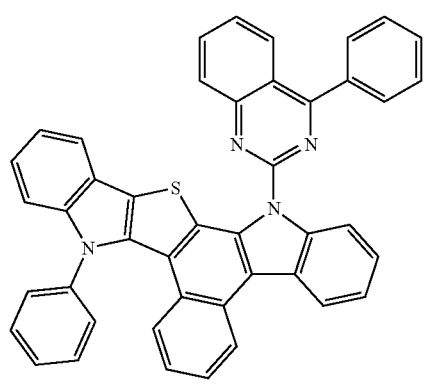
155
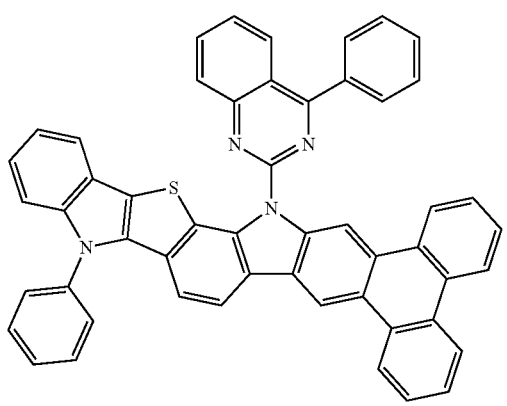
156
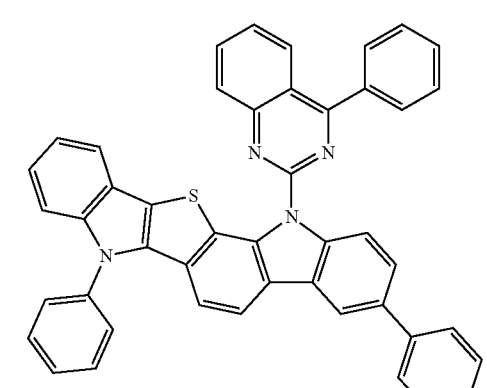

327
-continued
157
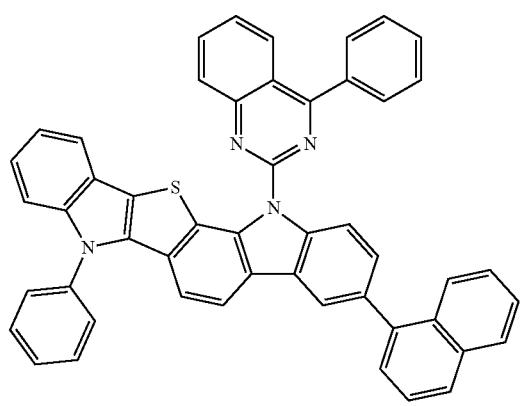
158
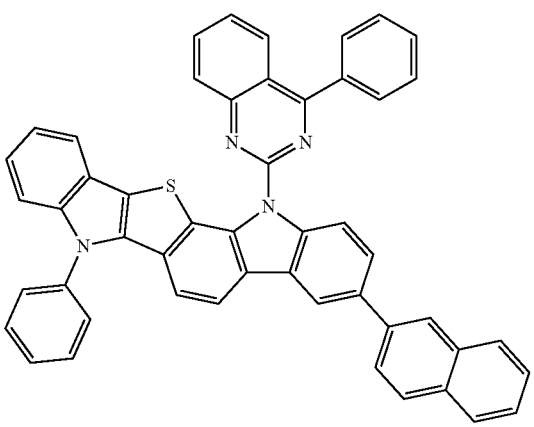
159
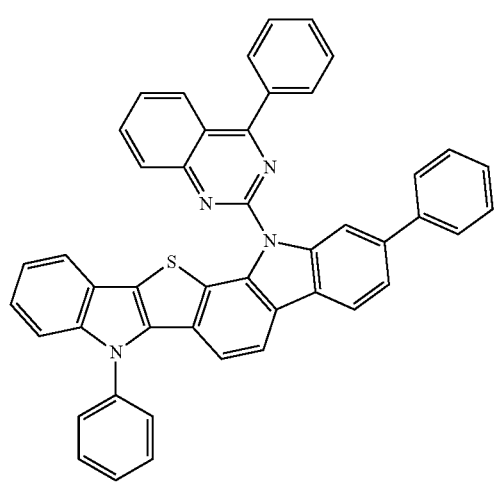
328
-continued
160
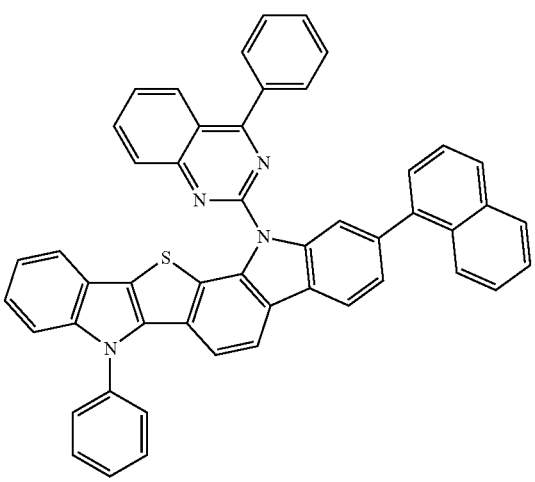
161
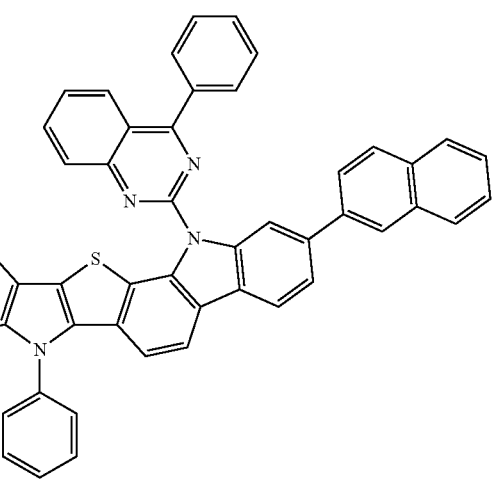
162
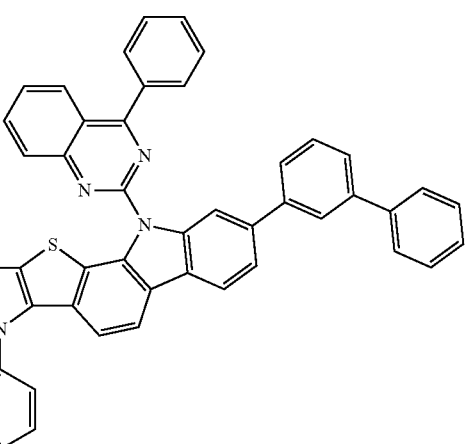

| 329 -continued | 330 -continued |
|---|---|
| 163 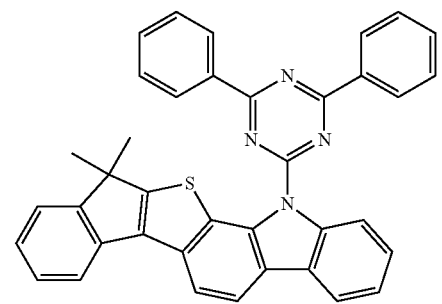 | 167 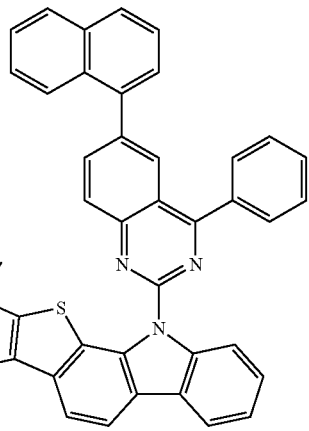 |
| 164 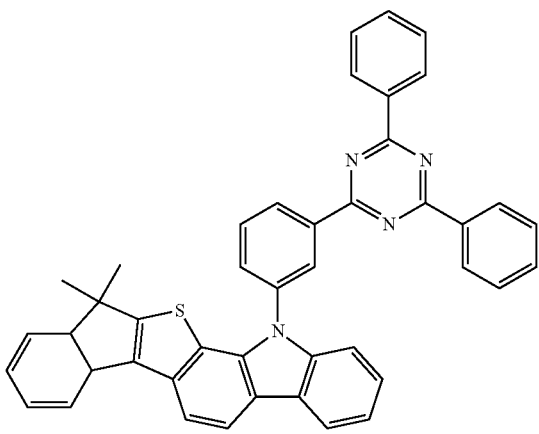 | 168 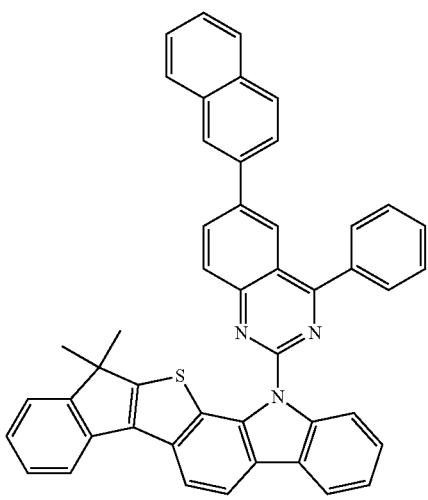 |
| 165 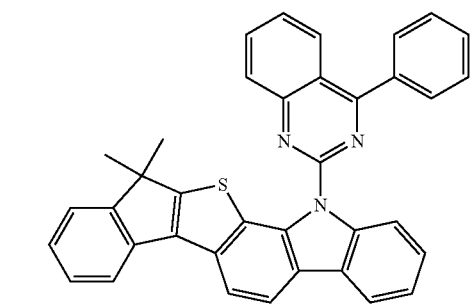 | 169 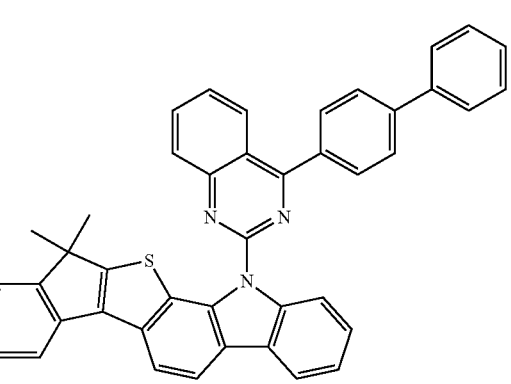 |
| 166 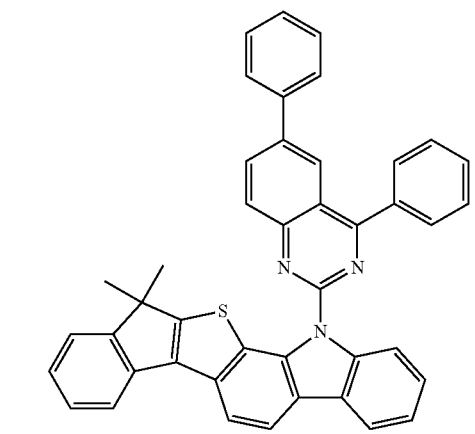 | 170 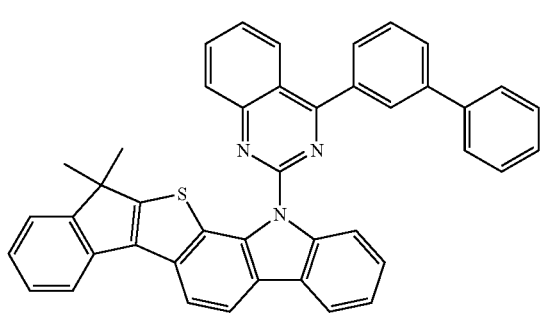 |

331
-continued
171
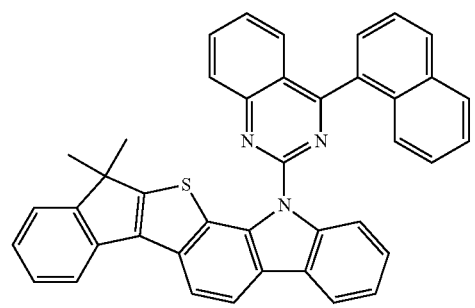
172
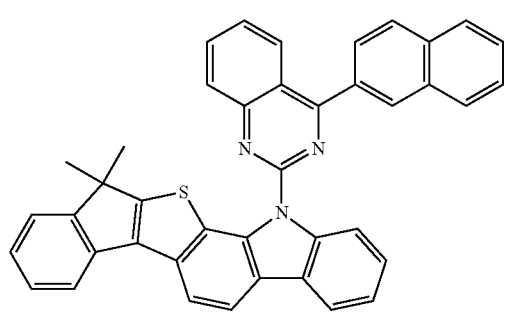
173
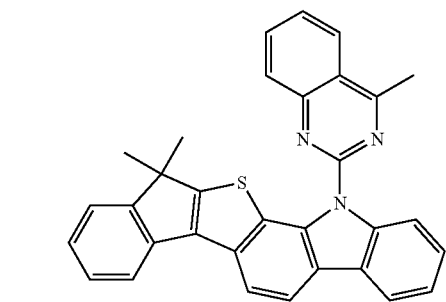
174
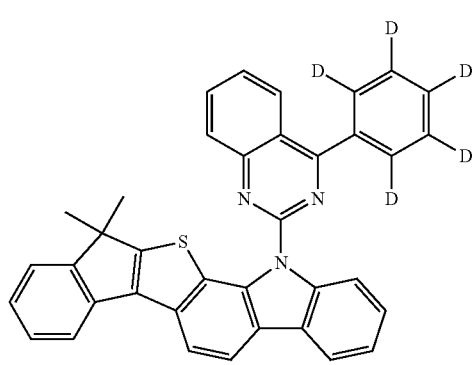
332
-continued
175
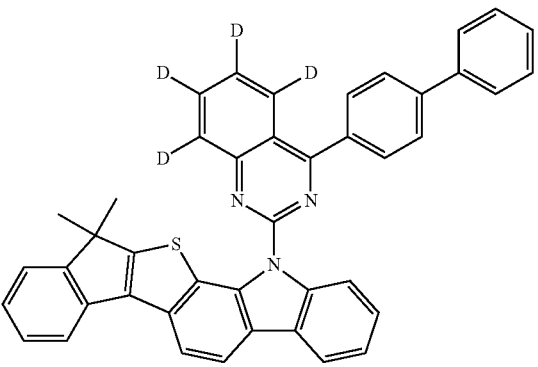
176
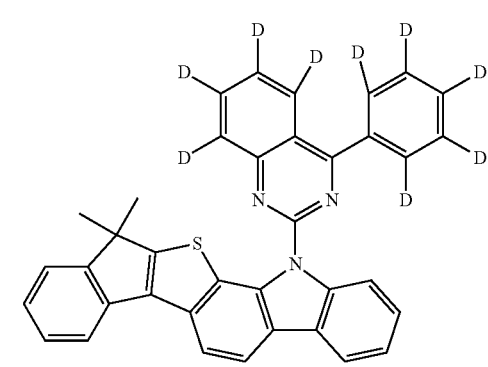
177
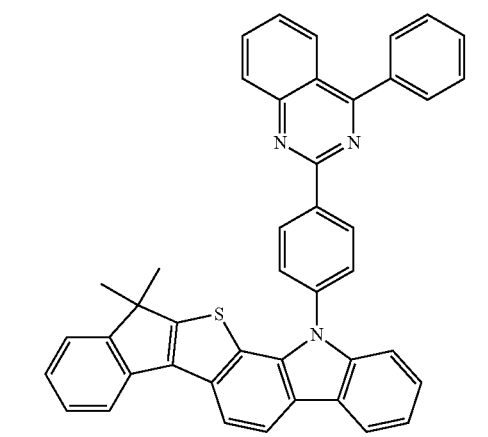
178
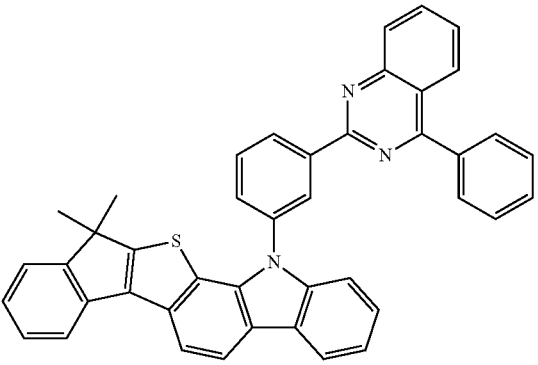

179
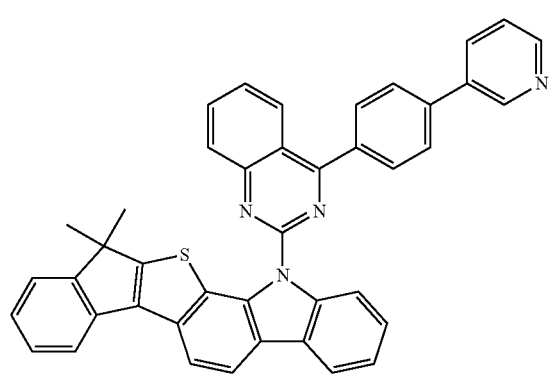
180
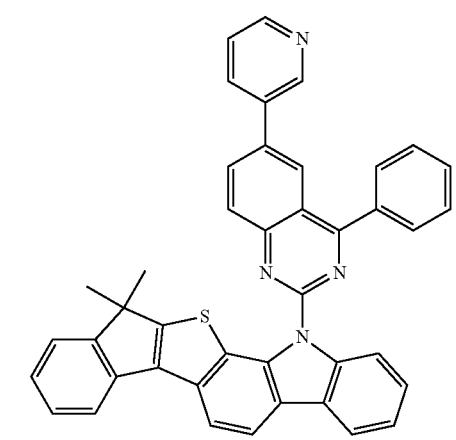
181
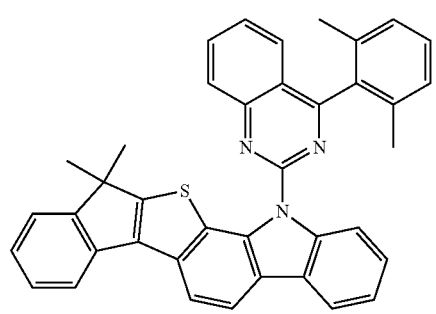
182
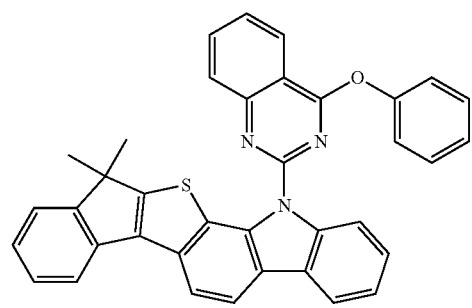
183
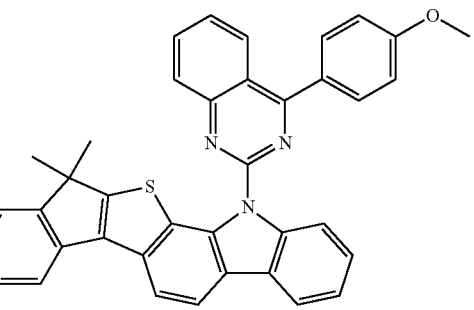
184
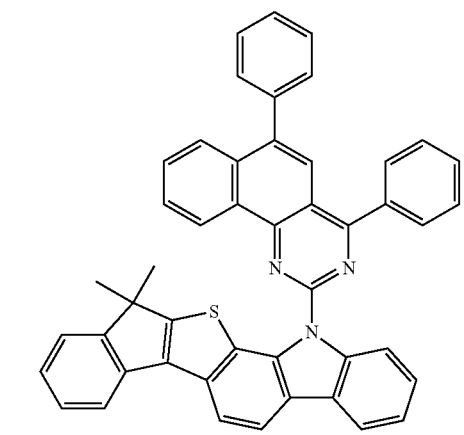
185
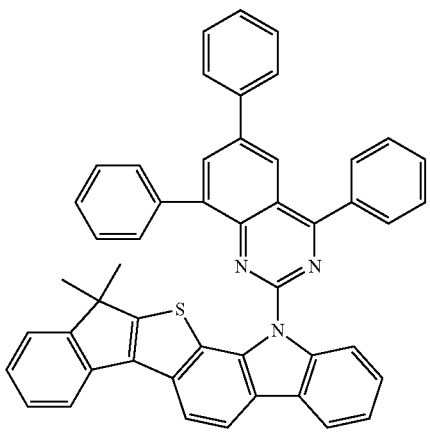
186
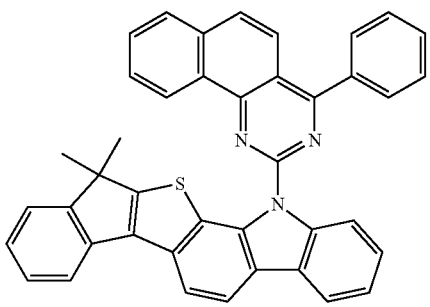

335
-continued
187
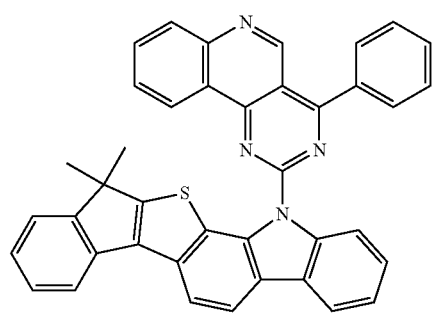
188
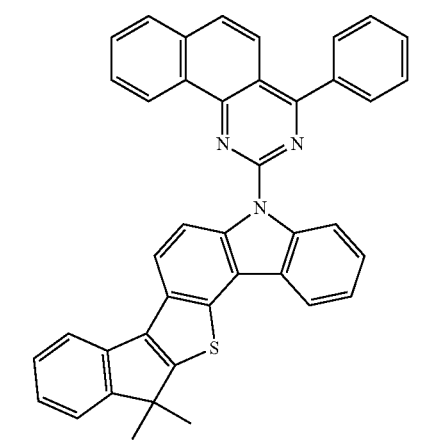
191
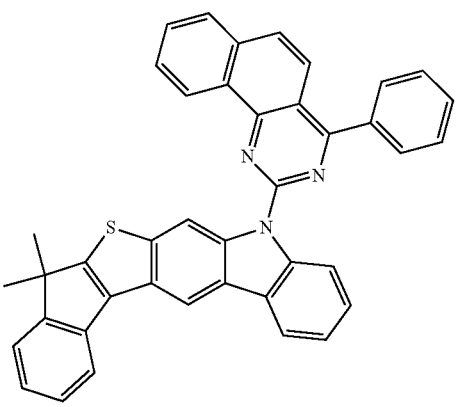
193
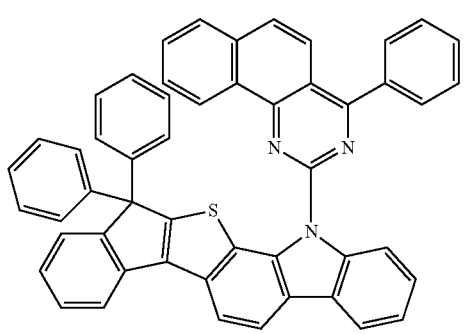
336
-continued
194
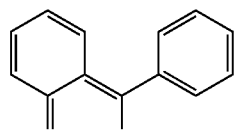
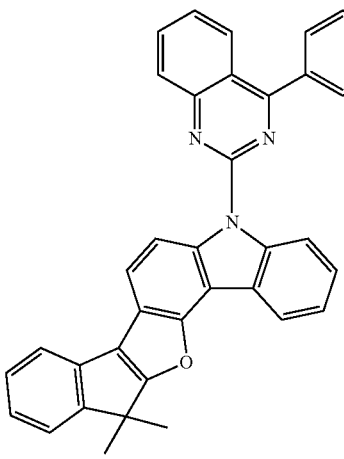
195
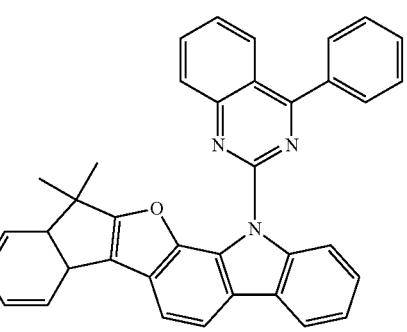
196
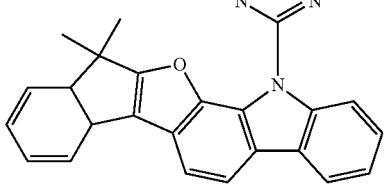
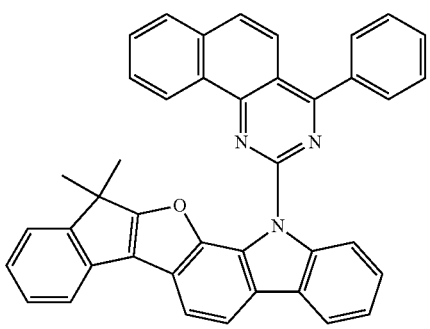
197

-continued
198
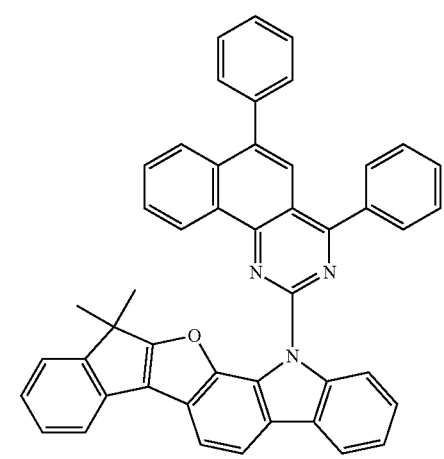
199
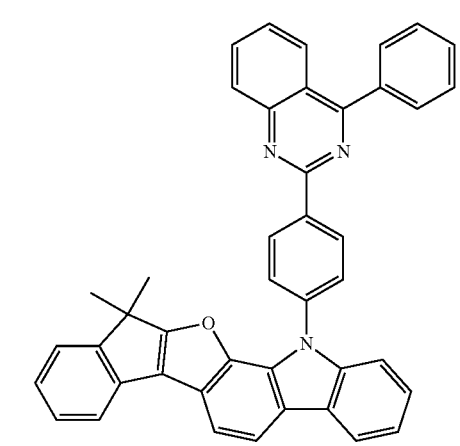
200
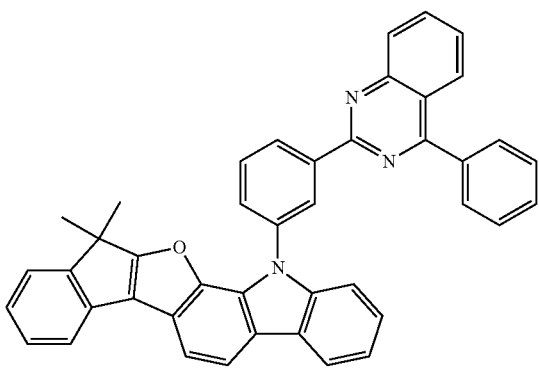
201
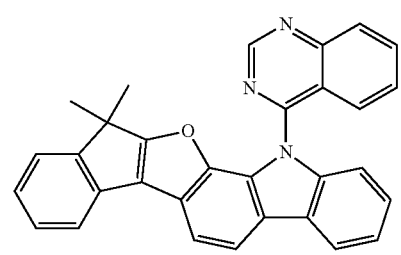
-continued
202
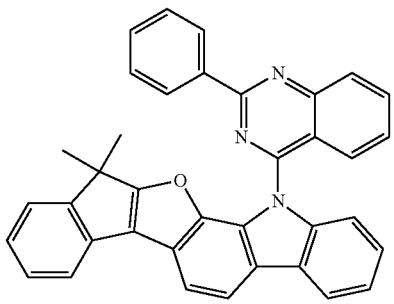
203
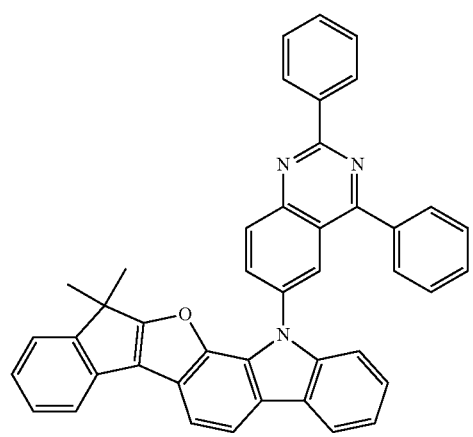
204
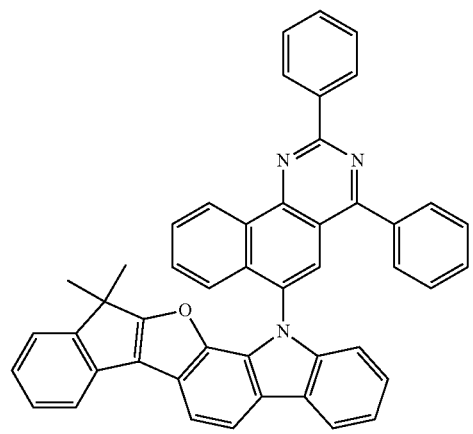
205
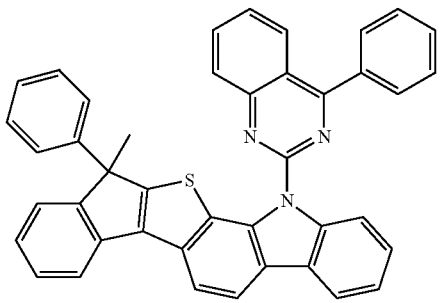

-continued
206
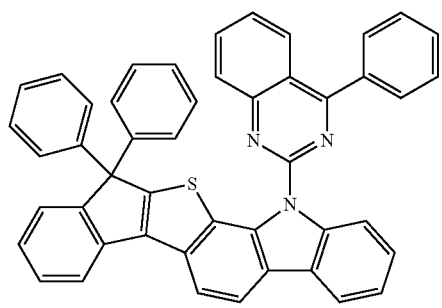
207
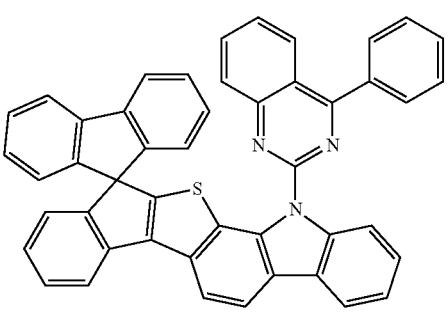
208
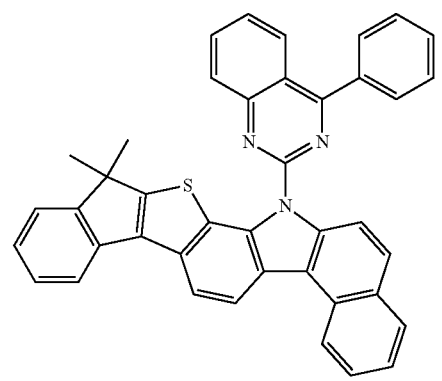
209
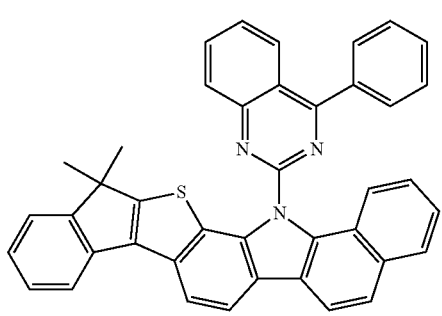
-continued
210
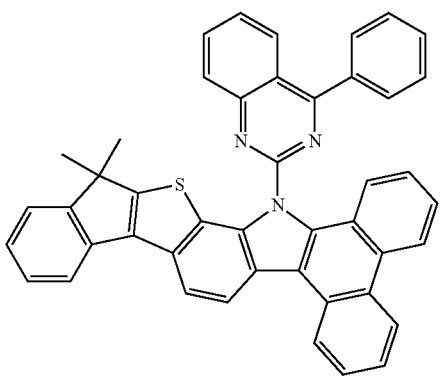
211
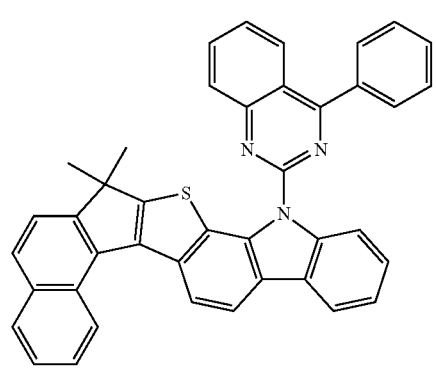
212
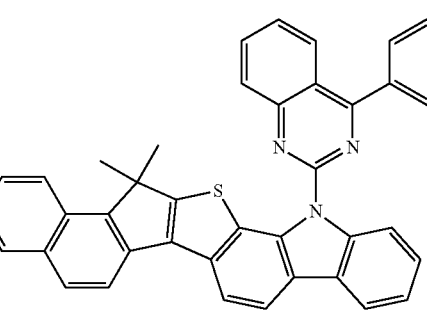
213
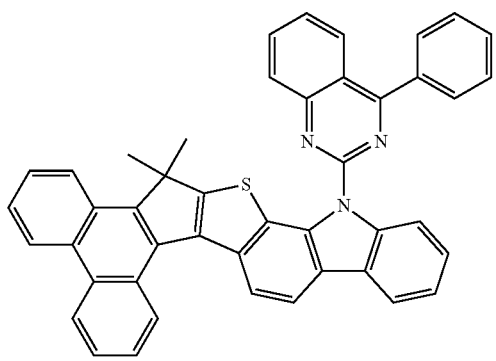

214
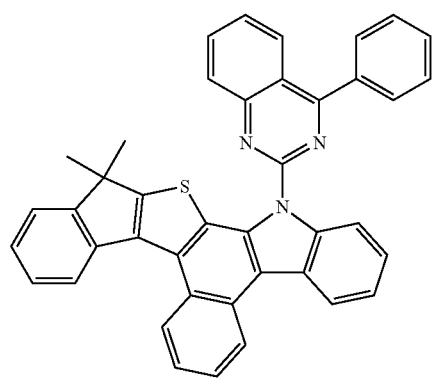
215
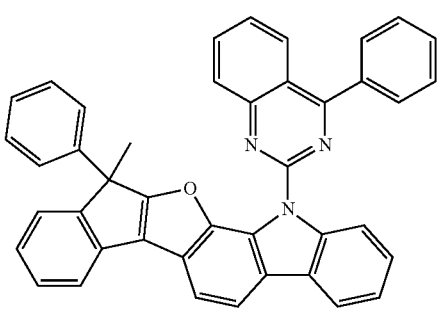
216
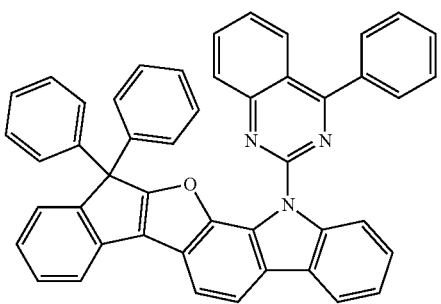
217
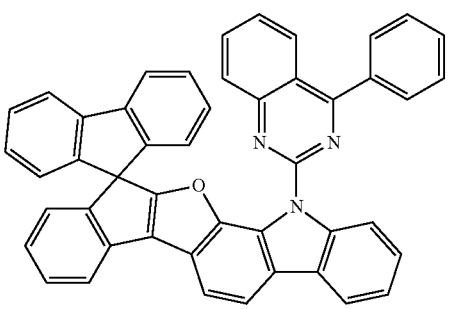
218
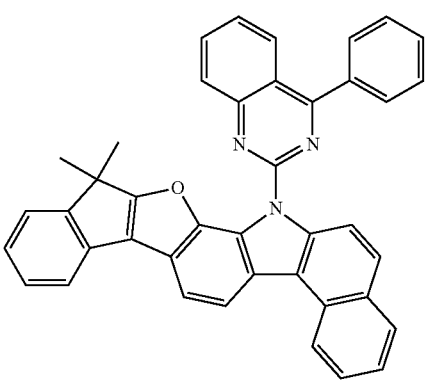
219
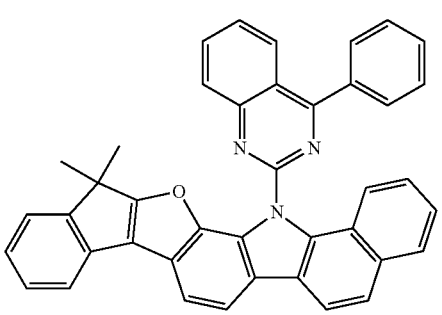
220
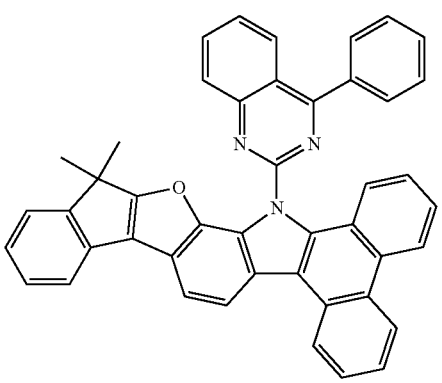
221
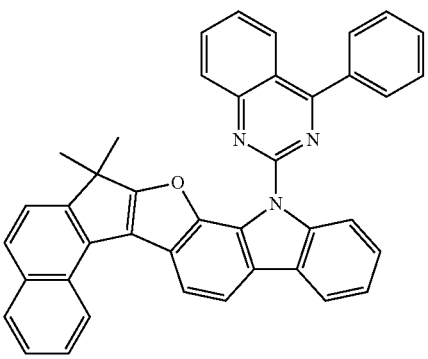

343
-continued
222
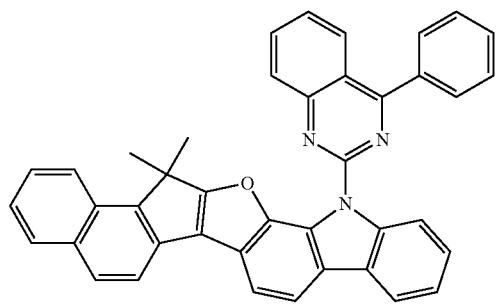
223
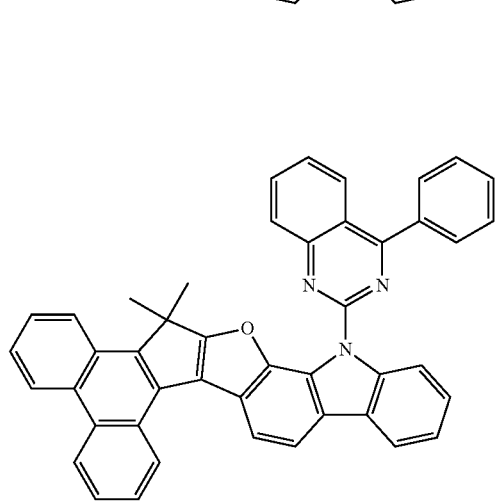
224
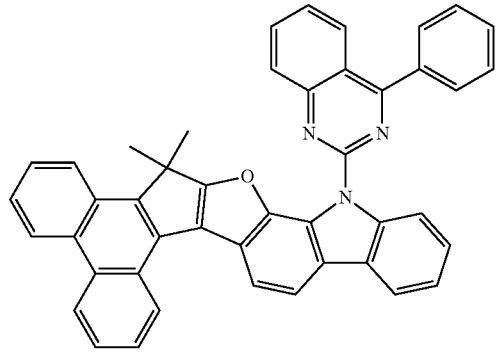
225
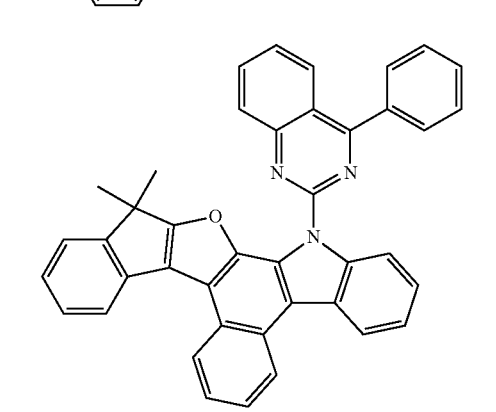
344
-continued
226
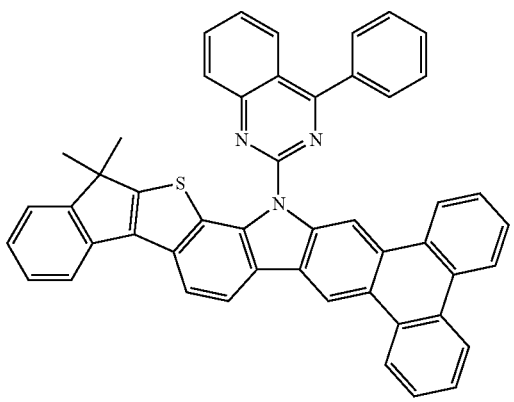
227
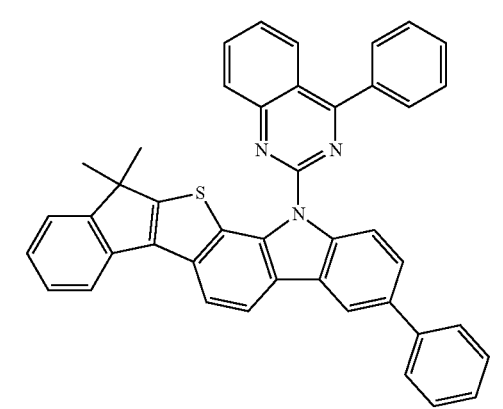
228
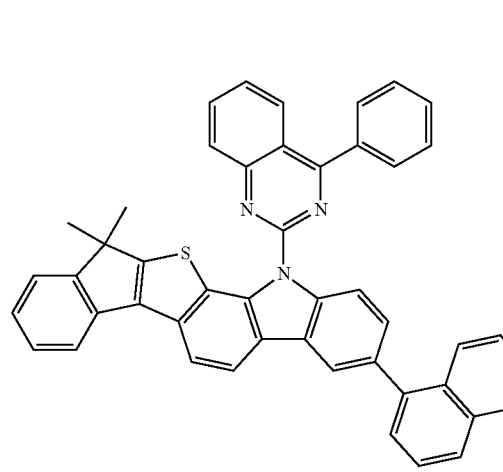

345
-continued
229
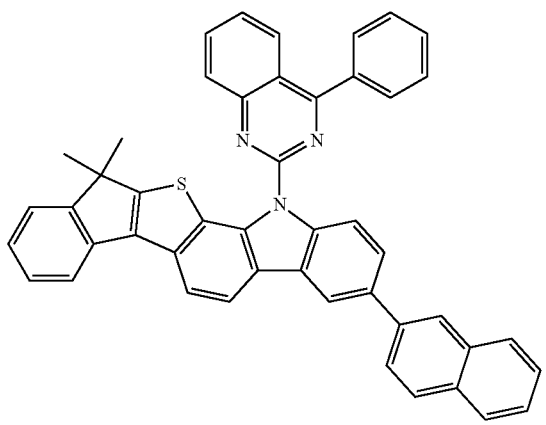
230
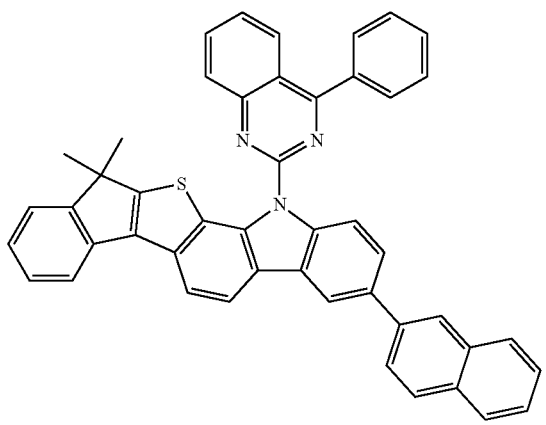
231
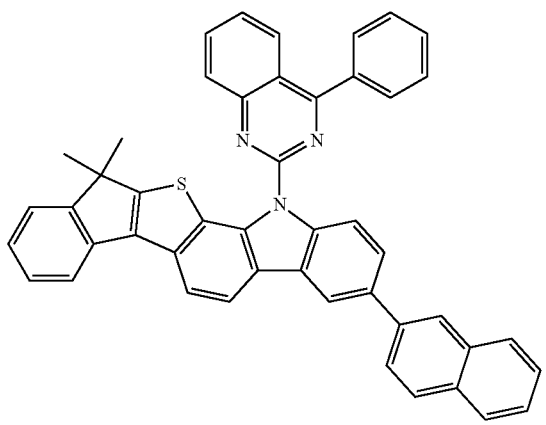
232
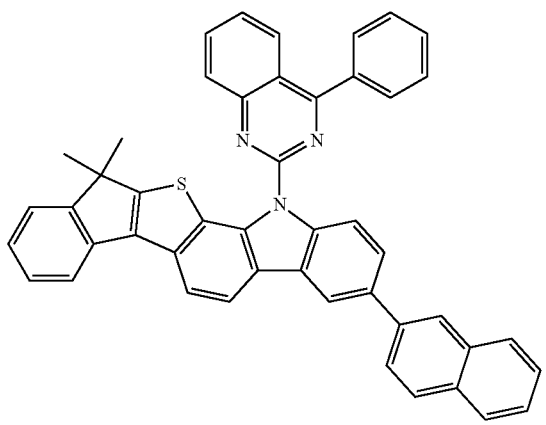
346
-continued
233
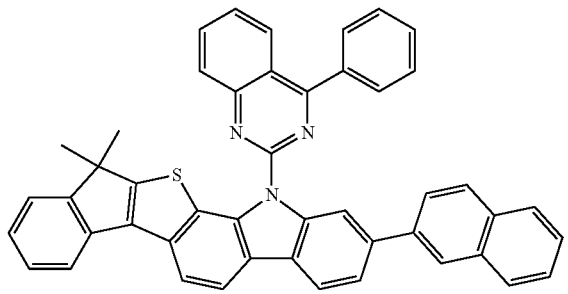
234
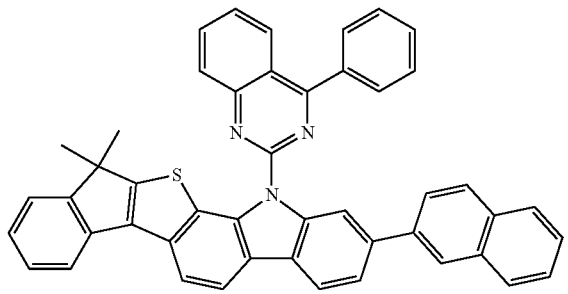
235
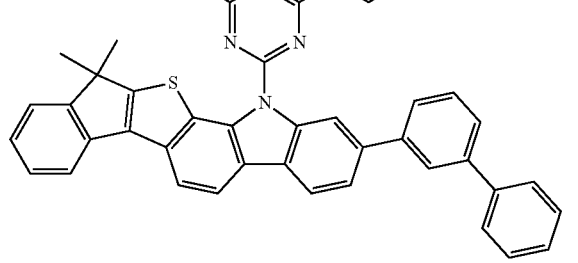
236
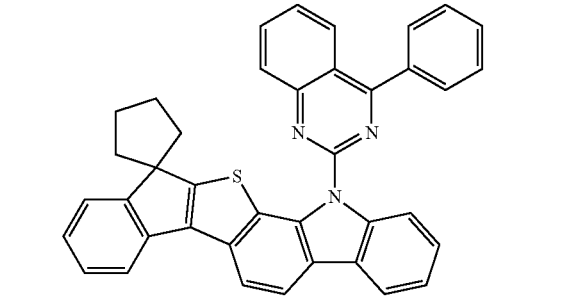
237
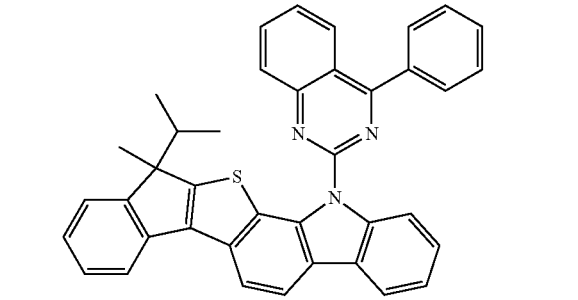

238
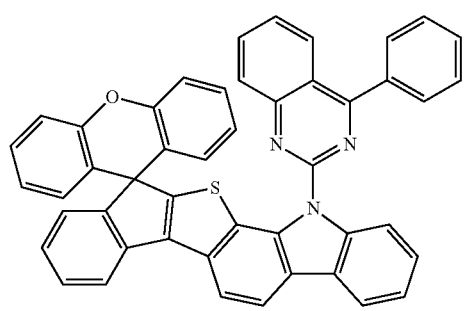
239
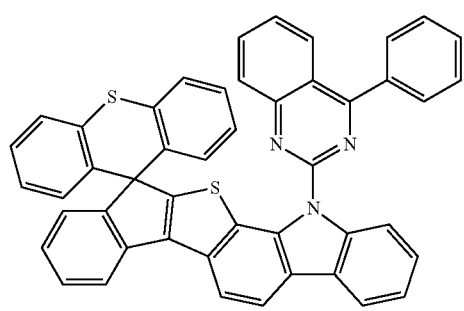
240
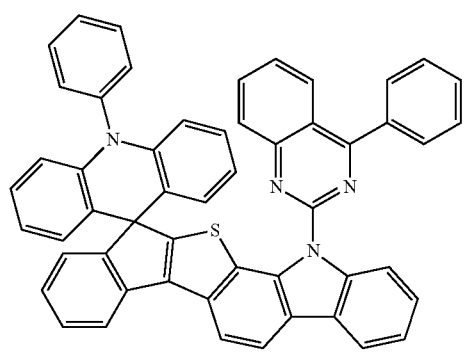
241
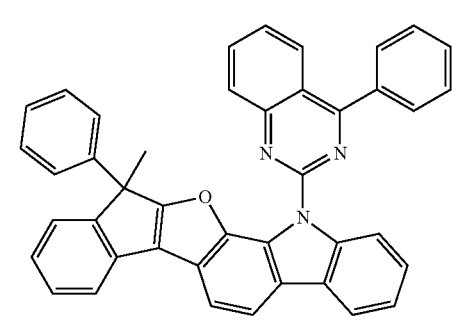
242
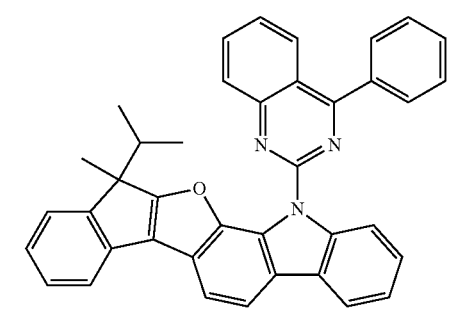
243
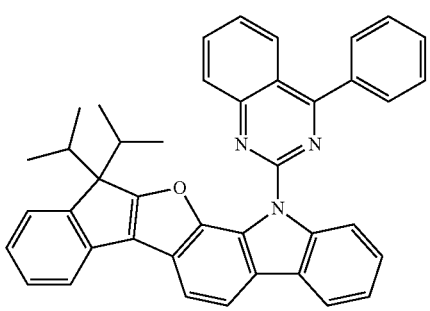
244
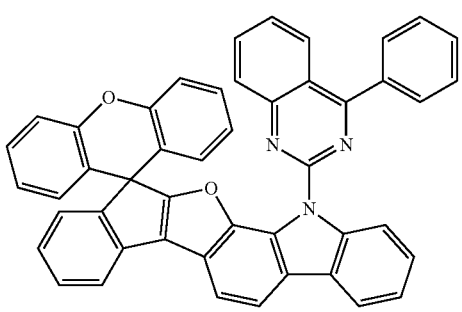
245
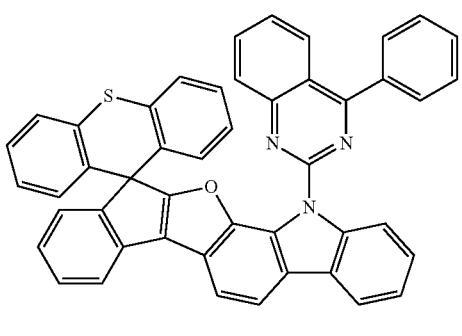
246
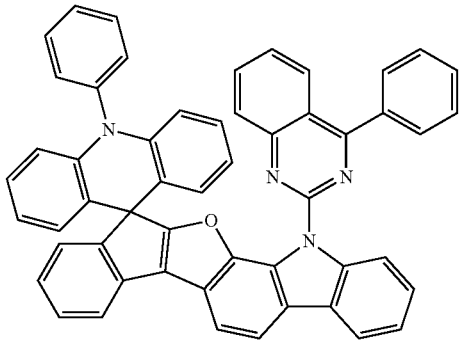
247
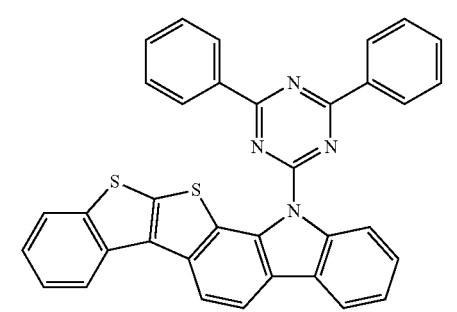

349
-continued
248
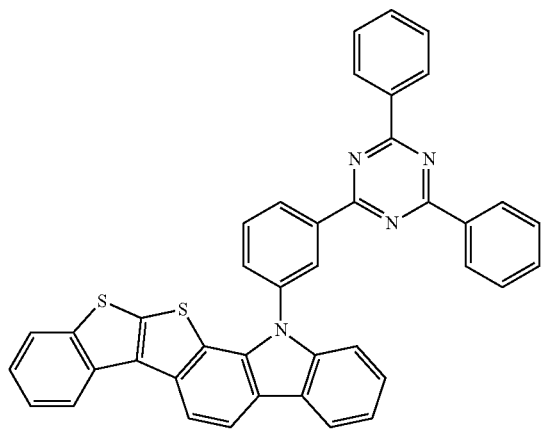
249
250
251
350
-continued
252
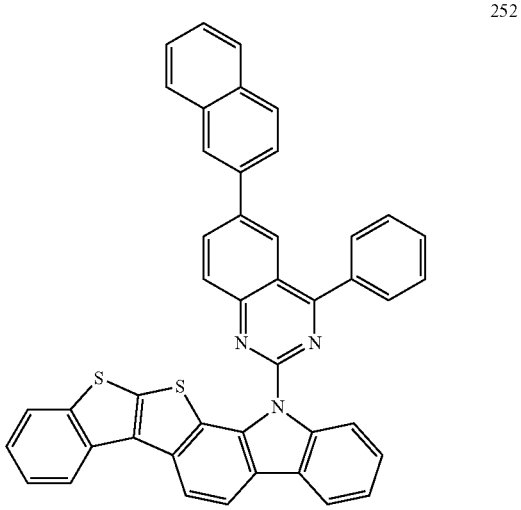
253
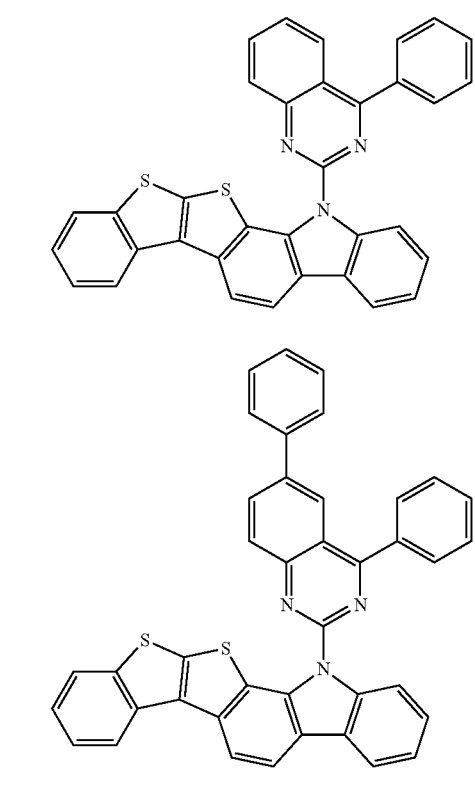
254
255
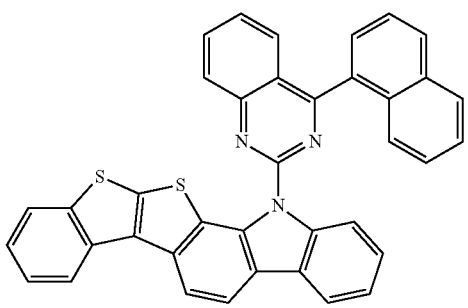
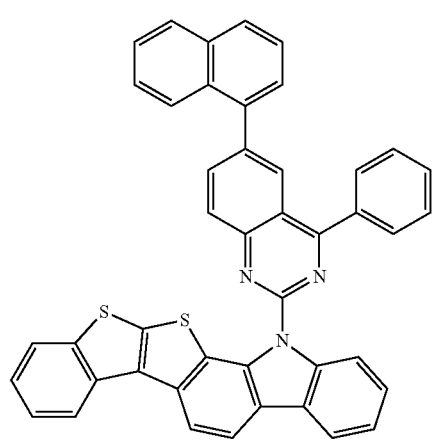

| 351 -continued | 352 -continued |
|---|---|
| 256 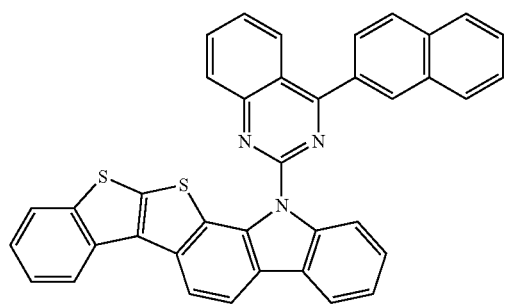 | 260 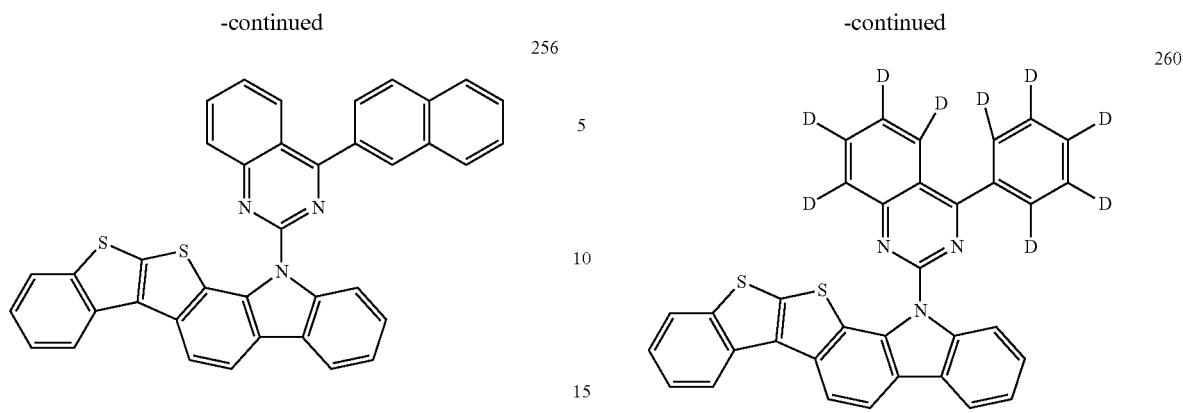 |
| 257 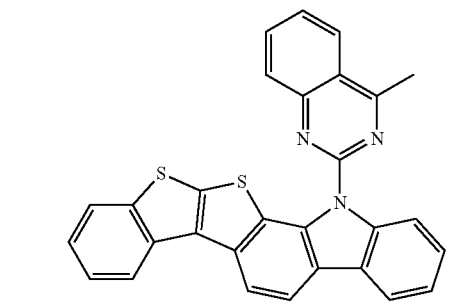 | 261 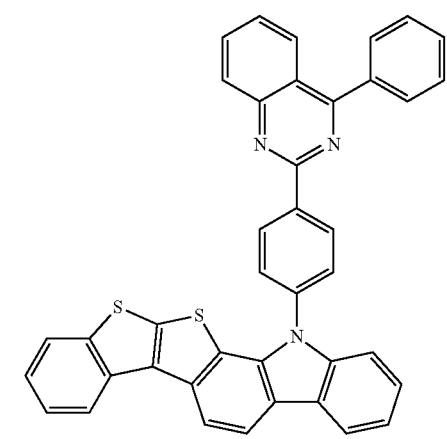 |
| 258 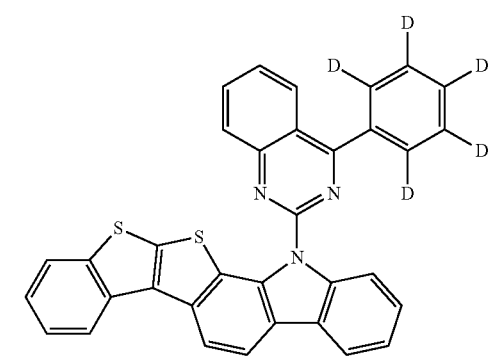 | 262 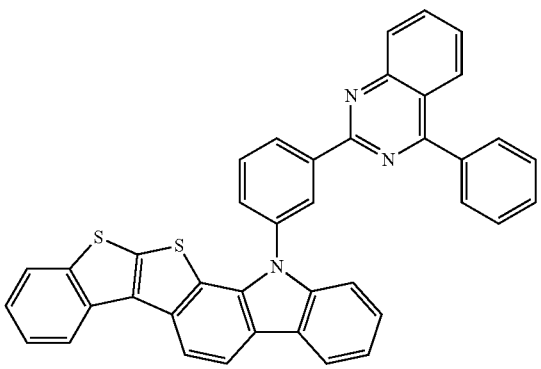 |
| 259 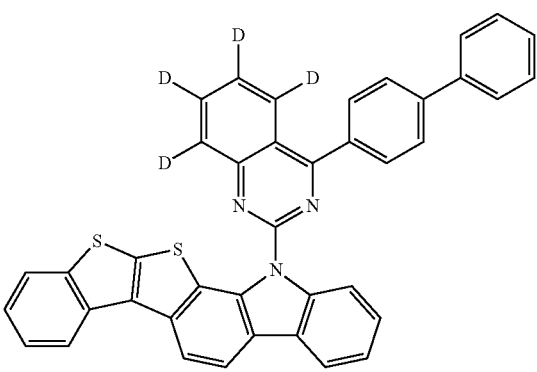 | 263 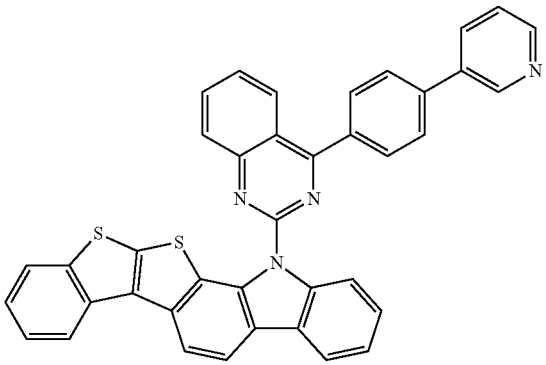 |

264
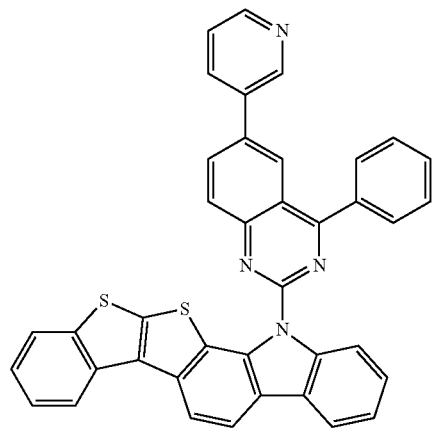
265
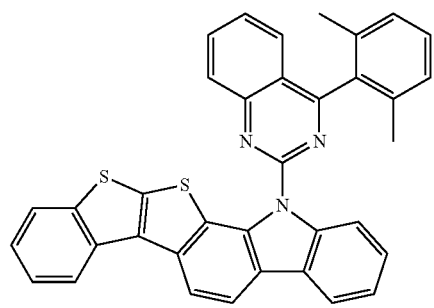
266
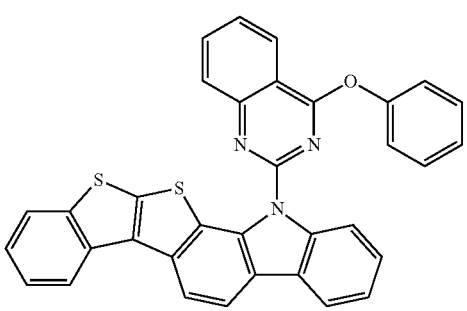
267
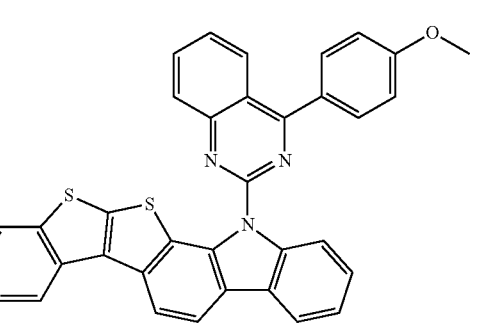
268
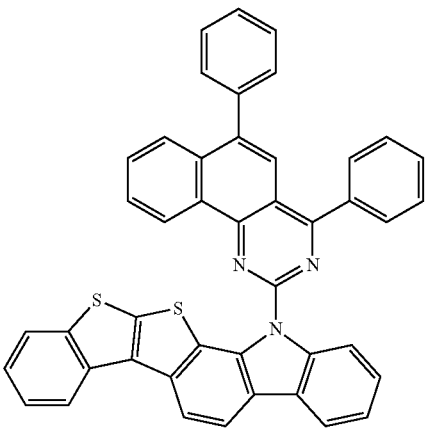
269
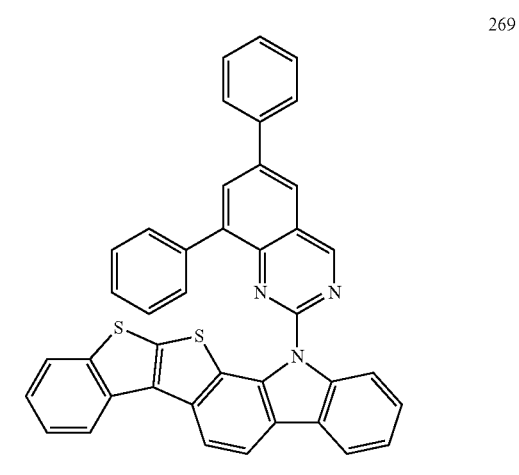
270
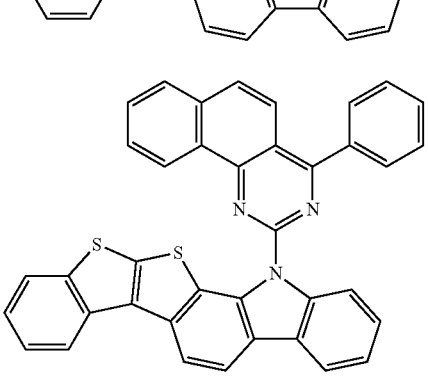
271
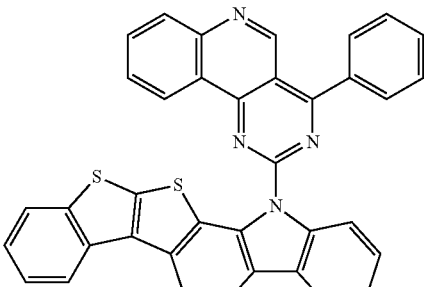

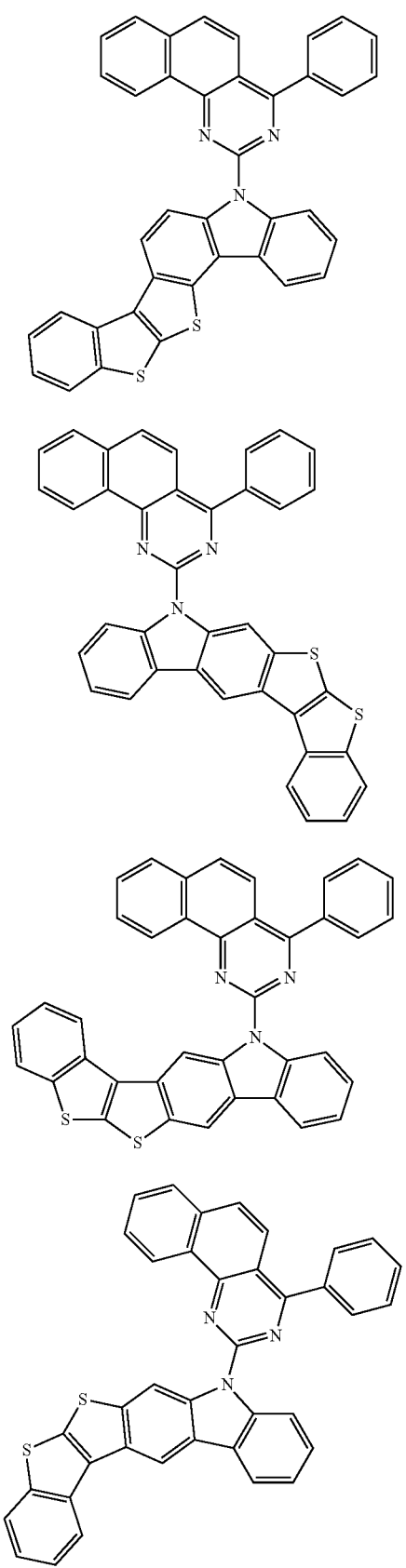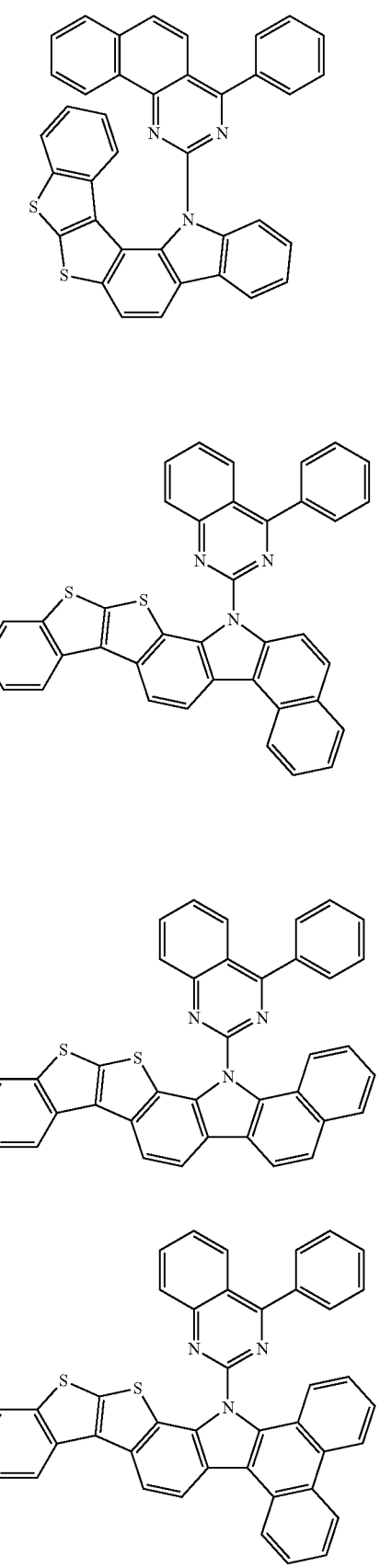

357
-continued
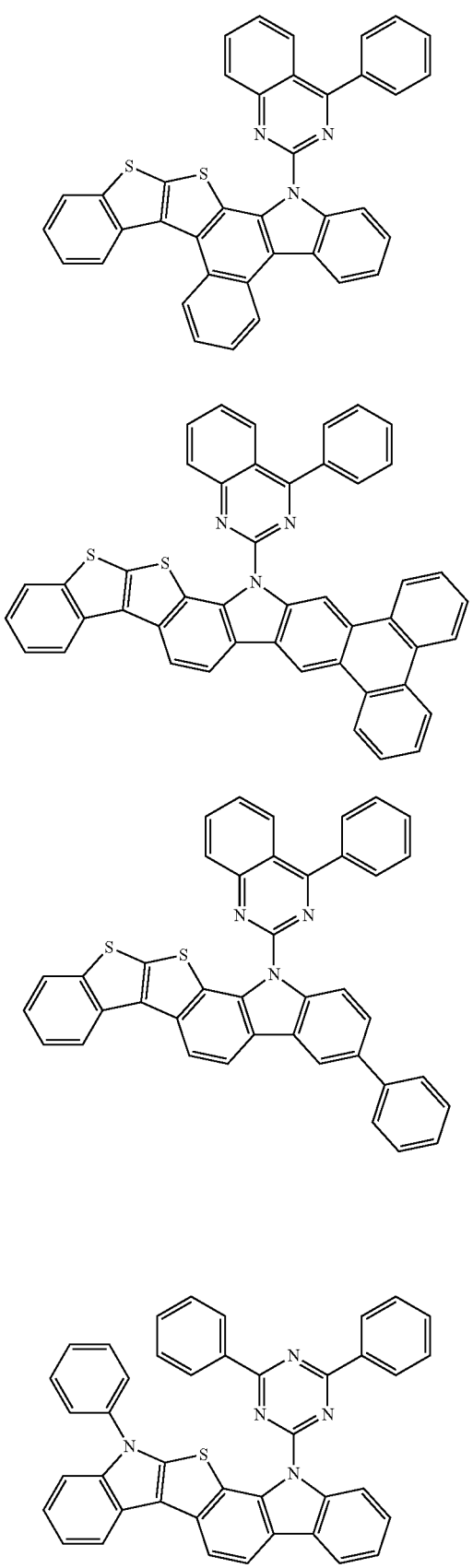
358
-continued
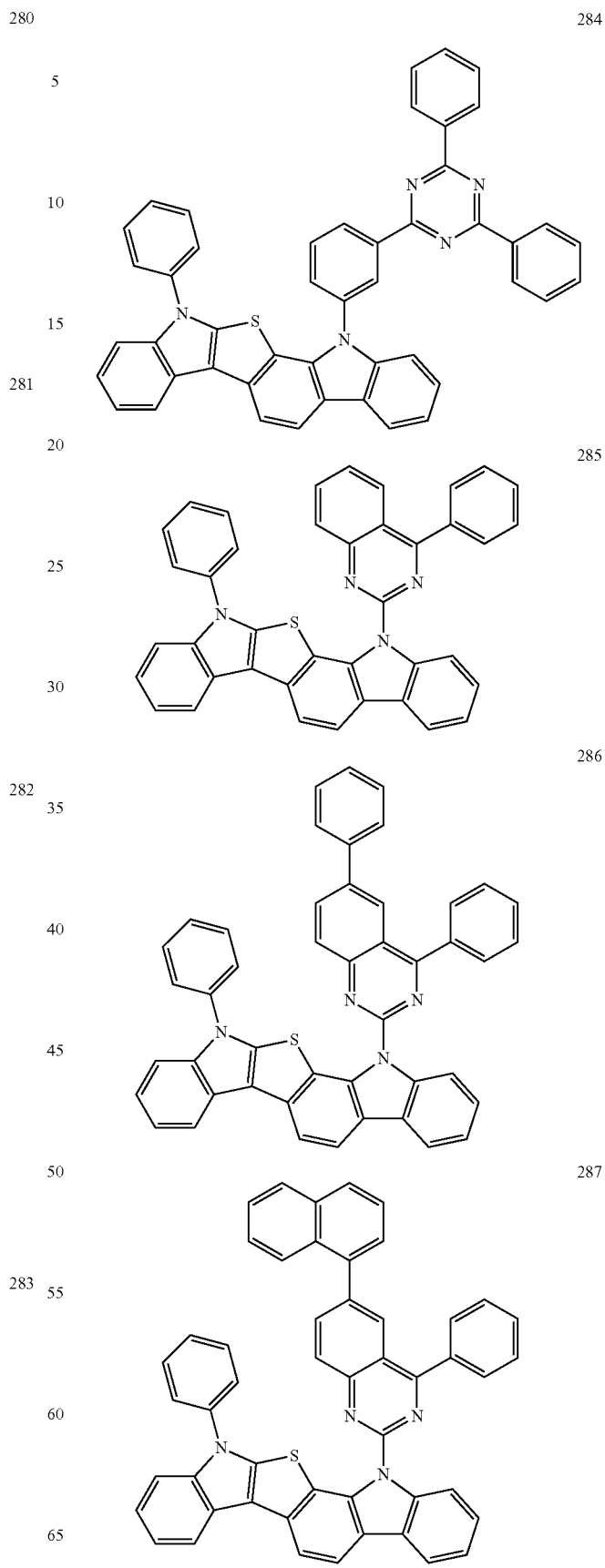

288
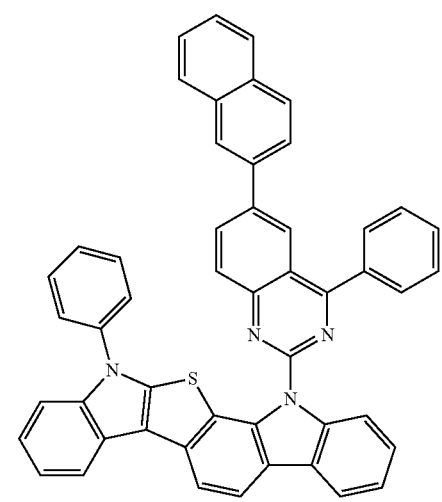
289
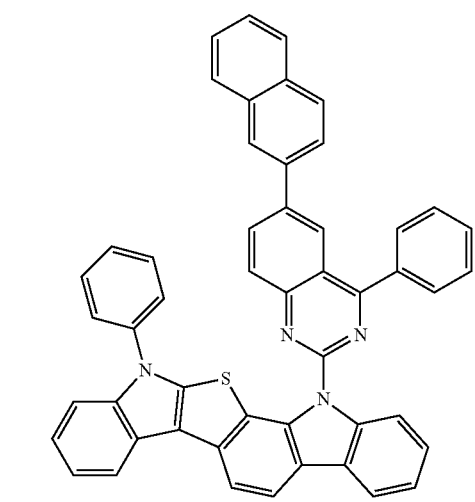
290
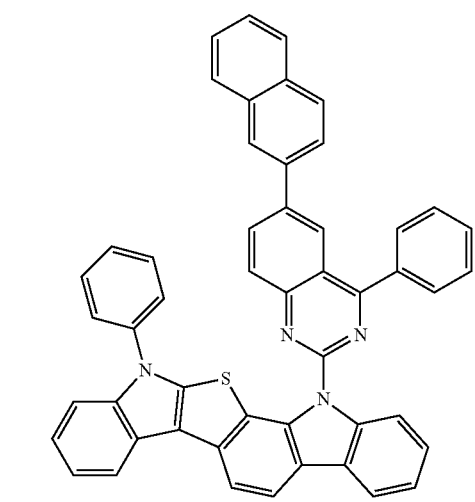
291
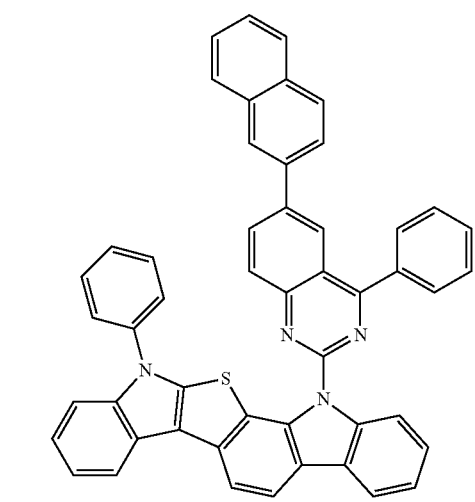
292
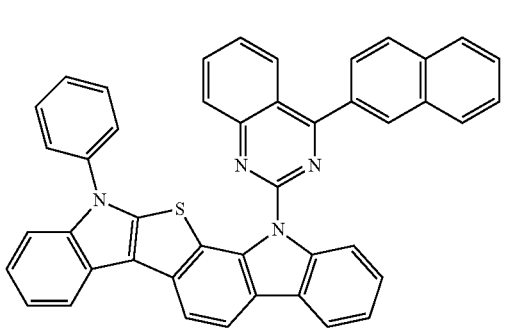
293
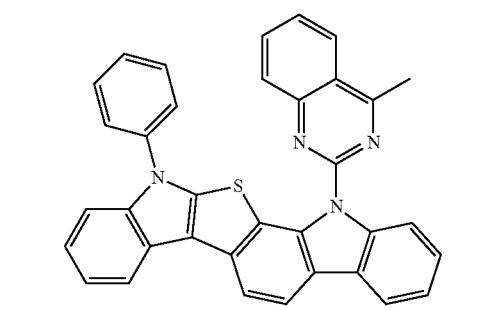
294
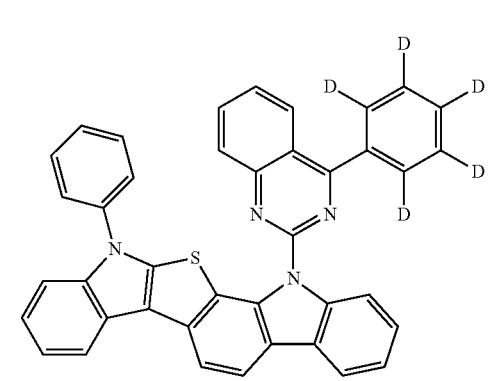
295
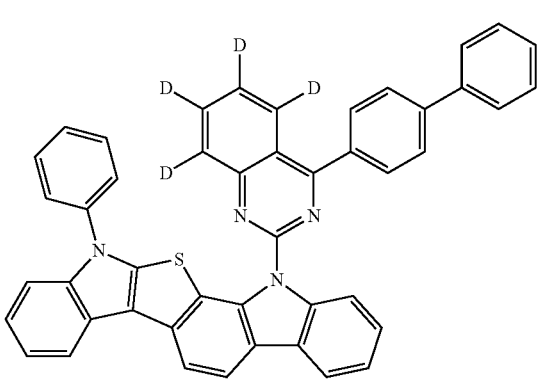

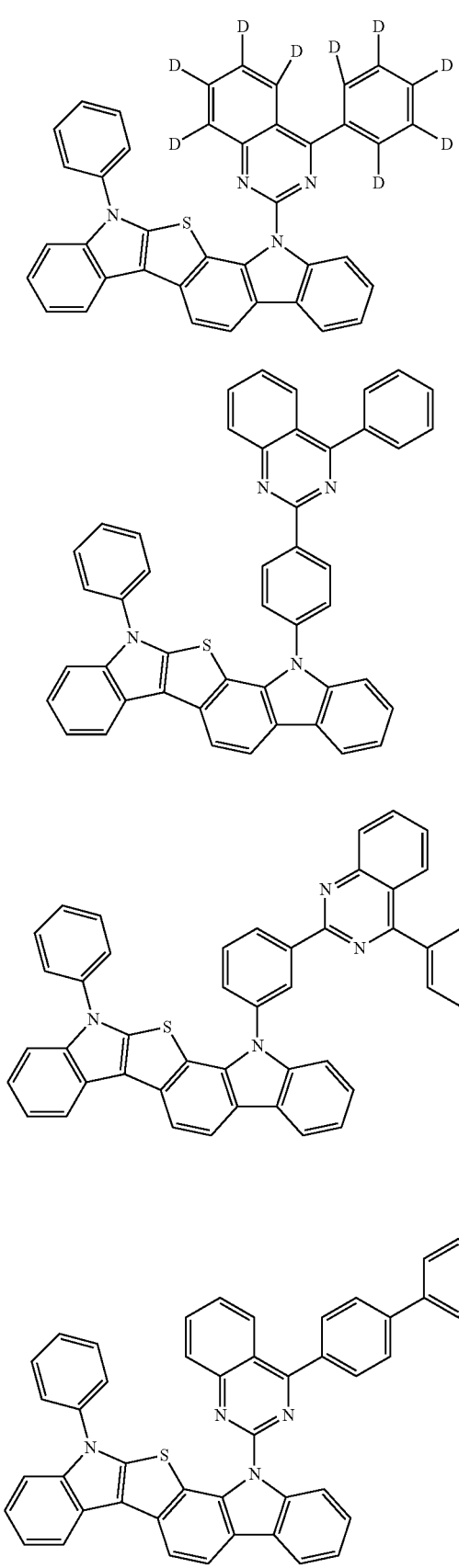
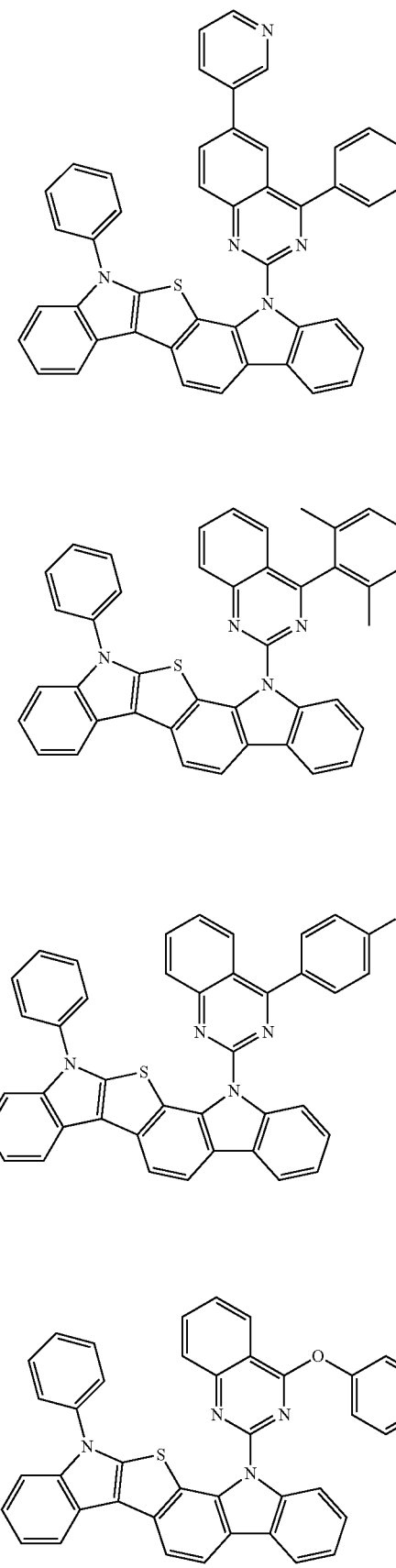

363
-continued
304
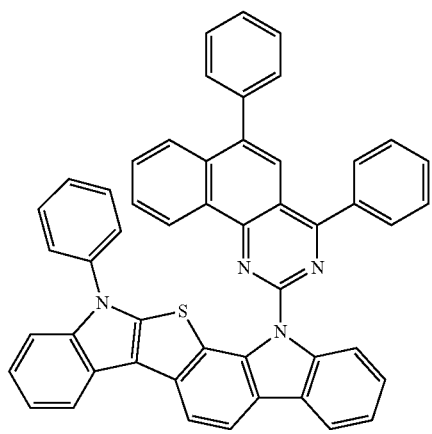
305
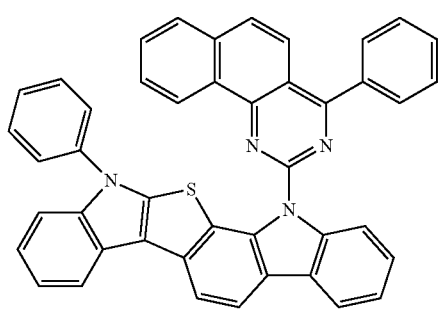
306
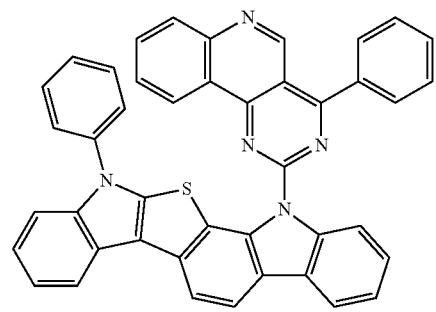
307
364
-continued
308
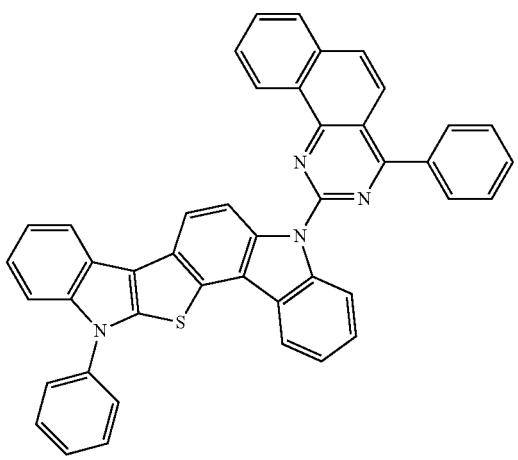
309
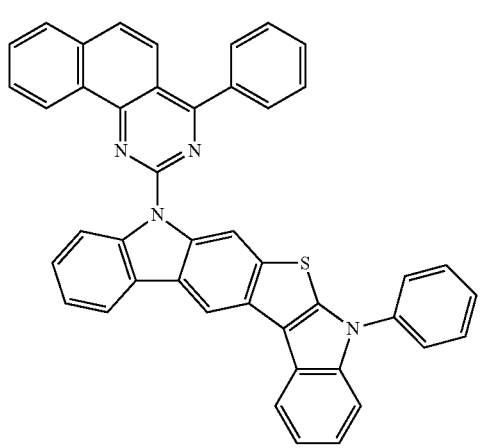
310
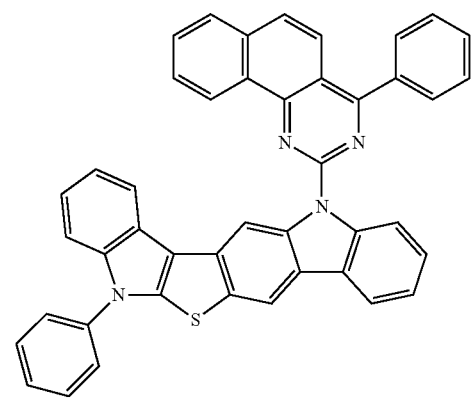

311
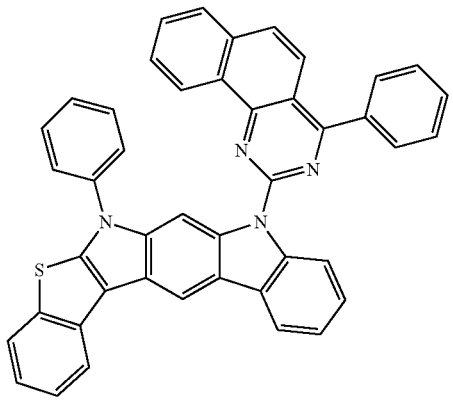
312
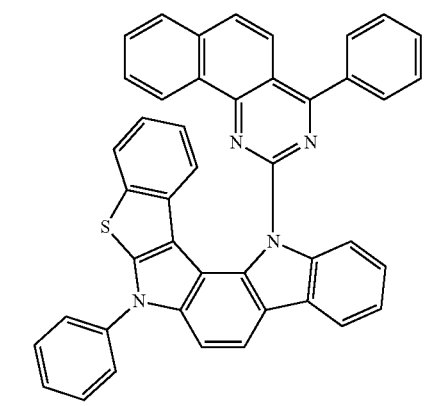
313
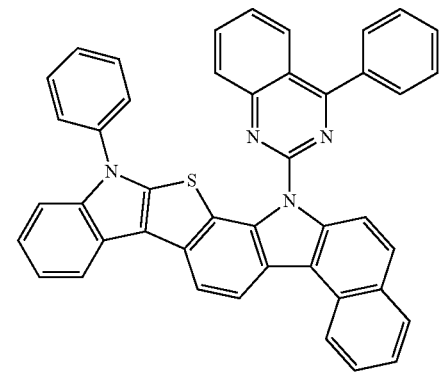
314
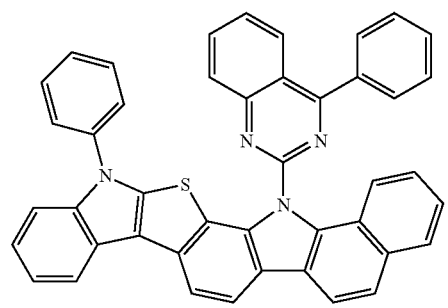
315
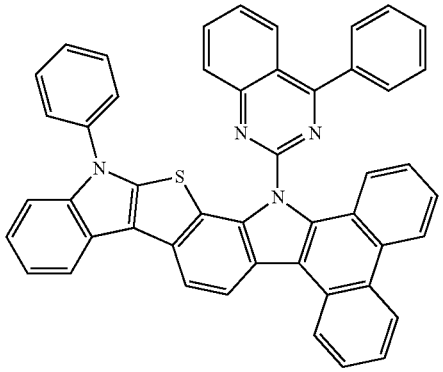
316
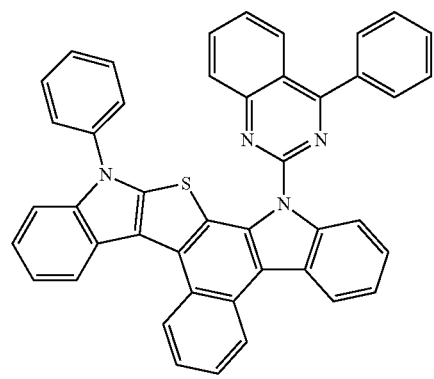
317
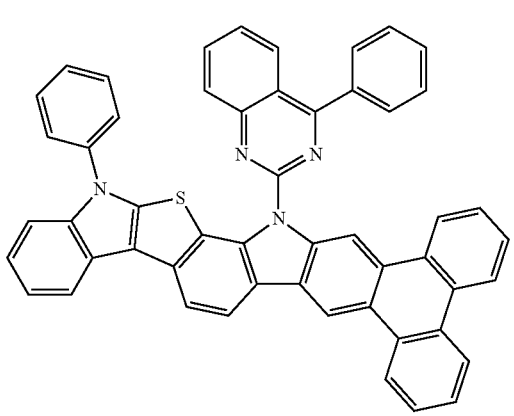
318
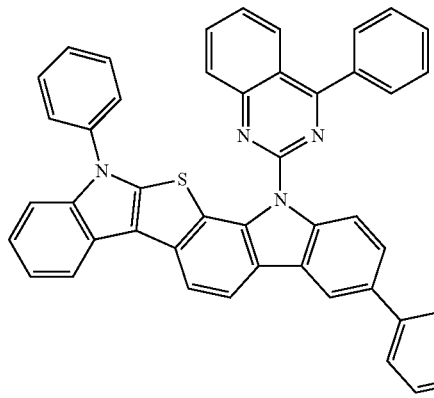

319
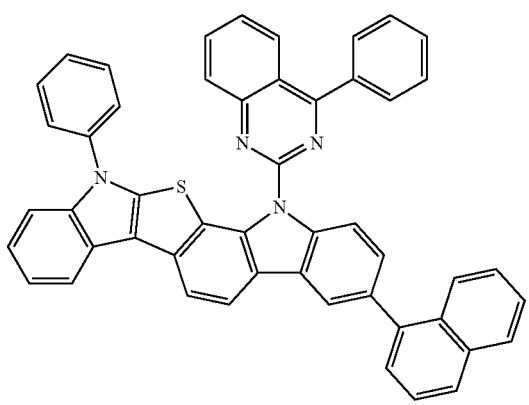
320
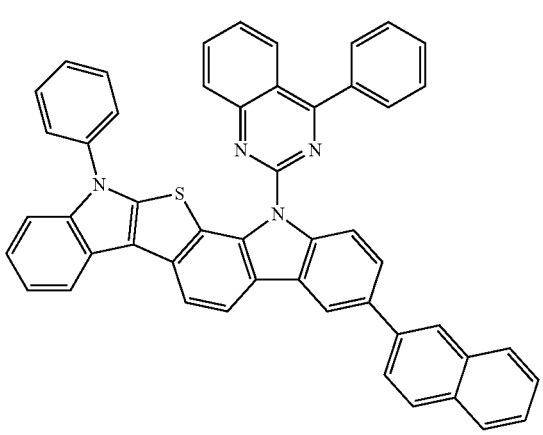
321
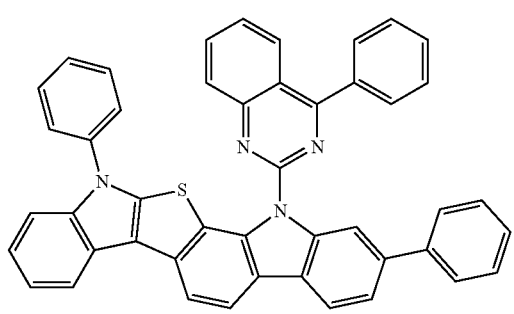
322
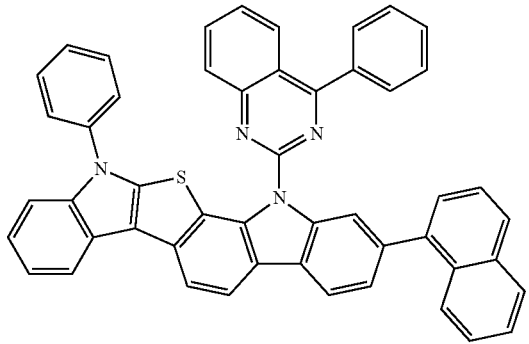
323
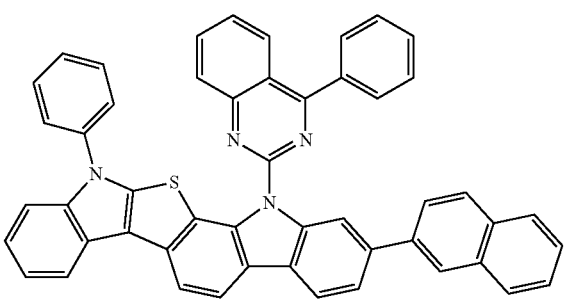
324
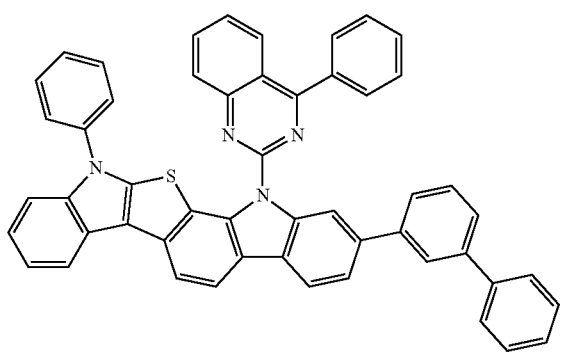
337
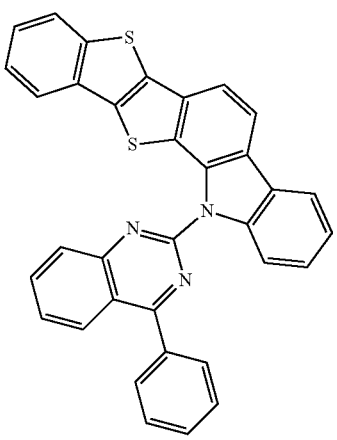
338
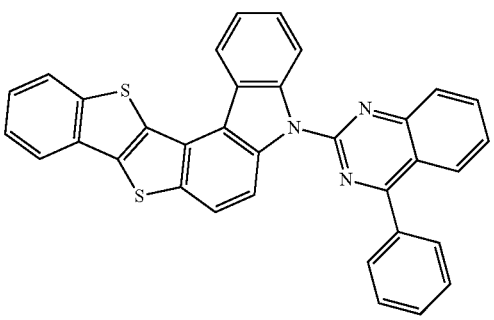

339
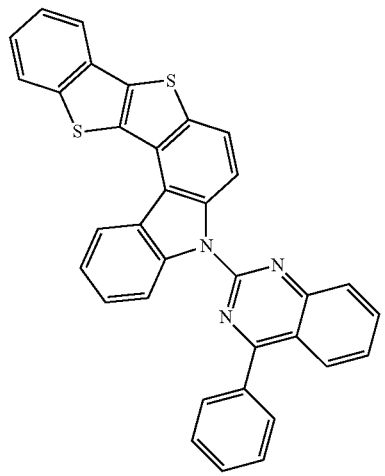
340
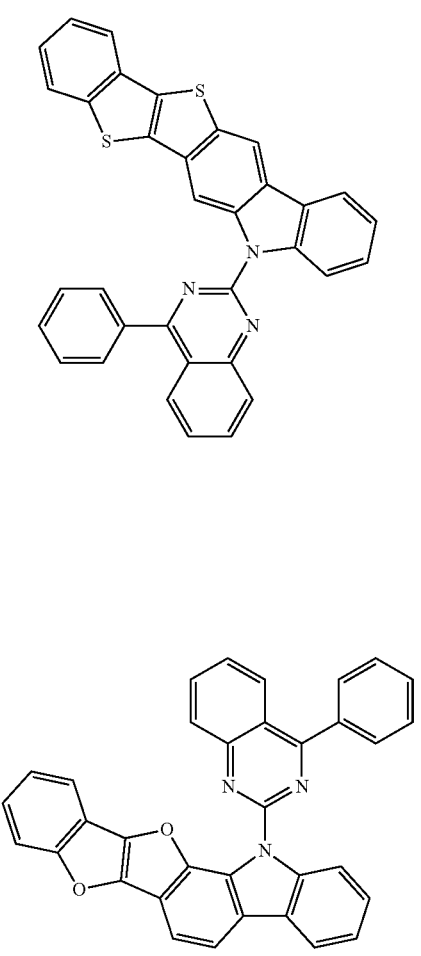
341
343
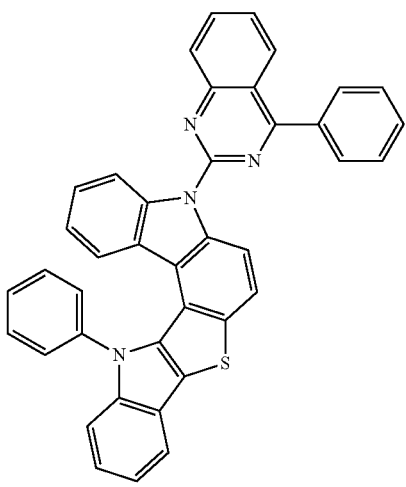
344
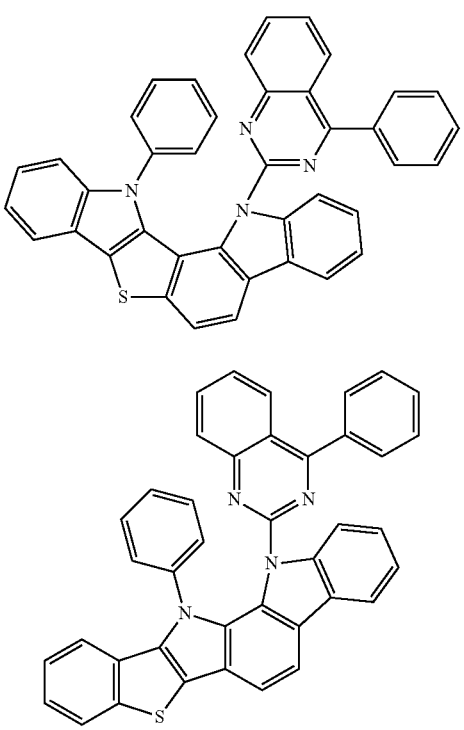
345
346
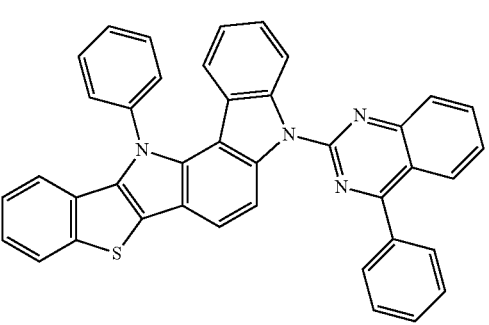

371
-continued
347
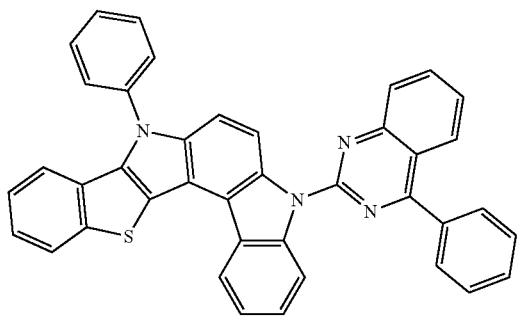
348
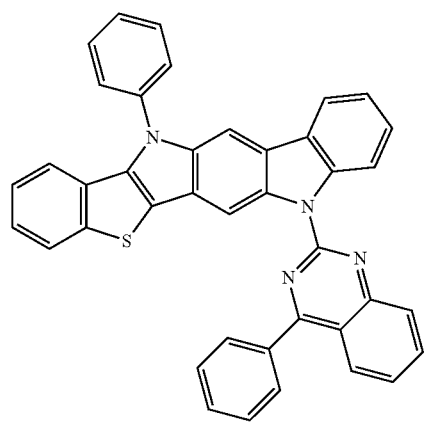
373
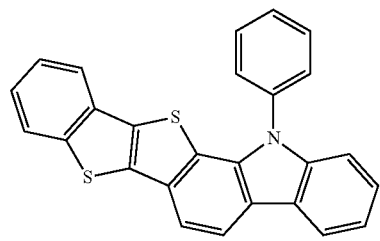
374
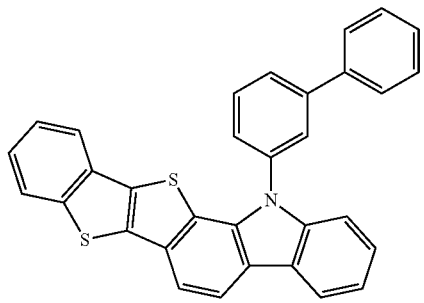
375
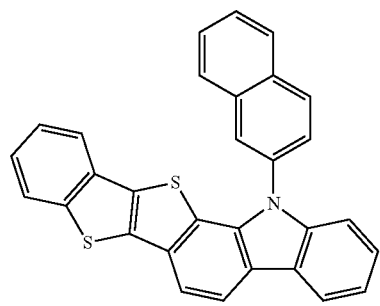
372
-continued
376
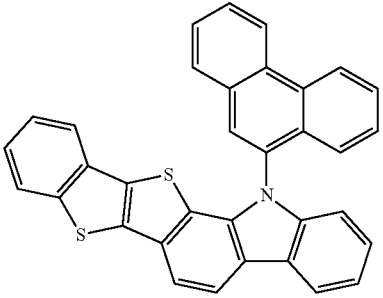
377
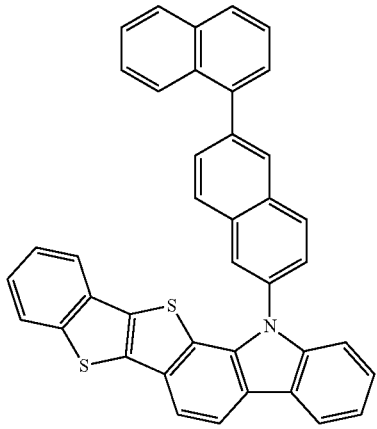
378
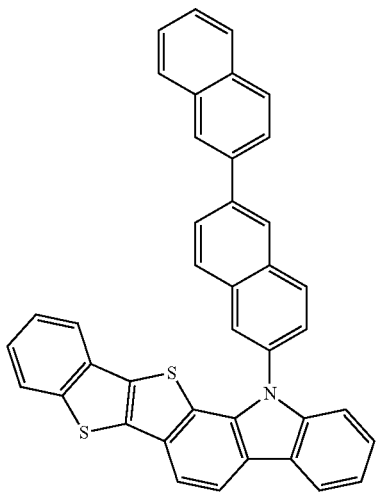
379
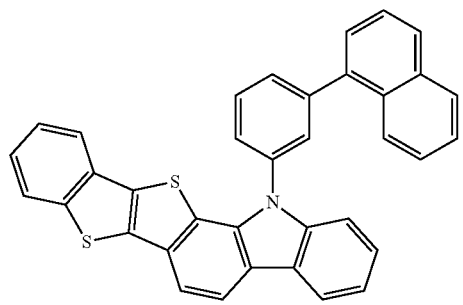

373
-continued
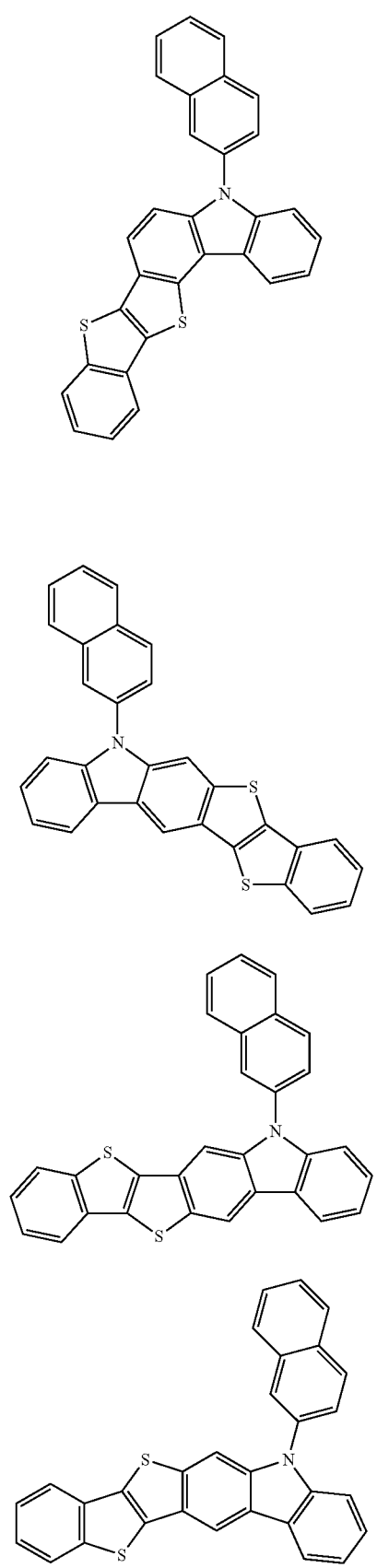
380
381
382
383
374
-continued
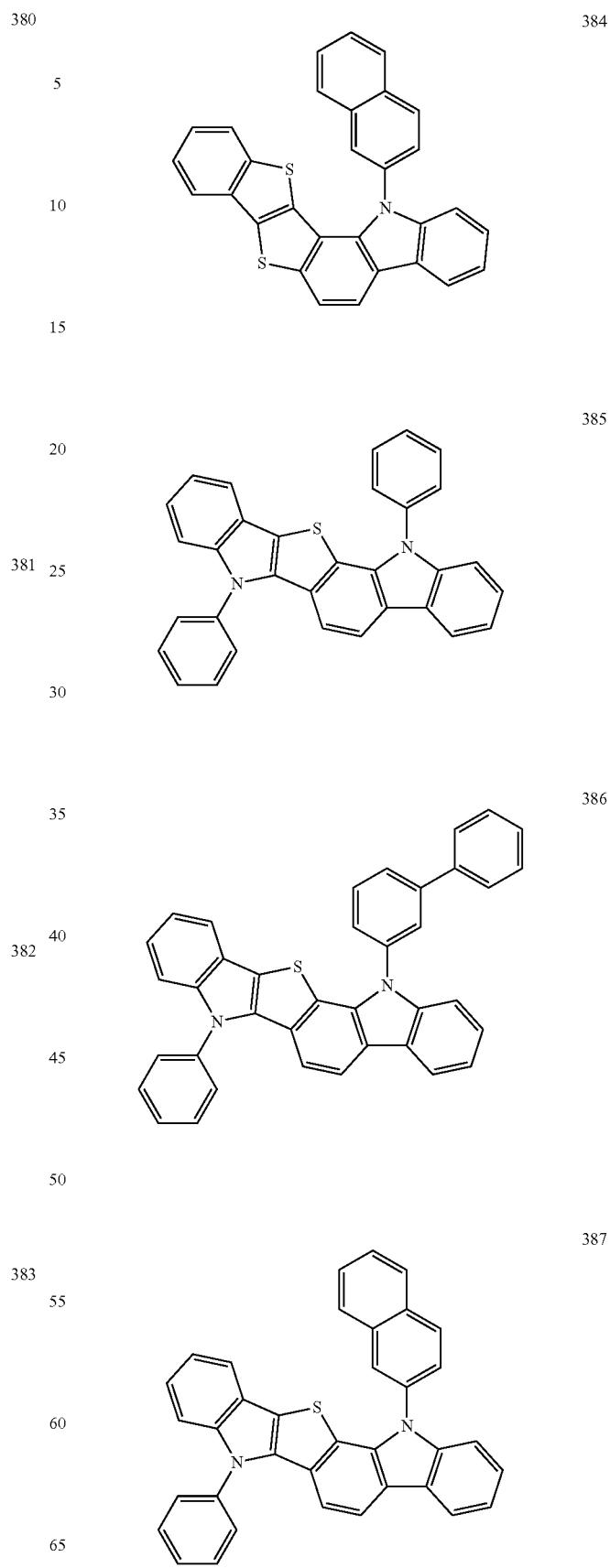
384
385
386
387

388
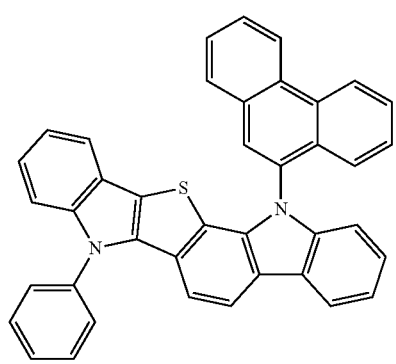
389
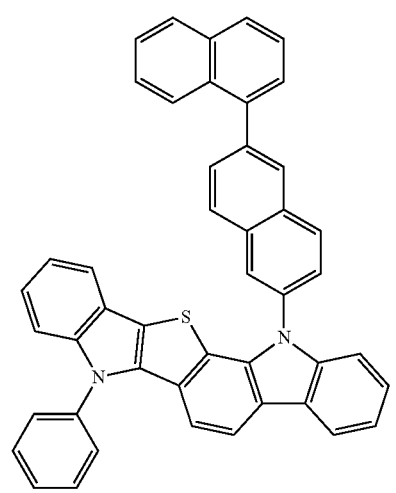
390
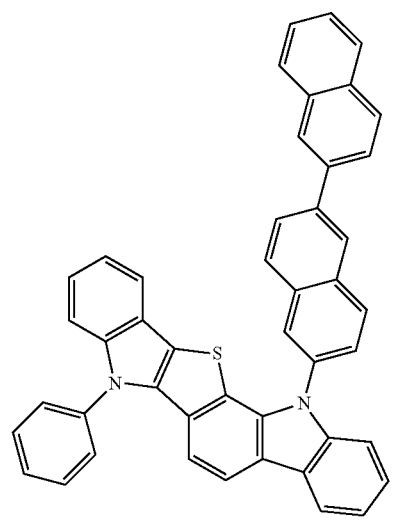
391
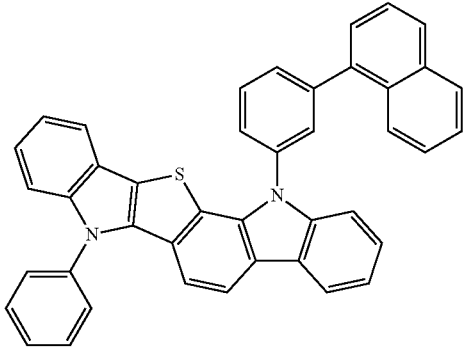
392
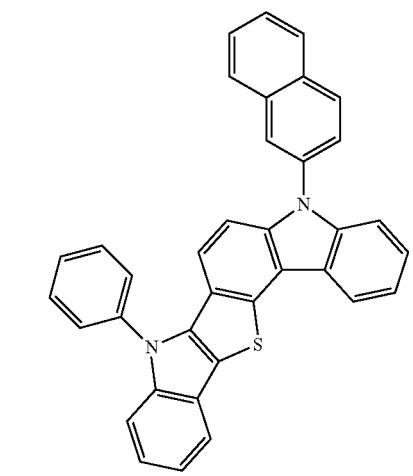
393
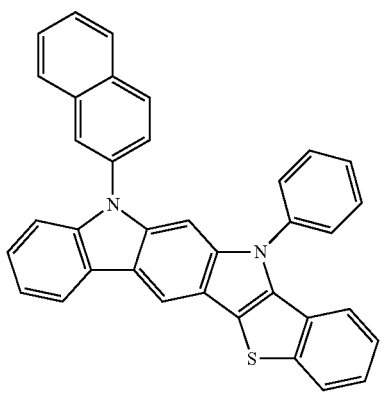
394
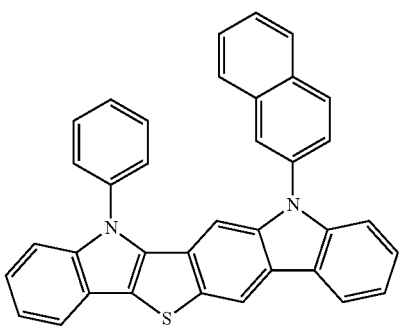

395
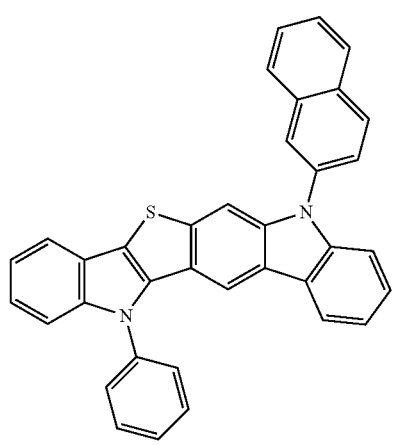
396
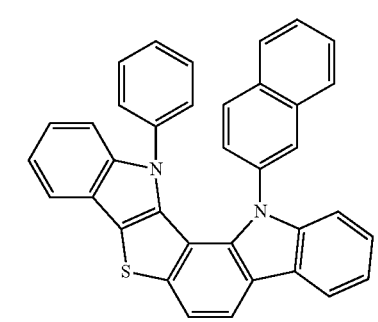
397
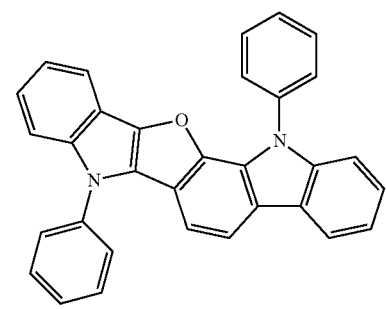
398
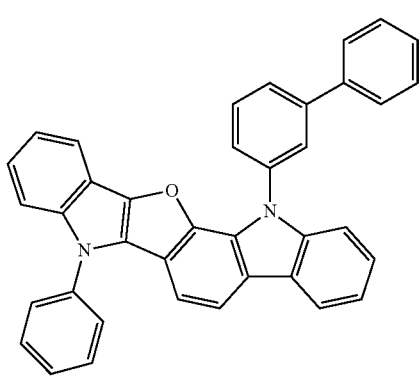
399
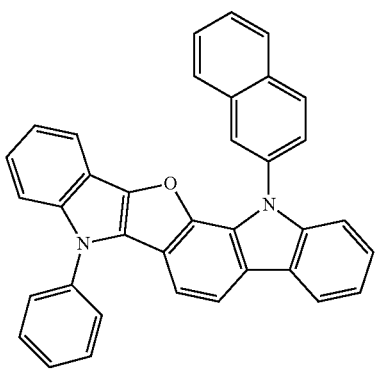
400
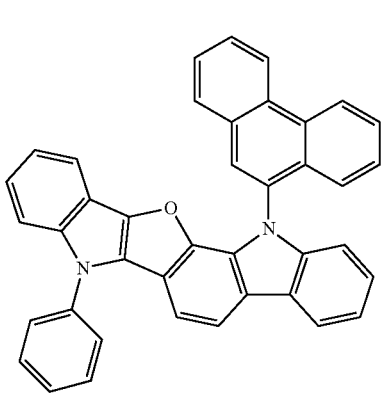
401
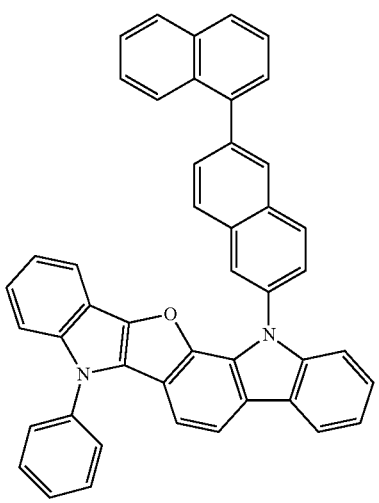

-continued
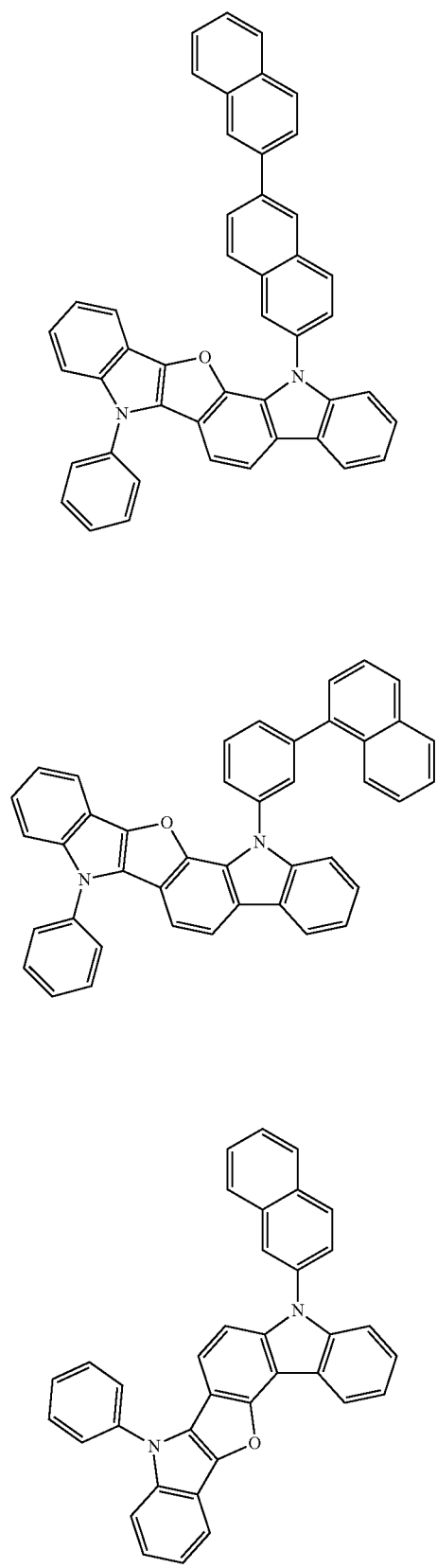
-continued
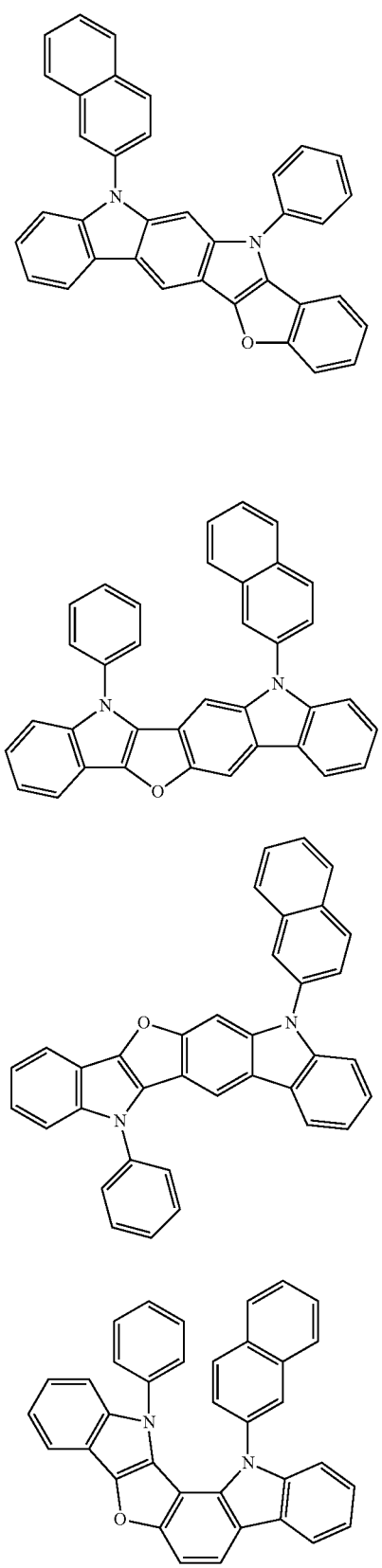

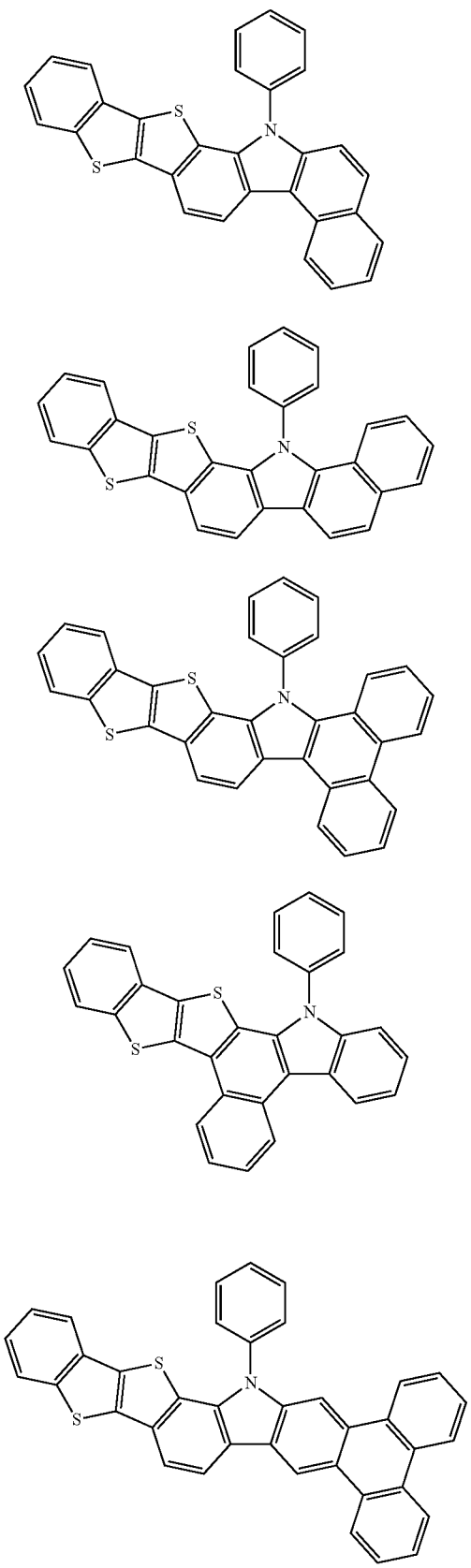
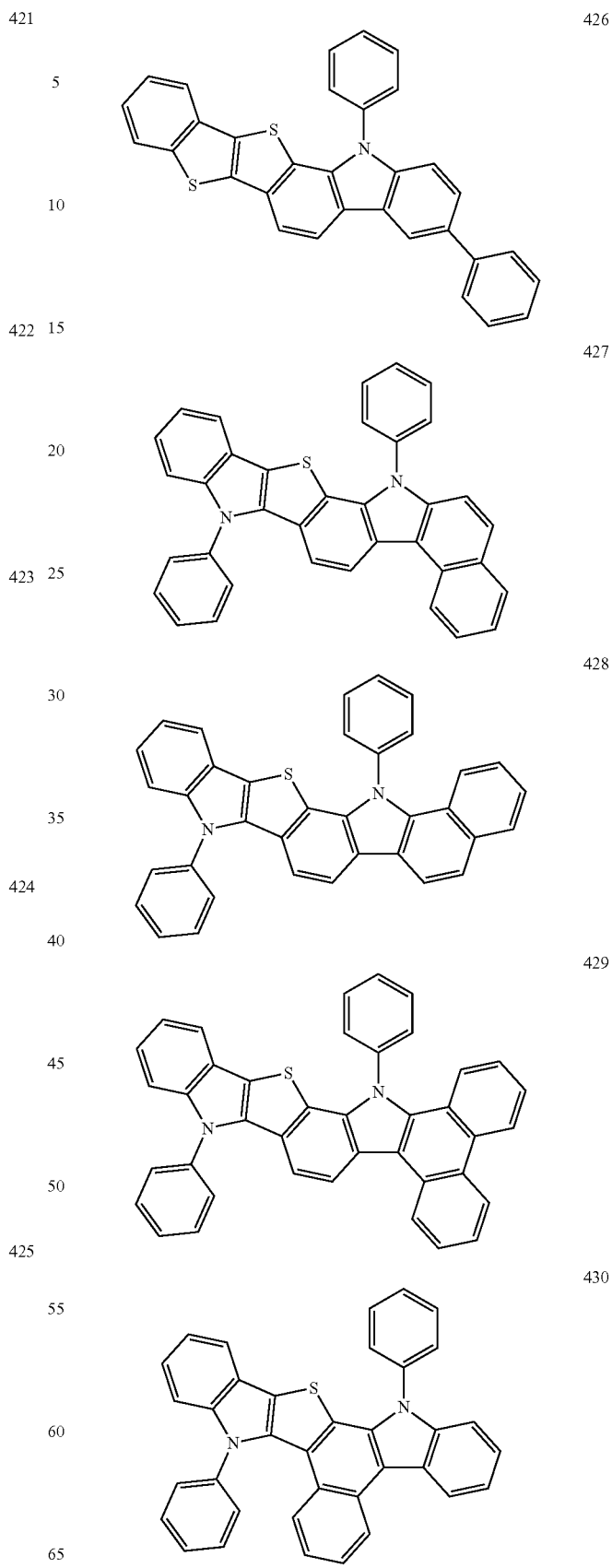

383
-continued
431
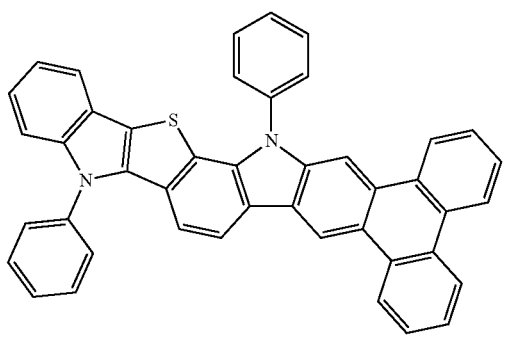
432
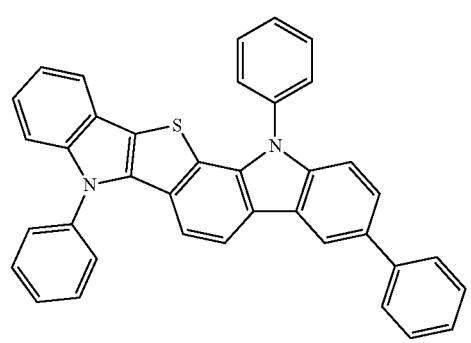
433
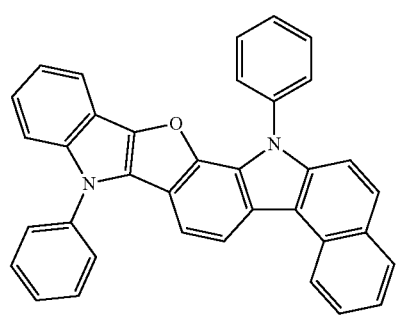
434
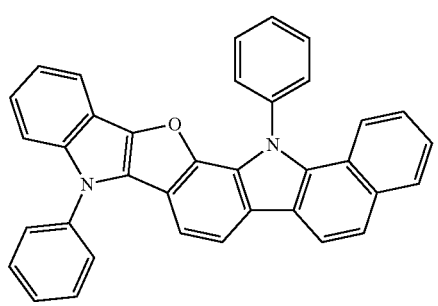
435
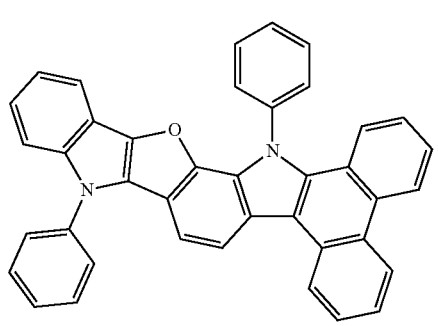
384
-continued
436
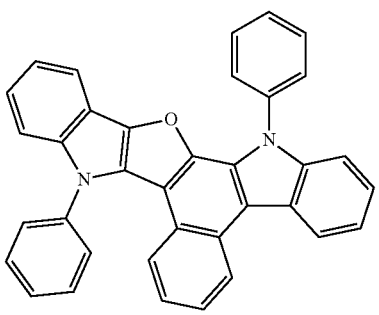
437
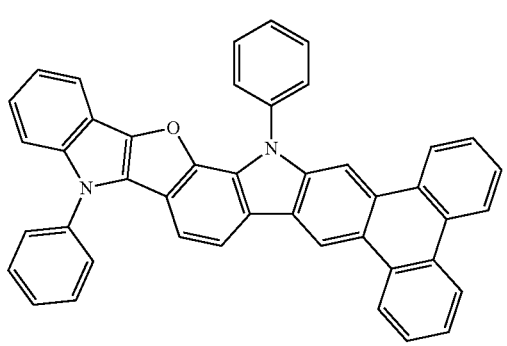
438
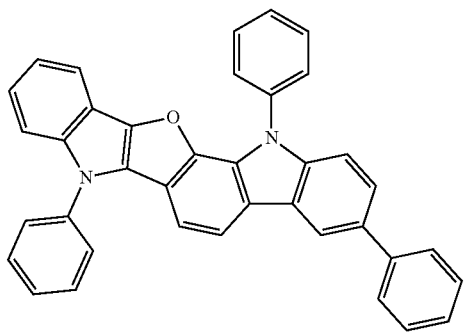
439
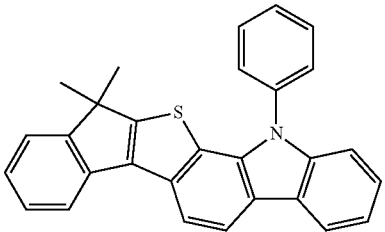
440
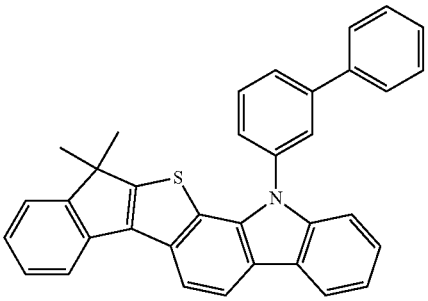

441
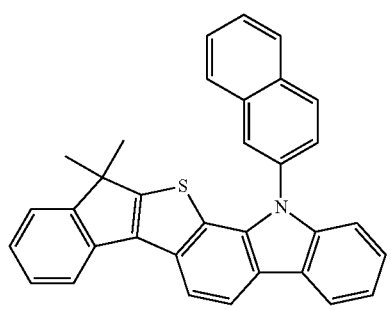
442
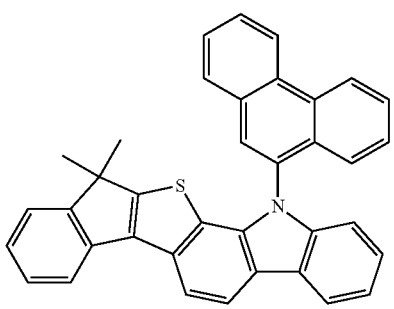
443
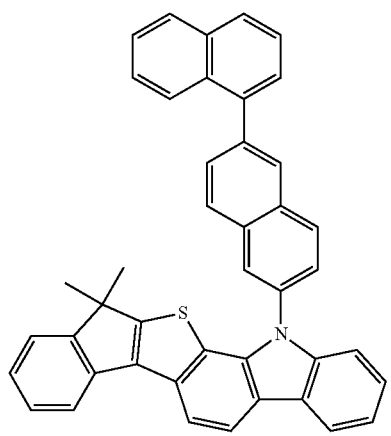
444
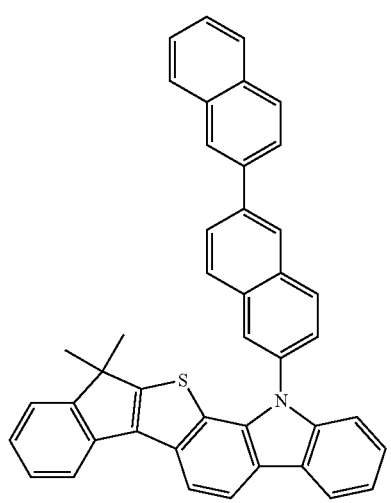
445
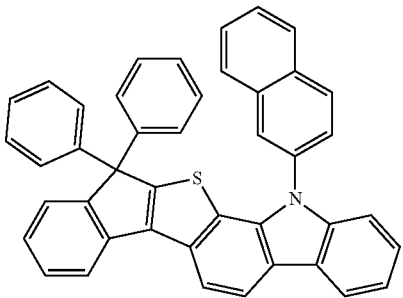
446
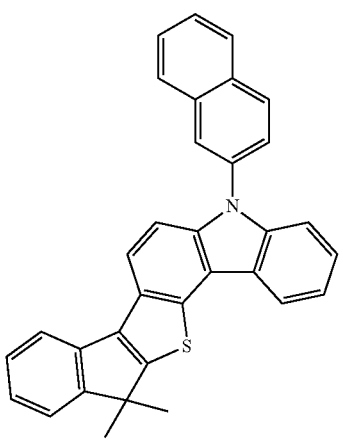
449
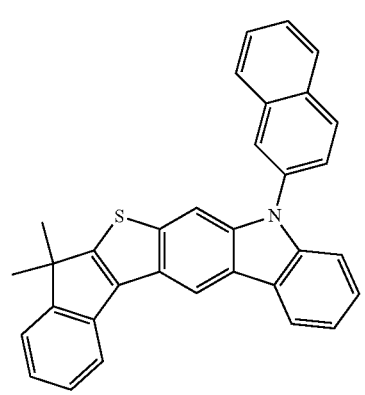
451
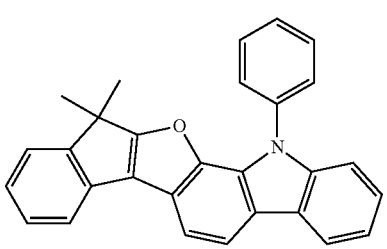

387
-continued
452
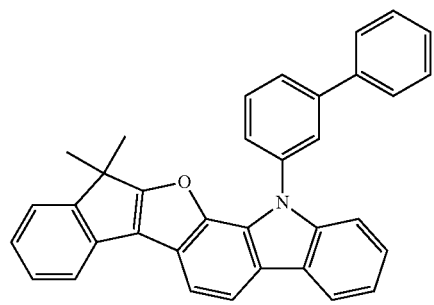
453
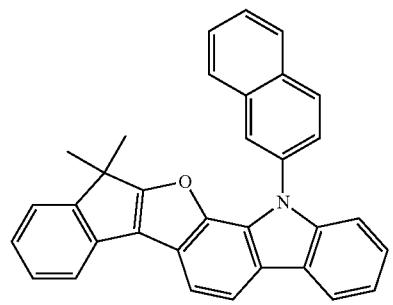
454
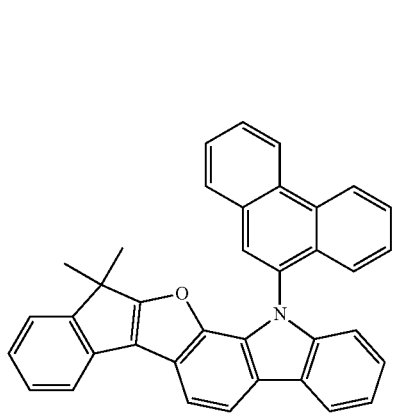
455
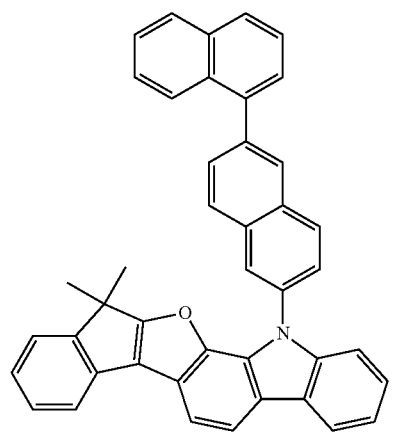
388
-continued
456
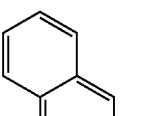
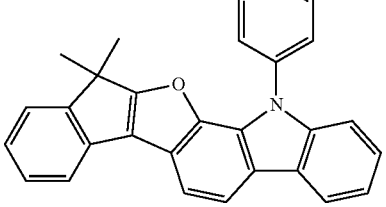
457
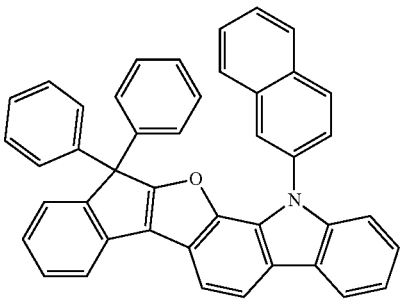
458
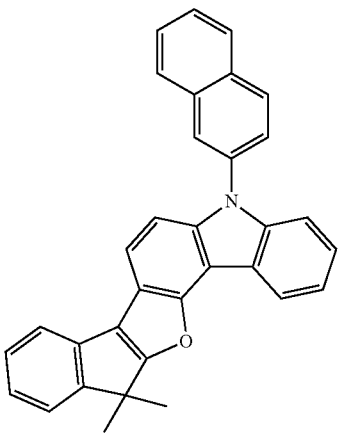
461
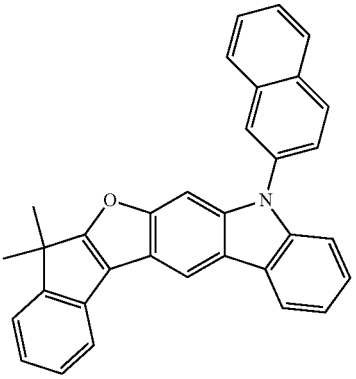

389
-continued
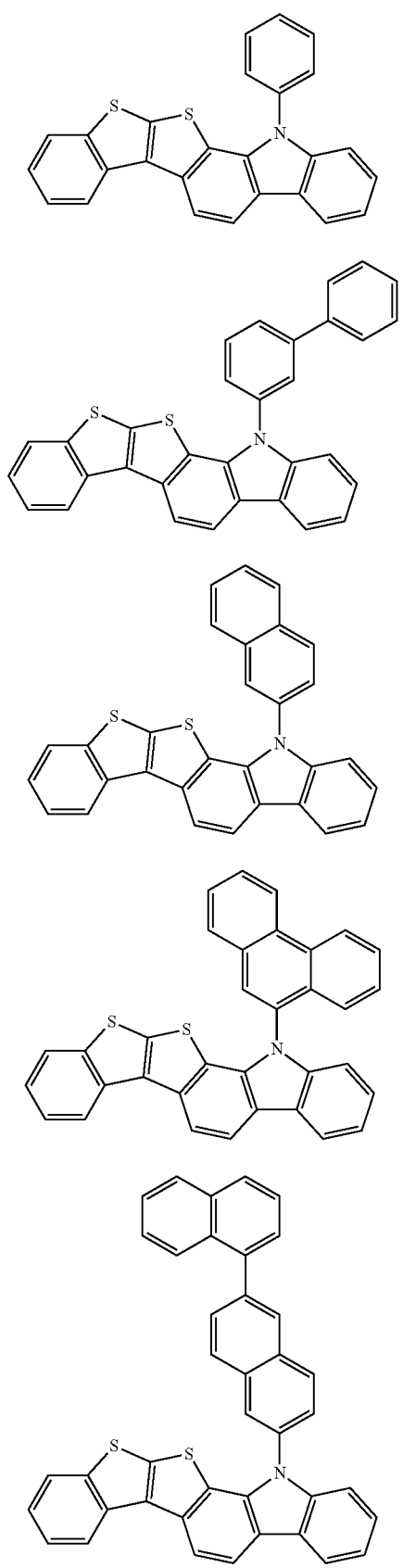
390
-continued
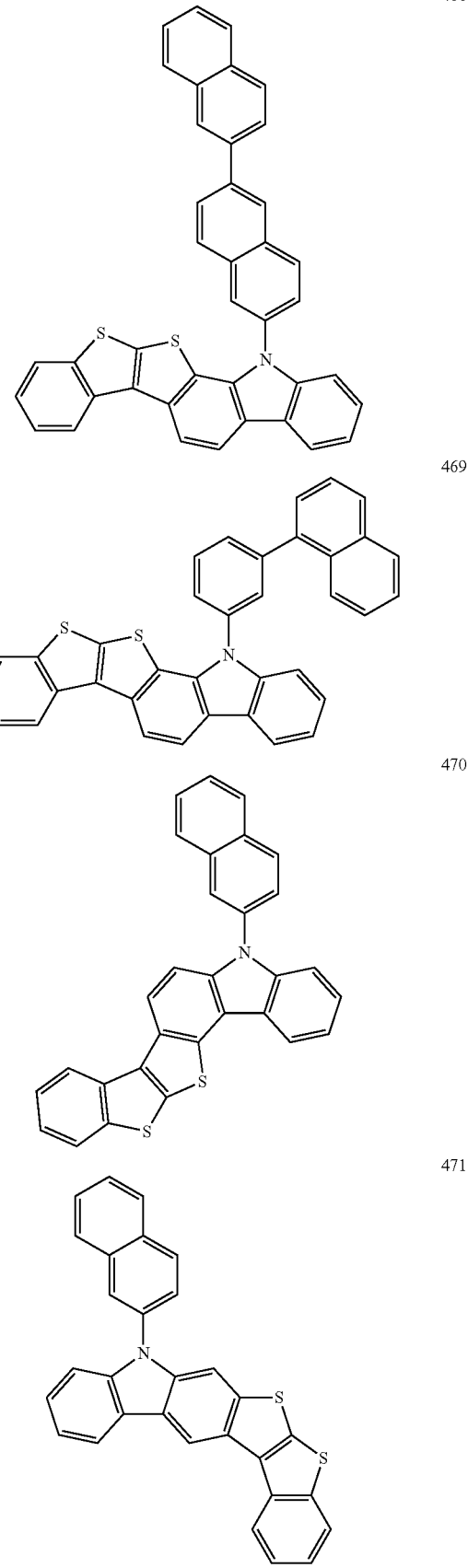

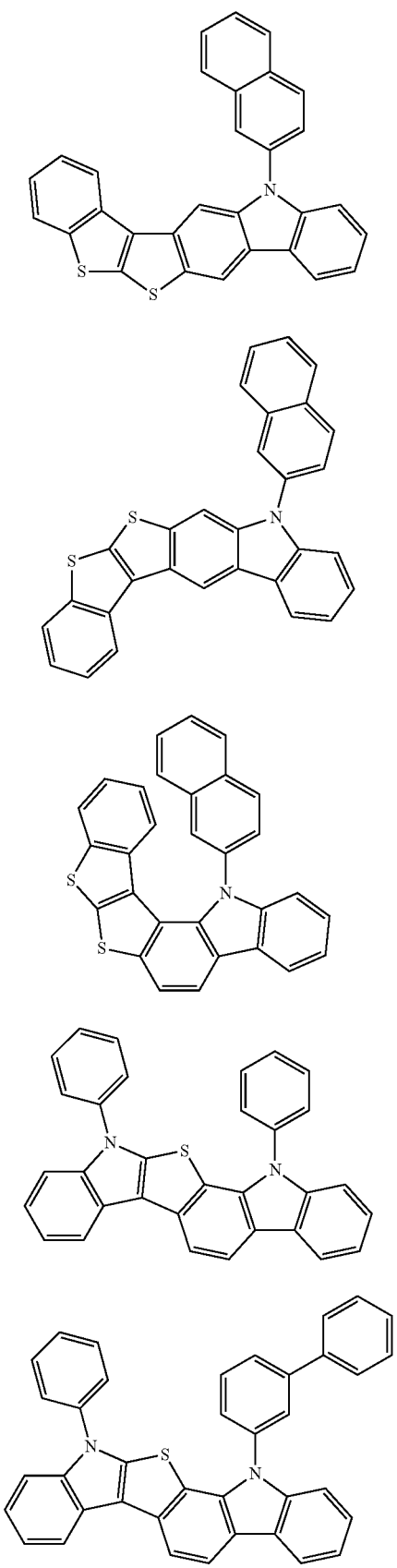

-continued
481
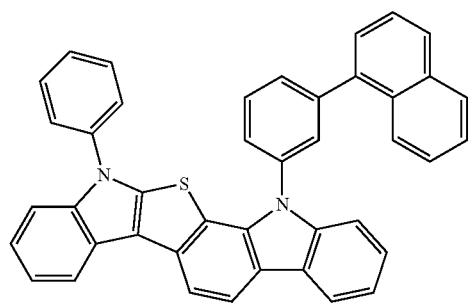
482
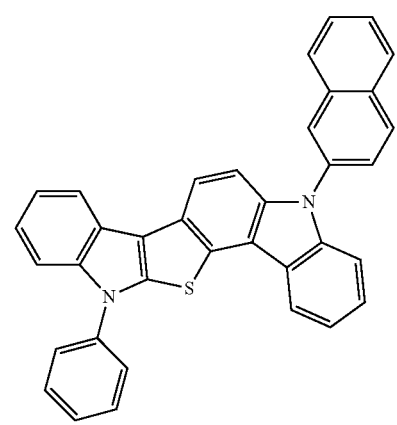
483
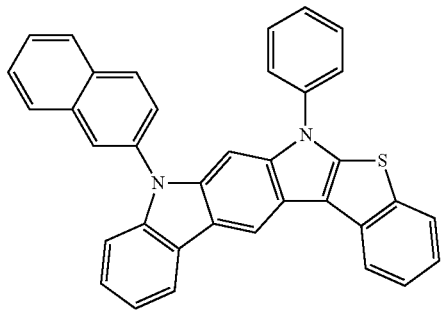
484
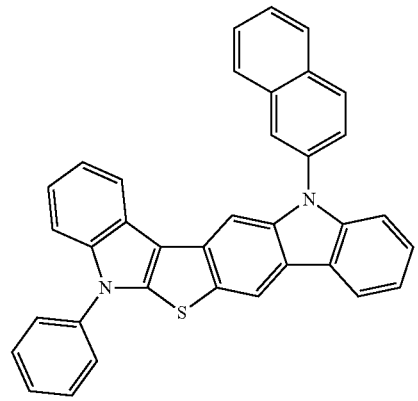
-continued
485
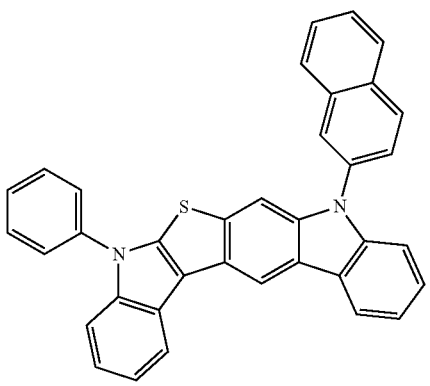
486
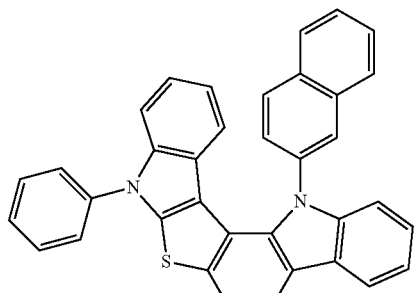
487
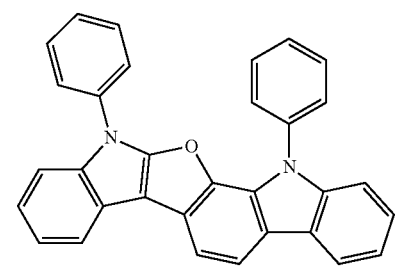
488
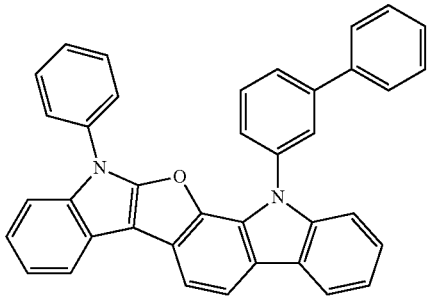
489
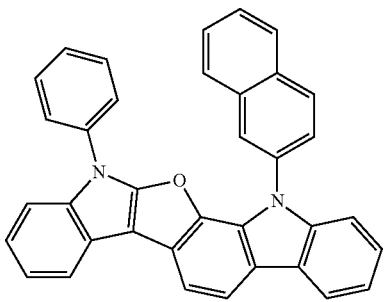

395
-continued
490
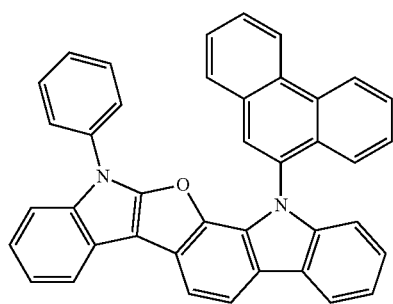
491
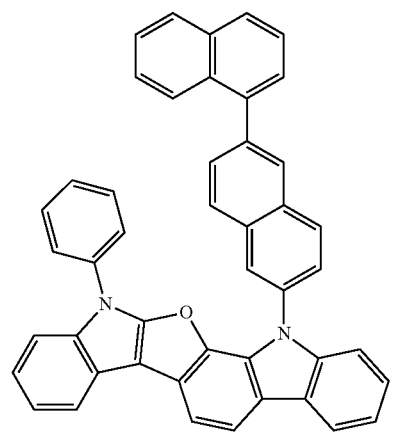
492
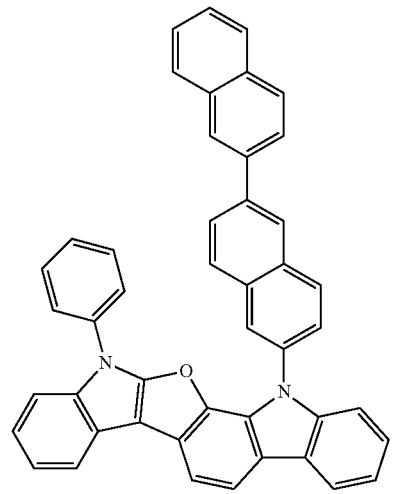
493
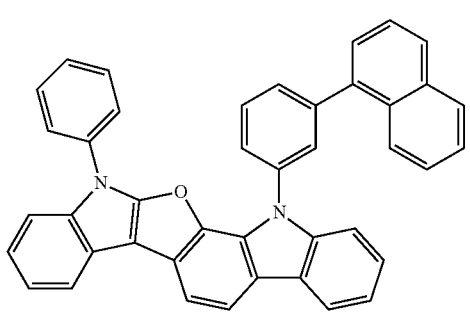
396
-continued
494
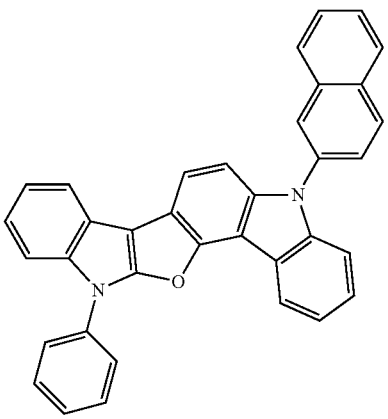
495
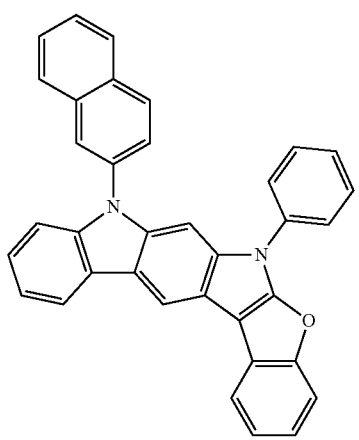
496
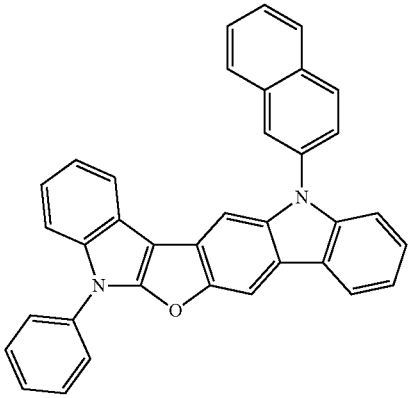
497
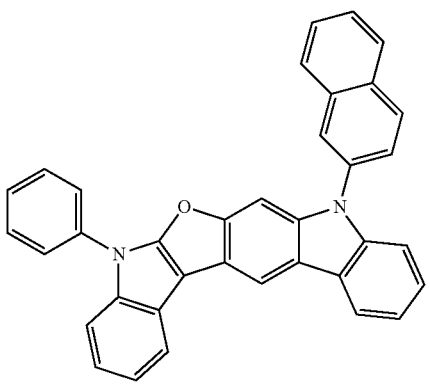

498
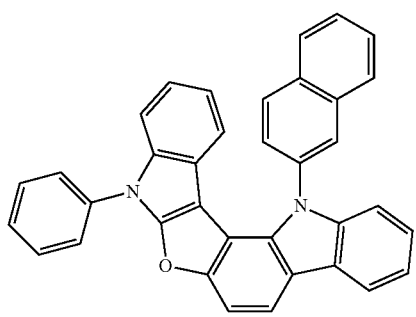
499
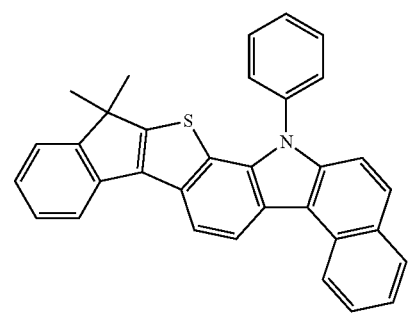
500
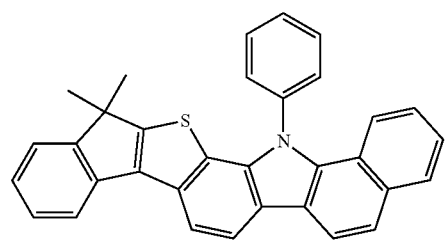
501
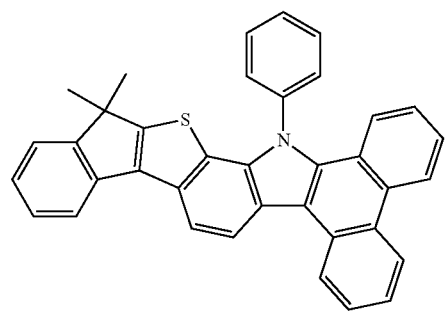
502
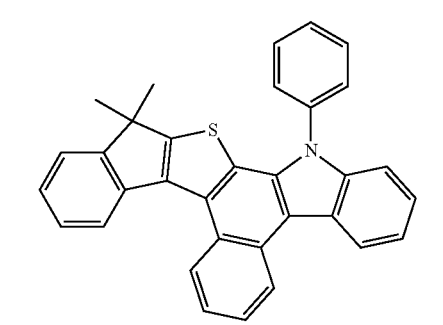
503
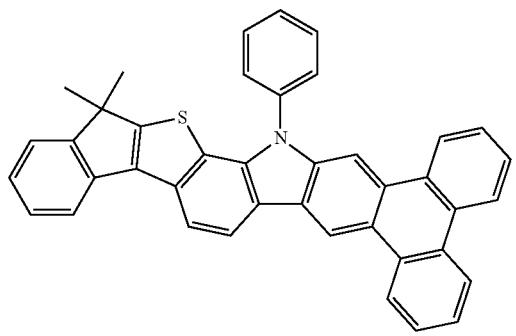
504
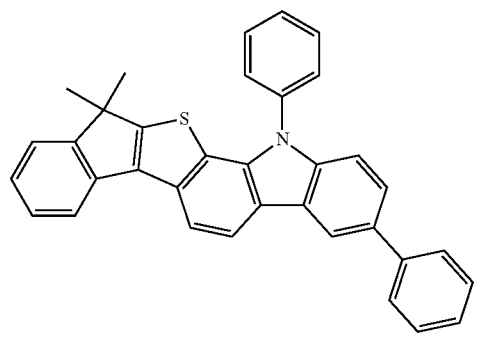
505
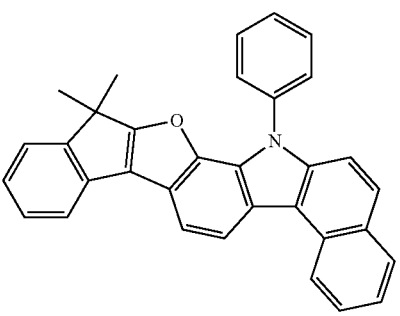
506
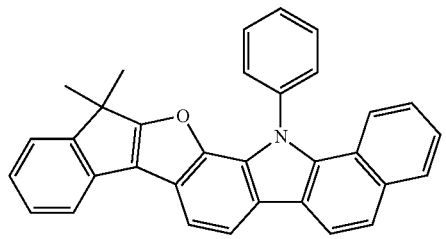
507
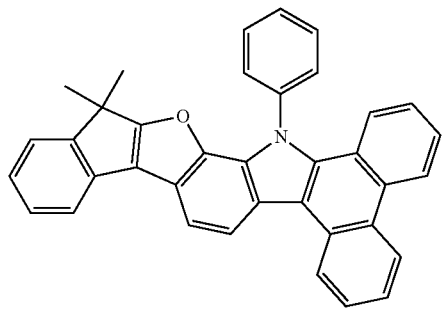

508
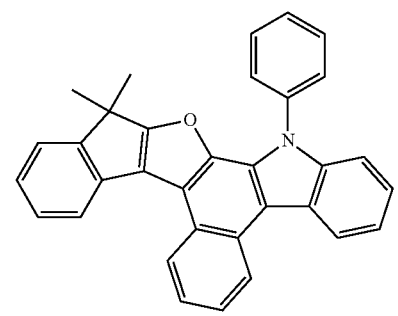
509
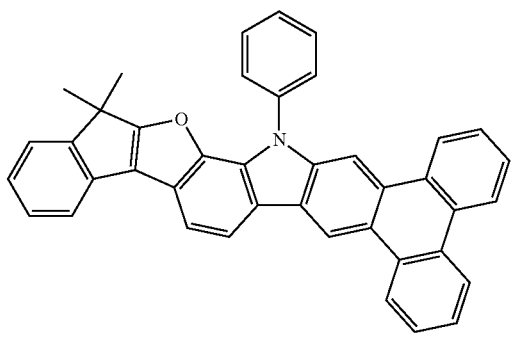
510
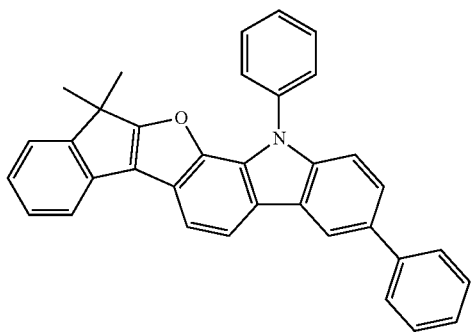
511
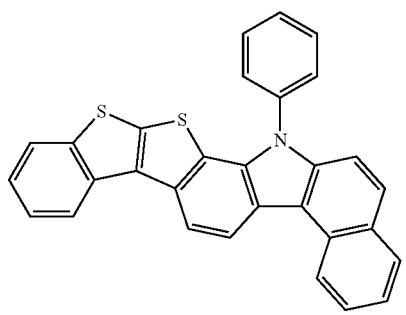
512
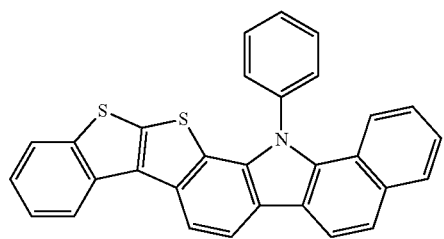
513
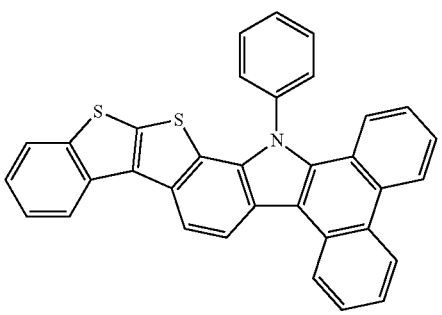
514
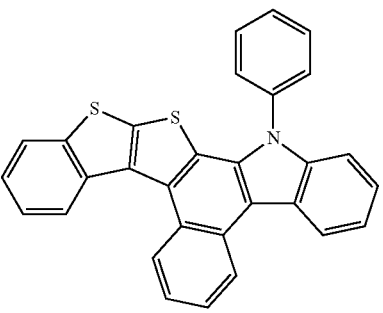
515
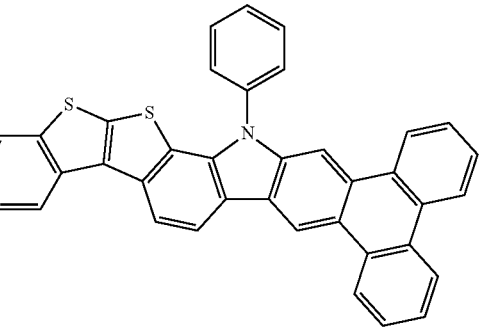
516
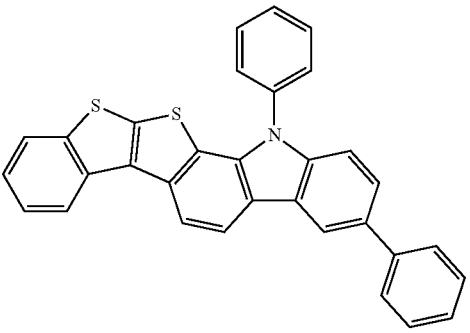

517 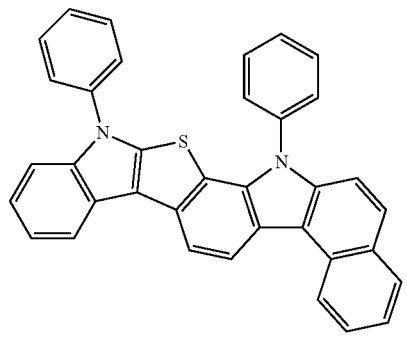
521 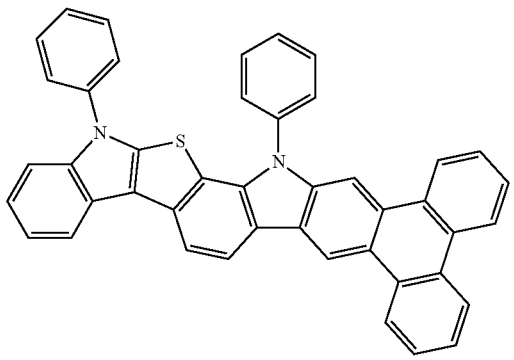
518 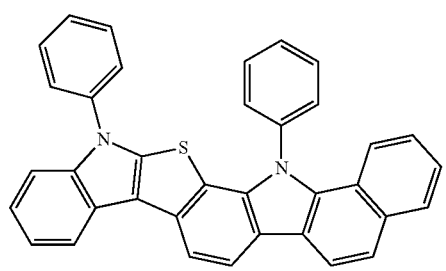
522 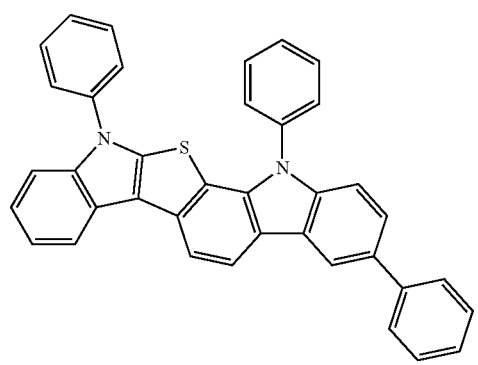
519 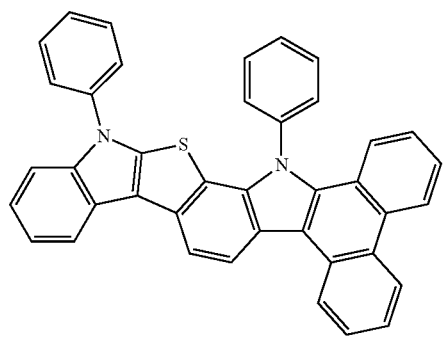
523 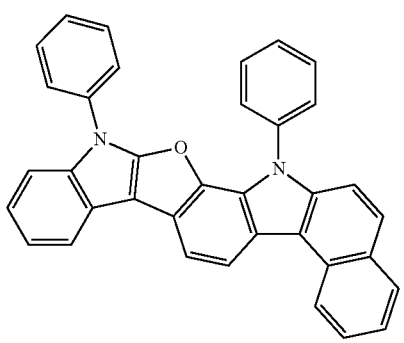
520 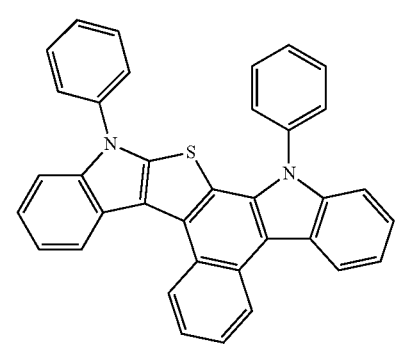
524 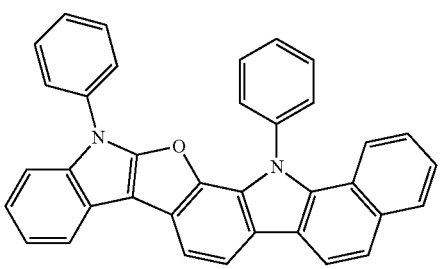

525
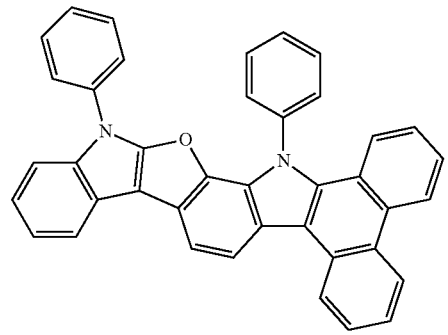
526
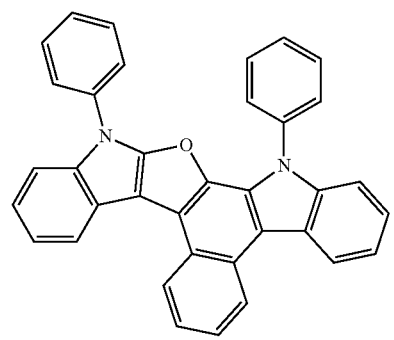
527
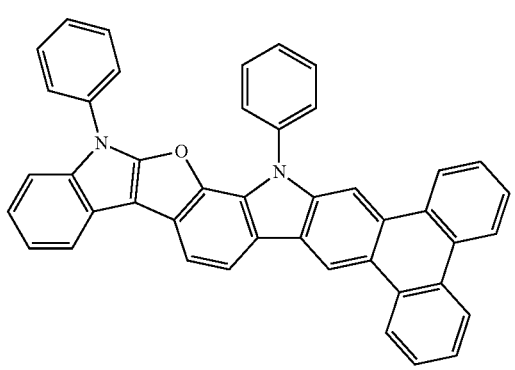
528
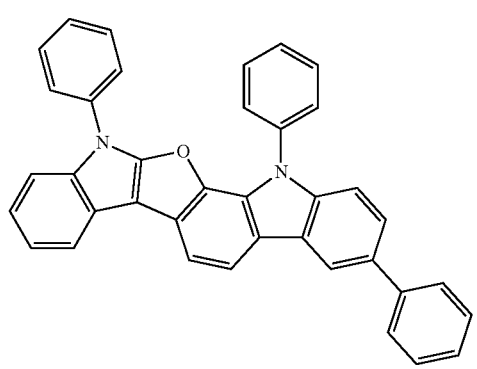
529
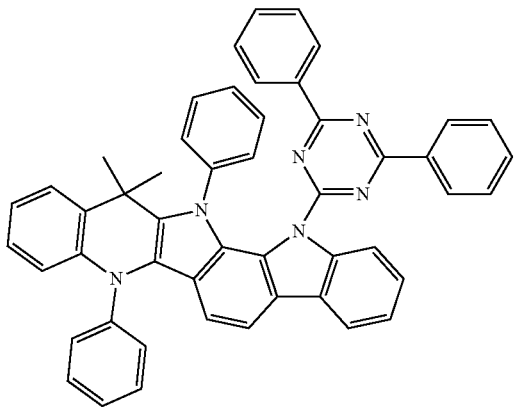
530
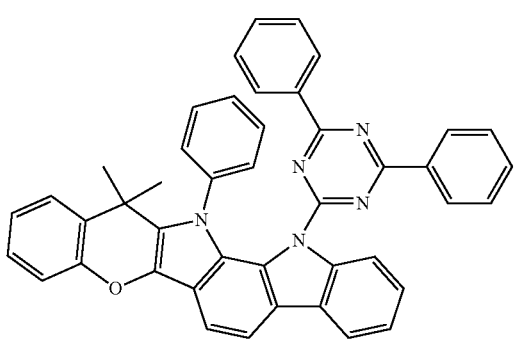
531
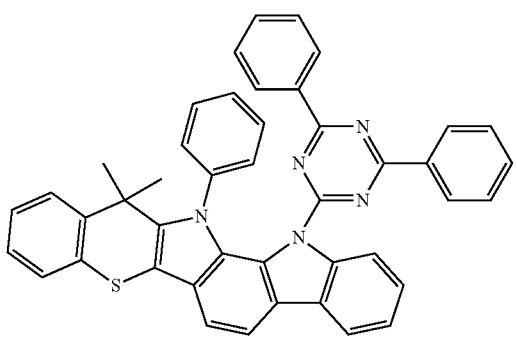
532
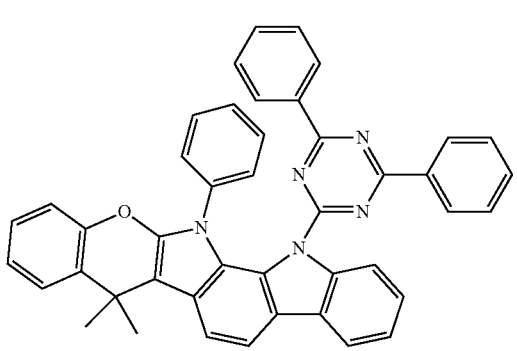

533
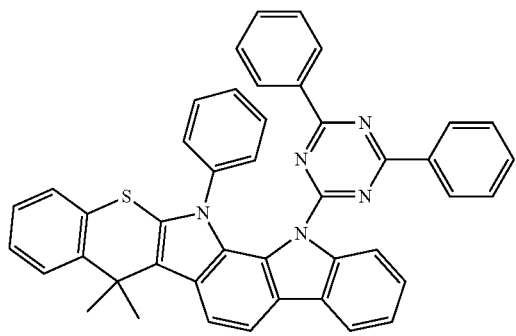
534
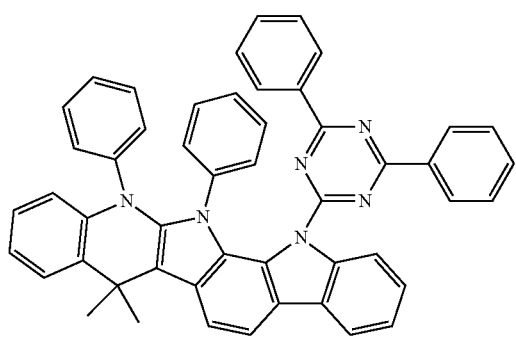
535
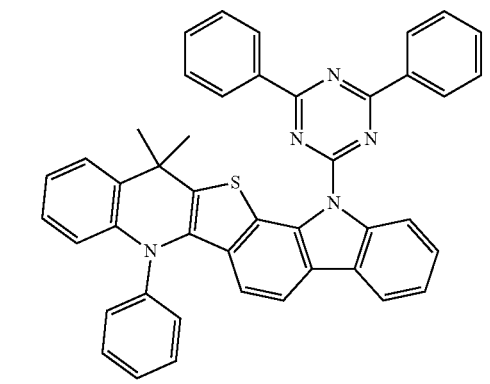
538
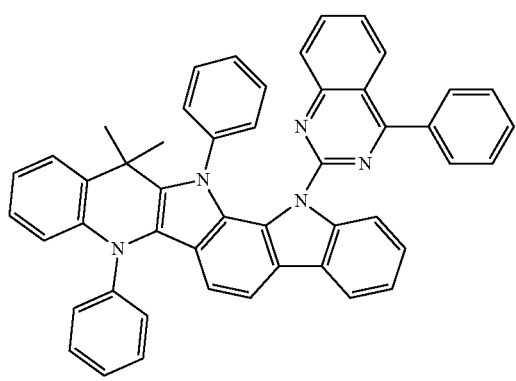
539
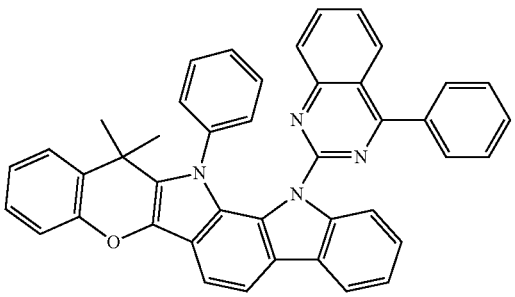
540
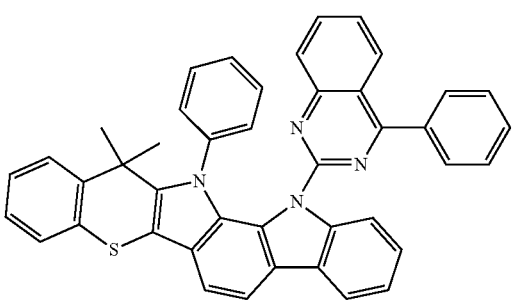
541
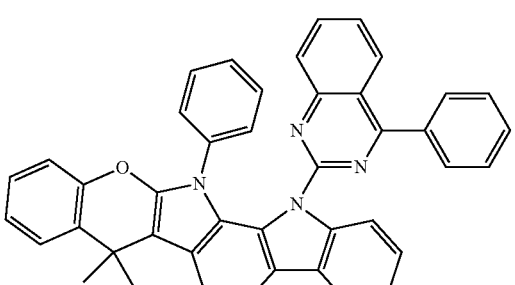
542
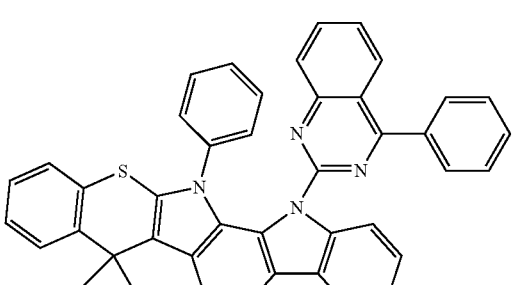
543
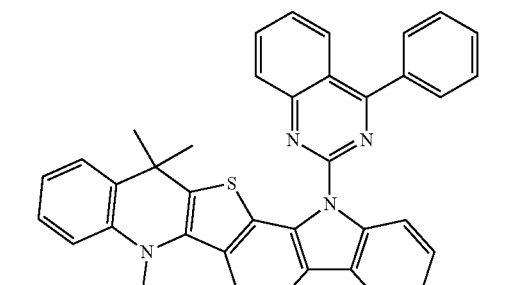

546
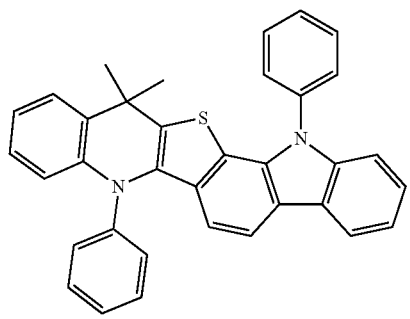
549
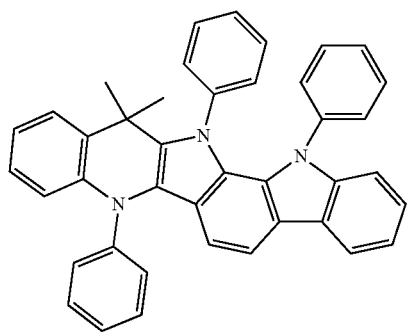
550
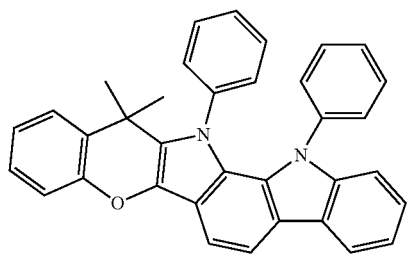
551
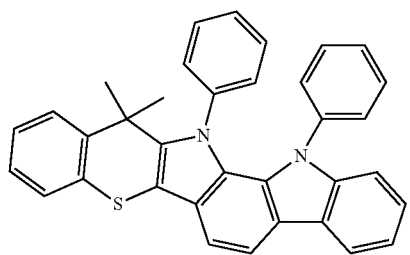
552
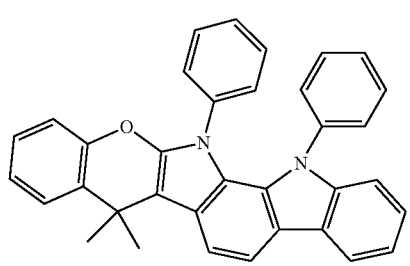
553
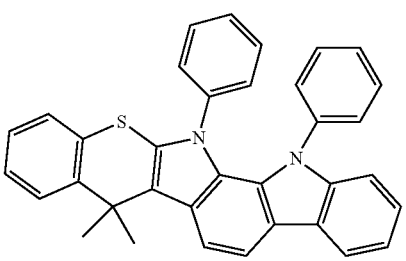
554
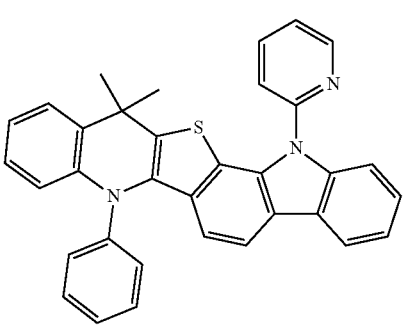
560
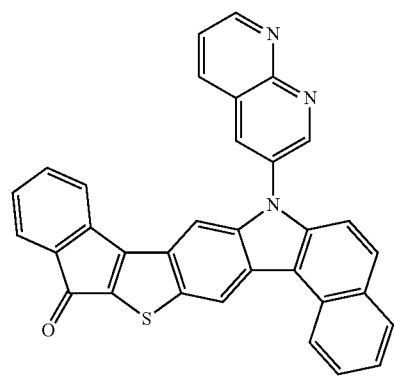
561
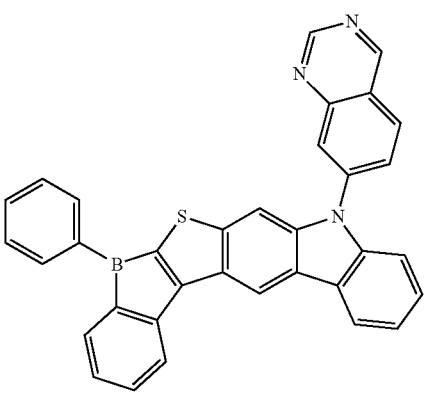

409
-continued
562
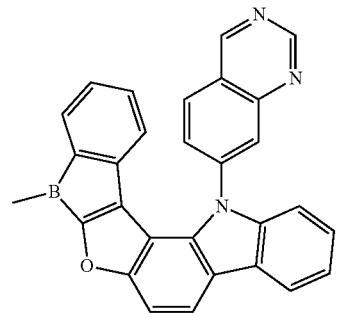
565
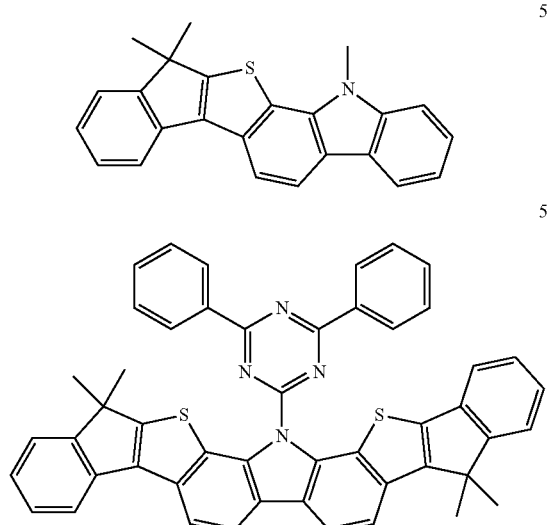
567
568
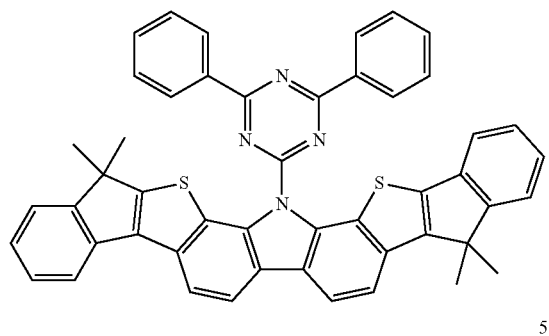
569
410
-continued
570
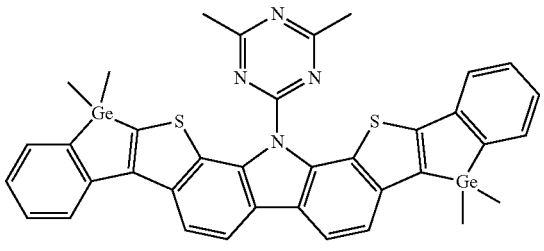
571
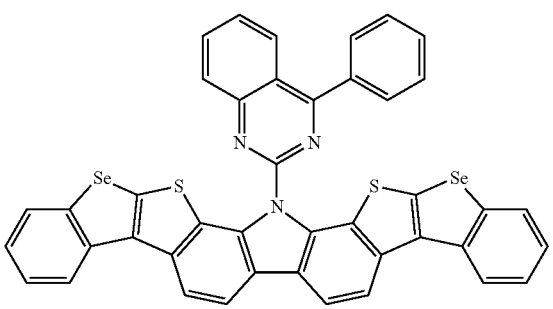
574
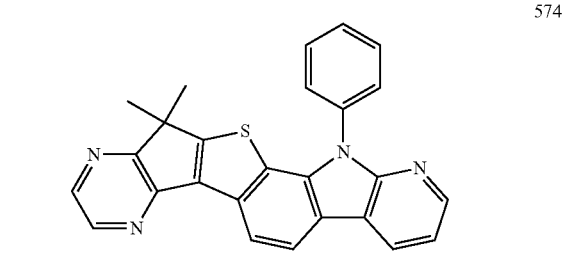
575
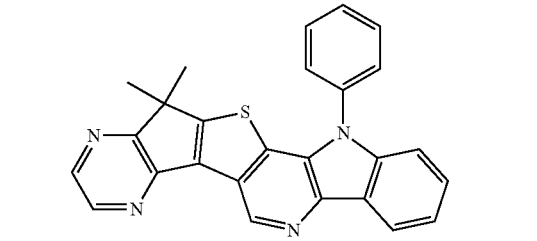
576
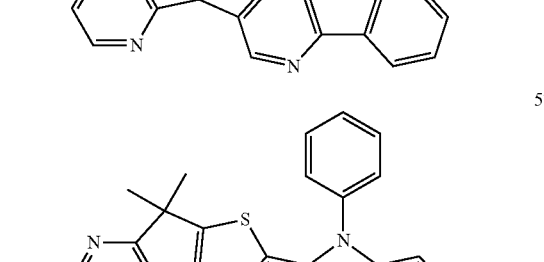

411
-continued

577
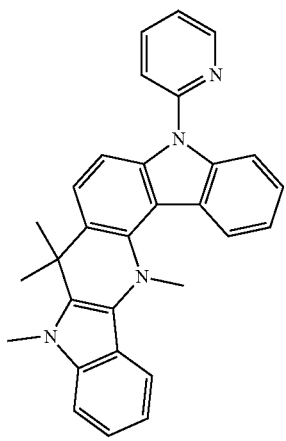

578
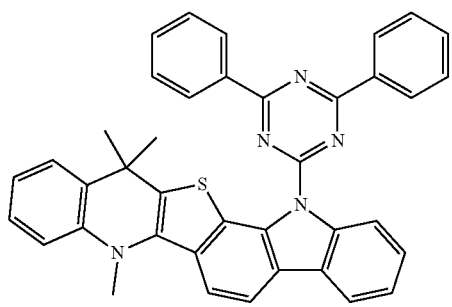

412
-continued

579
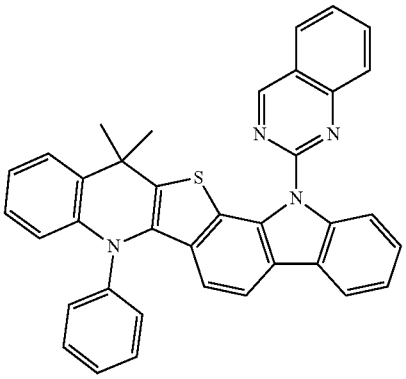

580
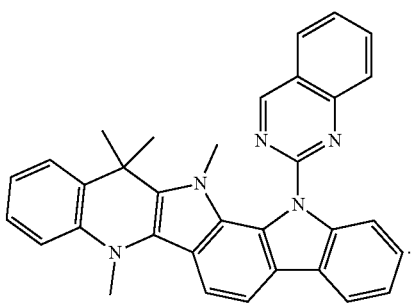

18. An organic light-emitting device comprising:
    a first electrode;
    a second electrode facing the first electrode; and
    an organic layer between the first electrode and the second electrode and comprising an emission layer, wherein the organic layer comprises the heterocyclic compound of claim 1.

19. The organic light-emitting device of claim 18, wherein the emission layer further comprises a dopant and wherein the heterocyclic compound is a host.

20. The organic light-emitting device of claim 19, wherein the dopant is a phosphorescent dopant.

* * * * *